(12) United States Patent
Barber et al.

(10) Patent No.: US 11,684,616 B2
(45) Date of Patent: Jun. 27, 2023

(54) AZALACTAM COMPOUNDS AS HPK1 INHIBITORS

(71) Applicant: PFIZER INC., New York, NY (US)

(72) Inventors: Joyann Barber, San Diego, CA (US); Sujin Cho-Schultz, San Diego, CA (US); Matthew L. Del Bel, San Diego, CA (US); Rebecca Anne Gallego, San Diego, CA (US); Mingying He, San Diego, CA (US); Mehran Jalaie, San Diego, CA (US); Robert Steven Kania, Del Mar, CA (US); Michele Ann McTigue, Encinitas, CA (US); Sajiv Krishnan Nair, Vista, CA (US); Anne-Marie Dechert Schmitt, Westerly, RI (US); Jamison Bryce Tuttle, Marblehead, MA (US); Dahui Zhou, Groton, CT (US); Ru Zhou, Carlsbad, CA (US)

(73) Assignee: PFIZER INC., New York, NY (US)

( * ) Notice: Subject to any disclaimer, the term of this patent is extended or adjusted under 35 U.S.C. 154(b) by 103 days.

(21) Appl. No.: 17/246,551

(22) Filed: Apr. 30, 2021

(65) Prior Publication Data

US 2022/0401424 A1 Dec. 22, 2022

Related U.S. Application Data

(60) Provisional application No. 63/018,689, filed on May 1, 2020.

(51) Int. Cl.
*C07D 471/04* (2006.01)
*C07D 519/00* (2006.01)
*A61K 31/444* (2006.01)
*A61K 45/06* (2006.01)

(52) U.S. Cl.
CPC ............ *A61K 31/444* (2013.01); *A61K 45/06* (2013.01); *C07D 471/04* (2013.01); *C07D 519/00* (2013.01)

(58) Field of Classification Search
CPC .. C07D 471/04; C07D 519/00; A61K 31/444; A61K 45/00
USPC ........................................................ 514/300
See application file for complete search history.

(56) References Cited

U.S. PATENT DOCUMENTS

| | | | |
|---|---|---|---|
| 2011/0230482 A1 | 9/2011 | Zhang et al. | |
| 2020/0172539 A1* | 6/2020 | Gallego | ............... C07D 471/04 |

FOREIGN PATENT DOCUMENTS

| | | |
|---|---|---|
| EP | 3572401 | 11/2019 |
| EP | 3590931 | 1/2020 |
| WO | 2018/049324 | 3/2018 |
| WO | 2018/151830 | 8/2018 |
| WO | 2018/167147 | 9/2018 |
| WO | 2018/187506 | 10/2018 |
| WO | 2019/015559 | 1/2019 |
| WO | 2019/148005 | 8/2019 |
| WO | 2020/100027 | 5/2020 |
| WO | 2021/224818 | 11/2021 |

OTHER PUBLICATIONS

PCT/IB2019/059702 International Search Report, dated Feb. 4, 2020.
PCT/IB2021/053522 International Search Report dated Jun. 21, 2021.
PCT/IB2021/053522 Written Opinion of the International Searching Authority dated Jun. 21, 2021.
Sawasdikosol, S., et al., "HPK1 as a novel target for cancer immunotherapy," Immunol Res, 2012, 262-265, vol. 54, No. 1.
Zhang, Q., et al., "Interactions between hematopoietic progenitor kinase 1 and its adaptor proteins," Molecular Medicine Reports, 2017, 6472-6482, vol. 16, No. 5.

* cited by examiner

*Primary Examiner* — Niloofar Rahmani
(74) *Attorney, Agent, or Firm* — Alexey Kuznetsov; Bryan C. Zielinski

(57) ABSTRACT

This invention relates to compounds of general Formula I

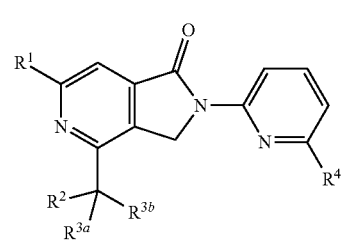

and pharmaceutically acceptable salts thereof, in which $R^1$, $R^2$, $R^{3a}$, $R^{3b}$, and $R^4$ are as defined herein, to pharmaceutical compositions comprising such compounds and salts, and to methods of using such compounds, salts and compositions for the treatment of abnormal cell growth, including cancer.

33 Claims, No Drawings

Specification includes a Sequence Listing.

AZALACTAM COMPOUNDS AS HPK1 INHIBITORS

This application claims the benefit of U.S. Provisional Application No. 63/018,689 filed on May 1, 2020, the contents of which is hereby incorporated by reference in its entirety.

REFERENCE TO SEQUENCE LISTING

This application is being filed electronically via EFS-Web and includes an electronically submitted sequence listing in .txt format. The .txt file contains a sequence listing entitled "PC72605A_SEQListing_ST25.txt" created on Apr. 30, 2021 and having a size of 12 KB. The sequence listing contained in this .txt file is part of the specification and is herein incorporated by reference in its entirety.

FIELD OF THE INVENTION

The present invention relates to compounds of Formula I, and their pharmaceutically acceptable salts, to pharmaceutical compositions comprising such compounds and salts, and to the uses thereof. The compounds, salts and compositions of the present invention are HPK1 inhibitors and as such may be used to enhance the activation of the immune system in the treatment or amelioration of abnormal cell proliferative disorders, such as cancer and amelioration of vaccine therapies.

BACKGROUND

Hematopoietic progenitor kinase 1 (HPK1), also known as mitogen activated protein kinase kinase kinase kinase 1 (MAP4K1), is a member of the mammalian Ste20-like family of serine/threonine kinases that operates via the JNK and ERK signalling pathways. HPK1 is mainly expressed in hematopoietic organs and cells (e.g., T-cells, B-cells, and dendritic cells), suggesting potential involvement of HPK1 in the regulation of signaling in hematopoietic lineages, including lymphocytes. (Shui, et al, "Hematoppietic progenitor kinase 1 negatively regulates T cell receptor signaling and T cell-mediated immune responses", Nature Immunology 8, 84-91 (2006)).

For example, stimulation of the T-Cell Receptor (TCR) induces HPK1 tyrosine 379 phosphorylation and relocation to the plasma membrane. Enzymatic activation of HPK1 is accompanied by phosphorylation of regulatory sites in the HPK1 kinase activation loop. Full activation of HPK1 is dependent on autophosphorylation of threonine 165 and phosphorylation by protein kinase D (PKD) of serine 171 (Arnold et al., "Activation of Hematopoietic Progenitor Kinase 1 Involves Relocation, Autophosphorylation, and Transphosphorylation by Protein Kinase D1.", Mol Cell Biol 25 (6), 2364-83 (2005)). HPK1 mediated phosphorylation of adaptor protein SLP76 ultimately leads to the destabilization of the TCR signaling complex which impedes and attenuates downstream mitogen-activated protein (MAP) kinase signaling events necessary for T-cell activation and proliferation. (Hernandez, et al., "The kinase activity of hematopoietic progenitor kinase 1 is essential for the regulation of T cell function", Cell Reports 25, (1), 80-94, (2018)). HPK1 kinase has also been shown to negatively regulate T-cell signaling by the $PGE_2$ receptor in a PKA-dependent manner. Furthermore, HPK1 kinase has been reported to play roles in: i) activation-induced cell death (AICD) and JNK activation; ii) regulation of leukocyte function-associated antigen-1 (LFA-1) integrin activation on T-cells by direct competition with adhesion and degranulation promoting adaptor protein (ADAP) for binding of the SLP76 SH2-domain; and iii) regulation of activation via nuclear factor KB (NF-κB) signaling by interacting with IKK-α and -β. Studies have also shown HPK1 negatively regulates MAP kinase pathway signaling and AP-1 transcription in T-cells. (reviewed in Hernandez, et al. 2018).

The research conducted to date on HPK1 kinases suggests that HPK1 inhibition plays a role in enhancing dendritic and T-cell responses and thereby heightening anti-tumor immunity, virus clearance and response to vaccine therapy.

SUMMARY

The present invention provides, in part, compounds of Formula I, and a pharmaceutically acceptable salt thereof. Such compounds can inhibit the activity of HPK1 kinase, thereby effecting biological functions. Also provided are pharmaceutical compositions and medicaments, comprising the compounds or salts of the invention, alone or in combination with additional anticancer therapeutic agents or palliative agents.

The present invention also provides, in part, methods for preparing the compounds, pharmaceutically acceptable salts and compositions of the invention, and methods of using the foregoing.

In one embodiment the invention provides a compound of Formula I:

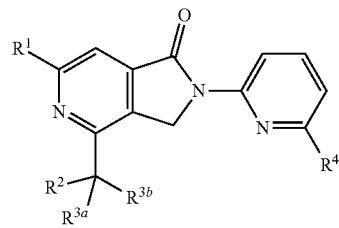

or a pharmaceutically acceptable salt thereof, wherein:

$R^1$ is $(C_1-C_6)$alkyl, halo$(C_1-C_6)$alkyl, $(C_1-C_6)$alkoxy, halo$(C_1-C_6)$alkoxy, —N$(R^5)(R^6)$, or $(C_3-C_6)$cycloalkyl, wherein said $(C_1-C_6)$alkyl, halo$(C_1-C_6)$alkyl, and $(C_3-C_6)$cycloalkyl are substituted with 0 or 1 substituent that is hydroxy, cyano, $(C_1-C_6)$alkyl, or $(C_1-C_6)$alkoxy, wherein:

$R^5$ and $R^6$ are each independently hydrogen or $(C_1-C_6)$ alkyl that is substituted with 0, 1, or 2 substituents independently selected from the group consisting of halogen, $(C_1-C_6)$alkoxy, cyano, and hydroxy, or $R^5$ and $R^6$ taken together with the nitrogen to which they are attached form a (4- to 8-membered)heterocycloalkyl that is substituted with 0, 1, or 2 substituents independently selected from the group consisting of halogen, $(C_1-C_6)$alkyl, halo$(C_1-C_6)$alkyl, $(C_1-C_6)$ alkoxy, and halo$(C_1-C_6)$alkoxy;

$R^2$ is $N(R^7)(R^8)$, wherein:

$R^7$ and $R^8$ are each independently hydrogen or $(C_1-C_6)$ alkyl that is substituted with 0, or 1 substituent that is halogen, $(C_1-C_6)$alkoxy, cyano, or hydroxy; or $R^7$ is hydrogen or $(C_1-C_6)$alkyl that is substituted with 0, or 1 substituent that is halogen, $(C_1-C_6)$alkoxy, cyano, or hydroxy; and $R^a$ taken together with the nitrogen to which it is attached and taken together with $R^{3a}$ and the carbon to which it is attached form a (4- to 6-membered)heterocycloalkyl that is substituted with 0, 1, or 2 substituents independently selected from halogen, hydroxy, ($C_1$-$C_3$)alkyl, halo($C_1$-$C_3$)alkyl, ($C_1$-$C_3$) alkoxy, and halo($C_1$-$C_6$)alkoxy; or $R^7$ and $R^8$ taken together with the nitrogen to which they are attached form a (4- to 6-membered)heterocycloalkyl that is substituted with 0, 1, or 2 substituents independently selected from halogen, hydroxy, ($C_1$-$C_6$) alkyl, halo($C_1$-$C_6$)alkyl, ($C_1$-$C_6$)alkoxy, and halo($C_1$-$C_6$)alkoxy;

$R^{3a}$ is hydrogen, or ($C_1$-$C_3$)alkyl that is substituted with 0 or 1 substituent that is hydroxy, or ($C_1$-$C_3$)alkoxy;

$R^{3b}$ is hydrogen, or ($C_1$-$C_3$)alkyl, provided that $R^{3a}$ and $R^{3b}$ are not both H when $R^4$ is ($R^4$-i);

$R^4$ is ($R^4$-i) or ($R^4$-ii):

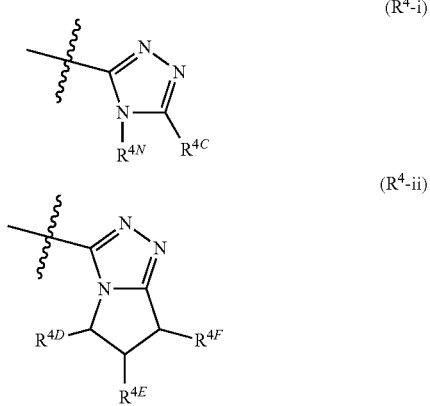

wherein:
$R^{4N}$ is ($C_1$-$C_6$)alkyl, halo($C_1$-$C_6$)alkyl, or ($C_3$-$C_6$)cycloalkyl, wherein said ($C_1$-$C_6$)alkyl is substituted with 0 or 1 substituent that is hydroxy;

$R^{4C}$ is hydrogen, ($C_1$-$C_6$)alkyl, halo($C_1$-$C_6$)alkyl, ($C_1$-$C_6$) alkoxy, halo($C_1$-$C_6$)alkoxy, or ($C_3$-$C_6$)cycloalkyl, wherein said ($C_1$-$C_6$)alkyl and halo($C_1$-$C_6$)alkyl are substituted with 0 or 1 substituent that is hydroxy, cyano, or ($C_1$-$C_6$)alkoxy;

$R^{4D}$ is hydrogen, ($C_1$-$C_6$)alkyl, halo($C_1$-$C_6$)alkyl, ($C_1$-$C_6$) alkoxy, halo($C_1$-$C_6$)alkoxy, or ($C_3$-$C_6$)cycloalkyl, wherein said ($C_1$-$C_6$)alkyl and halo($C_1$-$C_6$)alkyl are substituted with 0 or 1 substituent that is hydroxy, cyano, or ($C_1$-$C_6$)alkoxy;

$R^{4E}$ is hydrogen, halogen, cyano, hydroxy, or ($C_1$-$C_6$) alkyl; and $R^{4F}$ is hydrogen, halogen, cyano, hydroxy, ($C_1$-$C_6$)alkyl, halo($C_1$-$C_6$)alkyl, ($C_1$-$C_6$)alkoxy, halo($C_1$-$C_6$)alkoxy, or ($C_3$-$C_6$)cycloalkyl, wherein said ($C_1$-$C_6$)alkyl and halo($C_1$-$C_6$)alkyl are substituted with 0 or 1 substituent that is hydroxy, cyano, or ($C_1$-$C_6$)alkoxy.

The invention also provides therapeutic methods and uses comprising administering a compound of the invention, or a pharmaceutically acceptable salt thereof.

In another embodiment, the invention provides a method for the treatment of abnormal cell growth, in particular cancer, in a subject in need thereof, comprising administering to the subject a therapeutically effective amount of a compound of the invention, or a pharmaceutically acceptable salt thereof. Compounds of the invention may be administered as single agents, or may be administered in combination with other anti-cancer therapeutic agents, in particular standard of care agents appropriate for the particular cancer.

In a further embodiment, the invention provides a method for the treatment of abnormal cell growth, in particular cancer, in a subject in need thereof, comprising administering to the subject an amount of a compound of the invention, or a pharmaceutically acceptable salt thereof, in combination with an amount of an additional anti-cancer therapeutic agent, which amounts are together effective in treating said abnormal cell growth.

In another embodiment, the invention relates to a compound of the invention, or a pharmaceutically acceptable salt thereof, for use as a medicament, in particular a medicament for treatment of cancer.

In another embodiment, the invention relates to a compound of the invention, or a pharmaceutically acceptable salt thereof, for use in the treatment of abnormal cell growth, in particular cancer, in a subject.

In a further embodiment, the invention provides the use of a compound of the invention, or a pharmaceutically acceptable salt thereof, for the treatment of abnormal cell growth, in particular cancer, in a subject.

In another embodiment, the invention relates to a pharmaceutical composition for use in the treatment of abnormal cell growth in a subject in need thereof, which composition comprises a compound of the invention, or a pharmaceutically acceptable salt thereof, and a pharmaceutically acceptable carrier or excipient.

In yet another embodiment, the invention provides the use of a compound of Formula I as described herein, or a pharmaceutically acceptable salt thereof, for the preparation of a medicament for the treatment of abnormal cell or pathogen growth in a subject.

In frequent embodiments of the foregoing compounds, methods and uses, the abnormal cell growth is cancer.

In some embodiments, the methods and uses provided result in one or more of the following effects: (1) inhibiting cancer cell proliferation; (2) inhibiting cancer cell invasiveness; (3) inducing apoptosis of cancer cells; (4) inhibiting cancer cell metastasis; (5) inhibiting angiogenesis; (6) enhancing T-cell responses; or (7) enhancing dendritic and B cell responses; (8) heightening of anti-tumor activity; (9) enhancing vaccine therapies; and (10) enhancing immune-system mediated removal of pathogens such as viruses, bacteria, or parasite (e.g., intestinal worms).

In another embodiment, the invention provides a method for the treatment of HPK1-dependent disorders and enhancing an immune response in a subject, comprising administering to the subject a compound of the invention, or a pharmaceutically acceptable salt thereof, in an amount that is effective for treating said disorder or enhancing said immune response.

In some embodiments, the methods and uses described herein further comprise administering to the subject an amount of an additional anticancer therapeutic agent, vaccine, antibacterial agent, antiviral agent, or a palliative agent, which amounts are together effective in treating said abnormal cell growth or pathogen. Each of the embodiments of the compounds of the present invention described below can be combined with one or more other embodiments of the compounds of the present invention described herein not inconsistent with the embodiment(s) with which it is combined.

It is to be understood that both the foregoing general description and the following detailed description are exemplary and explanatory only and are not restrictive of the invention, as claimed.

In addition, each of the embodiments below describing the invention envisions within its scope the pharmaceutically acceptable salts of the compounds of the invention. Accordingly, the phrase "or a pharmaceutically acceptable salt thereof" is implicit in the description of all compounds described herein.

DETAILED DESCRIPTION

Definitions and Exemplifications

The present invention may be understood more readily by reference to the following detailed description of the preferred embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art.

As used herein, the singular form "a", "an", and "the" include plural references unless indicated otherwise. For example, "a" substituent includes one or more substituents.

The term "about" refers to a relative term denoting an approximation of plus or minus 10% of the nominal value it refers, in one embodiment, to plus or minus 5%, in another embodiment, to plus or minus 2%. For the field of this disclosure, this level of approximation is appropriate unless the value is specifically stated to require a tighter range.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to include $C_1$ alkyl (methyl), $C_2$ alkyl (ethyl), $C_3$ alkyl, $C_4$ alkyl, $C_5$ alkyl, and $C_6$ alkyl.

As used herein, a "HPK1 antagonist" or a "HPK1 inhibitor" is a molecule that reduces, inhibits, or otherwise diminishes one or more of the biological activities of HPK1 (e.g., serine/threonine kinase activity, recruitment to the TCR complex upon TCR activation, interaction with a protein binding partner, such as SLP76). Antagonism using the HPK1 antagonist does not necessarily indicate a total elimination of the HPK1 activity. Instead, the activity could decrease by a statistically significant amount. For example, a compound of the present invention may decrease HPK1 activity by at least about 2.5% to about 100%, from about 10% to about 90%, from about 20% to about 70%, from about 30% to about 60%, from about 40% to about 50% compared to an appropriate control. In some embodiments, the HPK1 antagonist reduces, inhibits, or otherwise diminishes the serine/threonine kinase activity of HPK1. In some of these embodiments, the HPK1 antagonist reduces, inhibits, or otherwise diminishes the HPK1-mediated phosphorylation of SLP76 and/or Gads. The presently disclosed compounds bind directly to HPK1 and inhibit its kinase activity.

The invention described herein suitably may be practiced in the absence of any element(s) not specifically disclosed herein. Thus, for example, in each instance herein any of the terms "comprising", "consisting essentially of", and "consisting of" may be replaced with either of the other two terms.

The term "$(C_x-C_y)$alkyl", as used herein, refers to a saturated, branched- or straight-chain alkyl group containing from x to y carbon atoms. For example, "$(C_1-C_6)$alkyl", is an alkyl group containing from 1 to 6 carbon atoms and includes, but is not limited to, methyl, ethyl, n-propyl, isopropyl, n-butyl, sec-butyl, isobutyl, tert-butyl, n-pentyl, isopentyl, neopentyl, and n-hexyl. The term "$(C_1-C_3)$alkyl" contains from 1 to 3 carbon atoms and is included within "$(C_1-C_6)$alkyl".

The term "halo$(C_x-C_y)$alkyl" as used herein, refers to a $(C_x-C_y)$alkyl group as defined above wherein the alkyl group is substituted with one or more halogen atoms. A representative number of halogen substituents is from 1 to 3 substituents. Representative examples of a halo$(C_x-C_y)$alkyl, include, but are not limited to, fluoromethyl, fluoroethyl, difluoromethyl, difluoroethyl, trifluoromethyl, and trifluoroethyl.

The term "$(C_x-C_y)$alkoxy" as used herein, refers to a $(C_x-C_y)$alkyl group, as defined above, attached to the parent molecular moiety through an oxygen atom. Representative examples of a $(C_1-C_6)$alkoxy include, but are not limited to, methoxy, ethoxy, propoxy, 2-propoxy, butoxy, tert-butoxy, pentyloxy, and hexyloxy.

The term "halo$(C_x-C_y)$alkoxy" as used herein, refers to a $(C_c-C_y)$alkoxy group as defined above wherein the alkoxy group is substituted with one or more halogen atoms. A representative number of halogen substituents is from 1 to 3 substituents. Representative examples of a halo$(C_x-C_y)$alkoxy, include, but are not limited to, fluoromethoxy, fluoroethoxy, difluoromethoxy, difluoroethoxy, and trifluoromethoxy, trifluoroethoxy.

As used herein, the term "cycloalkyl" refers to a cyclic, monovalent hydrocarbon group of formula —$C_nH_{(2n-1)}$— containing at least three carbon atoms. A "$(C_x-C_y)$cycloalkyl" refers to a cycloalkyl having 3 to y carbon atoms. A "$(C_3-C_6)$cycloalkyl" may be a monocyclic ring, examples of which include cyclopropyl, cyclobutyl, cyclopentyl, and cyclohexyl.

A "heterocycloalkyl," as used herein, refers to a cycloalkyl as defined above, wherein at least one of the ring carbon atoms is replaced with a heteroatom selected from nitrogen, oxygen and sulfur. As used herein, the term "n-membered" where n is an integer typically describes the number of ring-forming atoms in a moiety where the number of ring-forming atoms is n. The term "(4- to 6-membered)heterocycloalkyl" means the heterocycloalkyl substituent contains a total of 4 to 6 ring atoms, at least one of which is a heteroatom. The term "(4- to 8-membered)heterocycloalkyl" means the heterocycloalkyl substituent contains a total of 4 to 8 ring atoms, at least one of which is a heteroatom. A "(6-membered)heterocycloalkyl" means the heterocycloalkyl substituent contains a total of 6 ring atoms, at least one of which is a heteroatom. A "(5-membered)heterocycloalkyl" means the heterocycloalkyl substituent contains a total of 5 ring atoms at least one of which is a heteroatom. The heterocycloalkyl substituent may be attached via a nitrogen atom having the appropriate valence, or via any ring carbon atom. The heterocycloalkyl moiety may be optionally substituted with one or more substituents, such as $(C_1-C_6)$alkyl, at a nitrogen atom having the appropriate valence, or at any available carbon atom.

Examples of heterocycloalkyl rings include, but are not limited to, azetidinyl, tetrahydrofuranyl, tetrahydropyrazolyl, tetrahydrooxazinyl, imidazolidinyl, pyrrolidinyl, piperidinyl, piperazinyl, oxazolidinyl, tetrahydropyranyl, tetrahydro-oxazolyl, morpholinyl, and oxetanyl.

"halo" or "halogen", as used herein, refers to a chlorine, fluorine, bromine, or iodine atom.

"hydroxy" or "hydroxyl", as used herein, means an —OH group.

"cyano", as used herein, means a —CN group, which also may be depicted:

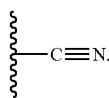

"Patient" or "subject" refers to warm-blooded animals such as, for example, pigs, cows, chickens, horses, guinea pigs, mice, rats, gerbils, cats, rabbits, dogs, monkeys, chimpanzees, and humans.

"Pharmaceutically acceptable" indicates that the substance or composition must be compatible, chemically and/or toxicologically, with the other ingredients comprising a formulation, and/or the mammal being treated therewith.

The term "therapeutically effective amount" as used herein refers to that amount of the compound being administered which will relieve to some extent one or more of the symptoms of the disorder being treated. In reference to the treatment of an HPK1 kinase-mediated disorder (e.g., cancer), a therapeutically effective amount refers to that amount which has the effect of relieving to some extent (or, for example, eliminating) one or more symptoms associated with the HPK1 kinase-mediated disorder. For example, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth or tumor invasiveness, and/or (4) relieving to some extent (or, preferably, eliminating) one or more signs or symptoms associated with the cancer.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined herein. The term "treating" also includes adjuvant and neo-adjuvant treatment of a subject.

"Isomer" means "stereoisomer" and "geometric isomer" as defined below.

"Stereoisomer" refers to compounds that possess one or more chiral centers, which may each exist in the R or S configuration. Stereoisomers include all diastereomeric, enantiomeric and epimeric forms as well as racemates and mixtures thereof.

"Geometric isomer" refers to compounds that may exist in cis, trans, anti, entgegen (E), and zusammen (Z) forms as well as mixtures thereof.

This specification uses the terms "substituent," "radical," and "group" interchangeably.

If substituents are described as being "independently selected" from a group, each instance of a substituent is selected independent of any other. Each substituent therefore may be identical to or different from the other substituent(s).

Compounds

The compounds of Formula I, as described herein, contain an azalactam (2,3-dihydro-1H-pyrrolo[3,4-c]pyridin-1-one) core wherein the pyrrolo ring is attached via its nitrogen atom to pyridine that is substituted with $R^4$.

In another embodiment, the invention provides a compound of Formula I, or a pharmaceutically acceptable salt thereof, wherein $R^4$ is ($R^4$-i);

$R^{4N}$ is $(C_1-C_6)$alkyl, or $(C_3-C_6)$cycloalkyl; and $R^{4C}$ is hydrogen, or $(C_1-C_3)$alkyl; wherein $R^1$, $R^2$, $R^{3a}$, and $R^{3b}$ are as defined in any of the herein described embodiments.

In another embodiment, the invention provides a compound of Formula I, or a pharmaceutically acceptable salt thereof, wherein $R^4$ is ($R^4$-i), wherein $R^1$ is —$N(R^5)(R^6)$, or $(C_3-C_6)$cycloalkyl, wherein said $(C_3-C_6)$cycloalkyl is cyclopropyl and is substituted with 0 or 1 substituent that is $(C_1-C_6)$alkyl, wherein said $(C_1-C_6)$alkyl is methyl;

$R^5$ and $R^6$ are each independently hydrogen or $(C_1-C_3)$alkyl, or $R^5$ and $R^6$ taken together with the nitrogen to which they are attached form a (5-membered)heterocycloalkyl that is substituted with 0, or 1 substituent that is $(C_1-C_6)$alkyl;

$R^2$ is $N(R^7)(R^8)$, wherein $R^7$ and $R^8$ are each independently hydrogen or $(C_1-C_6)$alkyl that is methyl;

$R^{3a}$ is $(C_1-C_3)$alkyl that is substituted with 0 or 1 substituent that is $(C_1-C_3)$alkoxy; and $R^{3b}$ is hydrogen, or $(C_1-C_3)$alkyl.

In another embodiment, the invention provides a compound of Formula I, or a pharmaceutically acceptable salt thereof, wherein $R^4$ is ($R^4$-ii);

$R^{4D}$ is hydrogen, $(C_1-C_6)$alkyl, or halo$(C_1-C_6)$alkyl, wherein said $(C_1-C_6)$alkyl is substituted with 0 or 1 substituent that is hydroxy;

$R^{4E}$ is hydrogen; and $R^{4F}$ is hydrogen, $(C_1-C_6)$alkyl, or halo$(C_1-C_6)$alkyl, wherein said $(C_1-C_6)$alkyl is substituted with 0 or 1 substituent that is hydroxy; and wherein $R^1$, $R^2$, $R^{3a}$, and $R^{3b}$ are as defined in any of the herein described embodiments.

In another embodiment, the invention provides a compound of Formula I, or a pharmaceutically acceptable salt thereof, wherein $R^4$ is ($R^4$-ii), and wherein $R^1$ is —$N(R^5)(R^6)$, or $(C_3-C_6)$cycloalkyl, wherein said $(C_3-C_6)$cycloalkyl is cyclopropyl and is substituted with 0 or 1 substituent that is $(C_1-C_6)$alkyl, wherein said $(C_1-C_6)$alkyl is methyl;

$R^5$ and $R^6$ are each independently hydrogen or $(C_1-C_3)$alkyl, or $R^5$ and $R^6$ taken together with the nitrogen to which they are attached form a (5-membered)heterocycloalkyl that is substituted with 0, or 1 substituent that is $(C_1-C_6)$alkyl;

$R^2$ is $N(R^7)(R^8)$, wherein $R^7$ and $R^8$ are each independently hydrogen or $(C_1-C_6)$alkyl that is methyl;

$R^{3a}$ is hydrogen, or $(C_1-C_3)$alkyl that is substituted with 0 or 1 substituent that is $(C_1-C_3)$alkoxy; and $R^{3b}$ is hydrogen, or $(C_1-C_3)$alkyl.

In another embodiment, the invention provides a compound of Formula I, or a pharmaceutically acceptable salt thereof, wherein $R^1$ is 2-methyl-pyrrolidin-1-yl, or 2(R)-methyl-pyrrolidin-1-yl; and wherein $R^2$, $R^{3a}$, $R^{3b}$ and $R^4$ are as defined in any of the herein described embodiments.

In another embodiment, the invention provides a compound of Formula I, or a pharmaceutically acceptable salt thereof, wherein $R^2$ is $N(R^7)(R^8)$, wherein $R^7$ and $R^3$ are each hydrogen, and wherein $R^1$, $R^{3a}$, $R^{3b}$ and $R^4$ are as defined in any of the herein described embodiments.

In another embodiment, the invention provides a compound of Formula I, or a pharmaceutically acceptable salt thereof, wherein $R^{3a}$ is $(C_1-C_3)$alkyl that is substituted with 0 or 1 substituent that is $(C_1-C_3)$alkoxy; and wherein $R^1$, $R^2$, $R^{3b}$ and $R^4$ are as defined in any of the herein described embodiments.

In another embodiment, the invention provides a compound of Formula I, or a pharmaceutically acceptable salt thereof, wherein $R^{3b}$ is $(C_1-C_3)$alkyl; and $R^1$, $R^2$, $R^{3a}$ and $R^4$ are as defined in any of the herein described embodiments.

In another embodiment, the invention provides a compound of Formula I, or a pharmaceutically acceptable salt thereof, wherein $R^2$ is $N(R^7)(R^8)$, wherein $R^7$ and $R^3$ are each hydrogen; and wherein $R^1$, $R^{3a}$, $R^{3b}$ and $R^4$ are as defined in any of the herein described embodiments.

In another embodiment, the invention provides a compound of Formula I, or a pharmaceutically acceptable salt thereof, wherein $R^2$ is $N(R^7)(R^8)$, wherein $R^7$ is hydrogen; and and $R^8$ is $(C_1-C_3)$alkyl; and wherein $R^1$, $R^{3a}$, $R^{3b}$ and $R^4$ are as defined in any of the herein described embodiments.

In another embodiment, the invention provides a compound of Formula I-A (a compound of Formula I, wherein $R^4$ is ($R^4$-i)):

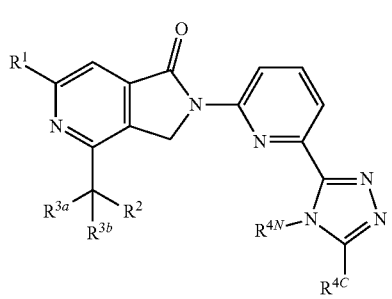

I-A or a pharmaceutically acceptable salt thereof, wherein:

$R^1$ is —$N(R^5)(R^6)$, or $(C_3-C_6)$cycloalkyl, wherein said $(C_3-C_6)$cycloalkyl is cyclopropyl and is substituted with 0 or 1 substituent that is $(C_1-C_6)$alkyl, wherein said $(C_1-C_6)$alkyl is methyl;

$R^5$ and $R^6$ are each independently hydrogen or $(C_1-C_3)$alkyl, or $R^5$ and $R^6$ taken together with the nitrogen to which they are attached form a (5-membered)heterocycloalkyl that is substituted with 0, or 1 substituent that is $(C_1-C_6)$alkyl;

$R^2$ is $N(R^7)(R^8)$, wherein $R^7$ and $R^8$ are each independently hydrogen or $(C_1-C_6)$alkyl that is methyl;

$R^{3a}$ is $(C_1-C_3)$alkyl that is substituted with 0 or 1 substituent that is $(C_1-C_3)$alkoxy;

$R^{3b}$ is hydrogen, or $(C_1-C_3)$alkyl;

$R^{4N}$ is $(C_1-C_6)$alkyl, or $(C_3-C_6)$cycloalkyl; and $R^{4C}$ is hydrogen, or $(C_1-C_3)$alkyl.

In another embodiment, the invention provides a compound of Formula I-A, or a pharmaceutically acceptable salt thereof, wherein $R^{3a}$ is $(C_1-C_3)$alkyl that is substituted with 0 or 1 substituent that is $(C_1-C_3)$alkoxy; and $R^{3b}$ is $(C_1-C_3)$alkyl.

In some embodiments, when $R^4$ is ($R^4$-i), the compound of Formula I-A has the absolute stereochemistry as shown in Formula I-A-i or I-A-ii:

Formula I-A-i

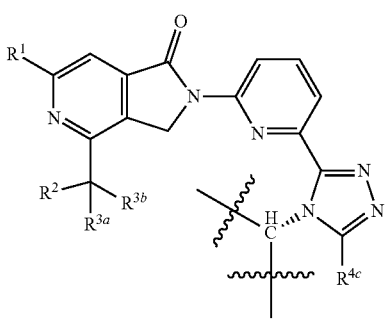

Formula I-A-ii

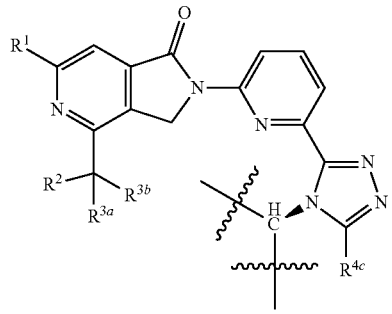

or a pharmaceutically acceptable salt thereof, where $R^1$, $R^2$, $R^{3a}$, $R^{3b}$, and $R^{4C}$ are defined in any embodiment for Formula I-A.

In another embodiment, the invention provides a compound of Formula I-B (a compound of Formula I, wherein $R^4$ is ($R^4$-ii)):

I-B

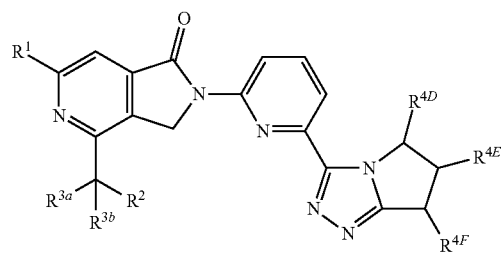

or a pharmaceutically acceptable salt thereof, wherein:

$R^1$ is $(C_1-C_6)$alkyl, halo$(C_1-C_6)$alkyl, $(C_1-C_6)$alkoxy, halo $(C_1-C_6)$alkoxy, —$N(R^5)(R^6)$, or $(C_3-C_6)$cycloalkyl, wherein said $(C_1-C_6)$alkyl, halo$(C_1-C_6)$alkyl, and $(C_3-C_6)$cycloalkyl are substituted with 0 or 1 substituent that is hydroxy, cyano, $(C_1-C_6)$alkyl, or $(C_1-C_6)$alkoxy, wherein:

$R^5$ and $R^6$ are each independently hydrogen or $(C_1-C_6)$ alkyl that is substituted with 0, 1, or 2 substituents independently selected from the group consisting of halogen, $(C_1-C_6)$alkoxy, cyano, and hydroxy, or $R^5$ and $R^6$ taken together with the nitrogen to which they are attached form a (4- to 8-membered)heterocycloalkyl that is substituted with 0, 1, or 2 substituents independently selected from the group consisting of halogen, $(C_1-C_6)$alkyl, halo$(C_1-C_6)$alkyl, $(C_1-C_6)$ alkoxy, and halo$(C_1-C_6)$alkoxy;

$R^2$ is $N(R^7)(R^8)$, wherein:

$R^7$ and $R^3$ are each independently hydrogen or $(C_1-C_6)$ alkyl that is substituted with 0, or 1 substituent that is halogen, $(C_1-C_6)$alkoxy, cyano, or hydroxy; or $R^7$ is hydrogen or $(C_1-C_6)$alkyl that is substituted with 0, or 1 substituent that is halogen, $(C_1-C_6)$alkoxy, cyano, or hydroxy; and $R^8$ taken together with the nitrogen to which it is attached and taken together with $R^{3a}$ and the carbon to which it is attached form a (4- to 6-membered)heterocycloalkyl that is substituted with 0, 1, or 2 substituents independently selected from halogen, hydroxy, $(C_1-C_3)$alkyl, halo$(C_1-C_3)$alkyl, $(C_1-C_3)$ alkoxy, or halo$(C_1-C_6)$alkoxy; or $R^7$ and $R^8$ taken together with the nitrogen to which they are attached form a (4- to 6-membered)heterocycloalkyl that is substituted with 0, 1, or 2 substituents independently selected from halogen, hydroxy, ($C_1$-$C_6$)alkyl, halo($C_1$-$C_6$)alkyl, ($C_1$-$C_6$)alkoxy, and halo($C_1$-$C_6$)alkoxy;

$R^{3a}$ is hydrogen, or ($C_1$-$C_3$)alkyl that is substituted with 0 or 1 substituent that is hydroxy, or ($C_1$-$C_3$)alkoxy;

$R^{3b}$ is hydrogen, or ($C_1$-$C_3$)alkyl;

$R^{4D}$ is hydrogen, ($C_1$-$C_6$)alkyl, halo($C_1$-$C_6$)alkyl, ($C_1$-$C_6$)alkoxy, halo($C_1$-$C_6$)alkoxy, or ($C_3$-$C_6$)cycloalkyl, wherein said ($C_1$-$C_6$)alkyl and halo($C_1$-$C_6$)alkyl are substituted with 0 or 1 substituent that is hydroxy, cyano, or ($C_1$-$C_6$)alkoxy;

$R^{4E}$ is hydrogen, halogen, cyano, hydroxy, or ($C_1$-$C_6$)alkyl; and $R^{4F}$ is hydrogen, halogen, cyano, hydroxy, ($C_1$-$C_6$)alkyl, halo($C_1$-$C_6$)alkyl, ($C_1$-$C_6$)alkoxy, halo($C_1$-$C_6$)alkoxy, or ($C_3$-$C_6$)cycloalkyl, wherein said ($C_1$-$C_6$)alkyl and halo($C_1$-$C_6$)alkyl are substituted with 0 or 1 substituent that is hydroxy, cyano, or ($C_1$-$C_6$)alkoxy; and wherein $R^2$ is as defined in any of the herein described embodiments.

In another embodiment, the invention provides a compound of Formula I-B, or a pharmaceutically acceptable salt thereof, wherein:

$R^1$ is —N($R^5$)($R^6$), or ($C_3$-$C_6$)cycloalkyl, wherein said ($C_3$-$C_6$)cycloalkyl is substituted with 0 or 1 substituent that is ($C_1$-$C_3$)alkyl, wherein:

$R^5$ and $R^6$ are each independently hydrogen or ($C_1$-$C_6$)alkyl or $R^5$ and $R^6$ taken together with the nitrogen to which they are attached form a (4- to 8-membered)heterocycloalkyl that is substituted with 0, 1, or 2 substituents that is ($C_1$-$C_6$)alkyl;

$R^2$ is N($R^7$)($R^8$), wherein $R^7$ and $R^8$ are each independently hydrogen or ($C_1$-$C_6$)alkyl;

$R^{3a}$ is hydrogen, or ($C_1$-$C_3$)alkyl that is substituted with 0 or 1 substituent that is ($C_1$-$C_3$)alkoxy;

$R^{3b}$ is hydrogen, or ($C_1$-$C_3$)alkyl;

$R^{4D}$ is hydrogen, ($C_1$-$C_3$)alkyl, or halo($C_1$-$C_3$)alkyl, wherein said ($C_1$-$C_3$)alkyl is substituted with 0 or 1 substituent that is hydroxy, cyano, or ($C_1$-$C_3$)alkoxy;

$R^{4E}$ is hydrogen; and $R^{4F}$ is hydrogen, ($C_1$-$C_3$)alkyl, or halo($C_1$-$C_3$)alkyl, wherein said ($C_1$-$C_3$)alkyl is substituted with 0 or 1 substituent that is hydroxy.

In another embodiment, the invention provides a compound of Formula I-B, or a pharmaceutically acceptable salt thereof, wherein $R^{3b}$ is hydrogen, or ($C_1$-$C_3$)alkyl.

In another embodiment, the invention provides a compound of Formula I-B, or a pharmaceutically acceptable salt thereof, wherein $R^{4D}$ is hydrogen, ($C_1$-$C_3$)alkyl, or halo($C_1$-$C_3$)alkyl, wherein said ($C_1$-$C_3$)alkyl is substituted with 0 or 1 substituent that is hydroxy; and wherein $R^1$, $R^{3a}$, $R^{3b}$, $R^{4E}$ and $R^{4F}$ are as defined in any of the herein described embodiments.

In another embodiment, the invention provides a compound of Formula I-B, or a pharmaceutically acceptable salt thereof, wherein $R^{3a}$ is ($C_1$-$C_3$)alkyl that is substituted with 0 or 1 substituent that is ($C_1$-$C_3$)alkoxy; and $R^{3b}$ is ($C_1$-$C_3$)alkyl; and wherein $R^1$, $R^2$, $R^{4D}$, $R^{4E}$ and $R^{4F}$ are as defined in any of the herein described embodiments.

In another embodiment, the invention provides a compound of Formula I-B, or a pharmaceutically acceptable salt thereof, wherein:

$R^1$ is —N($R^5$)($R^6$), or ($C_3$-$C_6$)cycloalkyl, wherein the ($C_3$-$C_6$)cycloalkyl is substituted with 0 or 1 ($C_1$-$C_3$)alkyl;

$R^5$ and $R^6$ are each independently selected from the group consisting of ($C_1$-$C_6$)alkyl, or $R^5$ and $R^6$ taken together with the nitrogen to which they are attached form a (5-membered) heterocycloalkyl that is substituted with 0 or 1 ($C_1$-$C_6$)alkyl;

$R^2$ is N($R^7$)($R^8$), wherein $R^7$ and $R^8$ are each hydrogen;

$R^{3a}$ is hydrogen, or ($C_1$-$C_3$)alkyl, wherein said ($C_1$-$C_3$) alkyl is substituted with 0 or 1 ($C_1$-$C_3$)alkoxy;

$R^{3b}$ is hydrogen, or ($C_1$-$C_3$)alkyl;

$R^{4D}$ is hydrogen, or ($C_1$-$C_3$)alkyl, wherein ($C_1$-$C_3$)alkyl is substituted with 0 to 1 substituent selected from OH, and F;

$R^{4E}$ is hydrogen; and $R^{4F}$ is hydrogen, or ($C_1$-$C_3$)alkyl.

In another embodiment, the invention provides a compound of Formula I-B, or a pharmaceutically acceptable salt thereof, wherein:

$R^1$ is —N($R^5$)($R^6$), or cyclopropyl that is substituted with 0 or 1 substituent that is methyl;

$R^5$ and $R^6$ are each independently hydrogen or ($C_1$-$C_3$) alkyl, or $R^5$ and $R^6$ taken together with the nitrogen to which they are attached form a (5-membered)heterocycloalkyl that is substituted with 0, or 1 substituent that is methyl;

$R^2$ is N($R^7$)($R^8$), wherein $R^7$ and $R^8$ are each independently hydrogen or methyl;

$R^{3a}$ is ($C_1$-$C_3$)alkyl that is substituted with 0 or 1 substituent that is ($C_1$-$C_3$)alkoxy; and $R^{3b}$ is hydrogen, or ($C_1$-$C_3$)alkyl; and wherein $R^{4D}$, $R^{4E}$, and $R^{4F}$ are as defined in any of the herein described embodiments.

In another embodiment, the invention concerns a compound of Formula I, or a pharmaceutically acceptable salt thereof, wherein $R^4$ is ($R^4$-ii);

$R^{4D}$ is hydrogen, ($C_1$-$C_6$)alkyl, or halo($C_1$-$C_6$)alkyl, wherein said ($C_1$-$C_6$)alkyl is substituted with 0 or 1 substituent that is hydroxy;

$R^{4E}$ is hydrogen; and $R^{4F}$ is hydrogen, ($C_1$-$C_6$)alkyl, or halo($C_1$-$C_6$)alkyl, wherein said ($C_1$-$C_6$)alkyl is substituted with 0 or 1 substituent that is hydroxy; and wherein $R^1$, $R^2$, $R^{3a}$, and $R^{3b}$ are as defined in any of the herein described embodiments.

In another embodiment, the invention concerns a compound of Formula I, or a pharmaceutically acceptable salt thereof, wherein $R^4$ is ($R^4$-ii);

$R^{4D}$ is hydrogen, methyl, fluoromethyl, hydroxymethyl, or ethyl;

$R^{4E}$ is hydrogen; and $R^{4F}$ is hydrogen; and wherein $R^1$, $R^2$, $R^{3a}$, and $R^{3b}$ are as defined in any of the herein described embodiments.

In another embodiment, the invention concerns compounds of Formula I, or a pharmaceutically acceptable salt thereof, having specific stereochemistry with regard to the orientation of $R^2$, $R^{3a}$, and $R^{3b}$, when $R^{3a}$ is different from $R^{3b}$. For example, when $R^{3b}$ is hydrogen ($R^{3b}$ is absent), compounds of Formula I would appear as the following:

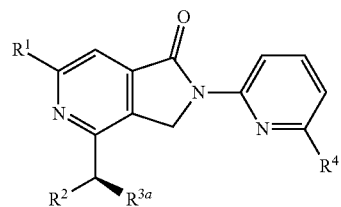

Formula I(R)

-continued

Formula I(S)

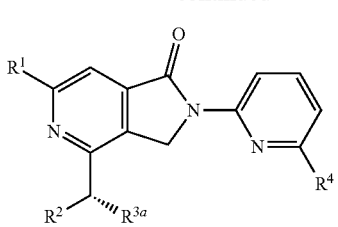

wherein $R^1$, $R^{3a}$, and $R^4$, are as defined in any of the herein described embodiments.

In another embodiment, the invention provides a compound of Formula I(R) or Formula I(S), or a pharmaceutically acceptable salt thereof, wherein:

$R^1$ is —N($R^5$)($R^6$), or cyclopropyl that is substituted with 1 substituent that is methyl;

$R^5$ and $R^6$ are each independently hydrogen or ($C_1$-$C_3$) alkyl, or $R^5$ and $R^6$ taken together with the nitrogen to which they are attached form a (5-membered)heterocycloalkyl that is substituted with 0, or 1 substituent that is methyl;

$R^2$ is N($R^7$)($R^8$), wherein $R^7$ and $R^8$ are each independently hydrogen or methyl;

$R^{3a}$ is ($C_1$-$C_3$)alkyl that is substituted with 0 or 1 substituent that is ($C_1$-$C_3$)alkoxy;

$R^{3b}$ is hydrogen;

$R^4$ is ($R^4$-ii);

$R^{4D}$ is hydrogen, methyl, fluoromethyl, hydroxymethyl, or ethyl;

$R^{4E}$ is hydrogen; and $R^{4F}$ is hydrogen, or methyl.

In yet another embodiment, the invention concerns compounds of Formula I(R), or a pharmaceutically acceptable salt thereof, wherein $R^{3b}$ is hydrogen ($R^{3b}$ is absent):

Formula I(R)

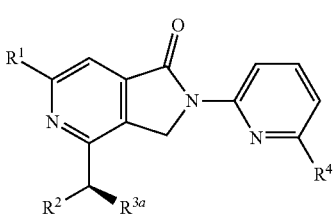

and wherein $R^1$, $R^{3a}$, and $R^4$, are as defined in any of the herein described embodiments.

In yet another embodiment, the invention concerns compounds of Formula I(S), or a pharmaceutically acceptable salt thereof, wherein $R^{3b}$ is hydrogen ($R^{3b}$ is absent):

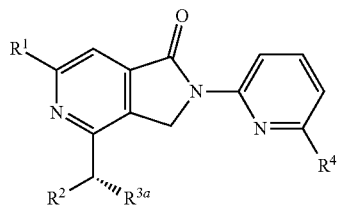

wherein $R^1$, $R^{3a}$, and $R^4$, are as defined in any of the herein described embodiments.

In another embodiment, the invention provides a compound of Formula I-B, or a pharmaceutically acceptable salt thereof, wherein $R^4$ is 5-methyl-6,7-dihydro-5H-pyrrolo[2,1-c][1,2,4]triazol-3-yl, (5R)-5-methyl-6,7-dihydro-5H-pyrrolo[2,1-c][1,2,4]triazol-3-yl, (5S)-5-methyl-6,7-dihydro-5H-pyrrolo[2,1-c][1,2,4]triazol-3-yl, 5-ethyl-6,7-dihydro-5H-pyrrolo[2,1-c][1,2,4]triazol-3-yl, (5S)-5-ethyl-6,7-dihydro-5H-pyrrolo[2,1-c][1,2,4]triazol-3-yl, or (5R)-5-ethyl-6,7-dihydro-5H-pyrrolo[2,1-c][1,2,4]triazol-3-yl, wherein said methyl is substituted with 0 or 1 substituent that is F or OH, and wherein $R^1$, $R^2$, $R^{3a}$, and $R^{3b}$ are as defined in any of the herein described embodiments.

In another embodiment, the invention provides a compound of Formula I-B, or a pharmaceutically acceptable salt thereof, wherein $R^4$ is (5S)-5-methyl-6,7-dihydro-5H-pyrrolo[2,1-c][1,2,4]triazol-3-yl, or (5S)-5-ethyl-6,7-dihydro-5H-pyrrolo[2,1-c][1,2,4]triazol-3-yl, wherein said methyl is substituted with 0 or 1 substituent that is F or OH, and wherein $R^1$, $R^2$, $R^{3a}$, and $R^{3b}$ are as defined in any of the herein described embodiments.

Each of the embodiments described herein with respect to Formula I is also applicable to compounds of Formulae I-A-i, I-A-ii, I-B-i, and I-B-ii.

In another embodiment, the invention provides a compound, wherein the compound is: 4-[1-aminopropyl]-2-{6-[5-methyl-6,7-dihydro-5H-pyrrolo[2,1-c][1,2,4]triazol-3-yl]pyridin-2-yl}-6-[2-methylpyrrolidin-1-yl]-2,3-dihydro-1H-pyrrolo[3,4-c]pyridin-1-one;

4-[1-aminoethyl]-2-{6-5-ethyl-6,7-dihydro-5H-pyrrolo[2,1-c][1,2,4]triazol-3-yl]pyridin-2-yl}-6-[2-methylpyrrolidin-1-yl]-2,3-dihydro-1H-pyrrolo[3,4-c]pyridin-1-one;

4-[1-aminoethyl]-2-{6-[5-ethyl-6,7-dihydro-5H-pyrrolo[2,1-c][1,2,4]triazol-3-yl]pyridin-2-yl}-6-[2-methylpyrrolidin-1-yl]-2,3-dihydro-1H-pyrrolo[3,4-c]pyridin-1-one;

4-[1-aminoethyl]-2-{6-[5-ethyl-6,7-dihydro-5H-pyrrolo[2,1-c][1,2,4]triazol-3-yl]pyridin-2-yl}-6-[methyl(propan-2-yl)amino]-2,3-dihydro-1H-pyrrolo[3,4-c]pyridin-1-one;

4-[1-aminopropyl]-2-{3-[5-methyl-6,7-dihydro-5H-pyrrolo[2,1-c][1,2,4]triazol-3-yl]phenyl}-6-[methyl(propan-2-yl)amino]-2,3-dihydro-1H-pyrrolo[3,4-c]pyridin-1-one; or 4-[1-amino-2-methoxyethyl]-6-(1-methylcyclopropyl)-2-{6-[5-methyl-6,7-dihydro-5H-pyrrolo[2,1-c][1,2,4]triazol-3-yl]pyridin-2-yl}-2,3-dihydro-1H-pyrrolo[3,4-c]pyridin-1-one; or a pharmaceutically acceptable salt thereof.

For example, the compound of the invention is a compound that is 4-[(1R)-1-aminopropyl]-2-{6-[(5S)-5-methyl-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one;

4-[(1R)-1-aminoethyl]-2-{6-[(5S)-5-ethyl-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one;

4-[(1S)-1-aminoethyl]-2-{6-[(5S)-5-ethyl-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one;

4-[(1R)-1-aminoethyl]-2-{6-[(5S)-5-ethyl-6,7-dihydro-5H-pyrrolo[2,1-c][1,2,4]triazol-3-yl]pyridin-2-yl}-6-[methyl(propan-2-yl)amino]-2,3-dihydro-1H-pyrrolo[3,4-c]pyridin-1-one;

4-[(1R)-1-aminopropyl]-2-{3-[(5S)-5-methyl-6,7-dihydro-5H-pyrrolo[2,1-c][1,2,4]triazol-3-yl]phenyl}-6-[methyl(propan-2-yl)amino]-2,3-dihydro-1H-pyrrolo[3,4-c]pyridin-1-one;

4-[(1R)-1-amino-2-methoxyethyl]-6-(1-methylcyclopropyl)-2-{6-[(5S)-5-methyl-6,7-dihydro-5H-pyrrolo[2,1-c][1,2,4]triazol-3-yl]pyridin-2-yl}-2,3-dihydro-1H-pyrrolo[3,4-c]pyridin-1-one; or 4-[(1S)-1-amino-2-methoxyethyl]-6-(1-methylcyclopropyl)-2-{6-[(5S)-5-methyl-6,7-dihydro-5H-pyrrolo[2,1-c][1,2,4]triazol-3-yl]pyridin-2-yl}-2,3-dihydro-1H-pyrrolo[3,4-c]pyridin-1-one; or a pharmaceutically acceptable salt thereof.

In another embodiment, the invention concerns compounds of Formula I, or a pharmaceutically acceptable salt thereof, wherein the compounds are compounds of Formula I(R) or compounds of Formula I(S), having specific stereochemistry with regard to the orientation of $R^2$, $R^{3a}$, and $R^{3b}$, when $R^{3a}$ is different from $R^{3b}$.

In another embodiment, the invention concerns a compound that is 4-[(1R)-1-aminopropyl]-2-{6-[(5S)-5-methyl-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one; or a pharmaceutically acceptable thereof.

In another embodiment, the invention concerns a compound that is 4-[(1R)-1-aminoethyl]-2-{6-[(5S)-5-ethyl-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one; or a pharmaceutically acceptable thereof.

In another embodiment, the invention concerns compounds that is 4-[(1 S)-1-aminoethyl]-2-{6-[(5S)-5-ethyl-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one; or a pharmaceutically acceptable thereof.

In another aspect, the invention provides a compound selected from the group consisting of the compounds exemplified herein, or a pharmaceutically acceptable salt thereof.

The compounds of the invention are selective against HPK1 kinase.

A "pharmaceutical composition" refers to a mixture of one or more of the compounds described herein, or a pharmaceutically acceptable salt, solvate, hydrate or prodrug thereof as an active ingredient, and at least one pharmaceutically acceptable carrier or excipient. In some embodiments, the pharmaceutical composition comprises two or more pharmaceutically acceptable carriers and/or excipients.

In some embodiments, the pharmaceutical composition further comprises at least one additional anti-cancer therapeutic agent or a palliative agent. In some such embodiments, the at least one additional agent is an anti-cancer therapeutic agent as described below. In some such embodiments, the combination provides an additive, greater than additive, or synergistic anti-cancer effect.

In one embodiment, the invention provides a method for the treatment of abnormal cell growth in a subject in need thereof, comprising administering to the subject a therapeutically effective amount of a compound of the invention, or a pharmaceutically acceptable salt thereof.

In another embodiment, the invention provides a method for the treatment of abnormal cell growth in a subject in need thereof, comprising administering to the subject an amount of a compound of the invention, or a pharmaceutically acceptable salt thereof, in combination with an amount of an additional therapeutic agent (e.g., an anticancer therapeutic agent), which amounts are together effective in treating said abnormal cell growth.

In frequent embodiments of the methods provided herein, the abnormal cell growth is cancer. Compounds of the invention may be administered as single agents, or may be administered in combination with other anti-cancer therapeutic agents, in particular standard of care agents appropriate for the particular cancer.

In some embodiments, the methods provided result in one or more of the following effects: (1) inhibiting cancer cell proliferation; (2) inhibiting cancer cell invasiveness; (3) inducing apoptosis of cancer cells; (4) inhibiting cancer cell metastasis; (5) inhibiting angiogenesis; (6) enhancing T-cell responses; (7) enhancing dendritic and B cell responses; (8) heightening of anti-tumor activity; (9) enhancing vaccine therapies; and (10) enhancing immune-system mediated removal of pathogens such as viruses, bacteria, worms.

In another aspect, the invention provides a method for the treatment of a disorder mediated by HPK1kinase activity, in a subject, such as certain cancers, comprising administering to the subject a compound of the invention, or a pharmaceutically acceptable salt thereof, in an amount that is effective for treating said disorder.

Unless indicated otherwise, all references herein to the inventive compounds include references to salts, solvates, hydrates and complexes thereof, and to solvates, hydrates and complexes of salts thereof, including polymorphs, stereoisomers, and isotopically labelled versions thereof.

Compounds of the invention may exist in the form of pharmaceutically acceptable salts such as, e.g., acid addition salts and base addition salts of the compounds of Formula I provided herein. As used herein, the term "pharmaceutically acceptable salt" refers to those salts which retain the biological effectiveness and properties of the parent compound. The phrase "pharmaceutically acceptable salt(s)", as used herein, unless otherwise indicated, includes salts of acidic or basic groups which may be present in the compounds of Formula I disclosed herein.

For example, the compounds of the invention that are basic in nature are capable of forming a wide variety of salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

The acids that may be used to prepare pharmaceutically acceptable acid addition salts of such basic compounds of those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Examples of salts include, but are not limited to, acetate, acrylate, benzenesulfonate, benzoate (such as chlorobenzoate, methylbenzoate, dinitrobenzoate, hydroxybenzoate, and methoxybenzoate), bicarbonate, bisulfate, bisulfite, bitartrate, borate, bromide, butyne-1,4-dioate, calcium edetate, camsylate, carbonate, chloride, caproate, caprylate, clavulanate, citrate, decanoate, dihydrochloride, dihydrogenphosphate, edetate, edislyate, estolate, esylate, ethylsuccinate, formate, fumarate, gluceptate, gluconate, glutamate, glycollate, glycollylarsanilate, heptanoate, hexyne-1,6-dioate, hexylresorcinate, hydrabamine, hydrobromide, hydrochloride, γ-hydroxybutyrate, iodide, isobutyrate, isothionate, lactate, lactobionate, laurate, malate, maleate, malonate, mandelate, mesylate, metaphosphate, methane-sulfonate, methylsulfate, monohydrogenphosphate, mucate, napsylate, naphthalene-1-sulfonate, naphthalene-2-sulfonate, nitrate, oleate, oxalate, pamoate (embonate), palmitate, pantothenate, phenylacetates, phenylbutyrate, phenylpropionate, phthalate, phosphate/diphosphate, polygalacturonate, propanesulfonate, propionate, propiolate, pyrophosphate, pyrosulfate, salicylate, stearate, subacetate, suberate, succinate, sulfate, sulfonate, sulfite, tannate, tartrate, teoclate, tosylate, triethiodode and valerate salts.

Illustrative examples of suitable salts include organic salts derived from amino acids, such as glycine and arginine, ammonia, primary, secondary, and tertiary amines and cyclic amines, such as piperidine, morpholine and piperazine, and inorganic salts derived from sodium, calcium, potassium, magnesium, manganese, iron, copper, zinc, aluminium and lithium.

The compounds of the invention that include a basic moiety, such as an amino group, may form pharmaceutically acceptable salts with various amino acids, in addition to the acids mentioned above.

Those compounds of the invention that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds herein. These salts may be prepared by any suitable method, for example, treatment of the free acid with an inorganic or organic base, such as an amine (primary, secondary or tertiary), an alkali metal hydroxide or alkaline earth metal hydroxide, or the like. These salts can also be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The chemical bases that may be used as reagents to prepare pharmaceutically acceptable base salts of the compounds of the invention that are acidic in nature are those that form non-toxic base salts with such compounds. Such non-toxic base salts include, but are not limited to, those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

Hemisalts of acids and bases may also be formed, for example, hemisulphate and hemicalcium salts.

For a review on suitable salts, see Handbook of Pharmaceutical Salts: Properties, Selection, and Use by Stahl and Wermuth (Wiley-VCH, 2002). Methods for making pharmaceutically acceptable salts of compounds of the invention are known to one of skill in the art.

Salts of the present invention can be prepared according to methods known to those of skill in the art. A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

It will be understood by those of skill in the art that the compounds of the invention in free base form having a basic functionality may be converted to the acid addition salts by treating with a stoichiometric excess of the appropriate acid. The acid addition salts of the compounds of the invention may be reconverted to the corresponding free base by treating with a stoichiometric excess of a suitable base, such as potassium carbonate or sodium hydroxide, typically in the presence of aqueous solvent, and at a temperature of between about 0° C. and 100° C. The free base form may be isolated by conventional means, such as extraction with an organic solvent.

In addition, acid addition salts of the compounds of the invention may be interchanged by taking advantage of differential solubilities of the salts, volatilities or acidities of the acids, or by treating with the appropriately loaded ion exchange resin. For example, the interchange may be affected by the reaction of a salt of the compounds of the invention with a slight stoichiometric excess of an acid of a lower pK than the acid component of the starting salt. This conversion is typically carried out at a temperature between about 0° C. and the boiling point of the solvent being used as the medium for the procedure. Similar exchanges are possible with base addition salts, typically via the intermediacy of the free base form.

The compounds of the invention may exist in both unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm. The term 'solvate' is used herein to describe a molecular complex comprising the compound of the invention and one or more pharmaceutically acceptable solvent molecules, for example, ethanol. The term 'hydrate' is employed when the solvent is water. Pharmaceutically acceptable solvates in accordance with the invention include hydrates and solvates wherein the solvent of crystallization may be isotopically substituted, e.g. $D_2O$, ds-acetone, ds-DMSO.

Also included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see J Pharm Sci, 64 (8), 1269-1288 by Haleblian (August 1975), the disclosure of which is incorporated herein by reference in its entirety.

The invention also relates to prodrugs of the compounds of Formula I provided herein. Thus, certain derivatives of compounds of the invention which may have little or no pharmacological activity themselves can, when administered to a patient, be converted into the inventive compounds, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association), the disclosures of which are incorporated herein by reference in their entireties.

Prodrugs in accordance with the invention can, for example, be produced by replacing appropriate functionalities present in the inventive compounds with certain moieties known to those skilled in the art as 'pro-moieties' as described, for example, in "Design of Prodrugs" by H Bundgaard (Elsevier, 1985), the disclosure of which is incorporated herein by reference in its entirety.

Some non-limiting examples of prodrugs in accordance with the invention include:

(i) where the compound contains a carboxylic acid functionality (—COOH), an ester thereof, for example, replacement of the hydrogen with ($C_1$-$C_8$)alkyl;

(ii) where the compound contains an alcohol functionality (—OH), an ether thereof, for example, replacement of the hydrogen with ($C_1$-$C_6$)alkanoyloxymethyl, or with a phosphate ether group; and (iii) where the compound contains a primary or secondary amino functionality (—$NH_2$ or —NHR where R≠H), an amide thereof, for example, replacement of one or both hydrogens with a suitably metabolically labile group, such as an amide, carbamate, urea, phosphonate, sulfonate, etc.

Further examples of replacement groups in accordance with the foregoing examples and examples of other prodrug types may be found in the aforementioned references.

Finally, certain inventive compounds may themselves act as prodrugs of other of the inventive compounds.

Also included within the scope of the invention are metabolites of compounds of Formula I as described herein, i.e., compounds formed in vivo upon administration of the drug.

The compounds of Formula I provided herein may have asymmetric carbon atoms. The carbon-carbon bonds of the compounds of the invention may be depicted herein using a solid line (———), a solid wedge (◥), or a dotted wedge (⋯⋯). The use of a solid line to depict bonds to asymmetric carbon atoms is meant to indicate that all possible stereoisomers (e.g. specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of the invention may contain more than one asymmetric carbon atom. In those compounds, the use of a solid line to depict bonds to asymmetric carbon atoms is meant to indicate that all possible stereoisomers are meant to be included and the attached stereocenter. For example, unless stated otherwise, it is intended that the compounds of the invention can exist as enantiomers and diastereomers or as racemates and mixtures thereof. The use of a solid line to depict bonds to one or more asymmetric carbon atoms in a compound of the invention and the use of a solid or dotted wedge to depict bonds to other asymmetric carbon atoms in the same compound is meant to indicate that a mixture of diastereomers is present.

Compounds of the invention that have chiral centers may exist as stereoisomers, such as racemates, enantiomers, or diastereomers.

Stereoisomers of the compounds of Formula I herein can include cis and trans isomers, optical isomers such as (R) and (S) enantiomers, diastereomers, geometric isomers, rotational isomers, atropisomers, conformational isomers, and tautomers of the compounds of the invention, including compounds exhibiting more than one type of isomerism; and mixtures thereof (such as racemates and diastereomeric pairs).

Also included are acid addition or base addition salts wherein the counterion is optically active, for example, d-lactate or l-lysine, or racemic, for example, dl-tartrate or dl-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of the invention may exhibit the phenomena of tautomerism and structural isomerism. For example, the compounds may exist in several tautomeric forms, including the enol and imine form, and the keto and enamine form and geometric isomers and mixtures thereof. All such tautomeric forms are included within the scope of compounds of the invention. Tautomers exist as mixtures of a tautomeric set in solution. In solid form, usually one tautomer predominates. Even though one tautomer may be described, the present invention includes all tautomers of the compounds of Formula I provided.

In addition, some of the compounds of the invention may form atropisomers (e.g., substituted biaryls). Atropisomers are conformational stereoisomers which occur when rotation about a single bond in the molecule is prevented, or greatly slowed, as a result of steric interactions with other parts of the molecule and the substituents at both ends of the single bond are unsymmetrical. The interconversion of atropisomers is slow enough to allow separation and isolation under predetermined conditions. The energy barrier to thermal racemization may be determined by the steric hindrance to free rotation of one or more bonds forming a chiral axis.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC) or superfluid critical chromatography (SFC).

Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art; see, for example, "Stereochemistry of Organic Compounds" by E L Eliel (Wiley, New York, 1994), the disclosure of which is incorporated herein by reference in its entirety.

The enantiomeric purity of compounds described herein may be described in terms of enantiomeric excess (ee), which indicates the degree to which a sample contains one enantiomer in greater amounts than the other. A racemic mixture has an ee of 0%, while a single completely pure enantiomer has an ee of 100%. Similarly, diastereomeric purity may be described in terms of diasteriomeric excess (de).

The present invention also includes isotopically-labeled compounds, which are identical to those recited in one of Formula I provided, but for the fact that one or more atoms are replaced by an atom having an atomic mass or mass number different from the atomic mass or mass number usually found in nature.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Examples of isotopes that may be incorporated into compounds of the invention include isotopes of hydrogen, carbon, nitrogen, oxygen, phosphorus, fluorine and chlorine, such as, but not limited to, $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$. Certain isotopically-labeled compounds of the invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically-labeled compounds of the invention may generally be prepared by carrying out the procedures disclosed in the Schemes and/or in the Examples and Preparations below, by substituting an isotopically-labeled reagent for a non-isotopically-labeled reagent.

Compounds of the invention intended for pharmaceutical use may be administered as crystalline or amorphous products, or mixtures thereof. They may be obtained, for example, as solid plugs, powders, or films by methods such as precipitation, crystallization, freeze drying, spray drying, or evaporative drying. Microwave or radio frequency drying may be used for this purpose. The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of Formula I may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^{-}$Na$^{+}$, —COO$^{-}$K$^{+}$, or —SO$_{3}$—Na$^{+}$) or non-ionic (such as —N$^{-}$N$^{+}$(CH$_{3}$)$_{3}$) polar head group. For more information, see *Crystals and the Polarizing Microscope* by N. H. Hartshorne and A. Stuart, 4$^{th}$ Edition (Edward Arnold, 1970).

The compounds of Formula I may exhibit polymorphism and/or one or more kinds of isomerism (e.g. optical, geometric or tautomeric isomerism). The compounds of Formula I may also be isotopically labelled. Such variation is implicit to the compounds of Formula I defined as they are by reference to their structural features and therefore within the scope of the invention.

Therapeutic Methods and Uses

The invention further provides therapeutic methods and uses comprising administering the compounds of the invention, or pharmaceutically acceptable salts thereof, alone or in combination with other therapeutic agents or palliative agents.

In one embodiment, the invention provides a method for the treatment of abnormal cell growth in a subject comprising administering to the subject a therapeutically effective amount of a compound of the invention, or a pharmaceutically acceptable salt thereof. In frequent embodiments, the abnormal cell growth is cancer.

In another embodiment, the invention provides a method for the treatment of cancer in a subject comprising administering to the subject an amount of a compound of the invention, or a pharmaceutically acceptable salt thereof, in combination with an amount of an additional anticancer therapeutic agent, which amounts are together effective in treating said cancer.

Compounds of the invention include compounds of Formula I as described herein, or a pharmaceutically acceptable salt thereof.

In still another embodiment, the invention provides a method of inhibiting cancer cell proliferation in a subject, comprising administering to the subject an effective amount of a compound of the invention, or a pharmaceutically acceptable salt thereof.

In another embodiment, the invention provides a method of inhibiting cancer cell invasiveness in a subject, comprising administering to the subject an effective amount of a compound of the invention, or a pharmaceutically acceptable salt thereof.

In another embodiment, the invention provides a method of causing cell death in cancer cells in a subject, comprising administering to the subject an effective amount of a compound of the invention, or a pharmaceutically acceptable salt thereof.

In still another embodiment, the invention provides a method of enhancing vaccine therapies in a mammal, comprising administering to the mammal a therapeutically effective amount of a vaccine, and further comprising administering to the mammal a therapeutically effective amount of a compound of any of claims 1 to 16, or a pharmaceutically acceptable salt thereof.

In still another embodiment, the invention provides a method of improving the immune system's ability to clear a viral infection, bacterial infection, or pathogen (including parasitic worms) in a subject, comprising administering to the subject an effective amount of a compound of the invention, or a pharmaceutically acceptable salt thereof. The invention provides a method for enhancing immune-system mediated removal of pathogens, comprising administering to the mammal a therapeutically effective amount of a compound of any of claims 1 to 16, or a pharmaceutically acceptable salt thereof. The method includes administering the compound of the invention as monotherapy or in combination with other agents to treat the infection or pathogen.

The presently disclosed compounds find use in inhibiting the activity of the HPK1 kinase. HPK1, also referred to as mitogen activated protein kinase kinase kinase kinase 1 or MAP4K1, is a member of the germinal center kinase subfamily of Ste20-related serine/threnonine kinases. HPK1 kinase functions as a MAP4K by phosphorylating and activating MAP3K proteins, including MEKKI, MLK3 and TAK1, leading to the activation of the MAPK Jnk.

HPK1 polynucleotides and polypeptides are known in the art (Hu et al. (1996) Genes Dev. 10: 2251-2264, which is herein incorporated by reference in its entirety). HPK1 polypeptides comprise a variety of conserved structural motifs. HPK1 polypeptides comprise an amino-terminal Ste20-like kinase domain that spans amino acid residues 17-293, which includes the ATP-binding site from amino acid residues 23-46. The kinase domain is followed by four pro line-rich (PR) motifs that serve as binding sites for SH3-containing proteins, such as CrkL, Grb2, HIP-55, Gads, Nek, and Crk. The four PR motifs span amino acid residues 308-407, 394-402, 432-443, and 468-477, respectively. HPK1 becomes phosphorylated and activated in response to TCR or BCR stimulation. TCR- and BCR-induced phosphorylation of the tyrosine at position 381, located between PR1 and PR2, mediates binding to SLP-76 in T cells or BLNK in B cells via a SLP-76 or BLNK SH2 domain, and is required for activation of the kinase. A citron homology domain found in the C-terminus of HPK1, approximately spanning residues 495-800, may act as a regulatory domain and may be involved in macromolecular interactions.

The presently disclosed compounds bind directly to HPK1 and inhibit its kinase activity. In some embodiments, the presently disclosed compounds reduce, inhibit, or otherwise diminish the HPK1-mediated phosphorylation of SLP76 and/or Gads. The presently disclosed compounds may or may not be a specific HPK1 inhibitor. A specific HPK1 inhibitor reduces the biological activity of HPK1 by an amount that is statistically greater than the inhibitory effect of the inhibitor on any other protein (e.g., other serine/threonine kinases). In certain embodiments, the presently disclosed compounds specifically inhibit the serine/threonine kinase activity of HPK1.

The presently disclosed compounds can be used in a method for inhibiting HPK1. Such methods comprise contacting HPK1 with an effective amount of a presently disclosed compound. The term "contacting" means bringing the compound within close enough proximity to an isolated HPK1 enzyme or a cell expressing HPK1 (e.g., T cell, B cell, dendritic cell) such that the compound is able to bind to and inhibit the activity of HPK1. The compound can be contacted with HPK1 in vitro or in vivo via administration of the compound to a subject.

Any method known in the art to measure the kinase activity of HPK1 may be used to determine if HPK1 has been inhibited, including in vitro kinase assays, immunoblots with antibodies specific for phosphorylated targets of HPK1, such as SLP76 and Gads, or the measurement of a downstream biological effect of HPK1 kinase activity, such as the recruitment of 14-3-3 proteins to phosphorylated SLP7 and Gads, release of the SLP76-Gads-14-3-3 complex from LAT-containing microclusters, or T or B cell activation.

The presently disclosed compounds can be used to treat a HPK1-dependent disorder. As used herein, a "HPK1-dependent disorder" is a pathological condition in which HPK1 activity is necessary for the genesis or maintenance of the pathological condition.

The presently disclosed compounds also find use in enhancing an immune response in a subject in need thereof. Such methods comprise administering an effective amount of a presently disclosed compound (i.e., any of the compounds of Formula I, or a pharmaceutically acceptable salt, prodrug, metabolite, or derivative thereof). The term "enhancing an immune response" refers to an improvement in any immunogenic response to an antigen. Non-limiting examples of improvements in an immunogenic response to an antigen include enhanced maturation or migration of dendritic cells, enhanced activation of T cells (e.g., CD4 T cells, CD8 T cells), enhanced T cell (e.g., CD4 T cell, CD8 T cell) proliferation, enhanced B cell proliferation, increased survival of T cells and/or B cells, improved antigen presentation by antigen presenting cells (e.g., dendritic cells), improved antigen clearance, increase in production of cytokines by T cells (e.g., interleukin-2), increased resistance to prostaglandin E2- or adenosine induced immune suppression, and enhanced priming and/or cytolytic activity of CD8 T cells. In some embodiments, the CD8 T cells in the subject have enhanced priming, activation, proliferation and/or cytolytic activity relative to prior to the administration of the compound of Formula I, or a pharmaceutically acceptable salt, prodrug, metabolite, or derivative thereof. In some embodiments, the CD8 T cell priming is characterized by elevated CD44 expression and/or enhanced cytolytic activity in CD8 T cells. In some embodiments, the CD8 T cell activation is characterized by an elevated frequency of IFNy$^+$ CD8 T cells. In some embodiments, the CD8 T cell is an antigen-specific T-cell.

In some embodiments, the antigen presenting cells in the subject have enhanced maturation and activation relative to prior to the administration of the compound of Formula I, or a pharmaceutically acceptable salt, prodrug, metabolite, or derivative thereof. In some embodiments, the antigen presenting cells are dendritic cells. In some embodiments, the maturation of the antigen presenting cells is characterized by an increased frequency of CD83$^+$ dendritic cells. In some embodiments, the activation of the antigen presenting cells is characterized by elevated expression of CD80 and CD86 on dendritic cells.

Engagement of the TCR leads to HPK1 activation, which functions as a negative regulator of TCR-induced AP-1 response pathway. It is believed that HPK1 negatively regulates T cell activation by reducing the persistence of signalling microclusters by phosphorylating SLP76 at Ser376 (Di Bartolo et al. (2007) JEM 204:681-691) and Gads at Thr254, which leads to the recruitment of 14-3-3 proteins that bind to the phosphorylated SLP76 and Gads, releasing the SLP76-Gads-14-3-3 complex from LAT-containing microclusters, which leads to T cell dysfunction, including anergy and exhaustion (Lasserre et al. (2011) J Cell Biol 195(5):839-853). The term "dysfunction" in the context of immune dysfunction, refers to a state of reduced immune responsiveness to antigenic stimulation. The term includes the common elements of both exhaustion and/or anergy in which antigen recognition may occur, but the ensuing immune response is ineffective to control infection or tumor growth.

The term "dysfunctional", as used herein, also includes refractory or unresponsive to antigen recognition, specifically, impaired capacity to translate antigen recognition into downstream T-cell effector functions, such as proliferation, cytokine production (e.g., IL-2, gamma-IFN) and/or target cell killing.

The term "anergy" refers to the state of unresponsiveness to antigen stimulation resulting from incomplete or insufficient signals delivered through the T-cell receptor {e.g. increase in intracellular Ca in the absence of ras-activation). T cell anergy can also result upon stimulation with antigen in the absence of co-stimulation, resulting in the cell becoming refractory to subsequent activation by the antigen even in the context of costimulation. The unresponsive state can often be overriden by the presence of Interleukin-2. Anergic T-cells do not undergo clonal expansion and/or acquire effector functions.

The term "exhaustion" refers to T cell exhaustion as a state of T cell dysfunction that arises from sustained TCR signalling that occurs during many chronic infections and cancer. It is distinguished from anergy in that it arises not through incomplete or deficient signalling, but from sustained signalling. It is defined by poor effector function, sustained expression of inhibitory receptors and a transcriptional state distinct from that of functional effector or memory T cells. Exhaustion prevents optimal control of infection and tumors. Exhaustion can result from both extrinsic negative regulatory pathways (e.g., immunoregulatory cytokines) as well as cell intrinsic negative regulatory (costimulatory) pathways (PD-1, B7-H3, B7-H4, etc.).

"Enhancing T cell function" means to induce, cause or stimulate a T cell to have a sustained or amplified biological function, or renew or reactivate exhausted or inactive T cells. Examples of enhancing T cell function include: increased secretion of cytokines (e.g., gamma-interferon, IL-2, IL-12, and TNFa), increased proliferation, increased antigen responsiveness (e.g., viral, pathogen, or tumor clearance) relative to such levels before the intervention, and increased effector granule production by CD8 T cells, such as granzyme B.

Accordingly, the presently disclosed compounds of Formula I, or pharmaceutically acceptable salts, prodrugs, metabolites, or derivatives thereof are useful in treating T cell dysfunctional disorders. A "T cell dysfunctional disorder" is a disorder or condition of T cells characterized by decreased responsiveness to antigenic stimulation. In a particular embodiment, a T cell dysfunctional disorder is a disorder that is specifically associated with increased kinase activity of HPK1. In another embodiment, a T cell dysfunctional disorder is one in which T cells are anergic or have decreased ability to secrete cytokines, proliferate, or execute cytolytic activity. In a specific aspect, the decreased responsiveness results in ineffective control of a pathogen or tumor expressing an immunogen. Examples of T cell dysfunctional disorders characterized by T-cell dysfunction include unresolved acute infection, chronic infection and tumor immunity.

Thus, the presently disclosed compounds can be used in treating conditions where enhanced immunogenicity is desired, such as increasing tumor immunogenicity for the treatment of cancer. "Immunogenecity" refers to the ability of a particular substance to provoke an immune response. Tumors are immunogenic and enhancing tumor immunogenicity aids in the clearance of the tumor cells by the immune response.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

In one aspect, provided herein is a method for treating of cancer in a subject in need thereof comprising administering to the subject an effective amount of a compound of Formula I, or a pharmaceutically acceptable salt, prodrug, metabolite, or derivative thereof. In some embodiments, the subject has melanoma. The melanoma may be at early stage or at late stage. In some embodiments, the subject has colorectal cancer. The colorectal cancer may be at early stage or at late stage. In some embodiments, the subject has non-small cell lung cancer. The non-small cell lung cancer may be at early stage or at late stage. In some embodiments, the subject has pancreatic cancer. The pancreatic cancer may be at early stage or late state. In some embodiments, the subject has a hematological malignancy. The hematological malignancy may be at early stage or late stage. In some embodiments, the subject has ovarian cancer. The ovarian cancer may be at early stage or at late stage. In some embodiments, the subject has breast cancer. The breast cancer may be at early stage or at late stage. In some embodiments, the subject has renal cell carcinoma. The renal cell carcinoma may be at early stage or at late stage. In some embodiments, the cancer has elevated levels of T-cell infiltration.

In some embodiments, the treatment results in a sustained response in the subject after cessation of the treatment. "Sustained response" refers to the sustained effect on reducing tumor growth after cessation of a treatment. For example, the tumor size may remain the same or smaller as compared to the size at the beginning of the administration phase.

The treatment methods disclosed herein may result in a partial or complete response. As used herein, "complete response" or "CR" refers to disappearance of all target lesions; "partial response" or "PR" refers to at least a 30 percent decrease in the sum of the longest diameters (SLD) of target lesions, taking as reference the baseline SLD; and "stable disease" or "SD" refers to neither sufficient shrinkage of target lesions to qualify for PR, nor sufficient increase to qualify for PD, taking as reference the smallest SLD since the treatment started. As used herein, "overall response rate" (ORR) refers to the sum of complete response (CR) rate and partial response (PR) rate.

The treatment methods disclosed herein can lead to an increase in progression free survival and overall survival of the subject administered the HPKI antagonist. As used herein, "progression free survival" (PFS) refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall survival" refers to the percentage of subjects in a group who are likely to be alive after a particular duration of time.

In some embodiments of the methods provided herein, the abnormal cell growth is cancer, wherein the cancer is selected from the group consisting of breast cancer, ovarian cancer, bladder cancer, uterine cancer, prostate cancer, lung cancer (including NSCLC, SCLC, squamous cell carcinoma or adenocarcinoma), esophageal cancer, head and neck cancer, colorectal cancer, kidney cancer (including RCC), liver cancer (including HCC), pancreatic cancer, stomach (e.g., gastric) cancer and thyroid cancer. In further embodiments of the methods provided herein, the cancer is selected from the group consisting of breast cancer, ovarian cancer, bladder cancer, uterine cancer, prostate cancer, lung cancer, esophageal cancer, liver cancer, pancreatic cancer and stomach cancer.

In some embodiments, the cancer is selected from the group consisting of breast cancer and ovarian cancer.

In some embodiments, the cancer is ovarian cancer.

In other embodiments, the cancer is breast cancer, including, e.g., ER-positive/HR-positive breast cancer, HER2-negative breast cancer; ER-positive/HR-positive breast cancer, HER2-positive breast cancer; triple negative breast cancer (TNBC); or inflammatory breast cancer. In some embodiments, the breast cancer is endocrine resistant breast cancer, trastuzumab resistant breast cancer, or breast cancer demonstrating primary or acquired resistance to CDK4/CDK6 inhibition. In some embodiments, the breast cancer is advanced or metastatic breast cancer.

In some embodiments, the compound of the invention is administered as first line therapy. In other embodiments, the compound of the invention is administered as second (or later) line therapy. In some embodiments, the compound of the invention is administered as second (or later) line therapy following treatment with an endocrine therapeutic agent and/or a CDK4/CDK6 inhibitor. In some embodiments, the compound of the invention is administered as second (or later) line therapy following treatment with an endocrine therapeutic agent. In some embodiments, the compound of the invention is administered as second (or later) line therapy following treatment with a CDK4/CDK6 inhibitor. In some embodiments, the compound of the invention is administered as second (or later) line therapy following treatment with one or more chemotherapy regimens, e.g., including taxanes or platinum agents. In some embodiments, the compound of the invention is administered as second (or later) line therapy following treatment with HER2 targeted agents, e.g., trastuzumab.

The terms "abnormal cell growth" and "hyperproliferative disorder" are used interchangeably in this application.

"Abnormal cell growth", as used herein, unless otherwise indicated, refers to cell growth that is independent of normal regulatory mechanisms (e.g., loss of contact inhibition). Abnormal cell growth may be benign (not cancerous), or malignant (cancerous).

Abnormal cell growth includes the abnormal growth of tumors that are resistant to endocrine therapy, HER2 antagonists or CDK4/6 inhibition.

The term "additional anticancer therapeutic agent" as used herein means any one or more therapeutic agent, other than a compound of the invention, that is or can be used in the treatment of cancer, such as agents derived from the following classes: mitotic inhibitors, alkylating agents, antimetabolites, antitumor antibiotics, topoisomerase I and II inhibitors, plant alkaloids, hormonal agents and antagonists, growth factor inhibitors, radiation, inhibitors of protein tyrosine kinases and/or serine/threonine kinases, cell cycle inhibitors, biological response modifiers, enzyme inhibitors, antisense oligonucleotides or oligonucleotide derivatives, cytotoxics, and immuno-oncology agents (immuno-oncology agents include monoclonal antibodies, bispecific antibodies, cytokines, CAR-t cells).

As used herein "cancer" refers to any malignant and/or invasive growth or tumor caused by abnormal cell growth. Cancer includes solid tumors named for the type of cells that form them, cancer of blood, bone marrow, or the lymphatic system. Examples of solid tumors include sarcomas and carcinomas. Cancers of the blood include, but are not limited to, leukemia, lymphoma and myeloma. Cancer also includes primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of a different type from the latter one.

In some embodiments of the methods provided herein, the cancer is selected from the group consisting of breast cancer, ovarian cancer, bladder cancer, uterine cancer, prostate cancer, lung cancer, esophageal cancer, liver cancer, pancreatic cancer and stomach cancer.

Dosage Forms and Regimens

Administration of the compounds of the invention may be effected by any method that enables delivery of the compounds to the site of action. These methods include oral routes, intraduodenal routes, parenteral injection (including intravenous, subcutaneous, intramuscular, intravascular or infusion), topical, and rectal administration.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens for administration of the chemotherapeutic agent are well-known in the relevant art and would be understood to be encompassed by the skilled artisan once provided the teachings disclosed herein.

The amount of the compound of the invention administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.1 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

Formulations and Routes of Administration

As used herein, a "pharmaceutically acceptable carrier" refers to a carrier or diluent that does not cause significant irritation to an organism and does not abrogate the biological activity and properties of the administered compound.

The pharmaceutical acceptable carrier may comprise any conventional pharmaceutical carrier or excipient. The choice of carrier and/or excipient will to a large extent depend on factors such as the particular mode of administration, the effect of the carrier or excipient on solubility and stability, and the nature of the dosage form.

Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Examples, without limitation, of excipients include calcium carbonate, calcium phosphate, various sugars and types of starch, cellulose derivatives, gelatin, vegetable oils and polyethylene glycols. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulations, solution suspension, for parenteral injection as a sterile solution, suspension or emulsion, for topical administration as an ointment or cream or for rectal administration as a suppository.

Exemplary parenteral administration forms include solutions or suspensions of active compounds in sterile aqueous solutions, for example, aqueous propylene glycol or dextrose solutions. Such dosage forms may be suitably buffered, if desired.

The pharmaceutical composition may be in unit dosage forms suitable for single administration of precise dosages.

Pharmaceutical compositions suitable for the delivery of compounds of the invention and methods for their preparation will be readily apparent to those skilled in the art. Such compositions and methods for their preparation can be found, for example, in 'Remington's Pharmaceutical Sciences', 19th Edition (Mack Publishing Company, 1995), the disclosure of which is incorporated herein by reference in its entirety.

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Other conventional ingredients include anti-oxidants, colorants, flavoring agents, preservatives and taste-masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tableting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., N.Y., 1980 (ISBN 0-8247-6918-X), the disclosure of which is incorporated herein by reference in its entirety.

Solid formulations for oral administration may be formulated to be immediate and/or modified release. Modified release formulations include delayed-, sustained-, pulsed-, controlled-, targeted and programmed release.

Suitable modified release formulations are described in U.S. Pat. No. 6,106,864. Details of other suitable release technologies such as high energy dispersions and osmotic and coated particles can be found in Verma et al, Pharmaceutical Technology On-line, 25(2), 1-14 (2001). The use of chewing gum to achieve controlled release is described in WO 00/35298. The disclosures of these references are incorporated herein by reference in their entireties.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including micro needle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J Pharm Sci, 88 (10), 955-958 by Finnin and Morgan (October 1999). Other means of topical administration include delivery by electroporation, iontophoresis, phonophoresis, sonophoresis and micro needle or needle-free (e.g. Powderject™, Bioject™, etc.) injection. The disclosures of these references are incorporated herein by reference in their entireties.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may include a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as I-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 µg to 20 mg of the compound of the invention per actuation and the actuation volume may vary from 1 µL to 100 µL. A typical formulation includes a compound of the invention, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing a desired mount of the compound of the invention. The overall daily dose may be administered in a single dose or, more usually, as divided doses throughout the day.

Compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Compounds of the invention may also be administered directly to the eye or ear, typically in the form of drops of a micronized suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

Compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in PCT Publication Nos. WO 91/11172, WO 94/02518 and WO 98/55148, the disclosures of which are incorporated herein by reference in their entireties.

Dosage

The amount of the active compound administered will be dependent on the subject being treated, the severity of the disorder or condition, the rate of administration, the disposition of the compound and the discretion of the prescribing physician. However, an effective dosage is typically in the range of about 0.001 to about 100 mg per kg body weight per day, preferably about 1 to about 35 mg/kg/day, in single or divided doses. For a 70 kg human, this would amount to about 0.05 to about 7000 mg/day, preferably about 0.1 to about 2500 mg/day. In some instances, dosage levels below the lower limit of the aforesaid range may be more than adequate, while in other cases still larger doses may be used without causing any harmful side effect, with such larger doses typically divided into several smaller doses for administration throughout the day.

Kit-of-Parts

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions. Thus, the kit of the invention includes two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

Combination Therapy

As used herein, the term "combination therapy" refers to the administration of a compound of the invention together with an at least one additional pharmaceutical or medicinal agent (e.g., an anti-cancer agent, vaccine, antibacterial agent, antiviral agent, or antiparasitic agent), either sequentially or simultaneously.

As noted above, the compounds of the invention may be used in combination with one or more additional agents, such as anti-cancer agents. The efficacy of the compounds of the invention in certain tumors may be enhanced by combination with other approved or experimental cancer therapies, e.g., radiation, surgery, chemotherapeutic agents, targeted therapies, agents that inhibit other signaling pathways that are dysregulated in tumors, and other immune enhancing agents, such as PD-1 antagonists and the like.

When a combination therapy is used, the one or more additional agents may be administered sequentially or simultaneously with the compound of the invention. In one embodiment, the additional agent is administered to a mammal (e.g., a human) prior to administration of the compound of the invention. In another embodiment, the additional agent is administered to the mammal (e.g., a human) after administration of the compound of the invention. In another embodiment, the additional agent is administered to the mammal (e.g., a human) simultaneously with the administration of the compound of the invention.

The invention also relates to a pharmaceutical composition for the treatment of abnormal cell growth in a mammal, including a human, which comprises an amount of a compound of the invention, as defined above (including hydrates, solvates, polymorphs, isomers, prodrugs, and/or metabolites of said compound or pharmaceutically acceptable salts thereof), in combination with one or more (preferably one to three) anti-cancer therapeutic agents.

In particular embodiments, a compound of the invention may be administered in combination with one or more: targeted agents, such as inhibitors of PI3 kinase, mTOR, PARP, Kras, IDO, TDO, ALK, ROS, MEK, VEGF, FLT3, AXL, ROR2, EGFR, FGFR, Src/Abl, RTK/Ras, Myc, Raf, PDGF, AKT, c-Kit, erbB, CDK2, CDK4, CDK4/CDK6, CDK5, CDK7, CDK9, SMO, CXCR4, HER2, GLS1, EZH2 or Hsp90, or immunomodulatory agents, such as PD-1 antagonists, PD-L1 antagonists, CTLA-4 antagonists, OX40 agonists, 4-1BB agonists, or CD80 agonists.

In other embodiments, a compound of the invention may be administered in combination with a standard of care agent, such as tamoxifen, docetaxel, paclitaxel, cisplatin, capecitabine, gemcitabine, vinorelbine, exemestane, letrozole, fulvestrant, anastrozole or trastuzumab.

Synthetic Methods

The compounds of Formula I, may be prepared by the methods described below, together with synthetic methods known in the art of organic chemistry, or modifications and transformations that are familiar to those of ordinary skill in the art. The starting materials used herein are commercially available or may be prepared by routine methods known in the art [such as those methods disclosed in standard reference books such as the *Compendium of Organic Synthetic Methods*, Vol. I-XIII (published by Wiley-Interscience)]. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999, which are hereby incorporated by reference.

Compounds of Formula I, or their pharmaceutically acceptable salts, can be prepared according to the reaction Schemes discussed herein below. Unless otherwise indicated, the substituents in the Schemes are defined as above.

Isolation and purification of the products is accomplished by standard procedures, which are known to a chemist of ordinary skill.

It will be understood by one skilled in the art that the various symbols, superscripts, and subscripts used in the schemes, methods, and examples are used for convenience of representation and/or to reflect the order in which they are introduced in the schemes, and are not intended to necessarily correspond to the symbols, superscripts, or subscripts in the appended claims. Additionally, one skilled in the art will recognize that in many cases, these compounds will be mixtures and enantiomers that may be separated at various stages of the synthetic schemes using conventional techniques, such as, but not limited to, crystallization, normal-phase chromatography, reversed-phase chromatography, and chiral chromatography, to afford single enantiomers. The schemes are representative of methods useful in synthesizing the compounds of the present invention. They are not to constrain the scope of the invention in any way.

Compounds of the invention are prepared according to the exemplary procedures provided herein and modifications thereof known to those of skill in the art.

The following abbreviations are used throughout the Examples: "Ac" means acetyl, "ACN" means acetonitrile, "BOC", "Boc" or "boc" means N-tert-butoxycarbonyl, "Bu" means butyl, "tBu" means tert-butyl, "DCM" ($CH_2Cl_2$) means methylene chloride, "de" means diastereomeric excess, "DMF" means N,N-dimethyl formamide, "DMSO" means dimethylsulfoxide, "ee" means enantiomeric excess, "Et" means ethyl, "EtOAc" means ethyl acetate, "EtOH" means ethanol, "i-Pr" or "iPr" means isopropyl, "Me" means methyl, "MeOH" means methanol, "MS" means mass spectrometry, "MTBE" means methyl tert-butyl ether, "Ph" means phenyl, "THF" means tetrahydrofuran, "SFC" means supercritical fluid chromatography, "TLC" means thin layer chromatography, "Rf" means retention factor, "~" means approximately, "RT" means room temperature that includes ambient temperature (generally 20° C. to 25° C.), "h" means hours, "min" means minutes, "equiv" means equivalents, "sat." means saturated.

The compounds of Formula I can be prepared by the procedures described in the general Methods presented below or by routine modifications thereof. Unless otherwise indicated, the substituents in the Methods are as defined herein. Although $R^4$ is in the compounds of Formula I, it will be clear from the intermediates used within the respective synthetic route whether $R^4$ is $R^4$-i or $R^4$-ii. The present invention also encompasses any one or more of these processes for preparing the compounds of Formula I, in addition to any novel intermediates used therein. The person skilled in the art will appreciate that the following reactions may be cooled, heated thermally, heated under microwave irradiation or run under flow chemistry conditions. It will be further appreciated that it may be necessary or desirable to carry out the transformations in a different order from that described in the Methods, or to modify one or more of the transformations, to provide the desired compound of the invention.

Method A

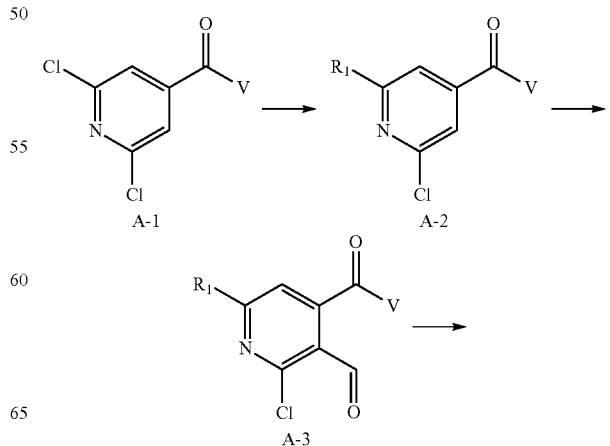

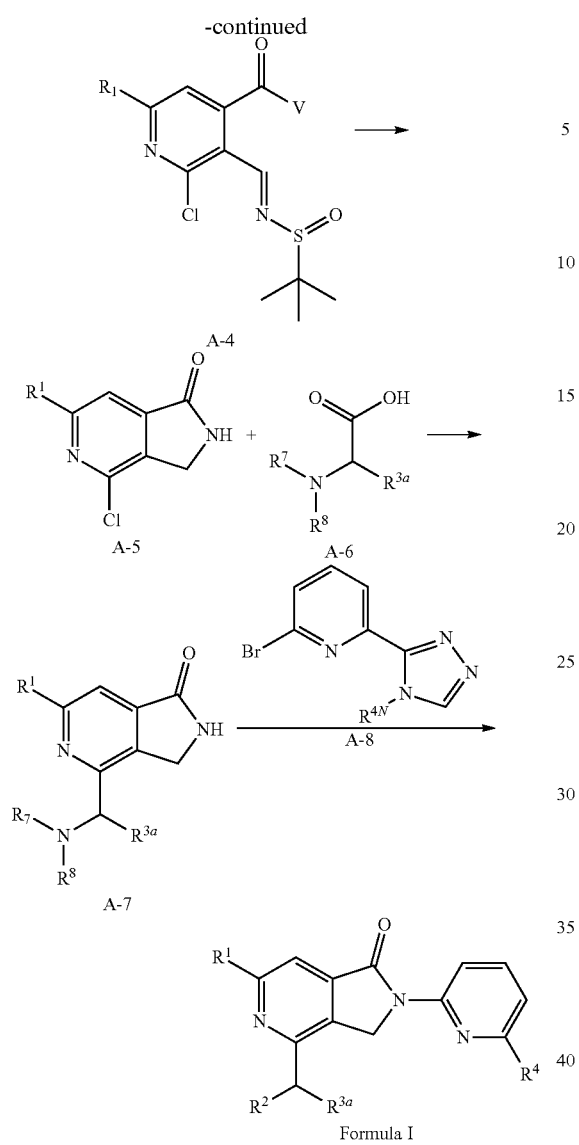

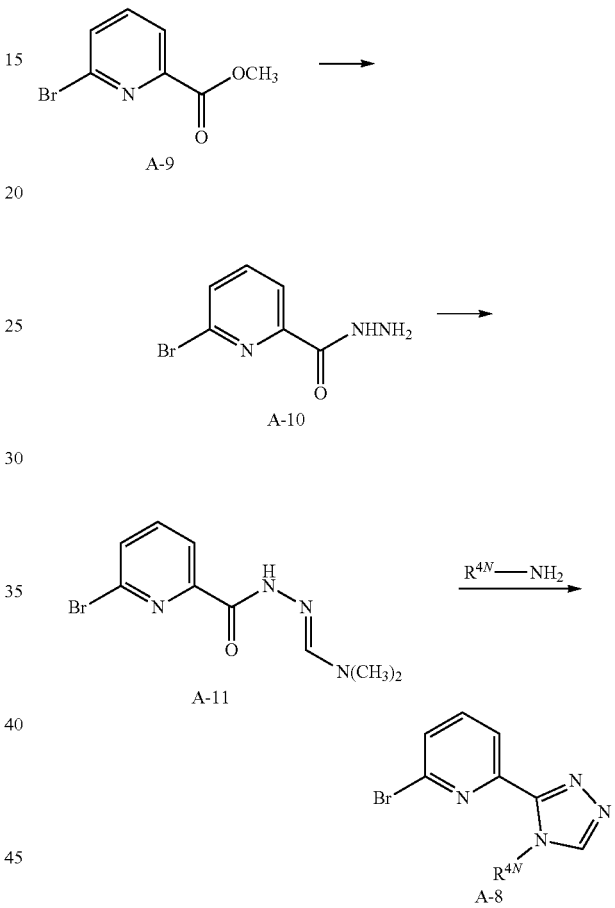

Method A presents a preparation of compounds of Formula I, where $R^{3b}$ is hydrogen. In Method A, cross coupling or nucleophilic aromatic substitution between requisite coupling partner or amine, providing $R^1$ is as in Formula I (or protected version thereof), yields A-2. For the dichloropyridine of formula A-1, V is $N(CH_3)_2$, OH, piperidine, morpholine, OMe, OEt, or OiPr. Formylation of A-2 then provides aldehyde A-3. Subsequent condensation with Ellman's sulfinamide provides the compound of formula A-4. Reduction and base-mediated cyclization of the compound of formula A-4 furnishes the compound of formula A-5. Alternatively, compounds of Formula I, wherein $R^1$ is cyclopropylmethyl, compound of formula A-5 can be prepared using the synthetic route described in making intermediate 15c described herein. In a next step, iridium and nickel-mediated decarboxylative photoredox coupling between the chloropyridine of the formula A-5 and the carboxylic acid of the formula A-6 provides the compound of the formula A-7. In this step, the $R^{3a}$ substituent of A-6 should be represented by the same moiety as is desired in the final product, Formula I, or a protected variation thereof. Additionally, the $R^7$ and $R^8$ substituent can be H, Boc, alternative protecting group or alkyl; or alternatively, the $R^{3a}$ and $R^8$ substituents can be part of a cyclic system as is desired in the final product, Formula I. Coupling of the compound of the formula A-7 with the bromopyridine triazole A-8 under palladium or copper catalysis followed by cleavage of any protecting group(s) under standard conditions provides the pyrrolo[3,4-c]pyridin-1-one of the Formula I. In this step, the $R^{4N}$ substituent of A-8 should be represented by the same moiety as is desired in the final product, Formula I, or a protected variation thereof.

Hydrazinolysis of bromopyridine ester A-9 (J. Med. Chem., 60(2), 722-748; 2017) followed by reaction of the corresponding hydrazide A-10 with dimethylformamide dimethyl acetal provides the formamidine A-11. Condensation of the formamidine A-11 with an amine gives the triazole A-8.

Method B

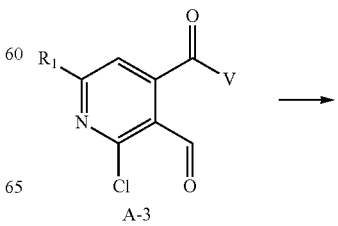

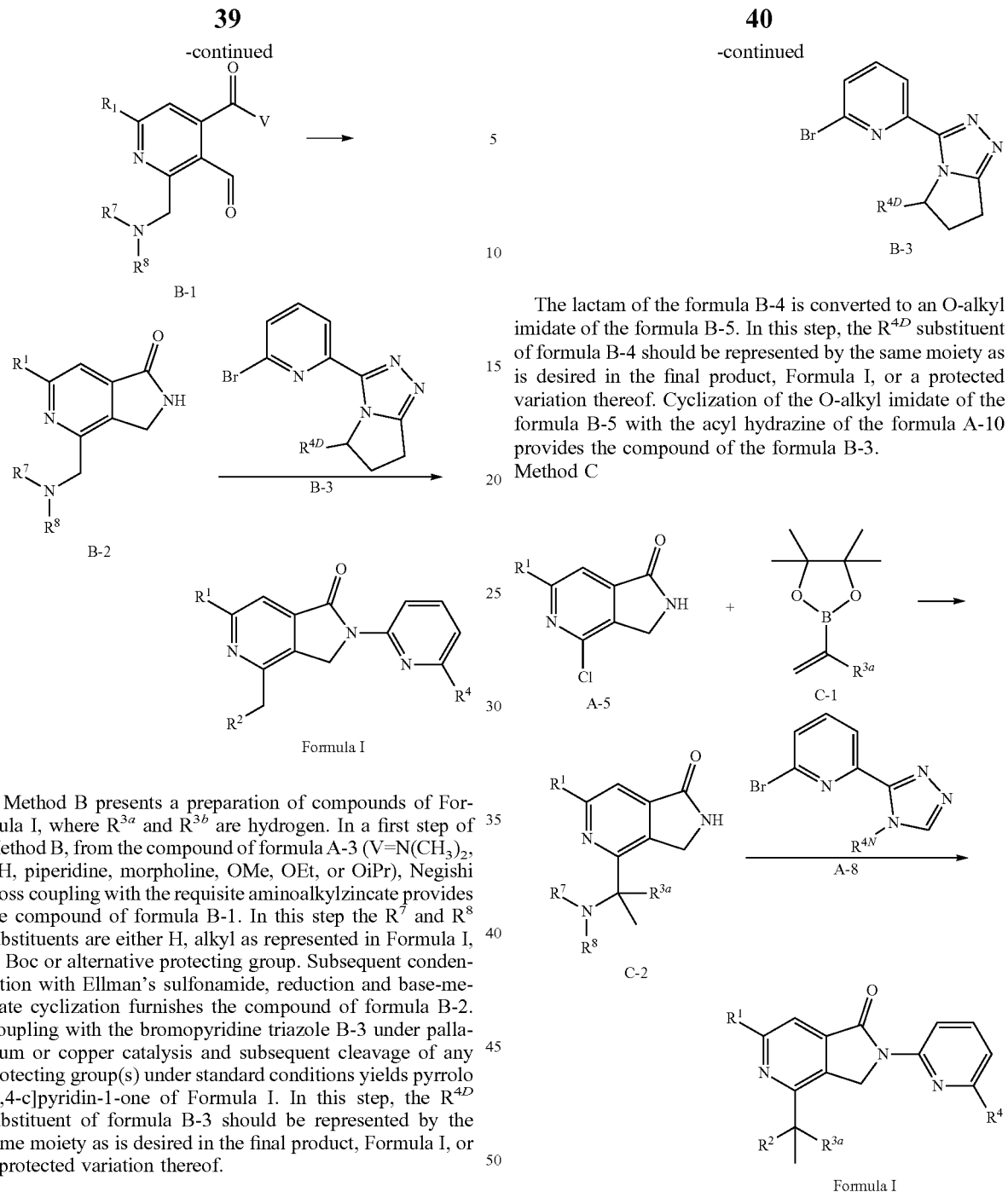

Method B presents a preparation of compounds of Formula I, where $R^{3a}$ and $R^{3b}$ are hydrogen. In a first step of Method B, from the compound of formula A-3 (V=N(CH$_3$)$_2$, OH, piperidine, morpholine, OMe, OEt, or OiPr), Negishi cross coupling with the requisite aminoalkylzincate provides the compound of formula B-1. In this step the $R^7$ and $R^8$ substituents are either H, alkyl as represented in Formula I, or Boc or alternative protecting group. Subsequent condensation with Ellman's sulfonamide, reduction and base-mediate cyclization furnishes the compound of formula B-2. Coupling with the bromopyridine triazole B-3 under palladium or copper catalysis and subsequent cleavage of any protecting group(s) under standard conditions yields pyrrolo[3,4-c]pyridin-1-one of Formula I. In this step, the $R^{4D}$ substituent of formula B-3 should be represented by the same moiety as is desired in the final product, Formula I, or a protected variation thereof.

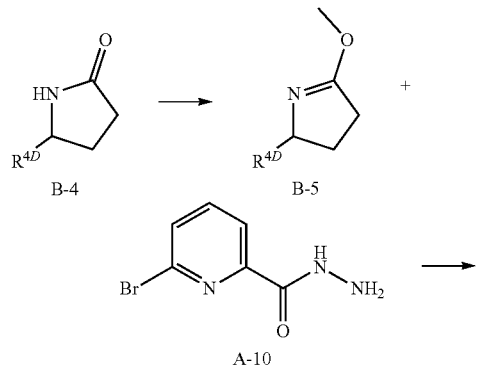

The lactam of the formula B-4 is converted to an O-alkyl imidate of the formula B-5. In this step, the $R^{4D}$ substituent of formula B-4 should be represented by the same moiety as is desired in the final product, Formula I, or a protected variation thereof. Cyclization of the O-alkyl imidate of the formula B-5 with the acyl hydrazine of the formula A-10 provides the compound of the formula B-3.

Method C

Method C presents a preparation of compounds of Formula I, where $R^{3b}$ is methyl. In a first step of Method C, palladium-mediated cross coupling between the compound of the formula A-5 and the boronic ester of the formula C-1 followed by iron-mediated hydroazidation of the olefin or alkene, reduction and optional protection of the resulting amine, provides the compound of the formula C-2. In this step, the $R^{3a}$ substituent of formula C-1 and the $R^1$ substituent of A-5 should be as represented in the desired product, Formula I, or a protected version thereof. Cross coupling of the compound of the formula C-2 with the bromopyridine triazole A-8 under palladium or copper catalysis followed by cleavage of any protecting group(s) under standard conditions provides the pyrrolo[3,4-c]pyridin-1-one of the Formula I. In this step, the $R^{4N}$ substituent of A-8 should be represented by the same moiety as is desired in $R^4$ of the final product, Formula I, or a protected variation thereof.

Method D

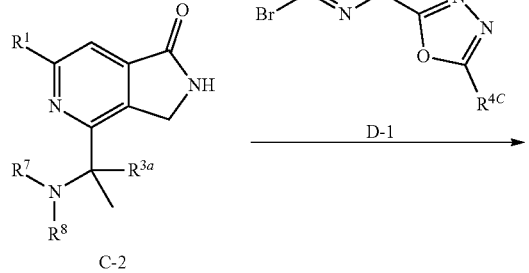

C-2

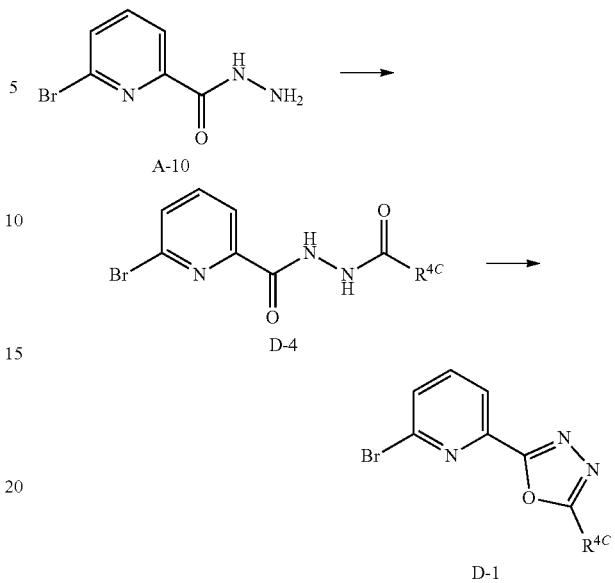

Method D presents a preparation of compounds of Formula I, where $R^{3b}$ is methyl. In the first step of Method D, coupling of the compound of the formula C-2 with the bromopyridine D-1 under copper or palladium catalysis provides the compound of the formula D-2. In this step, the $R^1$, $R^7$, $R^8$, and $R^{3a}$ substituents of C-2 and the $R^{4C}$ substituent of D-1 should be represented by the same moiety as is desired in the final product, D-3, or a protected variation thereof. $R^7$ and/or $R^8$ can also optionally be represented by protecting groups in this step. Reaction of the compound of formula D-2 with the requisite amine provides the compound of the formula D-3. In this step, the $R^{4N}$ substituent should be represented by the same moiety as is desired in the final product, D-3, or a protected variation thereof. Cleavage of any protecting group(s) in the compound of formula D-3, ultimately provides the pyrrolo[3,4-c]pyridin-1-one of the Formula I-A.

To access the compound of formula D-1, the compound of the formula A-10 undergoes reaction with the appropriate acyl chloride to provide the compound of the formula D-4. In this step, the $R^{4C}$ substituent of the acyl chloride is as represented in the final product, Formula I, or a protected version thereof. Cyclization of the compound of the formula D-4 provides the compound of formula D-1.

Method E

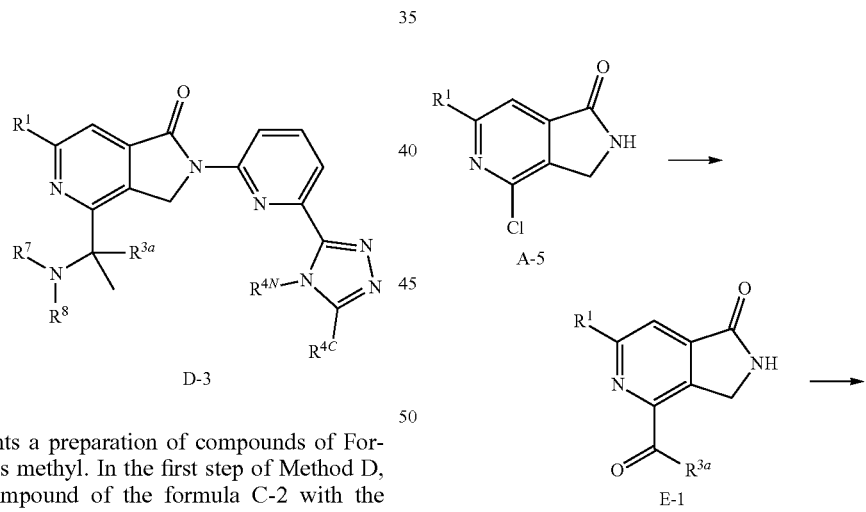

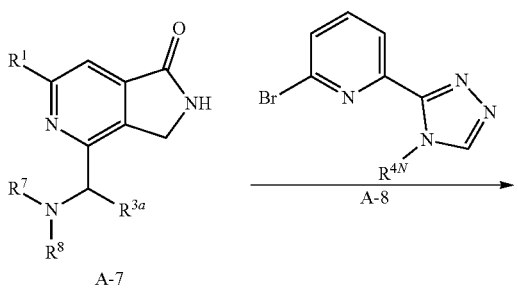

-continued

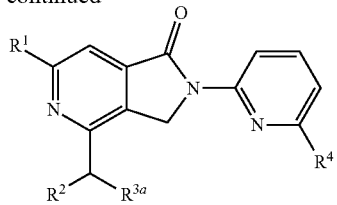

Formula I

Method E presents a preparation of compounds of Formula I, where $R^{3b}$ is hydrogen. In the first step of Method E, either i. Palladium-mediated cross coupling between the compound of the formula A-5 and tributyl(1-ethoxyvinyl)tin, followed by hydrolysis of the vinyl ether, provides the ketone of the formula E-1, where the $R^{3a}$ substituent should be represented by the same moiety as is desired in the final product, Formula I or ii. Palladium-mediated cross coupling between the compound of the formula A-5 and zinc cyanide, followed by reaction with alkyl Grignard reagent, provides the ketone of the formula E-1 where the $R^{3a}$ substituent should be represented by the same moiety as is desired in the final product, Formula I.

In this step, the $R^1$ substituent of A-5 should be represented by the same moiety as is desired in the final product, Formula I, or a protected variation thereof.

From the compound of the formula E-1, either i. Reduction of the ketone, followed by activation as the mesylate or chloride, displacement with azide and reduction and optional protection provides the compound of formula A-7 ($R^7$ and $R^3$ are both H or $R^7$ is H and $R^a$ is Boc or an alternative protecting group), or ii. Reduction of the ketone, followed by activation as the mesylate or chloride, displacement with an alkyl amine and optional protection provides the compound of formula A-7 ($R^7$ and/or $R^a$ are H, alkyl, Boc or an alternative protecting group), or iii. Condensation with a sulfinamide followed by reduction provides the compound of formula A-7 ($R^7$ is H and $R^8$ is SOtBu).

Coupling of the compound of the formula A-7 with the bromopyridine triazole A-8 under palladium or copper catalysis followed by cleavage of any protecting group(s) under standard conditions provides the pyrrolo[3,4-c]pyridin-1-one of the Formula I. In this step, the $R^{4N}$ substituent of A-8 should be represented by the same moiety as is desired in the final product, Formula I, or a protected variation thereof, within $R^4$.

Method F

A-7

-continued

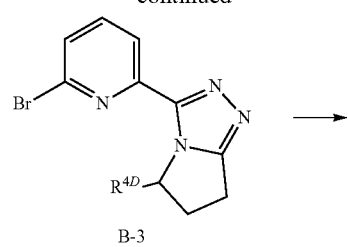

B-3

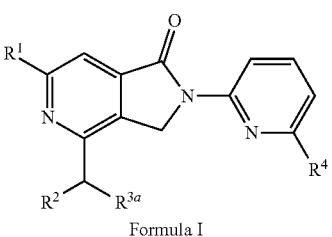

Formula I

Method F presents a preparation of compounds of Formula I, where $R^{3b}$ is hydrogen. In Method F, coupling of the compound of the formula A-7 with the bromopyridine triazole B-3 under palladium or copper catalysis followed by cleavage of any protecting group(s) under standard conditions provides the pyrrolo[3,4-c]pyridin-1-one of the Formula I. In this step the $R^{4C}$ substituent of B-3 and the $R^1$, $R^7$, $R^8$ and $R^{3a}$ substituents of formula A-7 should be represented by the same moiety as is desired in the final product, Formula I, or a protected variation thereof. In this step, the $R^7$ and/or $R^8$ substituents of formula A-7 may also be represented by Boc or another protecting group.

Method G

D-1

G-1

A-7

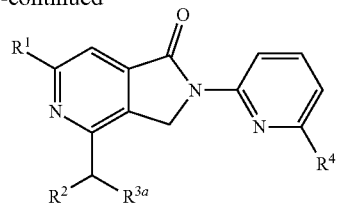

Formula I

Method G presents a preparation of compounds of Formula I, where $R^{3b}$ is hydrogen. In the first step of Method G, a bromopyridine of the formula D-1 undergoes reaction with the requisite amine to provide the compound of the formula G-1. In this step, the $R^{4C}$ and $R^{4N}$ substituents should be represented by the same moiety as is desired in the final product, Formula I, or a protected variation thereof. Coupling of the compound of the formula G-1 with A-7 under palladium or copper catalysis followed by cleavage of any protecting group(s) under standard conditions provides the pyrrolo[3,4-c]pyridin-1-one of the Formula I. In this step, the $R^1$, $R^7$, $R^8$ and $R^{3a}$ substituents of formula A-7 should be represented by the same moiety as is desired in the final product, Formula I, or a protected variation thereof. In this step, the $R^7$ and/or $R^8$ substituents of formula A-7 may also be represented by Boc or another protecting group.

Method H

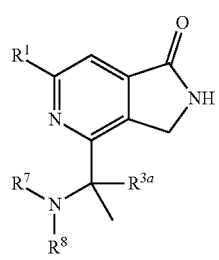

C-2

+

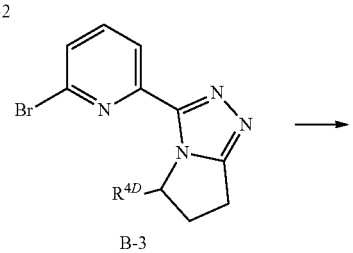

B-3

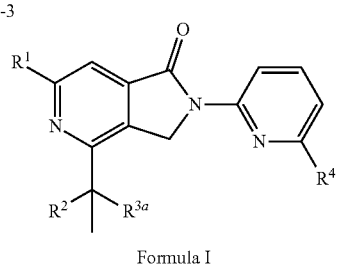

Formula I

Method H presents a preparation of compounds of Formula I, where $R^{3b}$ is methyl. In a first step of Method H, coupling of the compound of the formula C-2 with the bromopyridine triazole B-3 under palladium or copper catalysis followed by cleavage of any protecting group(s) under standard conditions provides the pyrrolo[3,4-c]pyridin-1-one of the Formula I. In this step, the $R^1$, $R^7$, $R^8$, and $R^{3a}$ substituents of C-2 and the $R^{4D}$ substituent of B-3 should be represented by the same moiety as is desired in the final product, Formula I, or a protected variation thereof. $R^7$ and/or $R^8$ of formula C-2 can also optionally be represented by a protecting group in this step.

Method I

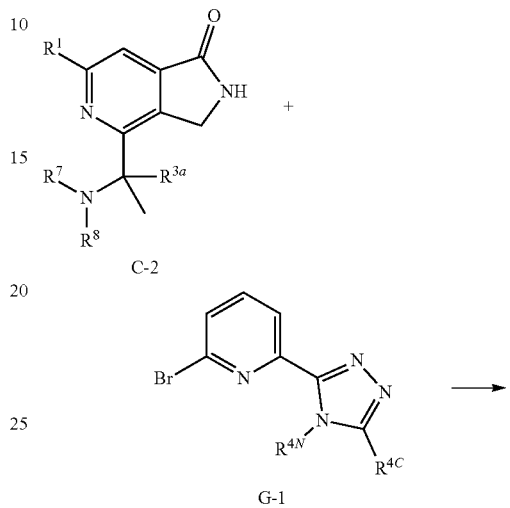

Method I presents a preparation of compounds of Formula I, where $R^{3b}$ is methyl. In the first step of Method I, coupling of the compound of the formula C-2 with the bromopyridine triazole G-1 under palladium or copper catalysis followed by cleavage of any protecting group(s) under standard conditions provides the pyrrolo[3,4-c]pyridin-1-one of the Formula I where $R^{3b}$ is methyl. In this step, the $R^1$, $R^7$, $R^8$, and $R^{3a}$ substituents of C-2 and the $R^{4C}$ and $R^{4N}$ substituents of G-1 should be represented by the same moiety as is desired in the final product, Formula I, or a protected variation thereof. $R^7$ and/or $R^8$ of formula C-2 can also optionally be represented by a protecting group in this step.

Method J

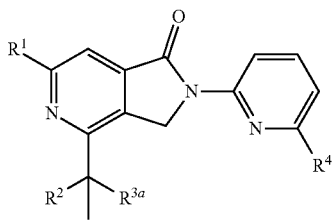

J-1    J-2

Method K

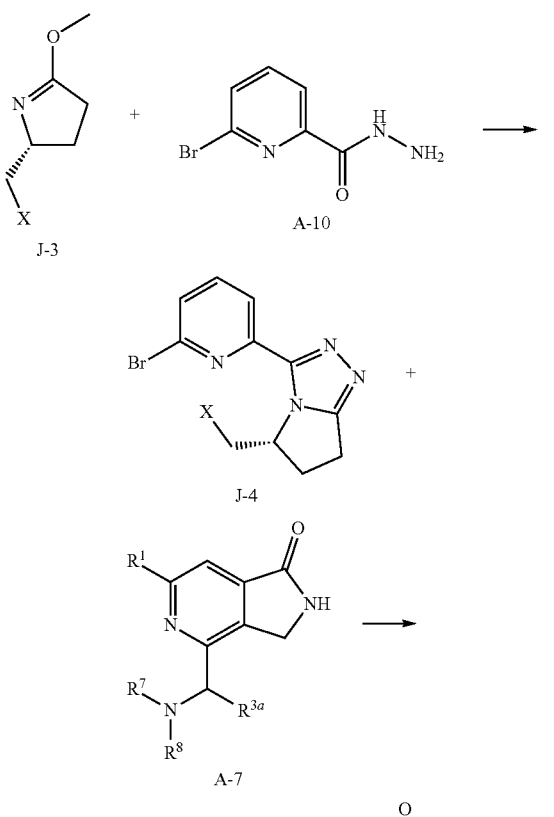

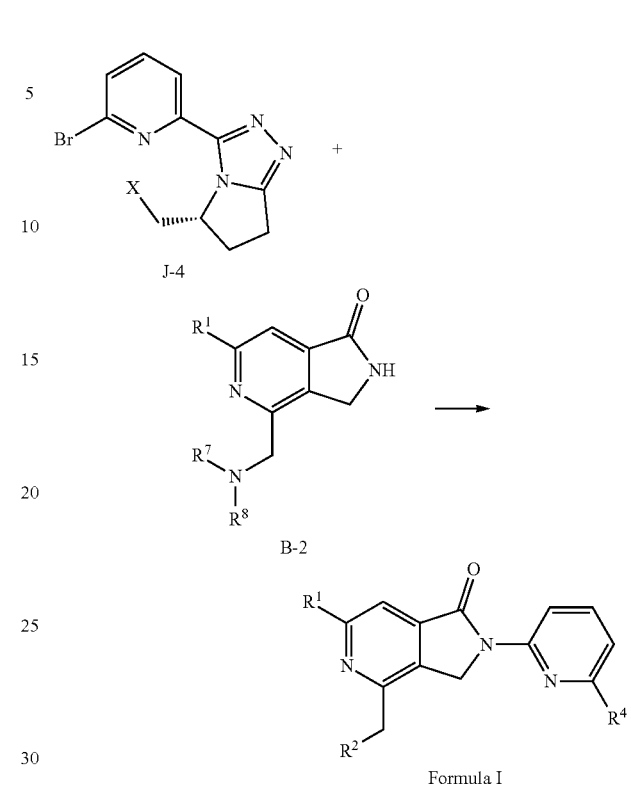

Method J presents a preparation of compounds of Formula I, where $R^{3b}$ is hydrogen. In the first step of Method J, the alcohol of formula J-1 is protected to provide the compound of formula J-2 (e.g. X=OTBDMS). The compound of formula J-2 is converted to an O-alkyl imidate of the formula J-3. Cyclization of the O-alkyl imidate of the formula J-3 with the acyl hydrazine of the formula A-10 provides the compound of the formula J-4. The compound of the formula J-4 undergoes coupling with the compound of the formula A-7 under palladium or copper followed by cleavage of any protecting group(s) under standard conditions to yield the pyrrolo[3,4-c]pyridin-1-one of Formula I. In this step, the $R^1$, $R^7$, $R^8$ and $R^{3a}$ substituents of A-7 should be represented by the same moiety as is desired in the final product, Formula I, or a protected variation thereof. In this step, the $R^7$ and/or $R^a$ substituents of formula A-7 can also optionally be represented by a protecting group.

Alternatively, to obtain compounds of Formula I, where $R^4$ is $R^4$-ii and $R^{4D}$ is alkyl substituted by a F atom (X=fluorine), from the compound of formula J-4 (X is protected hydroxy group) cleavage of the protecting group provides the compound of formula J-4 where X is hydroxy. The alcohol can then be converted to an alkyl fluoride to provide the compound of formula J-4 where X is fluorine.

Method K presents a preparation of compounds of Formula I, where $R^{3a}$ and $R^{3b}$ are hydrogen. In Method K, the compound of the formula J-4 (X is fluorine) undergoes coupling with the compound of the formula B-2 under palladium or copper catalysis to followed by cleavage of the protecting group(s) under standard conditions yields the pyrrolo[3,4-c]pyridin-1-one of Formula I. In this step the $R^1$, $R^7$ and $R^8$ substituents of B-2 and the X substituent of formula J-4 should be represented by the same moiety as is desired in the final product, Formula I, or a protected variation thereof. $R^7$ and/or $R^8$ of formula B-2 can also optionally be represented by a protecting group in this step.

Method L

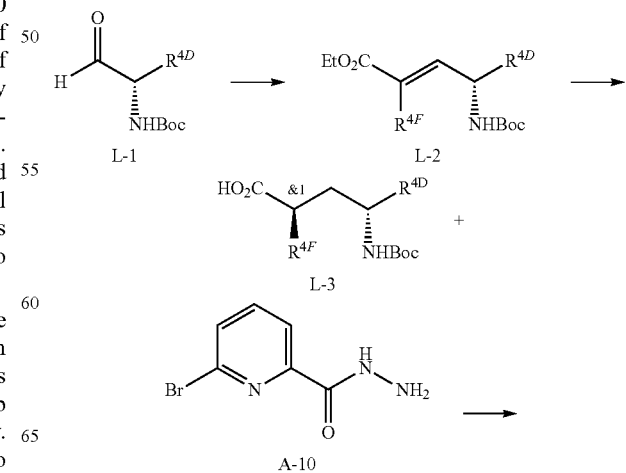

Method M

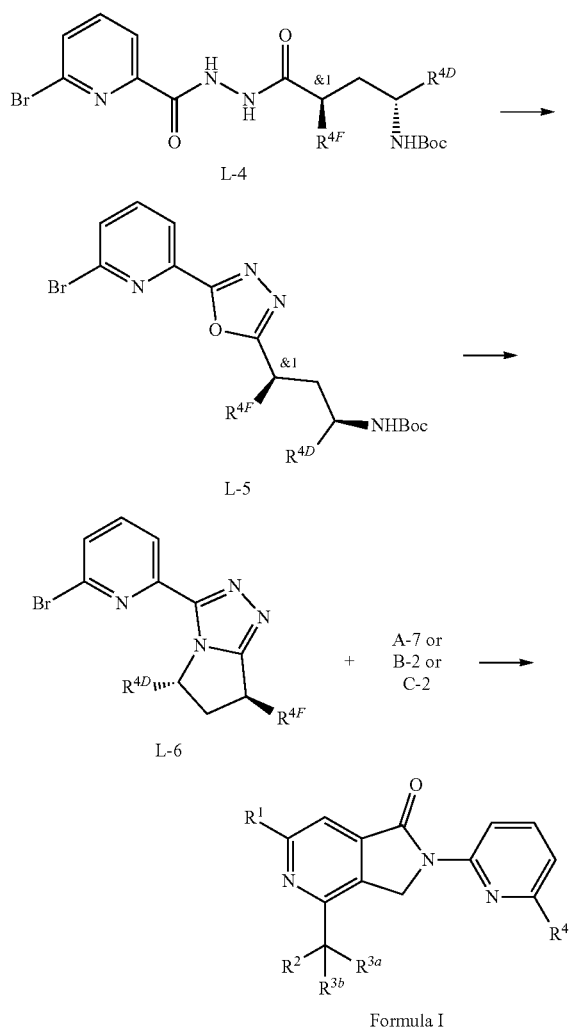

Method M presents a preparation of compounds of Formula I, where $R^{3a}$ and $R^{3b}$ are hydrogen. In Method M, coupling of the compound of the formula B-2 with the bromopyridine triazole A-8 under palladium or copper catalysis provides the protected pyrrolo[3,4-c]pyridin-1-one of Formula I. In this step the $R^1$, $R^7$ and $R^8$ substituents of the formula B-2 and the $R^{4N}$ substituent of formula A-8 should be represented by the same moiety as is desired in the final product, Formula I, or as a protected variation thereof or as a protecting group (ex. $R^7$=Boc). Cleavage of any protecting group(s) under standard conditions yields the pyrrolo[3,4-c]pyridin-1-one of Formula I.

Preparation of Synthetic Intermediates

In the first step of Method L, the compound of the formula L-1 undergoes Wittig olefination to provide the compound of formula L-2. Reduction and subsequent saponification of the compound of the formula L-2 provides the compound of the formula L-3. In these steps, the $R^{4D}$ substituent of L-1, and the $R^{4D}$ and $R^{4F}$ substituents of L-2 and L-3, and subsequent intermediates, are as represented in the final product, Formula I (as within $R^4$), or a protected version thereof. Alternatively, some compounds of the formula L-3 are commercially available. In a next step, the compound of formula L-3 undergoes reaction with the compound of formula A-10 to provide the compound of formula L-4. Cyclization of the compound of formula L-4 provides the oxadiazole of formula L-5. A subsequent cyclization preceded by thermal or acid-mediated deprotection of the compound of formula L-5 provides the compound of formula L-6. The compound of the formula L-6 undergoes coupling with the compound of the formula A-7, B-2, or C-2 under palladium or copper followed by cleavage of any protecting group(s) under standard conditions to yield the pyrrolo[3,4-c]pyridin-1-one of Formula I. The $R^1$, $R^2$, $R^{3a}$, and $R^{3b}$ substituents of Formula I depend on their definitions in previous Methods for A-7, B-2, or C-2, or a protected version thereof.

For the intermediates and Examples prepared herein, where the stereochemistry is known, the stereochemistry is as drawn and the name designates specific stereochemistry as (R) or (S). The stereochemistry as assigned herein is known because the compound was synthesized from known, chiral starting materials, or racemic mixtures were separated and the stereochemistry of certain examples or intermediates was confirmed using X-ray crystallography. In the case of the latter, the stereochemistry of other examples or intermediates would then be inferred based on the known chirality of the aforementioned examples or intermediates and the synthetic route. Where stereochemistry is not known but enantiomers are separated, "or1," or "or2" is at the chiral carbon atom. In the name, the carbon with the resolved but not confirmed stereochemical center, is identified with the symbol "ξ." The bond drawn at that carbon is a representation of the stereochemistry; meaning, the carbon would have that bond configuration drawn (solid wedge) or the opposite configuration (hashed wedge). See, e.g., Example 6a and Example 6b. Racemic compounds are indicated by the annotation "&1" and the bond is drawn as a defined stereochemistry meaning that the carbon would have that bond configuration drawn (solid wedge) and the opposite configuration (hashed wedge). See, e.g. Intermediate 15.

Intermediate 1: 2-bromo-6-(4-ethyl-4H-1,2,4-triazol-3-yl)pyridine

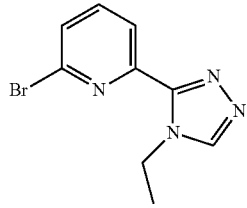

Step 1: 6-bromopyridine-2-carbohydrazide (1a)

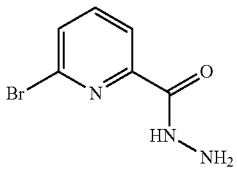

To a solution of methyl 6-bromo-2-pyridinecarboxylate (16.0 g, 74.0 mmol) in MeOH (120 mL) was added hydrazine monohydrate (5.23 g, 88.8 mmol, 85%) and the mixture was stirred for 16 hours at RT. The resultant solution was concentrated to approximately half the volume and then triturated by adding 40 mL of methyl tert-butyl ether and stirring for 10 min. The resultant white solid was filtered and dried under vacuum to provide the title compound (1a) (15 g, 94%). $^1$H NMR (400 MHz, CDCl$_3$) δ 8.82 (br. s, 1H), 8.13 (dd, J=0.9, 7.5 Hz, 1H), 7.76-7.71 (m, 1H), 7.64 (dd, J=0.9, 8.0 Hz, 1H), 4.08 (br. s, 2H). m/z (ESI) for (C$_6$H$_6$BrN$_3$O) 217.5 (M+H)$^+$.

Step 2: N'-[(6-bromopyridin-2-yl)carbonyl]-N,N-dimethylhydrazonoformamide (1b)

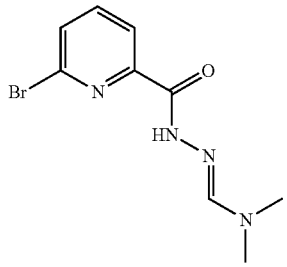

A solution of 6-bromopyridine-2-carbohydrazide (1a) (15.0 g, 69.4 mmol) in dimethyl formamide dimethyl acetal (80 mL) was stirred at 80° C. for 16 hours. The resulting mixture was concentrated under reduced pressure to give a residue. Methyl tert-butyl ether (60 mL) was added to this residue and it was stirred for 40 min. The resultant yellow solid was filtered and dried to provide the title compound (1b) (16 g, 85%). $^1$H NMR (400 MHz, DMSO-d$_6$) δ 10.74 (s, 1H), 8.06 (s, 1H), 8.01-7.97 (m, 1H), 7.91 (t, J=7.7 Hz, 1H), 7.80 (dd, J=1.0, 7.8 Hz, 1H), 2.84 (s, 6H). m/z (ESI) for (C$_9$H$_{11}$BrN$_4$O) 272.7 (M+H)$^+$.

Step 3: Intermediate 1

A flask was charged with N'-[(6-bromopyridin-2-yl)carbonyl]-N,N dimethylhydrazonoformamide (1b) (2.0 g, 7.4 mmol), ethylamine (0.5 mL, 333 mg, 7.4 mmol), acetic acid (3 mL) and MeCN (15 mL, 0.5 M). The solution was heated for 16 h at 95° C. EtOAc (10 mL) and H$_2$O (10 mL) were added. Solid KCO$_3$ was added until the pH of the aqueous layer was ~pH 8. The layers were separated, and the aqueous layer was extracted with EtOAc (3×30 mL). The combined organic layers were washed with brine (30 mL), dried over Na$_2$SO$_4$, filtered, and concentrated to dryness. The residue was slurried with EtOAc (0.3 mL) and petroleum ether (3 mL) for 5 min. The solids were collected by filtration to provide Intermediate 1 (1.5 g, 80%) as a pale-yellow solid. $^1$H NMR (400 MHz, DMSO-d$_6$) δ 8.75 (s, 1H), 8.19 (dd, J=7.7, 0.9 Hz, 1H), 7.99-7.90 (m, 1H), 7.79 (dd, J=8.0, 0.9 Hz, 1H), 4.47 (q, J=7.2 Hz, 2H), 1.38 (t, J=7.2 Hz, 3H); m/z (APCI+) for (C$_9$H$_9$BrN$_4$), 252.7 (M+H)$^+$.

Intermediate 2: (5S)-3-(6-bromopyridin-2-yl)-5-methyl-6,7-dihydro-5H-pyrrolo[2,1-c][1,2,4]triazole

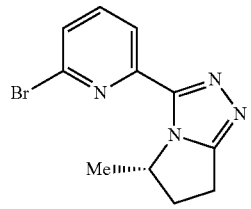 [SMILES: C[C@H]1CCc2nnc(-c3cccc(Br)n3)n21]

Step 1: tert-butyl {(2S)-5-[2-(6-bromopyridine-2-carbonyl)hydrazinyl]-5-oxopentan-2-yl}carbamate (2a)

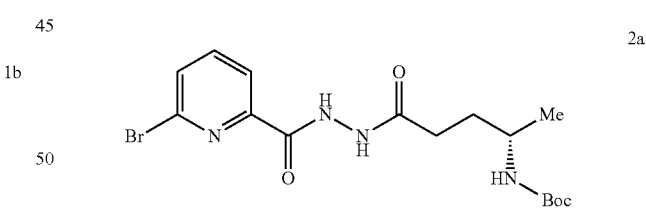

A solution of (4S)-4-[(tert-butoxycarbonyl)amino]pentanoic acid (600 mg, 2.76 mmol) in THF (13.8 mL, 0.2 M) was cooled to 0° C. Propylphosphonic anhydride solution (50% solution in EtOAc, 3.62 mL, 6.08 mmol) was added to the solution at 0° C. before the bath was removed and the reaction mixture was stirred for 30 min at RT. Then, N,N-diisopropylethylamine (2.89 mL, 16.6 mmol) and 6-bromopicolinohydrazide (656 mg, 3.04 mmol) were added and the reaction mixture was stirred at RT for 22 h. LCMS analysis showed consumption of the starting material. The reaction was quenched with water (15 mL) and transferred to a separatory funnel with EtOAc (20 mL). The layers were separated, and the organic phase was washed sequentially with 20% citric acid (20 mL), a saturated solution of NaHCO$_3$ (20 mL), and brine (20 mL). The organic extract was then dried over MgSO$_4$, filtered, and concentrated to dryness to provide the title compound (2a) (1.07 g, 93% yield) as an off-white solid, which was taken on without further purification. $^1$H NMR (400 MHz, CDCl$_3$) δ 9.76 (br. s, 1H), 9.36 (br. s, 1H), 8.15 (dd, J=0.9, 7.5 Hz, 1H), 7.77-7.71 (m, 1H), 7.69-7.64 (m, 1H), 4.45 (br. d, J=1.0 Hz, 1H), 3.91 (br. s, 1H), 2.47-2.35 (m, 2H), 2.00-1.89 (m, 1H), 1.75-1.66 (m, 1H), 1.48 (s, 9H), 1.22 (d, J=6.6 Hz, 3H). LCMS m/z (APCI) for (C$_{11}$H$_{15}$BrN$_4$O$_2$), 315.0 (M+H-Boc)$^+$.

Step 2: tert-butyl {(2S)-4-[5-(6-bromopyridin-2-yl)-1,3,4-oxadiazol-2-yl]butan-2-yl}carbamate (2b)

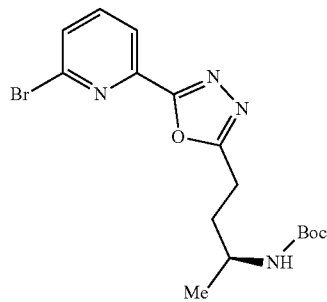

2b

To a solution of tert-butyl {(2S)-5-[2-(6-bromopyridine-2-carbonyl)hydrazinyl]-5-oxopentan-2-yl}carbamate (2a) (290 mg, 0.698 mmol) in DCM (2.8 mL, 0.25 M) was added triethylamine (0.292 mL, 2.09 mmol) and p-toluenesulfonyl chloride (160 mg, 0.838 mmol). The reaction was stirred at RT for 16 h. LCMS analysis showed consumption of the starting material. Ethylenediamine (0.047 mL, 0.698 mmol) was added to scavenge excess p-toluenesulfonyl chloride; during the addition, a precipitate formed immediately. After stirring at RT for 30 min, the reaction was washed with 20% citric acid (5 mL) and the layers were separated. The aqueous layer was extracted with DCM (5 mL), then the combined organic layers were washed with brine (10 mL), dried over MgSO$_4$, filtered and concentrated to dryness to provide the title compound (2b) (274 mg, 98% yield) as a light yellow solid, which was taken on without further purification. $^1$H NMR (400 MHz, CDCl$_3$) δ 8.21 (dd, J=0.9, 7.6 Hz, 1H), 7.76-7.69 (m, 1H), 7.68-7.65 (m, 1H), 4.39 (br. s, 1H), 3.85 (br. s, 1H), 3.08-3.01 (m, 2H), 2.17-2.03 (m, 1H), 2.03-1.90 (m, 1H), 1.44 (s, 9H), 1.22 (d, J=6.6 Hz, 3H). LCMS m/z (APCI) for (C$_{11}$H$_{13}$BrN$_4$O), 297.0 (M+H-Boc)$^+$.

Step 3: Intermediate 2

A microwave vial was charged with tert-butyl {(2S)-4-[5-(6-bromopyridin-2-yl)-1,3,4-oxadiazol-2-yl]butan-2-yl}carbamate (2b) (150 mg, 0.378 mmol) and trifluoroethanol (1.89 mL, 0.2 M) and was sealed before heating in the microwave to 180° C. for 30 min. LCMS analysis showed consumption of the starting material. The reaction mixture was concentrated, and the residue was purified by flash chromatography (SiO$_2$, 100% heptane to 1:10 MeOH/EtOAc) to provide Intermediate 2 (74.3 mg, 71% yield) as a tan, gummy solid. $^1$H NMR (400 MHz, CDCl$_3$) δ 8.38 (d, J=7.7 Hz, 1H), 7.74 (t, J=7.8 Hz, 1H), 7.58 (d, J=7.9 Hz, 1H), 5.22-5.08 (m, 1H), 3.21-3.16 (m, 1H), 3.16-3.02 (m, 2H), 2.55-2.44 (m, 1H), 1.60 (d, J=6.6 Hz, 3H). LCMS m/z (APCI) for (C$_{11}$H$_{11}$BrN$_4$), 279.1 (M+H)$^+$. Determined to be a single enantiomer by SFC (10-60% methanol (0.5% NH$_3$) in carbon dioxide @ 400-450 bar, gradient time=2 min, flow rate=4 mL/min, Chiralpack IC-U 50 mm*3 mm*1.6 μm column). Stereochemistry of Intermediate 2 was assigned based on use of (4S)-4-[(tert-butoxycarbonyl)amino]pentanoic acid in step 1.

Absolute configuration of Intermediate 2 was unambiguously established by small molecule X-ray crystallography. The single crystal X-ray diffraction studies were carried out on a Bruker APEX II Ultra CCD diffractometer equipped with Mo K$_α$ radiation (λ=0.71073). Crystal where used as received (grown by vapor diffusion from dichloromethane) A 0.200×0.075×0.060 mm colorless crystal was mounted on a Cryoloop with Paratone oil. Data were collected in a nitrogen gas stream at 100(2) K using φ and ω scans. Crystal-to-detector distance was 45 mm using exposure time 1 s (depending on the 2 θ range) with a scan width of 0.80°. Data collection was 100.0% complete to 25.242° in θ. The data were integrated using the Bruker SAINT software program and scaled using the SADABS software program. Solution by direct methods (SHELXT) produced a complete phasing model consistent with the proposed structure. All nonhydrogen atoms were refined anisotropically by full-matrix least-squares (SHELXL-2014). All carbon bonded hydrogen atoms were placed using a riding model. Their positions were constrained relative to their parent atom using the appropriate HFIX command in SHELXL-2014. Positions of the C—H, N—H and O—H hydrogen atoms have been refined using appropriate HFIX commands. Crystallographic data are summarized in Table 1.

TABLE 1

| | | |
|---|---|---|
| Molecular formula | C$_{11}$ H$_{11}$ Br N$_4$ | |
| Formula weight | 279.15 | |
| Temperature | 100.15 K | |
| Wavelength | 0.71073 Å | |
| Crystal system | Monoclinic | |
| Space group | P2$_1$ | |
| Unit cell dimensions | a = 7.772(2) Å | α = 90°. |
| | b = 13.571(4) Å | β = 96.191(6)°. |
| | c = 10.676(3) Å | γ = 90°. |
| Volume | 1119.5(5) Å$^3$ | |
| Z | 4 | |
| Density (calculated) | 1.656 Mg/m$^3$ | |
| Absorption coefficient | 3.649 mm$^{-1}$ | |
| F(000) | 560 | |
| Crystal size | 0.2 × 0.075 × 0.06 mm$^3$ | |
| Crystal color, habit | colorless block | |
| Theta range for data collection | 1.919 to 26.755°. | |

TABLE 1-continued

| | |
|---|---|
| Index ranges | −9 <= h <= 9, −17 <= k <= 17, −13 <= l <= 13 |
| Reflections collected | 19401 |
| Independent reflections | 4760 [$R_{int}$ = 0.0524] |
| Completeness to theta = 25.242° | 100.0% |
| Absorption correction | Semi-empirical from equivalents |
| Max. and min. transmission | 0.4910 and 0.3848 |
| Refinement method | Full-matrix least-squares on $F^2$ |
| Data/restraints/parameters | 4760/1/291 |
| Goodness-of-fit on $F^2$ | 1.013 |
| Final R indices [I > 2sigma(I)] | R1 = 0.0243, wR2 = 0.0582 |
| R indices (all data) | R1 = 0.0258, wR2 = 0.0589 |
| Absolute structure parameter | −0.012(6) |
| Largest diff. peak and hole | 0.300 and −0.219e.Å$^{-3}$ |

Intermediate 3: (5S)-3-(6-bromopyridin-2-yl)-5-ethyl-6,7-dihydro-5H-pyrrolo[2,1-c][1,2,4]triazole

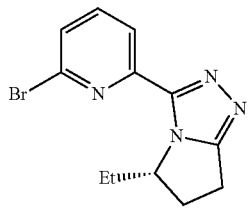 [SMILES: CC[C@H]1CCc2nnc(-c3cccc(Br)n3)n21]

Step 1: tert-butyl {(2S)-1-[methoxy(methyl)amino]-1-oxobutan-2-yl}carbamate (3a)

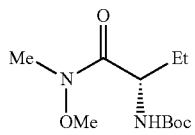

3a

A solution of (2S)-2-[(tert-butoxycarbonyl)amino]butanoic acid (2.0 g, 9.84 mmol) in THF (49.2 mL, O$_2$M) was cooled to 0° C. Propylphosphonic anhydride solution (50% solution in EtOAc, 12.9 mL, 21.6 mmol) was added to the solution at 0° C. before the bath was removed and the reaction mixture was allowed to warm to RT and stirred for 30 min. Then, N,N-diisopropylethylamine (10.3 mL, 59.0 mmol) and methoxy(methyl)amine hydrochloride (1.06 g, 10.8 mmol) were added and the reaction mixture was stirred at RT for 18 h. LCMS analysis showed consumption of the starting material. The reaction was quenched with water (40 mL) and transferred to a separatory funnel with EtOAc (40 mL). The layers were separated, and the organic phase was washed sequentially with 20% citric acid (40 mL), a saturated solution of NaHCO$_3$ (40 mL), and brine (40 mL). The organic extract was then dried over MgSO$_4$, filtered, and concentrated to dryness to provide the title compound (3a) (1.29 g, 53% yield) as a yellow oil, which was taken on without further purification. $^1$H NMR (400 MHz, CDCl$_3$) δ 5.28-5.12 (m, 1H), 4.74-4.52 (m, 1H), 3.79 (s, 3H), 3.23 (s, 3H), 1.85-1.73 (m, 1H), 1.64-1.54 (m, 1H), 1.46 (s, 9H), 0.96 (t, J=7.5 Hz, 3H). LCMS m/z (APCI) for (C$_{11}$H$_{22}$N$_2$O$_4$), 247.1 (M+H)$^+$.

Step 2: tert-butyl (S)-(1-oxobutan-2-yl)carbamate (3b)

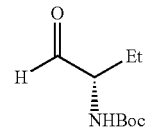

3b

A solution of tert-butyl {(2S)-1-[methoxy(methyl)amino]-1-oxobutan-2-yl}carbamate (3a) (1.29 g, 5.25 mmol) in THF (26.2 mL, O$_2$M) was cooled to 0° C. Lithium aluminum hydride (2.3 M solution in 2-MeTHF, 2.51 mL, 5.77 mmol) was added dropwise to the solution at 0° C. The reaction mixture was stirred for 40 min at 0° C. LCMS analysis showed consumption of the starting material. The reaction was quenched with EtOAc (10 mL) and 1 M HCl (10 mL) and transferred to a separatory funnel. The layers were separated, and the aqueous phase was extracted with EtOAc (3×10 mL). The combined organic extracts were then dried over MgSO$_4$, filtered, and concentrated to dryness. The residue was purified by flash chromatography (SiO$_2$, 100% heptane to 100% EtOAc) to provide to provide the title compound (3b) (0.575 g, 59% yield) as a white solid. $^1$H NMR (400 MHz, CDCl$_3$) δ 9.60 (s, 1H), 5.09 (br. s, 1H), 4.22 (br. s, 1H), 2.04-1.90 (m, 1H), 1.73-1.64 (m, 2H), 1.48 (s, 9H), 0.99 (t, J=7.5 Hz, 3H).

Step 3: ethyl (2E,4S)-4-[(tert-butoxycarbonyl)amino]hex-2-enoate (3c)

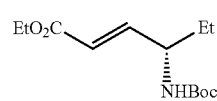

3c

To a solution of tert-butyl (S)-(1-oxobutan-2-yl)carbamate (3b) (575 mg, 3.07 mmol) in DCM (6.14 mL, 0.5 M) was added (ethoxycarbonylmethylene)triphenylphosphorane (1.60 g, 4.61 mmol). The reaction mixture was stirred at RT for 17 h. LCMS analysis showed consumption of the starting material. The reaction was concentrated to dryness before isopropanol (8.5 mL, 0.36 M) and zinc chloride (1.26 g, 9.21 mmol) were added to precipitate the triphenylphosphine oxide. After stirring at RT for 30 min, the reaction mixture was filtered and concentrated to dryness. The residue was purified by flash chromatography (SiO$_2$, 100% heptane to 100% EtOAc) to provide the title compound (3c) (653 mg, 83% yield, >20:1 ratio of E/Z isomers) as a colorless oil. ¹H NMR (400 MHz, CDCl₃) δ 6.86 (dd, J=5.4, 15.6 Hz, 1H), 5.94 (dd, J=1.7, 15.7 Hz, 1H), 4.50 (br. s, 1H), 4.31-4.16 (m, 3H), 1.65-1.63 (m, 1H), 1.60-1.51 (m, 1H), 1.47 (s, 9H), 1.32-1.30 (m, 3H), 0.99-0.95 (m, 3H). LCMS m/z (APCI) for (C₈H₁₅NO₂), 158.2 (M+H-Boc)⁺.

Step 4: ethyl (4S)-4-[(tert-butoxycarbonyl)amino] hexanoate (3d)

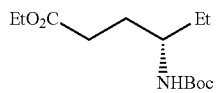

3d

To a solution of ethyl (2E,4S)-4-[(tert-butoxycarbonyl) amino]hex-2-enoate (3c) (653 mg, 2.54 mmol) in methanol (12.7 mL, 0.2 M) was added palladium on carbon (10% w/w, 270 mg, 0.254 mmol). The reaction vial was evacuated and refilled with H₂ under dynamic vacuum for 10 seconds. Then the reaction mixture was stirred at RT under 1 atm H₂ for 18 h. The mixture was stirred at RT for 17 h. LCMS analysis showed consumption of the starting material. The reaction was filtered over Celite® and concentrated to dryness. The residue was purified by flash chromatography (SiO₂, 100% heptane to 100% EtOAc) to provide the title compound (3d) (589 mg, 90% yield) as a colorless oil. ¹H NMR (400 MHz, CDCl₃) δ 4.37-4.23 (m, 1H), 4.20-4.11 (m, 2H), 3.61-3.46 (m, 1H), 2.42-2.33 (m, 2H), 1.93-1.82 (m, 1H), 1.71-1.62 (m, 1H), 1.57-1.51 (m, 1H), 1.46 (s, 9H), 1.44-1.38 (m, 1H), 1.30-1.26 (m, 3H), 0.94 (t, J=7.4 Hz, 3H).

Step 5: (4S)-4-[(tert-butoxycarbonyl)amino] hexanoic acid (3e)

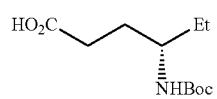

3e

To a solution of ethyl (4S)-4-[(tert-butoxycarbonyl) amino]hexanoate (3d) (589 mg, 2.27 mmol) in THF (11.4 mL, 0.2 M) and MeOH (5.7 mL, 0.4 M) was added a solution of LiOH (544 mg, 22.7 mmol) in water (2.84 mL, 0.8 M). The reaction mixture was stirred at RT for 24 h. The reaction was concentrated before the addition of water and 1M HCl until a pH of 5 was reached. The aqueous layer was extracted with EtOAc (3×20 mL). The combined organic layers were washed with brine, dried over MgSO₄, filtered, and concentrated to dryness to provide the title compound (3e) (260 mg, 50% yield) as a light-yellow oil, which was taken on without further purification.

Step 6: tert-butyl {(3S)-6-[2-(6-bromopyridine-2-carbonyl)hydrazinyl]-6-oxohexan-3-yl}carbamate (3f)

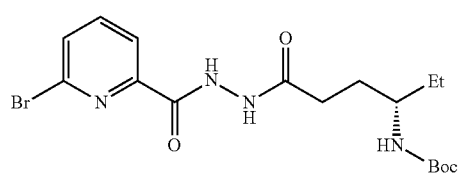

3f

A solution of (4S)-4-[(tert-butoxycarbonyl)amino] hexanoic acid (3e) (260 mg, 1.12 mmol) in THF (5.6 mL, 0.2 M) was cooled to 0° C. Propylphosphonic anhydride solution (50% solution in EtOAc, 1.47 mL, 2.47 mmol) was added to the solution at 0° C. before the bath was removed and the reaction mixture was stirred for 30 min at RT. Then, N,N-diisopropylethylamine (1.17 mL, 6.74 mmol) and 6-bromopicolinohydrazide (267 mg, 1.24 mmol) were added and the reaction mixture was stirred at RT for 18 h. The reaction was quenched with water (15 mL) and transferred to a separatory funnel with EtOAc (20 mL). The layers were separated, and the organic phase was washed sequentially with 20% citric acid (20 mL), a saturated solution of NaHCO₃ (20 mL), and brine (20 mL). The organic extract was then dried over MgSO₄, filtered, and concentrated to dryness. The residue was purified by flash chromatography (SiO₂, 100% heptane to 100% EtOAc) to provide the title compound (3f) (241 mg, 50% yield) as a white solid. ¹H NMR (400 MHz, CDCl₃) δ 9.76 (br. s, 1H), 9.29 (br. s, 1H), 8.15 (d, J=6.8 Hz, 1H), 7.76-7.71 (m, 1H), 7.68-7.64 (m, 1H), 4.45-4.31 (m, 1H), 3.69 (br. s, 1H), 2.45-2.37 (m, 2H), 2.04-1.94 (m, 1H), 1.69-1.62 (m, 1H), 1.49 (s, 9H), 1.45 (br. d, J=7.3 Hz, 2H), 0.99 (t, J=7.5 Hz, 3H). LCMS m/z (APCI) for (C₁₂H₁₇BrN₄O₂), 329.0 (M+H-Boc)⁺.

Step 7: tert-butyl {(3S)-1-[5-(6-bromopyridin-2-yl)-1,3,4-oxadiazol-2-yl]pentan-3-yl}carbamate

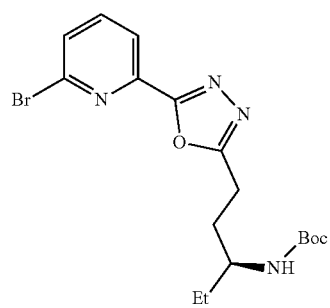

3g

To a solution of tert-butyl {(3S)-6-[2-(6-bromopyridine-2-carbonyl)hydrazinyl]-6-oxohexan-3-yl}carbamate (3f)

(241 mg, 0.561 mmol) in DCM (2.2 mL, 0.25 M) was added triethylamine (0.235 mL, 1.68 mmol) and p-toluenesulfonyl chloride (128 mg, 0.673 mmol). The reaction was stirred at RT for 16 h. LCMS analysis showed consumption of the starting material. Ethylenediamine (0.038 mL, 0.561 mmol) was added to scavenge excess p-toluenesulfonyl chloride; during the addition a precipitate formed immediately. After stirring at RT for 30 min, the reaction was washed with 20% citric acid (5 mL) and the layers were separated. The aqueous layer was extracted with DCM (5 mL) then the combined organic layers were washed with brine (10 mL), dried over $MgSO_4$, filtered and concentrated to dryness. The residue was purified by flash chromatography ($SiO_2$, 100% heptane to 100% EtOAc) to provide the title compound (3g) (178 mg, 77% yield) as a white solid. $^1$H NMR (400 MHz, $CDCl_3$) δ 8.22 (dd, J=0.7, 7.6 Hz, 1H), 7.77-7.72 (m, 1H), 7.68-7.65 (m, 1H), 4.35 (br. d, J=8.2 Hz, 1H), 3.65 (br. s, 1H), 3.07 (dt, J=6.1, 10.0 Hz, 2H), 2.21-2.11 (m, 1H), 1.93-1.83 (m, 1H), 1.65-1.61 (m, 1H), 1.53-1.48 (m, 1H), 1.46 (s, 9H), 0.98 (t, J=7.4 Hz, 3H). LCMS m/z (APCI) for ($C_{12}H_{15}BrN_4O$), 311.0 (M+H-Boc)$^+$.

Step 8: Intermediate 3

A microwave vial was charged with tert-butyl {(3S)-1-[5-(6-bromopyridin-2-yl)-1,3,4-oxadiazol-2-yl]pentan-3-yl}carbamate (3g) (178 mg, 0.431 mmol) and trifluoroethanol (2.16 mL, 0.2 M) and was sealed before heating in the microwave to 180° C. for 60 min. LCMS analysis showed consumption of the starting material. The reaction mixture was concentrated, and the residue was purified by flash chromatography ($SiO_2$, 100% heptane to 1:10 MeOH/EtOAc) to provide Intermediate 3 (116 mg, 91% yield) as a colorless oil. $^1$H NMR (400 MHz, $CDCl_3$) δ 8.26 (dd, J=0.7, 7.7 Hz, 1H), 7.67 (t, J=7.9 Hz, 1H), 7.49 (dd, J=0.7, 7.8 Hz, 1H), 4.90-4.83 (m, 1H), 3.07-2.89 (m, 3H), 2.58-2.49 (m, 1H), 2.04-1.97 (m, 1H), 1.83-1.70 (m, 1H), 0.96 (t, J=7.5 Hz, 3H). LCMS m/z (APCI) for ($C_{12}H_{13}BrN_4$), 293.0 (M+H)$^+$. Determined to be 97.4% ee by SFC (10-60% methanol (0.5% $NH_3$) in carbon dioxide @ 400-450 bar, gradient time=2 min, flow rate=4 mL/min, Kromasil (R,R) Whelk-O 50 mm*3 mm*1.8 μm column). Stereochemistry was assigned based on use of (2S)-2-[(tert-butoxycarbonyl)amino]butanoic acid in the first step. Absolute configuration of Intermediate 3 was unambiguously established by small molecule X-ray crystallography.

Table 2 provides the single crystal X-ray diffraction studies carried out on a Bruker APEX II Ultra CCD diffractometer equipped with Mo $K_\alpha$ radiation (λ=0.71073). Crystal were used as received (grown by vapor diffusion from ethyl acetate:methanol (10:1). A 0.180×0.065×0.055 mm colorless crystal was mounted on a Cryoloop with Paratone oil. Data were collected in a nitrogen gas stream at 100(2) K) using φ and $\overline{\omega}$ scans. Crystal-to-detector distance was 45 mm using exposure time 2 s (depending on the 2 θ range) with a scan width of 0.80°. Data collection was 100.0% complete to 25.242° in θ. The data were integrated using the Bruker SAINT software program and scaled using the SADABS software program. Solution by direct methods (SHELXT) produced a complete phasing model consistent with the proposed structure. All nonhydrogen atoms were refined anisotropically by full-matrix least-squares (SHELXL-2014). All carbon bonded hydrogen atoms were placed using a riding model. Their positions were constrained relative to their parent atom using the appropriate HFIX command in SHELXL-2014. Positions of the C—H, N—H and O—H hydrogen atoms have been refined using appropriate HFIX commands.

TABLE 2

| | | |
|---|---|---|
| Molecular formula | $C_{12} H_{13} Br N_4$ | |
| Formula weight | 293.17 | |
| Temperature | 100.15 K | |
| Wavelength | 0.71073 Å | |
| Crystal system | Orthorhombic | |
| Space group | $P2_12_12_1$ | |
| Unit cell dimensions | a = 7.1319(2) Å | α = 90°. |
| | b = 11.2187(3) Å | β = 90°. |
| | c = 15.5538(5) Å | γ = 90°. |
| Volume | 1244.47(6) Å$^3$ | |
| Z | 4 | |
| Density (calculated) | 1.565 Mg/m$^3$ | |
| Absorption coefficient | 3.286 mm$^{-1}$ | |
| F(000) | 592 | |
| Crystal size | 0.18 × 0.065 × 0.055 mm$^3$ | |
| Crystal color, habit | colorless irregular | |
| Theta range for data collection | 2.238 to 27.108°. | |
| Index ranges | −9 <= h <= 9, −14 <= k <= 14, −19 <= l <= 19 | |
| Reflections collected | 19687 | |
| Independent reflections | 2740 [$R_{int}$ = 0.0697] | |
| Completeness to theta = 25.242° | 100.0% | |
| Absorption correction | Semi-empirical from equivalents | |
| Max. and min. transmission | 0.4851 and 0.4153 | |
| Refinement method | Full-matrix least-squares on F$^2$ | |
| Data/restraints/parameters | 2740/0/155 | |
| Goodness-of-fit on F$^2$ | 1.047 | |
| Final R indices [l > 2sigma(l)] | R1 = 0.0237, wR2 = 0.0570 | |
| R indices (all data) | R1 = 0.0261, wR2 = 0.0581 | |
| Absolute structure parameter | −0.003(7) | |
| Largest diff. peak and hole | 0.307 and −0.255e.Å$^{-3}$ | |

Intermediate 4: (S,S)-2-methyl-N-[(1R)-1-{6-[(2R)-2-methylpyrrolidin-1-yl]-1-oxo-2,3-dihydro-1H-pyrrolo[3,4-c]pyridin-4-yl}ethyl]propane-2-sulfinamide

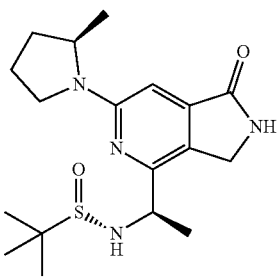

Step 1: {2-chloro-6-[(2R)-2-methylpyrrolidin-1-yl]pyridin-4-yl}(piperidin-1-yl)methanone (4a)

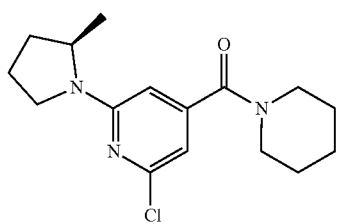

4a

A solution of (2,6-dichloropyridin-4-yl)(piperidin-1-yl)methanone (600 mg, 2.32 mmol) and (2R)-2-methylpyrrolidine (591 mg, 6.95 mmol) in DMF (1.5 mL) was stirred at 100° C. for 16 h. LCMS analysis showed consumption of the starting material. The reaction was cooled to RT, H$_2$O (40 mL) was added, and the reaction was extracted with DCM (3×4 0 mL). The combined organic layers were dried over Na$_2$SO$_4$, filtered, and concentrated. The residue was purified by flash chromatography (24 g SiO$_2$, 0-20% EtOAc/heptane) to provide the title compound (4a) (664 mg, 93% yield). $^1$H NMR (400 MHz, CDCl$_3$) δ 6.44 (d, J=1.0 Hz, 1H), 6.21 (d, J=1.0 Hz, 1H), 4.12 (q, J=7.1 Hz, 1H), 3.72-3.62 (m, 2H), 3.54 (ddd, J=10.5, 7.6, 2.9 Hz, 1H), 3.40-3.28 (m, 2H), 2.10-2.04 (m, 2H), 1.75-1.62 (m, 4H), 1.26 (t, J=7.2 Hz, 1H), 1.21 (d, J=6.3 Hz, 2H); m/z (APCI+) for (C$_{16}$H$_{22}$ClN$_3$O), 308.2 (M+H)$^+$.

Step 2: 2-chloro-6-[(2R)-2-methylpyrrolidin-1-yl]-4-(piperidine-1-carbonyl)pyridine-3-carbaldehyde (4b)

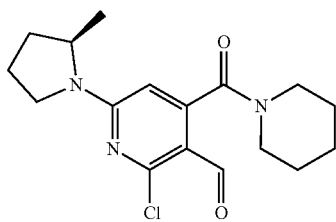

4b

To a solution of DMF (473 mg, 6.47 mmol) in DCM (3.0 mL) was added POCl$_3$ (992 mg, 6.47 mmol). The mixture was stirred for 10 min and then a solution of {2-chloro-6-[(2R)-2-methylpyrrolidin-1-yl]pyridin-4-yl}(piperidin-1-yl)methanone (4a) (664 mg, 2.16 mmol) in DCM (3.0 mL) was added. The mixture was stirred at reflux for 15 h. LCMS analysis showed consumption of the starting material. The reaction was concentrated to dryness and slowly poured into a saturated solution of NaHCO$_3$ (30 mL). The mixture was extracted with DCM (3×30 mL). The combined organics were dried over Na$_2$SO$_4$, filtered, and concentrated. The residue was purified by flash chromatography (24 g SiO$_2$, 0-40% EtOAc/heptane) to provide the title compound (4b) (568 mg, 78% yield). $^1$H NMR (400 MHz, CDCl$_3$) δ 10.07 (s, 1H), 5.99 (s, 1H), 4.13-4.65 (m, 1H), 3.68-3.83 (m, 1H), 3.55-3.68 (m, 2H), 3.35-3.55 (m, 1H), 2.98-3.20 (m, 2H), 1.88-2.17 (m, 3H), 1.71-1.83 (m, 2H), 1.55-1.67 (m, 3H), 1.46-1.55 (m, 1H), 1.31-1.42 (m, 1H), 1.17-1.26 (m, 3H); m/z (APCI+) for (C$_{17}$H$_{22}$Cl$_1$N$_3$O$_2$), 336.1 (M+H)$^+$.

Step 3: N-[(E)-{2-chloro-6-[(2R)-2-methylpyrrolidin-1-yl]-4-(piperidine-1-carbonyl)pyridin-3-yl}methylidene]-2-methylpropane-2-sulfinamide (4c)

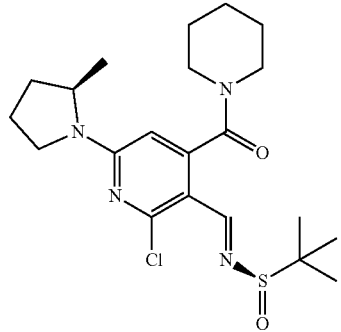

4c

A mixture of 2-chloro-6-[(2R)-2-methylpyrrolidin-1-yl]-4-(piperidine-1-carbonyl)pyridine-3-carbaldehyde (4b) (432 mg, 1.29 mmol), (R)-(+)-2-methyl-2-propanesulfinamide (187 mg, 1.54 mmol), and Ti(OEt)$_4$ (880 mg, 3.86 mmol) in THF (10.0 mL) was stirred at 45° C. for 16 h. LCMS analysis showed ~25% remaining starting material. Additional batches of (R)-(+)-2-methyl-2-propanesulfinamide (62.4 mg, 0.515 mmol), and Ti(OEt)$_a$(293 mg, 1.29 mmol) were added and the mixture was stirred at 50° C. for 16 h. LCMS analysis showed consumption of the starting material. The reaction was cooled to RT. The mixture was diluted with DCM (50 mL) and washed with a saturated solution of NaHCO$_3$ (35 mL) and brine (35 mL). The organic layer was dried over Na$_2$SO$_4$, filtered, and concentrated to provide the title compound (4c) (495 mg, 88% yield) as a white gum, which was taken on without further purification. m/z (APCI+) for (C$_{21}$H$_{31}$ClN$_4$O$_2$S), 440.2 (M+H)$^+$.

Step 4: 4-chloro-6-[(2R)-2-methylpyrrolidin-1-yl]-2,3-dihydro-1H-pyrrolo[3,4-c]pyridin-1-one (4d)

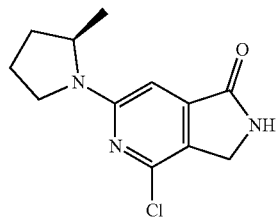

4d

A solution of N-[(E)-{2-chloro-6-[(2R)-2-methylpyrrolidin-1-yl]-4-(piperidine-1-carbonyl)pyridin-3-yl}methylidene]-2-methylpropane-2-sulfinamide (4c) (495 mg, 1.13 mmol) in THF (15.0 mL) was cooled to 0° C. and then a solution of LiBH$_4$ (2.0 M in THF, 620 mL, 1.24 mmol) was added. The mixture was stirred at 0° C. for 2 h and then a solution of NaOMe (25% in MeOH, 2.5 mL, 10.1 mmol) was added. The reaction was allowed warm to RT and then stirred for 16 h. The reaction was diluted with DCM (60 mL) and washed with saturated aqueous NH$_4$Cl (60 mL) and brine (60 mL). The organic layer was dried over Na$_2$SO$_4$, filtered, and concentrated. The residue was purified by flash chromatography (SiO$_2$, 50-100% EtOAc/heptane) to provide the title compound (4d) (199 mg, 70% yield) as a colorless foam. $^1$H NMR (400 MHz, CDCl$_3$) δ 6.68 (s, 1H), 6.45 (s, 1H), 4.35 (s, 2H), 4.21-4.14 (m, 1H), 3.58 (ddd, J=10.5, 7.6, 2.8 Hz, 1H), 3.39 (q, J=8.9 Hz, 1H), 2.13-1.97 (m, 2H), 1.75 (dt, J=5.2, 2.6 Hz, 1H), 1.23 (d, J=6.3 Hz, 3H). One hydrogen atom assumed obscured by water peak; m/z (APCI+) for (C$_{12}$H$_{14}$ClN$_3$O), 252.3 (M+H)$^+$.

Step 5: 6-[(2R)-2-methylpyrrolidin-1-yl]-1-oxo-2,3-dihydro-1H-pyrrolo[3,4-c]pyridine-4-carbonitrile (4e)

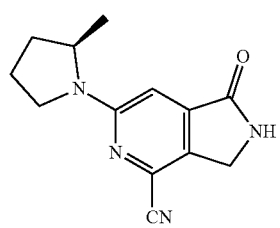

4e

A mixture of 4-chloro-6-[(2R)-2-methylpyrrolidin-1-yl]-2,3-dihydro-1H-pyrrolo[3,4-c]pyridin-1-one (4d) (438 mg, 1.74 mmol), Zn(CN)$_2$ (306 mg, 2.6 mmol), DMF (15 mL) and Pd(PPh$_3$)$_4$ (100 mg, 0.09 mmol) was heated to 140° C. in the microwave for 30 min. The reaction was diluted with DCM and filtered. The filter cake was washed with DCM. The filtrate was concentrated in vacuo and the crude compound was purified by flash chromatography (SiO$_2$, 0-100% 1:1 EtOAc:DCM/heptane) to the title compound (4e) as a yellow solid (375 mg, 89% yield). $^1$H NMR (400 MHz, CDCl$_3$) δ 7.00-6.94 (m, 1H), 6.46-6.32 (m, 1H), 4.55 (s, 2H), 4.29-4.19 (m, 1H), 3.61 (ddd, J=2.6, 7.6, 10.3 Hz, 1H), 3.46-3.34 (m, 1H), 2.22-2.02 (m, 3H), 1.86-1.72 (m, 1H), 1.25 (d, J=6.4 Hz, 3H); m/z (APCI+) for (C$_{13}$H$_{14}$N$_4$O), 243.1 (M+H)$^+$.

Step 6: 4-acetyl-6-[(2R)-2-methylpyrrolidin-1-yl]-2,3-dihydro-1H-pyrrolo[3,4-c]pyridin-1-one (4f)

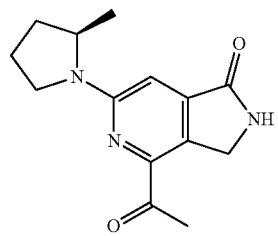

4f

To a solution of 6-[(2R)-2-methylpyrrolidin-1-yl]-1-oxo-2,3-dihydro-1H-pyrrolo[3,4-c]pyridine-4-carbonitrile (4e) (355 mg, 1.47 mmol) in THF (15 mL) at ice/water bath was added MeMgBr (4.88 mL, 14.7 mmol, 3.0 M in THF). The resulting mixture was stirred at this temperature for 10 min, then allowed warmed to RT and allowed to stir for 2 h. The mixture was quenched with 2 N HCl (6 mL) at 0° C. and stirred at RT for 15 min. The mixture was neutralized with a saturated solution of NaHCO$_3$ and extracted with DCM (3×40 mL). The combined organic layers were dried over Na$_2$SO$_4$ filtered, and concentrated. The crude compound was purified by flash chromatography (SiO$_2$, 20-50% EtOAc/heptane) to provide the title compound (4f) as a yellow solid (190 mg, 50% yield). $^1$H NMR (400 MHz, CDCl$_3$) 6.98 (s, 1H), 6.59 (br. s, 1H), 4.70 (s, 2H), 4.28 (br. t, J=5.7 Hz, 1H), 3.64 (ddd, J=2.6, 7.5, 10.1 Hz, 1H), 3.48-3.38 (m, 1H), 2.70 (s, 3H), 2.19-2.10 (m, 2H), 2.08-2.01 (m, 1H), 1.79 (td, J=2.6, 5.0 Hz, 1H), 1.30 (d, J=6.2 Hz, 3H); m/z (APCI+) for (C$_{14}$H$_{17}$N$_3$O$_2$), 260.2 (M+H)$^+$.

Step 7: Intermediate 4

To a 40 mL vial was added 4-acetyl-6-[(2R)-2-methylpyrrolidin-1-yl]-2,3-dihydro-1H-pyrrolo[3,4-c]pyridin-1-one (4f) (200 mg, 0.77 mmol), (S)-tert-butylsulfinamide (187 mg, 1.54 mmol), THF (1.54 mL) and Ti(OEt)$_4$ (1.54 mmol, 0.323 mL). The vial was capped and heated to 80° C. for 48 h. The reaction was then cooled to −78° C. (dry ice/acetone bath) and L-selectride (1.54 mmol, 1.54 mL, 1.0 M in THF) dropwise. The resulting mixture was stirred at −78° C. for 3 hr. The mixture was warmed to RT and quenched with saturated NH$_4$Cl (2 mL) dropwise, then added DCM (20 mL) and brine (20 mL). The mixture was filtered through Celite® and washed with DCM (40 mL). The organic layer was collected, and the aqueous layer was extracted with DCM (20 mL). The combined organic layers were dried over Na$_2$SO$_4$, filtered, and concentrated. The crude was purified by flash chromatography (SiO$_2$, solvent 0-10% MeOH in EtOAc) to provide Intermediate 4 as a yellow foam (127 mg, 45% yield). m/z (APCI+) for (C$_{18}$H$_{28}$N$_4$O$_2$S), 365.3 (M+H)$^+$. Stereochemistry was assigned based on use of (2R)-2-methylpyrrolidine in step 1 and (S)-tert-butylsulfinamide in step 7.

Intermediate 5: (S,R)-2-methyl-N-[(1R)-1-{6-[(2R)-2-methylpyrrolidin-1-yl]-1-oxo-2,3-dihydro-1H-pyrrolo[3,4-c]pyridin-4-yl}propyl]propane-2-sulfinamide Step 2: (S,S)-2-methyl-N-[(1E)-1-{6-[(2R)-2-methylpyrrolidin-1-yl]-1-oxo-2,3-dihydro-1H-pyrrolo[3,4-c]pyridin-4-yl}propylidene]propane-2-sulfinamide (5b)

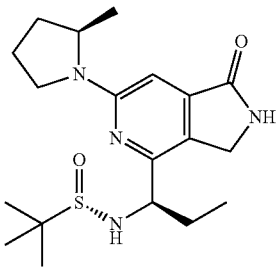 [SMILES: CC[C@@H](N[S@@](=O)C(C)(C)C)c1nc(N2CCC[C@H]2C)cc2c1CNC2=O]

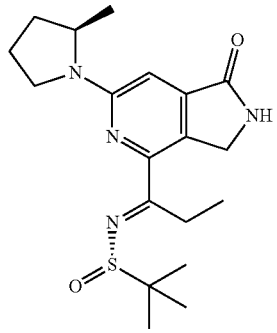

5b

Step 1: 6-[(2R)-2-methylpyrrolidin-1-yl]-4-propanoyl-2,3-dihydro-1H-pyrrolo[3,4-c]pyridin-1-one (5a)

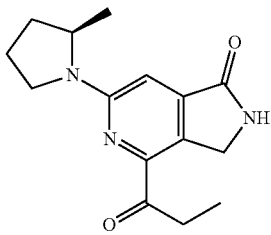

5a

A solution of 6-[(2R)-2-methylpyrrolidin-1-yl]-1-oxo-2,3-dihydro-1H-pyrrolo[3,4-c]pyridine-4-carbonitrile (4e) (808 mg, 3.33 mmol) in THF (8.0 mL) was cooled to 0° C. and then treated with a solution of ethylmagnesium bromide (3.0 M in Et$_2$O, 11.1 mL, 33.3 mmol). The mixture was stirred at RT for 1 h. LCMS analysis showed consumption of the starting material. The reaction was cooled to 0° C. and quenched by addition of 2 N HCl. The mixture was stirred at RT for 10 min, neutralized by addition of a saturated solution of NaHCO$_3$, and then extracted with DCM (2×30 mL). The combined organic layers were dried over Na$_2$SO$_4$, filtered, and concentrated. The residue was purified by flash chromatography (24 g SiO$_2$, 0-100% EtOAc/heptane) to provide the title compound (5a) (646 mg, 71% yield) as a yellow oil. $^1$H NMR (400 MHz, CDCl$_3$) δ 7.01 (s, 1H), 6.41 (br. s, 1H), 4.73 (s, 2H), 4.39-4.22 (m, 1H), 3.66 (ddd, J=2.6, 7.4, 10.1 Hz, 1H), 3.52-3.38 (m, 1H), 3.30-3.14 (m, 2H), 2.26-2.10 (m, 2H), 2.06-2.01 (m, 1H), 1.81 (td, J=2.5, 5.1 Hz, 1H), 1.31 (d, J=6.2 Hz, 3H), 1.24 (t, J=7.3 Hz, 3H); m/z (APCI+) for (C$_{15}$H$_{19}$N$_3$O$_2$), 274.2 (M+H)$^+$.

To a solution of 6-[(2R)-2-methylpyrrolidin-1-yl]-4-propanoyl-2,3-dihydro-1H-pyrrolo[3,4-c]pyridin-1-one (5a) (640 mg, 2.34 mmol) in THF (2.0 mL) were added (S)-(−)-2-methyl-2-propanesulfinamide (568 mg, 4.68 mmol) and Ti(OEt)$_4$ (2.14 g, 9.37 mmol). The mixture was stirred at 90° C. for 23 h. LCMS analysis showed consumption of the starting material. The mixture was cooled to RT and brine (40 mL) and DCM (30 mL) were then added. The mixture was stirred for 10 min and then filtered through Celite®. The layers were separated. The aqueous layer was extracted with DCM (30 mL). The combined organic layers were dried over Na$_2$SO$_4$, filtered, and concentrated to provide the title compound (5b) (779 mg, 88% yield) as a white foam which was directly taken on in the next step. m/z (APCI+) for (C$_{19}$H$_{23}$N$_4$O$_2$S), 377.2 (M+H)$^+$.

Step 3: Intermediate 5

A solution of (S,S)-2-methyl-N-[(1E)-1-{6-[(2R)-2-methylpyrrolidin-1-yl]-1-oxo-2,3-dihydro-1H-pyrrolo[3,4-c]pyridin-4-yl}propylidene]propane-2-sulfinamide (5b) (654 mg, 1.40 mmol) in THF (12.0 mL) was cooled to −78° C. and then treated dropwise with a solution of L-selectride (1.0 M in THF, 2.5 mL, 2.5 mmol). The mixture was stirred at −78° C. for 1.5 h. Additional L-selectride (1.0 M, 0.417 mL, 0.417 mmol) was added and the mixture was stirred at −78° C. for a further 1.5 h. The mixture was quenched with MeOH, diluted with brine (50 mL), and extracted with DCM (2×50 mL). The combined organic layers were dried over Na$_2$SO$_4$, filtered, and concentrated. The residue was purified by flash chromatography (12 g SiO$_2$, 0-10% MeOH/DCM) to provide Intermediate 5 (300 mg, 57% yield) as a yellow gum. $^1$H NMR (400 MHz, DMSO-d$_6$) δ 8.66 (s, 1H), 6.48 (s, 1H), 5.14 (d, J=6.6 Hz, 1H), 4.35 (s, 2H), 4.27-4.14 (m, 2H), 3.59-3.44 (m, 1H), 3.29-3.18 (m, 1H), 2.14-2.01 (m, 2H), 1.98-1.81 (m, 3H), 1.73-1.60 (m, 1H), 1.20 (d, J=6.2

Hz, 3H), 1.07 (s, 9H), 0.86-0.73 (m, 3H); m/z (APCI+) for (C$_{19}$H$_{30}$N$_4$O$_2$S), 379.2 (M+H)$^+$.

Stereochemistry was assigned based on use of (2R)-2-methylpyrrolidine in step 1 of the synthesis of Intermediate 4 and (S)-(−)-2-methyl-2-propanesulfinamide in step 2. Absolute configuration of Intermediate 5 was unambiguously established by small molecule X-ray crystallography.

Table 3 provides X-ray diffraction data confirming the stereochemistry of Intermediate 5. The single crystal X-ray diffraction studies were carried out on a Bruker Microstar APEX II CCD diffractometer equipped with Cu K$_\alpha$ radiation (λ=1.54178 Å). Absolute stereochemistry was conclusively assigned (Flack=0.003(12)). Crystals of Intermediate 5 were grown from ether/pentane at 4° C. A 0.12×0.04×0.02 mm piece of a colorless crystal was mounted on a Cryoloop with Paratone oil. Data were collected in a nitrogen gas stream at 100(2) K using φ and $\overline{\omega}$ scans. Crystal-to-detector distance was 45 mm and exposure time was 4, 6, 8, 10, 14, or 20 seconds depending on the 2θ range per frame using a scan width of 1.25°. Data collection was 97.0% complete to 67.500° in θ. The data were integrated using the Bruker SAINT Software program and scaled using the SADABS software program. Solution by direct methods (SHELXT) produced a complete phasing model consistent with the proposed structure. All nonhydrogen atoms were refined anisotropically by full-matrix least-squares (SHELXL-2014). All carbon bonded hydrogen atoms were placed using a riding model. Their positions were constrained relative to their parent atom using the appropriate HFIX command in SHELXL-2014.

Intermediate 6: 4-(2-aminopropan-2-yl)-6-[(2R)-2-methylpyrrolidin-1-yl]-2,3-dihydro-1H-pyrrolo[3,4-c]pyridin-1-one

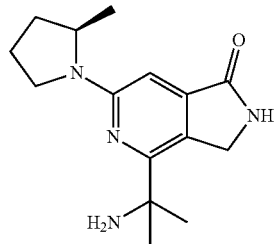 [SMILES: C[C@@H]1CCCN1c1cc2c(c(C(C)(C)N)n1)CNC2=O]

To a suspension of 6-[(2R)-2-methylpyrrolidin-1-yl]-1-oxo-2,3-dihydro-1H-pyrrolo[3,4-c]pyridine-4-carbonitrile (4e) (213 mg, 0.88 mmol) in THF (9 mL) at RT was added lanthanum (III) chloride bis(lithium chloride) complex (1.76 mmol, 2.93 mL, 0.6 M). The resulting mixture was stirred at RT for 30 min, and then was cooled to −78° C. (dry ice/acetone bath) and methyllithium (3.52 mmol, 2.20 mL, 1.6 M) was added dropwise. The resulting mixture was stirred at −78° C. for 1 h, then allowed warm to RT. The mixture was quenched with saturated NH$_4$Cl (20 mL), and brine (20 mL) and DCM (20 mL) were then added. The mixture was stirred at RT for 5 min and filtered through Celite®. The organic layer was collected, and the aqueous layer was extracted with DCM (20 mL). The combined organic layers were dried over Na$_2$SO$_4$, filtered, and concentrated. The residue was purified by flash chromatography (SiO$_2$, solvent 0-10% MeOH in DCM) to provide Intermediate 6 as a pale brown color solid (157 mg, 65% yield). $^1$H NMR (400 MHz, DMSO-d$_6$) δ 8.60 (s, 1H), 6.42 (s, 1H), 4.56 (s, 2H), 4.17 (br. t, J=5.7 Hz, 1H), 3.50 (ddd, J=2.4, 7.2,

TABLE 3

| | | |
|---|---|---|
| Empirical formula: | C$_{19}$ H$_{30}$ N$_4$ O$_2$ S | |
| Molecular weight | 378.53 | |
| Temperature | 100.0 K | |
| Wavelength | 1.54178 Å | |
| Crystal system | Triclinic | |
| Space group | P1 | |
| Unit cell dimensions: | a = 8.3400(3) Å | α = 92.724(2)°. |
| | b = 9.4731(3) Å | β = 104.495(2)°. |
| | c = 15.3569(5) Å | γ = 115.416(2)°. |
| Volume | 1044.18(6) Å$^3$ | |
| Z | 2 | |
| Density (calculated) | 1.204 Mg/m$^3$ | |
| Absorption coefficient | 1.532 mm$^{-1}$ | |
| F(000) | 408 | |
| Crystal size | 0.12 × 0.04 × 0.02 mm$^3$ | |
| Crystal color, habit | colorless plank | |
| Theta range for data collection | 3.020 to 68.664°. | |
| Index ranges | −10 <= h <= 10, −11 <= k <= 11, −18 <= l <= 18 | |
| Reflections collected | 21109 | |
| Independent reflections | 7199 [R(int) = 0.0654] | |
| Completeness to theta = 67.500° | 97.0% | |
| Absorption correction | Semi-empirical from equivalents | |
| Max. and min. transmission | 0.5210 and 0.4220 | |
| Refinement method | Full-matrix least-squares on F$^2$ | |
| Data/restraints/parameters | 7199/3/479 | |
| Goodness-of-fit on F$^2$ | 1.038 | |
| Final R indices [I > 2sigma(I)] | R1 = 0.0626, wR2 = 0.1561 | |
| R indices (all data) | R1 = 0.0774, wR2 = 0.1686 | |
| Absolute structure parameter | 0.003(12) | |
| Extinction coefficient | n/a | |
| Largest diff. peak and hole | 0.593 and −0.326e.Å$^{-3}$ | |

9.8 Hz, 1H), 3.30-3.22 (m, 1H), 2.07-2.02 (m, 1H), 2.00-1.92 (m, 2H), 1.68 (td, J=2.4, 4.9 Hz, 1H), 1.41 (s, 3H), 1.40 (s, 3H), 1.20 (d, J=6.2 Hz, 3H); m/z (APCI+) for ($C_{15}H_{22}N_4O$), 275.2 (M+H)+.

Intermediate 7: (5R)-3-(6-bromopyridin-2-yl)-5-(fluoromethyl)-6,7-dihydro-5H-pyrrolo[2,1-c][1,2,4]triazole

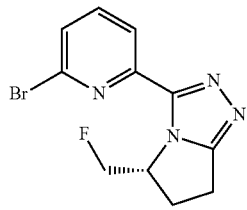 [SMILES: FC[C@H]1CCc2nnc(-c3cccc(Br)n3)n21]

Step 1: (5R)-5-(fluoromethyl)pyrrolidin-2-one (7a)

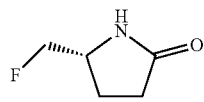

A solution of (5R)-5-(bromomethyl)pyrrolidin-2-one (600 mg, 3.37 mmol) in $CH_3CN$ (6.74 mL, 0.5 M) was covered with aluminum foil to exclude light. To this solution was added a suspension of AgF (1.07 g, 8.43 mmol) in $CH_3CN$ (12.5 mL, 0.27 M) in one portion. The reaction was stirred at RT in the dark for 36 h. The reaction was filtered over Celite® and concentrated to dryness. The crude residue was purified by flash chromatography ($SiO_2$, 100% EtOAc to 1:1 EtOAc/acetone) to provide the title compound (7a) (173 mg, 44% yield) as a colorless oil. $^1$H NMR (400 MHz, $CDCl_3$) δ 7.17 (br. s, 1H), 4.49-4.17 (m, 2H), 4.01-3.84 (m, 1H), 2.44-2.28 (m, 2H), 2.27-2.16 (m, 1H), 1.88-1.75 (m, 1H). $^{19}$F NMR (376 MHz, $CDCl_3$) δ-224.58 (s, 1F).

Step 2: tert-butyl (2R)-2-(fluoromethyl)-5-oxopyrrolidine-1-carboxylate (7b)

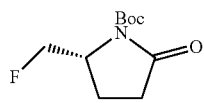

To a solution of (5R)-5-(fluoromethyl)pyrrolidin-2-one (7a) (170 mg, 1.45 mmol) in $CH_3CN$ (6.74 mL, 0.5 M) was added $Boc_2O$ (348 mg, 1.60 mmol) and 4-(dimethylamino)pyridine (17.7 mg, 0.145 mmol). The reaction was stirred at RT for 2 h. TLC analysis (2:1 EtOAc:acetone) showed consumption of the starting material. The reaction mixture was concentrated and purified by flash chromatography ($SiO_2$, 100% heptane to 100% EtOAc) to provide the title compound (7b) (277 mg, 88% yield) as a colorless oil. $^1$H NMR (400 MHz, $CDCl_3$) δ 4.78-4.42 (m, 2H), 4.40-4.25 (m, 1H), 2.76-2.62 (m, 1H), 2.50-2.39 (m, 1H), 2.29-2.14 (m, 1H), 2.13-2.03 (m, 1H), 1.56 (s, 9H). $^{19}$F NMR (376 MHz, $CDCl_3$) δ-233.52 (s, 1F).

Step 3: tert-butyl [(2R)-1-fluoro-5-hydrazinyl-5-oxopentan-2-yl]carbamate (7c)

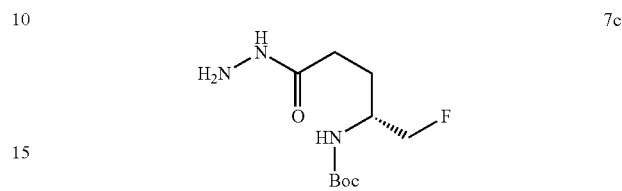

To a solution of tert-butyl (2R)-2-(fluoromethyl)-5-oxopyrrolidine-1-carboxylate (7b) (1.78 g, 8.19 mmol) in THF (41.0 mL, 0.2 M) was added hydrazine monohydrate (1.3 mL, 41.0 mmol) via syringe. The reaction was stirred at RT for 30 min. TLC analysis (1:1 heptane:EtOAc) showed consumption of the starting material. The reaction mixture was concentrated and then EtOAc (50 mL) and saturated aqueous $NH_4Cl$ (50 mL) were added. The layers were separated, and the aqueous layer was extracted with EtOAc (3×50 mL). The combined organic layers were dried over $MgSO_4$, filtered, and concentrated to dryness to provide the title compound (7c) (1.6 g, 78% yield) as a white solid, which was taken on without further purification. $^1$H NMR (400 MHz, $CDCl_3$) δ 5.15-5.00 (m, 1H), 4.52-4.44 (m, 1H), 4.39-4.33 (m, 1H), 3.93-3.75 (m, 1H), 2.40 (br. s, 2H), 2.00-1.81 (m, 2H), 1.46 (s, 9H). $^{19}$F NMR (376 MHz, $CDCl_3$) δ-232.02 (s, 1F).

Step 4: tert-butyl {(2R)-5-[2-(6-bromopyridine-2-carbonyl)hydrazinyl]-1-fluoro-5-oxopentan-2-yl}carbamate (7d)

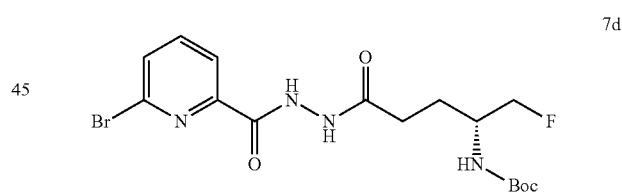

A solution of 6-bromopyridine-2-carboxylic acid (1.4 g, 6.93 mmol) in THF (34.7 mL, 0.2 M) was cooled to 0° C. Propylphosphonic anhydride solution (50% solution in EtOAc, 9.1 mL, 15.2 mmol) was added to the solution at 0° C. before the bath was removed and the reaction mixture was stirred for 30 min at RT. Then, N,N-diisopropylethylamine (7.24 mL, 41.6 mmol) and tert-butyl [(2R)-1-fluoro-5-hydrazinyl-5-oxopentan-2-yl]carbamate (7c) (1.90 g, 7.62 mmol) were added and the reaction mixture was stirred at RT for 17 h. LCMS analysis showed consumption of the starting material. The reaction was quenched with water (30 mL) and transferred to a separatory funnel with EtOAc (50 mL). The layers were separated, and the organic phase was washed sequentially with 20% citric acid (30 mL), a saturated solution of $NaHCO_3$ (30 mL), and brine (30 mL). The organic extract was then dried over $MgSO_4$, filtered, and concentrated to dryness to provide the title compound (7d)

(2.37 g, 78% yield) as a yellow solid, which was taken on without further purification. $^{1}$H NMR (400 MHz, CDCl$_3$) δ 9.74 (br. s, 1H), 9.15 (br. s, 1H), 8.14 (d, J=7.5 Hz, 1H), 7.77-7.71 (m, 1H), 7.70-7.65 (m, 1H), 4.95 (br. d, J=9.2 Hz, 1H), 4.62-4.36 (m, 2H), 4.12-3.98 (m, 1H), 2.49-2.37 (m, 2H), 2.03-1.95 (m, 2H), 1.49 (s, 9H). $^{19}$F NMR (376 MHz, CDCl$_3$) δ-232.01 (s, 1F). LCMS m/z (APCI) for (C$_{11}$H$_{14}$BrFN$_4$O$_2$), 333.1 (M+H-Boc)$^+$.

Step 5: tert-butyl {(2R)-4-[5-(6-bromopyridin-2-yl)-1,3,4-oxadiazol-2-yl]-1-fluorobutan-2-yl}carbamate (7e)

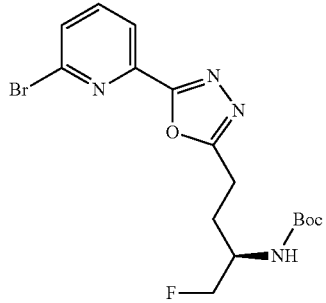

To a solution of tert-butyl {(2R)-5-[2-(6-bromopyridine-2-carbonyl)hydrazinyl]-1-fluoro-5-oxopentan-2-yl}carbamate (7d) (2.3 g, 5.3 mmol) in DCM (21.2 mL, 0.25 M) was added triethylamine (2.22 mL, 15.9 mmol) and p-toluenesulfonyl chloride (1.21 g, 6.37 mmol). The reaction was stirred at RT for 1.5 h. LCMS analysis showed consumption of the starting material. Ethylenediamine (0.355 mL, 5.31 mmol) was added to scavenge excess p-toluenesulfonyl chloride, during the addition a precipitate formed immediately. After stirring at RT for 30 min, the reaction was washed with 20% citric acid (20 mL) and the layers were separated. The aqueous layer was extracted with DCM (40 mL) then the combined organic layers were washed with brine (25 mL), dried over MgSO$_4$, filtered and concentrated to dryness to provide the title compound (7e) (2.07 g, 94% yield) as a yellow solid, which was taken on without further purification. $^{1}$H NMR (400 MHz, CDCl$_3$) δ 8.21 (d, J=7.6 Hz, 1H), 4.90-4.69 (m, 1H), 4.55 (br. d, J=2.8 Hz, 1H), 4.43 (br. s, 1H), 4.08-3.84 (m, 1H), 3.15-3.05 (m, 2H), 2.29-2.06 (m, 2H), 1.45 (s, 9H). $^{19}$F NMR (376 MHz, CDCl$_3$) δ-231.82 (s, 1F). LCMS m/z (APCI) for (C$_{11}$H$_{12}$BrFN$_4$O), 315.0 (M+H-Boc)$^+$.

Step 6: Intermediate 7

A microwave vial was charged with tert-butyl {(2R)-4-[5-(6-bromopyridin-2-yl)-1,3,4-oxadiazol-2-yl]-1-fluorobutan-2-yl}carbamate (7e) (1.00 g, 2.41 mmol) and trifluoroethanol (10.4 mL, 0.17 M) and was sealed before heating in the microwave to 180° C. for 30 min. LCMS analysis showed consumption of the starting material. The reaction mixture was concentrated, and the residue was purified by flash chromatography (SiO$_2$, 100% heptane to 1:10 MeOH/EtOAc) to provide Intermediate 7 (564 mg, 78% yield) as a yellow oil. $^{1}$H NMR (400 MHz, CDCl$_3$) δ 8.40 (d, J=7.3 Hz, 1H), 7.79-7.73 (m, 1H), 7.58 (d, J=7.9 Hz, 1H), 5.26-5.01 (m, 2H), 4.89-4.71 (m, 1H), 3.25-3.08 (m, 3H), 2.96-2.85 (m, 1H). $^{19}$F NMR (376 MHz, CDCl$_3$) δ-235.95 (s, 1F). LCMS m/z (APCI) for (C$_{11}$H$_{10}$BrFN$_4$), 297.0 (M+H)$^+$. Stereochemistry was assigned based on use of (5R)-5-(bromomethyl)pyrrolidin-2-one in step 1.

Intermediate 8: tert-butyl methyl({6-[(2R)-2-methylpyrrolidin-1-yl]-1-oxo-2,3-dihydro-1H-pyrrolo[3,4-c]pyridin-4-yl}methyl)carbamate

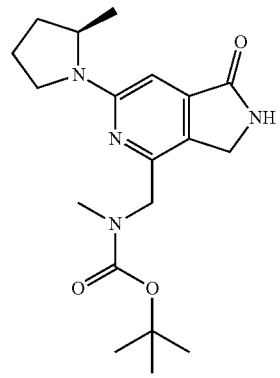 [SMILES: C[C@@H]1CCCN1c1cc2c(c(CN(C)C(=O)OC(C)(C)C)n1)CNC2=O]

Step 1: tert-butyl ({3-formyl-6-[(2R)-2-methylpyrrolidin-1-yl]-4-(piperidine-1-carbonyl)pyridin-2-yl}methyl)methylcarbamate (8a)

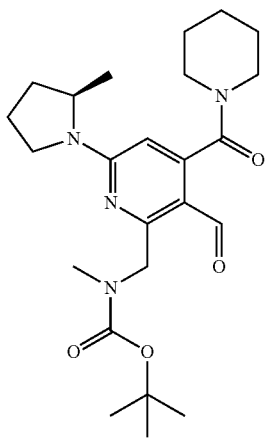

A solution of 2-chloro-6-[(2R)-2-methylpyrrolidin-1-yl]-4-(piperidine-1-carbonyl)pyridine-3-carbaldehyde (4b) (600 mg, 1.79 mmol) and PdCl$_2$(dppf) (261 mg, 0.357 mmol) in 1,4-dioxane (25.0 mL) was sparged with N$_2$ for 5 min and then heated to 80° C. A solution of {[(tert-butoxycarbonyl)(methyl)amino]methyl}(chlorido)zinc* (0.158 M in THF, 39.6 mL) was added at 80° C. and the mixture was stirred a further 35 min at the same temperature. LCMS analysis showed consumption of the starting material. The mixture was cooled to 30° C. and filtered through Celite®. The filter cake was washed with DCM (5×10 mL) and the filtrate was concentrated to dryness. The residue was combined with the crude material obtained from a parallel reaction run in identical fashion with 100 mg 2-chloro-6-[(2R)-2-methylpyrrolidin-1-yl]-4-(piperidine-1-carbonyl)pyridine-3-carbaldehyde. The mixture purified by flash chromatography (SiO$_2$, 1:1 EtOAc/petroleum ether) to provide the title compound (8a) (900 mg, 97% yield) as a yellow gum. $^1$H NMR (400 MHz, DMSO-d$_6$) δ 9.84 (s, 1H), 6.40-6.06 (m, 1H), 4.91-4.45 (m, 2H), 4.52-3.92 (m, 1H), 3.69-3.47 (m, 3H), 3.21-3.00 (m, 2H), 2.98-2.84 (m, 3H), 2.22-1.82 (m, 3H), 1.83-1.66 (m, 1H), 1.59 (s, 4H), 1.41 (s, 7H), 1.19 (d, J=18.2 Hz, 8H). m/z (ESI+) for (C$_{24}$H$_{36}$N$_4$O$_4$), 445.4 (M+H)$^+$.

*as prepared in: Angew. Chem. Int. Ed. 2014, 53, 2678.

Step 2: tert-butyl methyl{[3-{(E)-[(2-methylpropane-2-sulfinyl)imino]methyl}-6-[(2R)-2-methylpyrrolidin-1-yl]-4-(piperidine-1-carbonyl)pyridin-2-yl]methyl}carbamate (8b)

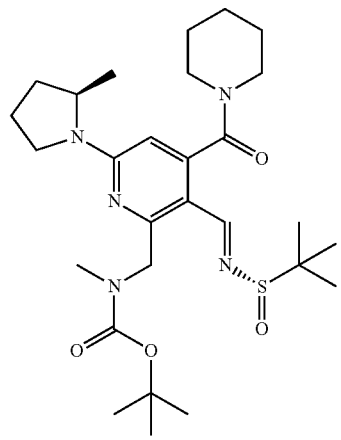

8b

A mixture of tert-butyl ({3-formyl-6-[(2R)-2-methylpyrrolidin-1-yl]-4-(piperidine-1-carbonyl)pyridin-2-yl}methyl)methylcarbamate (8a) (1.40 g, 3.15 mmol), Ti(OEt)$_4$ (1.44 g, 6.30 mmol), and (S)-(-)-2-methyl-2-propanesulfinamide (573 mg, 4.72 mmol) in THF (50.0 mL) was stirred at 50° C. for 18 h. Additional batches of Ti(OEt)$_4$ (359 mg, 1.57 mmol) and (S)-(-)-2-methyl-2-propanesulfinamide (115 mg, 0.945 mmol) were added and the mixture was stirred at 50° C. for an additional 20 h. LCMS analysis showed consumption of the starting material. The reaction was quenched with a saturated solution of Na$_2$CO$_3$ (150 mL) and DCM (100 mL) was added. The mixture was filtered through Celite® and the layers were separated. The aqueous layer was extracted with DCM (100 mL). The combined organic layers were washed with brine (150 mL), dried over Na$_2$SO$_4$, filtered, and concentrated to provide the title compound (8b) (1.7 g, >99% yield) as a yellow solid. m/z (ESI+) for (C$_{28}$H$_{45}$N$_5$O$_4$S), 548.5 (M+H)$^+$.

Step 5: Intermediate 8

To a solution of tert-butyl methyl{[3-{(E)-[(2-methylpropane-2-sulfinyl)imino]methyl}-6-[(2R)-2-methylpyrrolidin-1-yl]-4-(piperidine-1-carbonyl)pyridin-2-yl]methyl}carbamate (8b) (1.72 g. 3.41 mmol) in THF (20.0 mL) at 0° C. was added LiBH$_4$ (68.6 mg, 3.15 mmol). The reaction was stirred at 0° C. for 1 h. TLC analysis showed consumption of the starting material. The mixture was warmed to RT and a solution of NaOMe (30% in MeOH, 6.24 g, 34.6 mmol) was added. The mixture was stirred for 16 h. LCMS analysis showed formation of the desired product mass. The reaction was concentrated to dryness. The residue was dissolved in EtOAc (40 mL) and washed with H$_2$O (40 mL). The aqueous layer was extracted with EtOAc (30 mL). The combined organic layers were washed with brine (60 mL), dried over Na$_2$SO$_4$, filtered, and concentrated. The residue was purified by flash chromatography (SiO$_2$, EtOAc) to provide Intermediate 8 (750 mg, 66% yield) as a white solid. $^1$H NMR (400 MHz, CDCl$_3$) δ 7.04-6.79 (m, 1H), 6.68 (s, 1H), 4.56-4.43 (m, 2H), 4.43-4.33 (m, 2H), 4.27-4.16 (m, 1H), 3.58 (ddd, J=2.5, 7.3, 10.0 Hz, 1H), 3.45-3.30 (m, 1H), 3.01-2.91 (m, 3H), 2.17-1.96 (m, 3H), 1.80-1.72 (m, 1H), 1.53-1.37 (m, 9H), 1.26-1.23 (m, 3H); m/z (ESI+) for (C$_{19}$H$_{28}$N$_4$O$_3$), 361.2 (M+H)$^+$.

Stereochemistry was assigned based on use of (2R)-2-methylpyrrolidine in step 1 of the synthesis of Intermediate 4.

Intermediate 9: tert-butyl methyl({6-[methyl(propan-2-yl)amino]-1-oxo-2,3-dihydro-1H-pyrrolo[3,4-c]pyridin-4-yl}methyl)carbamate

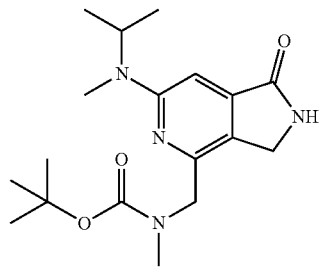 [SMILES: CC(C)N(C)c1cc2c(c(CN(C)C(=O)OC(C)(C)C)n1)CNC2=O]

Step 1: 2-chloro-N,N-dimethyl-6-[methyl(propan-2-yl)amino]pyridine-4-carboxamide (9a)

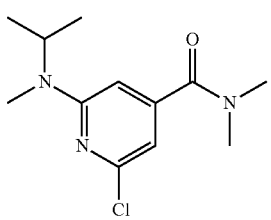

9a

A mixture of 2,6-dichloro-N,N-dimethylpyridine-4-carboxamide (30.0 g, 137 mmol) and N-methylpropan-2-amine (50.1 g, 685 mmol) in MeCN (120 mL) was portioned among three sealed reaction vessels and each was stirred at 100° C. for 60 h. LCMS analysis showed consumption of the starting material. The reaction mixtures were combined and concentrated to dryness. The residue was purified by flash chromatography (SiO$_2$, 1:1 EtOAc/petroleum ether) to provide the title compound (9a) (30.5 g, 87% yield) as a yellow solid. $^1$H NMR (400 MHz, CDCl$_3$) δ 6.45 (d, J=0.9 Hz, 1H), 6.31 (d, J=1.0 Hz, 1H), 4.82 (p, J=6.8 Hz, 1H), 3.08 (s, 3H), 2.97 (s, 3H), 2.83 (s, 3H), 1.16 (d, J=6.7 Hz, 6H); m/z (ESI+) for (C$_{12}$H$_{13}$ClN$_3$O), 255.9 (M+H)$^+$.

Step 2: 2-chloro-3-formyl-N,N-dimethyl-6-[methyl(propan-2-yl)amino]pyridine-4-carboxamide (9b)

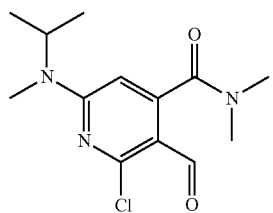

9b

To a solution of DMF (21.9 g, 299 mmol) in DCE (120 mL) was added POCl$_3$ (45.9 g, 299 mmol) dropwise at 5-15° C. The mixture was stirred at RT for 15 min and 2-chloro-N,N-dimethyl-6-[methyl(propan-2-yl)amino]pyridine-4-carboxamide (9a) (25.5 g, 99.7 mmol) was added. The reaction was stirred at 65° C. for 16 h. LCMS analysis showed consumption of the starting material. The reaction was cooled to RT and added dropwise to saturated aqueous Na$_2$CO$_3$ (900 mL). The mixture was extracted with DCM (2×300 mL). The combined organic layers were washed with brine (5×500 mL), dried over Na$_2$SO$_4$, filtered, and concentrated. The residue was purified by flash chromatography (SiO$_2$, 1:1 EtOAc/petroleum ether) to provide the title compound (9b) (23.7 g, 84% yield) as a brown solid. $^1$H NMR (400 MHz, CDCl$_3$) δ 10.19 (s, 1H), 6.25 (br. s, 1H), 3.12 (s, 3H), 3.02-2.85 (m, 3H), 2.77 (s, 3H), 1.22 (br. d, J=6.5 Hz, 6H); m/z (ESI+) for (C$_{13}$H$_{18}$ClN$_3$O$_2$), 283.9 (M+H)$^+$.

Step 3: 2-chloro-N,N-dimethyl-3-{(E)-[(2-methylpropane-2-sulfinyl)imino]methyl}-6-[methyl(propan-2-yl)amino]pyridine-4-carboxamide (9c)

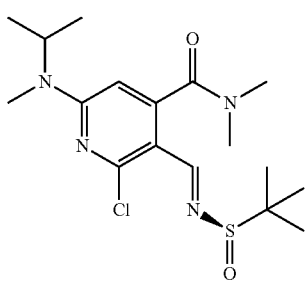

9c

A mixture of 2-chloro-3-formyl-N,N-dimethyl-6-[methyl(propan-2-yl)amino]pyridine-4-carboxamide (9b) (23.7 g, 83.5 mmol), (R)-(+)-2-methyl-2-propanesulfinamide (12.1 g, 100 mmol), and Ti(OEt)$_4$ (38.1 g, 167 mmol) in THF (250 mL) was stirred at 50° C. for 20 h. LMCS analysis showed consumption of the starting material. The reaction was concentrated to dryness. The residue was stirred with a saturated solution of NaHCO$_3$ (300 mL) for 30 min. The mixture was filtered. The filter cake was rinsed with H$_2$O (3×80 mL) and petroleum ether (3×50 mL) and dried under vacuum to provide the title compound (9c) (32.3 g, 99% yield) as a yellow solid. $^1$H NMR (400 MHz, DMSO-d$_6$) δ 9.07 (s, 1H), 6.74 (s, 1H), 5.36-5.10 (m, 1H), 3.30 (s, 3H), 3.26 (s, 3H), 3.10 (s, 3H), 1.54 (d, J=6.7 Hz, 6H), 1.49 (s, 9H); m/z (ESI+) for (C$_{17}$H$_{27}$ClN$_4$O$_2$S), 387.2 (M+H)$^+$.

Step 4: 4-chloro-6-[methyl(propan-2-yl)amino]-2,3-dihydro-1H-pyrrolo[3,4-c]pyridin-1-one (9d)

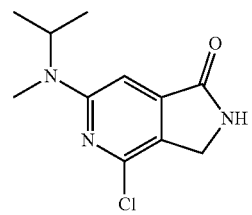

9d

A solution of 2-chloro-N,N-dimethyl-3-{(E)-[(2-methylpropane-2-sulfinyl)imino]methyl}-6-[methyl(propan-2-yl)amino]pyridine-4-carboxamide (9c) (32.3 g, 83.5 mmol) in THF (200 mL) was cooled to 0° C. and LiBH$_4$ (1.82 g, 83.5 mmol) was added. The mixture was stirred at RT for 1 h. LCMS analysis showed consumption of the starting material. NaOMe (165 g, 919 mmol) was added and the mixture was stirred at RT for 16 h. The reaction mixture was filtered and the filter cake was washed with EtOAc (3×200 mL). The combined filtrate was concentrated to dryness. The residue was dissolved in DCM (300 mL) and washed with H$_2$O (500 mL). The aqueous layer was extracted with DCM (2×300 mL). The combined organic layers were washed with brine (500 mL), dried over Na$_2$SO$_4$, filtered, and concentrated. The solid was slurried in a mixture of DCM (50 mL) and petroleum ether (120 mL) for 30 min. The solids were collected by filtration. The filter cake was dried under vacuum to provide the title compound (9d) (11.3 g, 56% yield) as an off-white solid. $^1$H NMR (400 MHz, CDCl$_3$) δ 7.19 (s, 1H), 6.79 (s, 1H), 4.82 (p, J=6.7 Hz, 1H), 4.35 (d, J=1.2 Hz, 2H), 2.88 (s, 3H), 1.18 (d, J=6.7 Hz, 6H); m/z (ESI+) for (C$_{11}$H$_{14}$ClN$_3$O), 239.9 (M+H)$^+$.

Step 5: methyl 6-[methyl(propan-2-yl)amino]-1-oxo-2,3-dihydro-1H-pyrrolo[3,4-c]pyridine-4-carboxylate (9e)

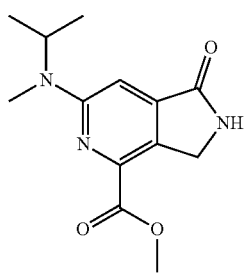

9e

A mixture of 4-chloro-6-[methyl(propan-2-yl)amino]-2,3-dihydro-1H-pyrrolo[3,4-c]pyridin-1-one (9d) (11.3 g, 47.1 mmol), PdCl$_2$(dppf) (2.16 g, 2.95 mmol), and TEA (14.3 g, 141 mmol) in MeOH (200 mL) was stirred at 80° C. for 40 h under an atmosphere of CO at 50 psi. TLC analysis (1:1 EtOAc/petroleum ether) showed consumption of the starting material. The reaction was concentrated to dryness. The residue was dissolved in H$_2$O (200 mL) and extracted with DCM (2×150 mL). The combined organic layers were washed with brine (200 mL), dried over Na$_2$SO$_4$, filtered, and concentrated. The residue was slurried in DCM (50 mL) for 30 min. The solids were collected by filtration. The filter cake was washed with petroleum ether (3×5 mL) and dried under vacuum. The filtrate was purified by flash chromatography (SiO$_2$, 40-70% EtOAc/DCM). The product-containing fractions were concentrated to dryness and combined with the above filter cake to provide the title compound (9e) (12.3 g, 99% yield) as a yellow solid. $^1$H NMR (400 MHz, CDCl$_3$) δ 7.12 (s, 1H), 6.79 (s, 1H), 4.89 (p, J=6.6 Hz, 1H), 4.68 (d, J=1.1 Hz, 2H), 3.97 (s, 3H), 2.96 (s, 3H), 1.21 (d, J=6.7 Hz, 6H); m/z (ESI+) for (C$_{13}$H$_{17}$N$_3$O$_3$), 263.9 (M+H)$^+$.

Step 6: 4-(hydroxymethyl)-6-[methyl(propan-2-yl) amino]-2,3-dihydro-1H-pyrrolo[3,4-c]pyridin-1-one (9f)

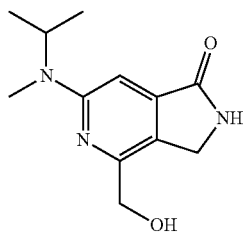

9f

To a mixture of methyl 6-[methyl(propan-2-yl)amino]-1-oxo-2,3-dihydro-1H-pyrrolo[3,4-c]pyridine-4-carboxylate (9e) (1.0 g, 3.80 mmol) in THF (60 mL) was added a solution of LiAlH$_4$ (2.5 M in THF, 1.67 mL, 4.18 mmol) dropwise at 0° C. The mixture was stirred at 0° C. for 1 h and then at 20° C. for 16 h. TLC analysis (1:1 EtOAc/petroleum ether) showed consumption of the starting material. The mixture was quenched by addition of 20% aqueous NaOH (0.5 mL). To the mixture was added Na$_2$SO$_4$ (4 g). The mixture was stirred for 30 min and then filtered. The filtrate was concentrated to dryness to provide the title compound (9f) (890 mg, 99% yield) as a yellow solid. $^1$H NMR (400 MHz, CDCl$_3$) δ 7.04 (s, 1H), 6.82 (s, 1H), 4.85 (p, J=6.6 Hz, 1H), 4.67 (d, J=4.7 Hz, 2H), 4.33 (s, 2H), 4.09 (t, J=4.6 Hz, 1H), 2.92 (s, 3H), 1.20 (d, J=6.7 Hz, 6H); m/z (ESI+) for (C$_{12}$H$_{17}$N$_3$O$_2$), 236.0 (M+H)$^+$.

Step 7: {6-[methyl(propan-2-yl)amino]-1-oxo-2,3-dihydro-1H-pyrrolo[3,4-c]pyridin-4-yl}methyl methanesulfonate (9g)

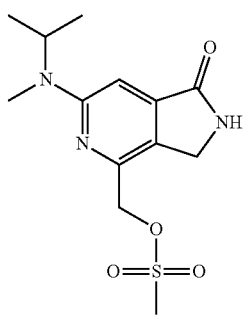

9g

To a mixture of 4-(hydroxymethyl)-6-[methyl(propan-2-yl)amino]-2,3-dihydro-1H-pyrrolo[3,4-c]pyridin-1-one (9f) (890 mg, 3.78 mmol) and TEA (957 mg, 9.46 mmol) in THF (20.0 mL) was added MsCl (953 mg, 8.23 mmol) dropwise at 0° C. under an atmosphere of N$_2$. The mixture was stirred at 0° C. LCMS analysis showed consumption of the starting material. The reaction was diluted with saturated aqueous Na$_2$CO$_3$ (30 mL) and extracted with EtOAc (2×20 mL). The combined organic layers were washed with brine (30 mL), dried over Na$_2$SO$_4$, filtered, and concentrated to provide the title compound (9g) (1.2 g, 99% yield) as a yellow solid, which was taken on without further purification. m/z (ESI+) for (C$_{13}$H$_{19}$N$_3$O$_4$S), 314.0 (M+H)$^+$.

Step 8: 4-[(methylamino)methyl]-6-[methyl(propan-2-yl)amino]-2,3-dihydro-1H-pyrrolo[3,4-c]pyridin-1-one (9h)

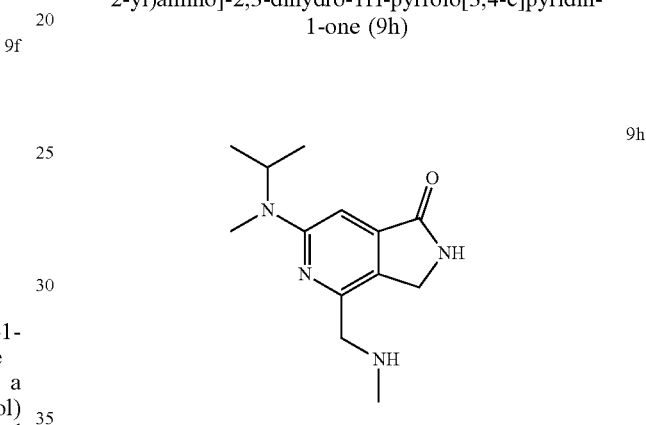

9h

To a mixture of {6-[methyl(propan-2-yl)amino]-1-oxo-2,3-dihydro-1H-pyrrolo[3,4-c]pyridin-4-yl}methyl methanesulfonate (9g) (1.18 g, 3.78 mmol) in THF (20.0 mL) was added a solution of methylamine (2.0 M in THF, 37.8 mL, 75.6 mmol). The mixture was stirred for 1 h. LCMS analysis indicated consumption of the starting material. The mixture was concentrated to dryness to provide the title compound (9h) (940 mg, 99% yield) as a brown solid, which was taken on without further purification. m/z (ESI+) for (C$_{13}$H$_{20}$N$_4$O), 249.0 (M+H)$^+$.

Step 9: Intermediate 9

To a solution of 4-[(methylamino)methyl]-6-[methyl(propan-2-yl)amino]-2,3-dihydro-1H-pyrrolo[3,4-c]pyridin-1-one (9h) (940 mg, 11.4 mmol) and TEA (1.15 g, 11.4 mmol) in DCM (20.0 mL) was added Boc$_2$O (1.65 mg, 7.57 mmol). The mixture was stirred for 30 min. LCMS analysis showed consumption of the starting material. The reaction was concentrated to dryness. The residue was purified by flash chromatography (SiO$_2$, EtOAc) to provide Intermediate 9 (600 mg, 46% yield) as a yellow solid. $^1$H NMR (400 MHz, CDCl$_3$) δ 6.81 (s, 1H), 6.57-6.42 (m, 1H), 4.91 (p, J=6.6 Hz, 1H), 4.48 (s, 2H), 4.35 (d, J=12.4 Hz, 2H), 2.92 (s, 3H), 2.88 (s, 3H), 1.48 (s, 5H), 1.41 (s, 4H), 1.17 (d, J=6.7 Hz, 6H); m/z (ESI+) for (C$_{18}$H$_{28}$N$_4$O$_3$), 349.2 (M+H)$^+$.

Intermediate 10: (S,S)-2-methyl-N-[(1R)-1-{6-[methyl(propan-2-yl)amino]-1-oxo-2,3-dihydro-1H-pyrrolo[3,4-c]pyridin-4-yl}propyl]propane-2-sulfinamide

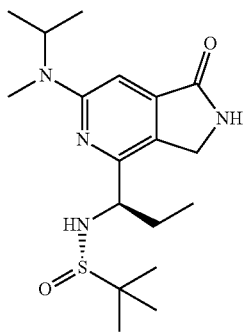 [SMILES: CC[C@@H](N[S@@](=O)C(C)(C)C)c1nc(N(C)C(C)C)cc2c1CNC2=O]

Step 1: 6-[methyl(propan-2-yl)amino]-1-oxo-2,3-dihydro-1H-pyrrolo[3,4-c]pyridine-4-carbonitrile

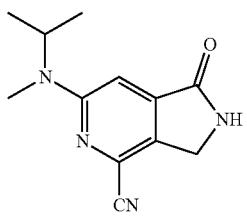

10a

A mixture of 4-chloro-6-[methyl(propan-2-yl)amino]-2,3-dihydro-1H-pyrrolo[3,4-c]pyridin-1-one (9d) (706 mg, 2.95 mmol), Zn(CN)$_2$ (519 mg, 4.42 mmol), DMF (10 mL) and Pd(PPh$_3$)$_4$ (170 mg, 0.147 mmol) was heated to 140° C. in the microwave for 30 min. The reaction was diluted with DCM and filtered. The filter cake was washed with DCM. The filtrate was concentrated in vacuo to provide the title compound (10a) as a yellow solid (544 mg, 80% yield) which was used without further purification. $^1$H NMR (400 MHz, DMSO-d$_6$) 9.01 (s, 1H), 7.13 (s, 1H), 4.80 (td, J=6.7, 13.4 Hz, 1H), 4.47 (s, 2H), 2.89 (s, 3H), 1.15 (d, J=6.7 Hz, 6H); m/z (APCI+) for (C$_{12}$H$_{14}$N$_4$O), 231.2 (M+H)$^+$.

Step 2: 6-[methyl(propan-2-yl)amino]-4-propanoyl-2,3-dihydro-1H-pyrrolo[3,4-c]pyridin-1-one (10b)

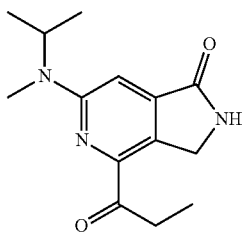

10b

A suspension of 6-[methyl(propan-2-yl)amino]-1-oxo-2,3-dihydro-1H-pyrrolo[3,4-c]pyridine-4-carbonitrile (10a) (511 mg, 2.22 mmol) in THF (20.0 mL) was cooled to 0° C. and then treated with a solution of ethylmagnesium bromide (3.0 M in Et$_2$O, 7.40 mL, 22.2 mmol). The mixture was stirred at RT for 1 h. LCMS analysis showed consumption of the starting material. The reaction was cooled to 0° C. and quenched by addition of saturated NH$_4$Cl (60 mL) and then extracted with DCM (2×80 mL). The combined organic layers were dried over Na$_2$SO$_4$, filtered, and concentrated. The residue was purified by flash chromatography (24 g SiO$_2$, 0-100% EtOAc/heptane) to provide the title compound (10b) (125 mg, 22% yield) as a yellow foam. m/z (APCI+) for (C$_{14}$H$_{19}$N$_3$O$_2$), 262.2 (M+H)$^+$.

Step 3: Intermediate 10

To a solution of 6-[methyl(propan-2-yl)amino]-4-propanoyl-2,3-dihydro-1H-pyrrolo[3,4-c]pyridin-1-one (10b) (124 mg, 0.475 mmol) in THF (6.0 mL) were added (S)-(−)-2-methyl-2-propanesulfinamide (92 mg, 0.759 mmol) and Ti(OEt)$_4$ (433 mg, 1.90 mmol). The mixture was stirred at reflux for 42 h. LCMS analysis showed consumption of the starting material. The mixture was cooled to −78° C. and then treated dropwise with a solution of L-selectride (1.0 M in THF, 1.9 mL, 1.90 mmol). The mixture was stirred at −78° C. for 4 h. The mixture was quenched with MeOH, diluted with brine (30 mL), and extracted with DCM (20×2 mL). The combined organic layers were dried over Na$_2$SO$_4$, filtered, and concentrated. The residue was purified by flash chromatography (12 g SiO$_2$, 0-10% MeOH/DCM) to provide Intermediate 10 (72 mg, 41% yield) as a yellow solid. $^1$H NMR (400 MHz, DMSO-d$_6$) δ 8.67 (s, 1H), 6.64 (s, 1H), 5.25 (d, J=6.7 Hz, 1H), 4.94 (quin, J=6.7 Hz, 1H), 4.34 (s, 2H), 4.21 (q, J=6.7 Hz, 1H), 2.84 (s, 3H), 1.98-1.80 (m, 2H), 1.13 (dd, J=3.6, 6.7 Hz, 6H), 1.06 (s, 9H), 0.83 (t, J=7.3 Hz, 3H). m/z (APCI+) for (C$_{18}$H$_{30}$N$_4$O$_2$S), 367.2 (M+H)$^+$. Stereochemistry was assigned based on use of (S)-(−)-2-methyl-2-propanesulfinamide in step 2.

Intermediate 11: tert-butyl {[6-(dimethylamino)-1-oxo-2,3-dihydro-1H-pyrrolo[3,4-c]pyridin-4-yl]methyl}methylcarbamate

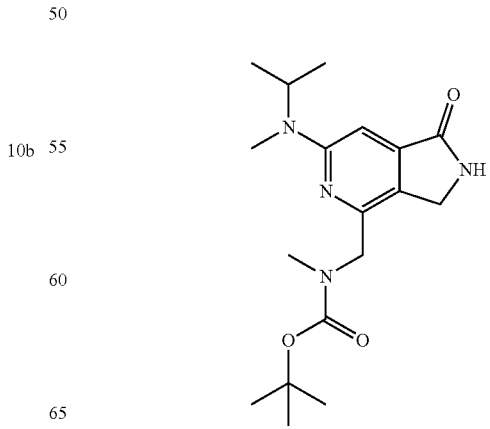

Step 1: 2-chloro-6-(dimethylamino)-N,N-dimethylpyridine-4-carboxamide (11a)

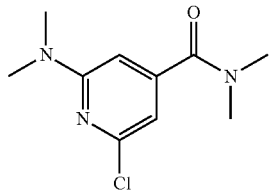

11a

To a 3.0 L round-bottom flask charged with methyl 2,6-dichloropyridine-4-carboxylate (58.0 g, 281 mmol) under an atmosphere of $N_2$ was added N,N-dimethylamine (38.1 g, 845 mmol) at 0-10° C. THF (200 mL) was added. A solution of i-PrMgCl (2.0 M in THF, 352 mL, 704 mmol) was added over 3 h, maintaining the reaction temperature at 0-10° C. The reaction was stirred a further 10 min at 0° C. and then at 25° C. for 18 h. LCMS analysis showed consumption of the starting material. The reaction was cooled in an ice bath and quenched by addition of cold saturated aqueous $NH_4Cl$ (500 mL), maintaining the reaction temperature<20° C. EtOAc (500 mL) was added and the layers were separated. The aqueous layer was extracted with EtOAc (500 mL). The combined organic layers were washed with brine, dried over $Na_2SO_4$, filtered, and concentrated. The resultant oil was taken up in heptane (200 mL) and concentrated on a rotary evaporator until solids formed. The suspension was stirred for 0.5 h and the solids were collected by filtration. The filter cake was washed with hexanes (3×50 mL). The filter cake was slurried in 1:20 EtOAc/petroleum ether (100 mL) and the solids were collected by filtration. The filter cake was washed with 1:20 EtOAc/petroleum ether (3×30 mL) and then dried under vacuum to provide the title compound (11a) (51 g, 80% yield) as a light-yellow solid. $^1$H NMR (400 MHz, CDCl$_3$) δ 6.49 (d, J=0.7 Hz, 1H), 6.35 (d, J=0.9 Hz, 1H), 3.13-3.09 (m, 9H), 2.98 (s, 3H); m/z (ESI+) for ($C_{10}H_{14}ClN_3O$), 227.9 (M+H)$^+$.

Step 2: 2-chloro-6-(dimethylamino)-3-formyl-N,N-dimethylpyridine-4-carboxamide (11b)

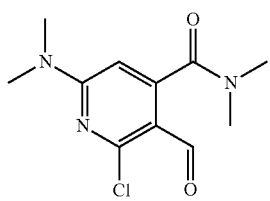

11b

Two sets of reactions were run in parallel. To a round-bottom flask containing DMF (250 mL), with stirring, was added POCl$_3$ (85.9 g, 560 mmol) at 15-25° C. The mixture was stirred at 15-25° C. for 15 min and then 2-chloro-6-(dimethylamino)-N,N-dimethylpyridine-4-carboxamide (11a) (25.5 g, 112 mmol) was added. The mixture was stirred at 50° C. for 16 h. LCMS analysis showed consumption of the starting material. The two reactions were combined and then quenched by slowly pouring into cold aqueous saturated Na$_2$CO$_3$, maintaining the pH~9. The mixture was extracted with EtOAc (4×1.0 L). The combined organics were washed with brine (5×600 mL), dried over Na$_2$SO$_4$, filtered, and concentrated. The crude product was combined with two additional reactions run in identical fashion with 7.5 g and 5.0 g 2-chloro-6-(dimethylamino)-N,N-dimethylpyridine-4-carboxamide. The material was taken up in EtOAc (200 mL) and slurried for 20 min. The suspension was filtered. The filter cake was washed with EtOAc (2×50 mL). The filter cake was slurried in 1:1 petroleum ether/EtOAc (80 mL) for 20 min. The suspension was filtered and the filter cake was washed with 1:1 petroleum ether/EtOAc (60 mL). The filter cake was dried under vacuum. The combined filtrate was concentrated to dryness. The residue was slurried with 1:1 petroleum ether/EtOAc (100 mL) for 30 min. The suspension was filtered and the filter cake was washed with 1:1 petroleum ether/EtOAc (2×50 mL) and dried under vacuum. The combined dried solids were slurried in petroleum either (200 mL) for 10 min and the solids were collected by filtration. The filter cake was washed with petroleum ether (100 mL) and then concentrated under vacuum. The combined filtrate was concentrated under vacuum to ~50 mL and then let stand for 2 d. The resultant solids were collected by filtration and the filter cake was washed with 3:2 petroleum ether/EtOAc (2×50 mL). The solids were combined to the title compound (11b) (52 g, 73% yield for the combined set of reactions) as a yellow solid. $^1$H NMR (400 MHz, CDCl$_3$) δ 10.21 (d, J=0.6 Hz, 1H), 6.28 (d, J=0.6 Hz, 1H), 3.19 (s, 6H), 3.13 (s, 3H), 2.77 (s, 3H); m/z (ESI+) for ($C_{11}H_{14}ClN_3O_2$), 255.9 (M+H)$^+$.

Step 3: tert-butyl {[6-(dimethylamino)-4-(dimethylcarbamoyl)-3-formylpyridin-2-yl]methyl}methylcarbamate (11c)

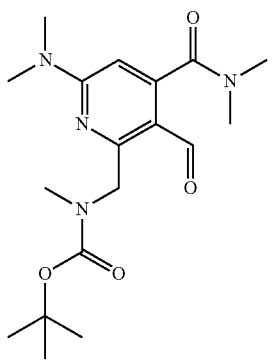

11c

A mixture of tert-butyl dimethylcarbamate (3.41 g, 23.5 mmol) and N,N,N,N-tetramethylenediamine (3.27 g, 28.2 mmol) in 135 mL THF was cooled to −55° C. under an atmosphere of $N_2$. A solution of s-BuLi (1.4 M in cyclohexane, 20.1 mL, 28.2 mmoL) was added slowly maintaining the solution temperature at less than −52° C. (internal). The mixture was stirred for an additional 30 min at −55° C. and then treated with a solution of $ZnCl_2$ (1.9 M in 2-methyltetrahydrofuran, 14.8 mL, 28.2 mmol), maintaining the reaction temperature at less than −52° C. The solution was stirred for an additional 40 min at −55° C. and then warmed to RT to provide a solution of {[(tert-butoxycarbonyl)(methyl)amino]methyl}(chlorido)zinc (c=0.195 M). A portion of the pre-formed zincate solution (90.2 mL, 17.6 mmoL) was transferred to an oven-dried 250 mL round bottom flask under an atmosphere of $N_2$ and concentrated to dryness to provide a white foam. The flask was back-filled with $N_2$. A separate flask was charged with 2-chloro-6-(dimethylamino)-3-formyl-N,N-dimethylpyridine-4-carboxamide (11b) (3.0 g, 10 mmol), $PdCl_2(dppf)$ (0.858 g, 1.17 mmol), 1,4-dioxane (50 mL) and $H_2O$ (0.159 g, 8.8 mmol). The suspension was transferred to the flask containing the zincate via cannulation and then the mixture was stirred at 80° C. for 80 min. LCMS showed formation of a product mass with some remaining starting material. An additional aliquot of {[(tert-butoxycarbonyl)(methyl)amino]methyl}(chlorido)zinc solution (2.0 mL) was added and the mixture was stirred at 80° C. for 20 min. No additional conversion was observed. The reaction was cooled to 0° C. and quenched by addition of saturated aqueous $NH_4Cl$ (10 mL) and $H_2O$ (20 mL). The mixture was stirred at 0° C. for 20 min and then filtered through a pad of Celite®. The filtrate was extracted with EtOAc (4×). The combined organics were dried over $Na_2SO_4$, filtered, and concentrated. The residue was purified by flash chromatography (80 g $SiO_2$, 0-100% EtOAc/heptane. The resultant white foam was triturated with MTBE and concentrated under vacuum to provide the title compound (11c) (3.8 g, 95% yield) as a light-yellow solid. $^1H$ NMR (400 MHz, DMSO-$d_6$) δ 9.84 (d, J=6.8 Hz, 1H), 6.45 (s, 1H), 4.71 (s, 2H), 3.15 (s, 6H), 2.99 (s, 3H), 2.90 (s, 3H), 2.75 (s, 3H), 1.33 (d, J=69.8 Hz, 9H); m/z (ESI+) for ($C_{18}H_{28}N_4O_4$), 365.3 (M+H)$^+$.

Step 4: tert-butyl {[6-(dimethylamino)-4-(dimethylcarbamoyl)-3-{(E)-[(2-methylpropane-2-sulfinyl)imino]methyl}pyridin-2-yl]methyl}methylcarbamate (11d)

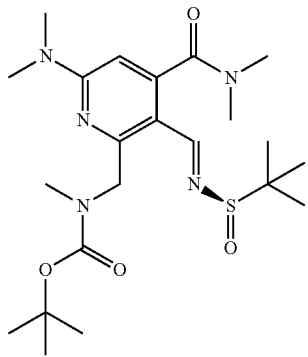

To a solution of tert-butyl {[6-(dimethylamino)-4-(dimethylcarbamoyl)-3-formylpyridin-2-yl]methyl}methylcarbamate (11c) (3.0 g, 8.0 mmol) and (R)-(+)-2-methyl-2-propanesulfinamide (1.2 g, 9.88 mmol) in THF (40 mL) was added Ti(OEt)$_4$ (5.63 g, 24.7 mmol). The mixture was stirred at 50° C. overnight. The reaction was cooled to RT, diluted with DCM (50 mL), and quenched by addition of a saturated solution of $NaHCO_3$ (20 mL). The solution was vigorously stirred for 20 min and then filtered through a pad of Celite®. The Celite® was washed with DCM (3×). The combined filtrate was dried over $Na_2SO_4$, filtered, and concentrated. The residue was purified by flash chromatography (80 g $SiO_2$, 0-100% EtOAc/heptane) to provide the title compound (11d) (3.89 g, 97% yield) as a colorless foam. $^1H$ NMR (400 MHz, DMSO-$d_6$) δ 8.39 (s, 1H), 6.46 (s, 1H), 4.77-4.55 (m, 2H), 3.12 (s, 6H), 2.95 (s, 3H), 2.93 (s, 3H), 2.74 (s, 3H), 1.41 (s, 4H), 1.20 (s, 5H), 1.12 (s, 9H); m/z (ESI+) for ($C_{22}H_{37}N_5O_4S$), 468.4 (M+H)$^+$.

Step 5: Intermediate 11

To round-bottom flask charged with tert-butyl {[6-(dimethylamino)-4-(dimethylcarbamoyl)-3-{(E)-[(2-methylpropane-2-sulfinyl)imino]methyl}pyridin-2-yl]methyl}methylcarbamate (11d) (3.89, 8.32 mmol) under an atmosphere of $N_2$ was added THF (42 mL). The mixture was cooled to 0° C. and then treated with a solution of $LiBH_4$ (2.0 M in THF, 4.37 mL, 8.73 mmol). The mixture was stirred at 0° C. for 1 h and then a solution of NaOMe (25% in MeOH, 17.1 mL, 74.9 mmol) was added at the same temperature. The reaction was allowed to warm slowly to RT and stirred for 16 h. LCMS analysis indicated consumption of the starting material. The mixture was diluted with DCM and washed with saturated aqueous $NH_4Cl$ and brine. The organic layer was dried over $Na_2SO_4$, filtered, and concentrated. The residue was purified by flash chromatography (80 g $SiO_2$, 0-100% EtOAc/heptanes) to provide Intermediate 11 (1.7 g, 64% yield) as a colorless foam. $^1H$ NMR (400 MHz, DMSO-$d_6$) δ 8.68 (s, 1H), 6.68 (s, 1H), 4.42 (s, 2H), 4.23 (s, 2H), 3.06 (s, 6H), 2.86 (s, 3H), 1.36 (m, 9H); LCMS m/z (ESI+) for ($C_{16}H_{24}N_4O_3$), 321.2 (M+H)$^+$.

Intermediate 12: 2-bromo-6-(4-propyl-4H-1,2,4-triazol-3-yl)pyridine

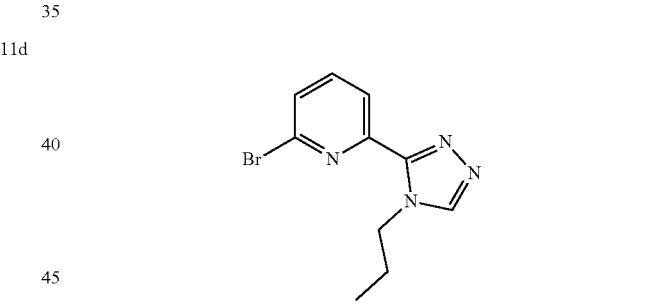

A mixture of N'-[(6-bromopyridin-2-yl)carbonyl]-N,N-dimethylhydrazonoformamide (1b) (29.0 g, 106.8 mmol) and propan-1-amine (31.6 g, 534 mmoL) in MeCN (440 mL) and acetic acid (110 mL) was stirred at 95° C. for 16 h. LCMS analysis showed consumption of the starting material. The reaction was concentrated to dryness. The residue was taken up in $H_2O$ (50 mL) and basified to pH~9 with 1 N NaOH (~500 mL). The mixture was extracted with EtOAc (3×150 mL). The combined organic layers were washed with brine (150 mL), dried over $Na_2SO_4$, filtered, and concentrated. The residue was slurried with EtOAc (50 mL) for 10 min and the solid was collected by filtration. The filter cake was washed with petroleum ether (2×50 mL) and dried in vacuum to provide the title compound (Intermediate 12) (21.0 g, 74% yield) as a yellow solid. $^1H$ NMR (400 MHz, DMSO-$d_6$) δ 8.74 (s, 1H), 8.20 (dd, J=0.7, 7.8 Hz, 1H), 7.98-7.91 (m, 1H), 7.78 (dd, J=0.7, 8.0 Hz, 1H), 4.45-4.36 (m, 2H), 1.77 (sxt, J=7.4 Hz, 2H), 0.87 (t, J=7.4 Hz, 3H); m/z (ESI+) for ($C_{10}H_{11}BrN_4$), 266.7 (M+H)$^+$.

Intermediate 13: (S,S)-2-methyl-N-[(1R)-1-{6-[methyl(propan-2-yl)amino]-1-oxo-2,3-dihydro-1H-pyrrolo[3,4-c]pyridin-4-yl}ethyl]propane-2-sulfinamide

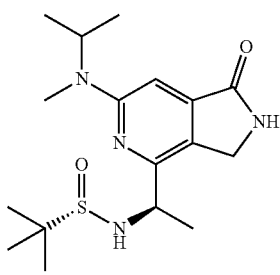 [SMILES: CC(C)N(C)c1cc2c(c([C@@H](C)N[S@@](=O)C(C)(C)C)n1)CNC2=O]

Step 1: 4-acetyl-6-(isopropyl(methyl)amino)-2,3-dihydro-1H-pyrrolo[3,4-c]pyridin-1-one

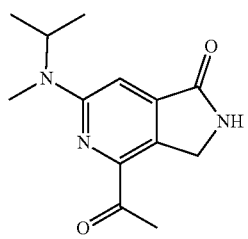

13a

Methylmagnesium bromide (9.11 g, 76.4 mmol, 25.9 mL, 3.0 M) was added to a solution of 6-(isopropyl(methyl)amino)-1-oxo-2,3-dihydro-1H-pyrrolo[3,4-c]pyridine-4-carbonitrile (Intermediate 10a) (1.76 g, 7.64 mmol) in THF (70 mL, c=0.11 M) at 0° C. The mixture was stirred at this temperature for 10 min and then allowed to warm to RT and allowed to stir for 3 h. The mixture was then quenched with 2 M HCl (7 mL) dropwise at RT and allowed to stir for 30 min. A saturated solution of NaHCO$_3$ (70 mL) was added to neutralize the solution and it was extracted with DCM (3×100 mL). The combined organic layers were dried over Na$_2$SO$_4$ and concentrated in vacuo. The resulting residue was purified by flash chromatography (40 g SiO$_2$, 10-40% EtOAc/heptane) to provide the title compound (13a) as a yellow solid (553 mg, 29% yield). $^1$H NMR (400 MHz, DMSO-d6) δ 8.82 (s, 1H) 7.06 (s, 1H) 4.88 (br. d, J=6.72 Hz, 1H) 4.49 (s, 2H) 2.94 (s, 3H) 2.61 (s, 3H) 1.19 (d, J=6.60 Hz, 6H); m/z (APCI+) for (C$_{13}$H$_{17}$N$_3$O$_2$), 248.2 (M+H)$^+$.

Step 2: Intermediate 13

A mixture of 4-acetyl-6-[methyl(propan-2-yl)amino]-2,3-dihydro-1H-pyrrolo[3,4-c]pyridin-1-one (13a) (8.10 g, 32.75 mmol), (S)-tert-butylsulfinamide (7.94 g, 65.5 mmol) in Ti(OEt)$_4$ (29.9 g, 131 mmol) in THF (100 mL) under N$_2$ was heated at 90° C. for 72 h and the reaction was monitored by LCMS. The reaction was then cooled to 0° C. and L-selectride (1 M in THF, 131 mmol, 131 mL) was added dropwise at 0° C. The mixture was stirred at 0° C. for 3 h. The mixture was quenched with saturated NH$_4$Cl (200 mL) and brine (200 mL) at 0-5° C. The suspension was filtered through a pad of Celite® and the filter cake was washed with DCM (500 mL). The filtrate layers were separated, and the aqueous layer was extracted with DCM (2×100 mL). The combined organic layers were washed with brine (250 mL), dried over Na$_2$SO$_4$, filtered and concentrated. The residue was purified by flash chromatography (SiO$_2$, 0-10% MeOH/DCM) to provide Intermediate 13 as a yellow solid (10 g, 87%). $^1$H NMR (400 MHz, CDCl$_3$) δ 6.83 (br. s, 1H), 6.75 (s, 1H), 4.89-4.76 (m, 1H), 4.48-4.39 (m, 1H), 4.37-4.26 (m, 3H), 2.83 (s, 3H), 1.55 (d, J=6.6 Hz, 3H), 1.19-1.07 (m, 15H). m/z (APCI+) for (C$_{17}$H$_{28}$N$_4$O$_2$S), 353.2 (M+H)$^+$. Stereochemistry was assigned based on use of (S)-tert-butylsulfinamide in step 1.

Intermediate 14: (S,R)-2-methyl-N-[(1 S)-1-{6-[(2R)-2-methylpyrrolidin-1-yl]-1-oxo-2,3-dihydro-1H-pyrrolo[3,4-c]pyridin-4-yl}ethyl]propane-2-sulfinamide

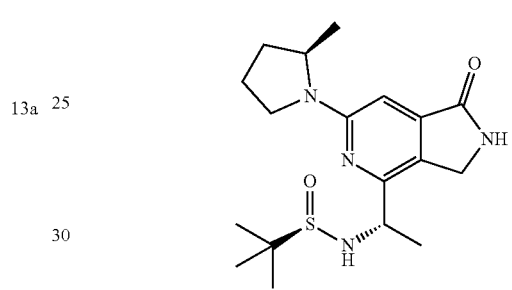

A mixture of 4-acetyl-6-[(2R)-2-methylpyrrolidin-1-yl]-2,3-dihydro-1H-pyrrolo[3,4-c]pyridin-1-one (4f) (4000 mg, 15.43 mmol), (R)-2-methylpropane-2-sulfinamide (2240 mg, 18.5 mmol) in Ti(OEt)$_4$ (20 mL) was stirred at 100° C. for 20 h under N$_2$. LCMS analysis showed consumption of the starting material. The yellow solution was cooled to 0° C. and was diluted with THF (50 mL). L-Selectride (38.6 mmol, 38.6 mL, 1M in THF) was added dropwise at 0° C. The mixture was then stirred at 10° C. for 20 h. LCMS showed starting material remaining. Additional L-Selectride (38.6 mmol, 38.6 mL 1M in THF) was added dropwise at 0° C. and the mixture was stirred at 10° C. for an additional 2 h. TLC analysis showed consumption of the starting material. The mixture was quenched with saturated aqueous NH$_4$Cl (200 mL) at 0-5° C. The suspension was filtered through a pad of Celite® and the cake was washed with EtOAc (2×50 mL). The filtrate layers were separated, and the aqueous layer was extracted with EtOAc (2×20 mL). The combined organic layers were washed with brine (30 mL), dried over Na$_2$SO$_4$, filtered and concentrated to provide a residue. The residue was first purified by flash chromatography (SiO$_2$, EtOAc/MeOH=10:1) and then further purified by prep HPLC (ACSSH-CA; Method column: YMC Triart C18 250*50 mm*7 μm; water (0.05% ammonia hydroxide v/v)-ACN to provide Intermediate 14 (2.5 g, 44%) as an off-white solid. $^1$H NMR (400 MHz, CDCl$_3$) δ 6.70 (s, 1H), 6.47 (br. s, 1H), 4.57-4.34 (m, 4H), 4.20 (br. t, J=5.9 Hz, 1H), 3.64-3.53 (m, 1H), 3.47-3.35 (m, 1H), 2.20-1.99 (m, 3H), 1.77 (br. dd, J=2.5, 4.7 Hz, 1H), 1.64 (d, J=6.5 Hz, 3H), 1.28 (d, J=6.2 Hz, 3H), 1.22 (s, 9H). m/z (ESI) for (C$_{18}$H$_{28}$N$_4$O$_2$S), 365.1 (M+H)$^+$. Stereochemistry was assigned based on use of (R)-tert-butylsulfinamide.

Intermediate 15: tert-butyl {2-methoxy-1-[6-(1-methylcyclopropyl)-1-oxo-2,3-dihydro-1H-pyrrolo[3,4-c]pyridin-4-yl]ethyl}carbamate

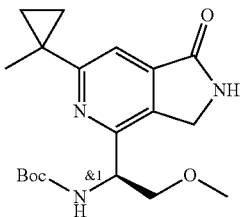

Step 1: ethyl 3-cyano-2-hydroxy-6-(1-methylcyclopropyl)pyridine-4-carboxylate (15a)

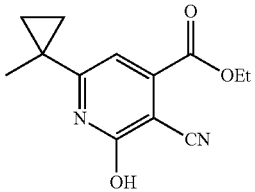

A mixture of 2-cyanoacetamide (10.0 g, 119 mmol) and TEA (12.0 g, 119 mmol) in EtOH (50 mL) was heated to 65° C. (internal temperature) until the solids dissolved and then ethyl 3-(1-methylcyclopropyl)-3-oxopropanoate (24.6 g, 124 mmol) was added. The mixture was stirred at 65° C. for 2 h. TLC analysis (1:10 EtOAc/petroleum ether) showed consumption of the starting material. The reaction was cooled to 10° C. The resultant precipitate was collected by filtration. The filter cake was washed with MTBE (3×10 mL) and dried under vacuum. The filtrate was concentrated to dryness. EtOH (10 mL) was added and then MTBE (30 mL) was added. The resultant solids were collected by filtration. The filter cake was washed with EtOH (5 mL) and MTBE (2×10 mL) and dried under vacuum. The solids were combined to provide the title compound (15a) (25.0 g, 85% yield) as a yellow solid. $^1$H NMR (400 MHz, DMSO-$d_6$) δ 12.74 (br. s, 1H), 6.63 (br. s, 1H), 4.36 (q, J=7.1 Hz, 2H), 1.45-1.27 (m, 6H), 1.16-1.06 (m, 2H), 0.92-0.75 (m, 2H).

Step 2: ethyl 2-chloro-3-cyano-6-(1-methylcyclopropyl)pyridine-4-carboxylate (15b)

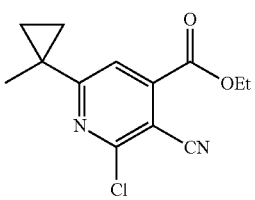

To a solution of ethyl 3-cyano-2-hydroxy-6-(1-methylcyclopropyl)pyridine-4-carboxylate (15a) (24.0 g, 97.5 mmol) in MeCN (487 mL) was added POCl$_3$ (74.7 g, 487 mmol) dropwise at 30° C. The mixture was stirred at 65° C. for 60 h. TLC analysis (EtOAc) showed consumption of the starting material. The solution was concentrated to remove residual POCl$_3$. The residue was poured onto ice and basified with a saturated solution of NaHCO$_3$ to pH~ 8. The mixture was extracted with EtOAc (2×100 mL). The combined organic layers were dried over Na$_2$SO$_4$, filtered, and concentrated. The residue was purified by flash chromatography (1:10 EtOAc/petroleum ether) to provide the title compound (15b) (21.9 g, 85% yield) as a light yellow solid. $^1$H NMR (400 MHz, CDCl$_3$) δ 7.79 (s, 1H), 4.50 (q, J=7.2 Hz, 2H), 1.55 (s, 3H), 1.50-1.40 (m, 5H), 1.03 (q, J=3.9 Hz, 2H); m/z (ESI+) for ($C_{13}H_{13}ClN_2O_2$), 264.9 (M+H)$^+$.

Step 3: 4-chloro-6-(1-methylcyclopropyl)-2,3-dihydro-1H-pyrrolo[3,4-c]pyridin-1-one (15c)

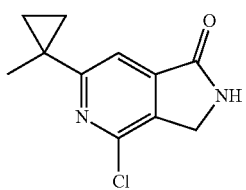

To a solution of ethyl 2-chloro-3-cyano-6-(1-methylcyclopropyl)pyridine-4-carboxylate (15b) (2.5 g, 9.44 mmol) in EtOH (500 mL) was added Raney Ni (2.0 g 34.1 mmol). The black mixture was stirred at 30° C. under an atmosphere of H$_2$ at 30 psi for 48 h. TLC analysis (1:10 EtOAc/petroleum ether) showed consumption of the starting material. The mixture was filtered through a pad of Celite®. The filter cake was washed with MeOH (250 mL). The combined filtrate was concentrated to dryness. The residue was slurried in EtOAc (5 mL) for 20 min and the suspension was filtered. The filter cake was washed with EtOAc (2 mL) and dried under vacuum to provide the title compound (15c) (1.1 g, 52% yield) as a grey solid. $^1$H NMR (400 MHz, CDCl$_3$) δ 7.66 (br. s, 1H), 7.23-7.05 (m, 1H), 4.56-4.34 (m, 2H), 1.55 (br. s, 3H), 1.39-1.11 (m, 2H), 0.99-0.66 (m, 2H); m/z (ESI+) for ($C_{11}H_{11}ClN_2O$), 222.8 (M+H)$^+$.

Step 4: Intermediate 15

A 40 mL vial was charged with 4-chloro-6-(1-methylcyclopropyl)-2,3-dihydro-1H-pyrrolo[3,4-c]pyridin-1-one (15c) (200 mg, 0.898 mmol), Cs$_2$CO$_3$ (644 mg, 1.98 mmol), N-(tert-butoxycarbonyl)-O-methylserine (394 mg, 1.80 mmol), NiCl$_2$·glyme (39.5 mg, 0.18 mmol), pyridine-2-yl-N-cyanoamidine (26.3 mg, 0.180 mmol), iridium(II) bis[2-(2,4-difluorophenyl)-5-methylpyridine]-4,40-di-tert-butyl-2,20-bipyridine hexafluorophosphate (18.2 mg, 0.018 mmol) and anhydrous DMF (27 mL). The mixture was sparged with N$_2$ for 2 min and irradiated with 365 nM light at 15-25° C. for 18 h (fan speed 5200 r/min, stir rate 1200 r/min, 100% LED). The mixture was concentrated and purified by flash chromatography (SiO$_2$, 10-20% [0% MeOH in EtOAc] in petroleum ether) to provide a yellow solid. Purification by prep. HPLC (Column: YMC Triart C18 150*25 μm*5 μm, water (0.05% ammonia hydroxide v/v)-CAN) provided Intermediate 15 as a white solid (315 mg, 32%). $^1$H NMR (400 MHz, CDCl$_3$) δ 7.65 (s, 1H), 6.77 (s, 1H), 5.66 (d, J=8.0 Hz, 1H), 4.94 (d, J=6.3 Hz, 1H), 4.63-4.48 (m, 2H), 3.77 (dd, J=8.9, 5.0 Hz, 1H), 3.58-3.44 (m, 1H), 3.26 (s, 3H), 1.62 (s, 3H), 1.45 (s, 9H), 1.30 (q, J=3.6 Hz, 2H), 0.88 (q, J=3.4 Hz, 2H); m/z (ESI+) for ($C_1H_{27}N_3O_4$), 362.3 (M+H)$^+$.

EXAMPLES

The Examples prepared herein have stereochemistry assigned based on use of intermediates with confirmed stereochemistry, e.g., Examples 1 and 2, or based on the use of intermediates prepared from stereospecific starting materials, e.g., Examples 3 and 4.

Example 1: 4-[(1R)-1-aminopropyl]-2-{6-[(5S)-5-methyl-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one

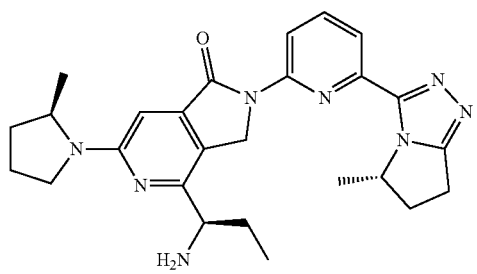 [SMILES: CC[C@@H](N)c1nc(N2CCC[C@H]2C)cc2c1CN(c1cccc(-c3nnc4n3[C@@H](C)CC4)n1)C2=O]

Step 1: (S,S)-2-methyl-N-[(1R)-1-(2-{6-[(5S)-5-methyl-6,7-dihydro-5H-pyrrolo[2,1-c][1,2,4]triazol-3-yl]pyridin-2-yl}-6-[(2R)-2-methylpyrrolidin-1-yl]-1-oxo-2,3-dihydro-1H-pyrrolo[3,4-c]pyridin-4-yl)propyl]propane-2-sulfinamide

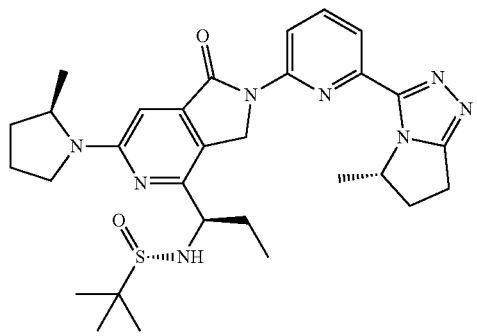 [SMILES: CC[C@@H](N[S@@](=O)C(C)(C)C)c1nc(N2CCC[C@H]2C)cc2c1CN(c1cccc(-c3nnc4n3[C@@H](C)CC4)n1)C2=O]

A mixture of (S,S)-2-methyl-N-[(1R)-1-{6-[(2R)-2-methylpyrrolidin-1-yl]-1-oxo-2,3-dihydro-1H-pyrrolo[3,4-c]pyridin-4-yl}propyl]propane-2-sulfinamide (Intermediate 5) (63.0 mg, 0.17 mmol), (5S)-3-(6-bromopyridin-2-yl)-5-methyl-6,7-dihydro-5H-pyrrolo[2,1-c][1,2,4]triazole (Intermediate 2) (147 mg, 0.528 mmol), $K_3PO_4$ (336 mg, 1.59 mmol), $Pd_2(dba)_3$ (30.4 mg, 0.0528 mmol) and XantPhos (61.1 mg, 0.106 mmol) in 1,4-dioxane (4.5 mL, c=0.1 M) was heated at 100° C. (block temp) in 40 mL vial (capped) for 18 h. The mixture was filtered through Celite®, washed with DCM. The filtrate was concentrated in vacuo and the crude compound was purified by flash chromatography ($SiO_2$, 0-10% MeOH/DCM) to provide the title compound as pale yellow color foam (194 mg, 64% yield). m/z (APCI+) for ($C_{29}H_{40}N_8O_2S$), 577.3 (M+H)$^+$.

Step 2: Example 1

A solution of 4 N HCl in 1,4-dioxane (1.01 mmol, 0.252 mL, 4 M) was added to a suspension of (S,S)-2-methyl-N-[(1R)-1-(2-{6-[(5S)-5-methyl-6,7-dihydro-5H-pyrrolo[2,1-c][1,2,4]triazol-3-yl]pyridin-2-yl}-6-[(2R)-2-methylpyrrolidin-1-yl]-1-oxo-2,3-dihydro-1H-pyrrolo[3,4-c]pyridin-4-yl)propyl]propane-2-sulfinamide (194 mg, 0.336 mmol) in MeOH (12 mL). The resulting mixture was stirred at RT for 2 h. The volatiles were removed under reduced pressure. The crude product was purified by Chiral SFC (Phenomenex Lux Cellulose-1 4.6×100 mm 3 µm column 30% MeOH+10 mM $NH_3$ in $CO_2$ @ 120 bar, 4 mL/min) to provide Example 1 (146 mg, 92% yield, >99% de) as pale yellow color solid. $^1$H NMR (600 MHz, DMSO-$d_6$) δ 8.48 (d, J=8.3 Hz, 1H), 8.01 (t, J=8.0 Hz, 1H), 7.91 (d, J=7.7 Hz, 1H), 6.67 (s, 1H), 5.22-5.03 (m, 3H), 4.33-4.21 (m, 2H), 3.60-3.50 (m, 1H), 3.41-3.32 (m, 1H), 3.06-2.98 (m, 1H), 2.97-2.89 (m, 1H), 2.88-2.76 (m, 1H), 2.37-2.27 (m, 1H), 2.09-1.86 (m, 5H), 1.69-1.62 (m, 1H), 1.44 (d, J=6.4 Hz, 3H), 1.15 (d, J=6.2 Hz, 3H), 0.86 (t, J=7.4 Hz, 3H); m/z (APCI+) for ($C_{26}H_{32}N_8O$), 473.2 (M+H)$^+$; [α]$D_{22}$=+37.0° (c=0.1 M, MeOH).

Table 4 provides single crystal X-ray diffraction data confirming the stereochemistry of Example 1. The single crystal X-ray diffraction studies were carried out on a Bruker Microstar APEX II CCD diffractometer equipped with Cu $K_α$ radiation (λ=1.54178 Å). Crystals of Example 1 were grown from acetonitrile/pentane. A 0.25×0.2×0.15 mm piece of a colorless crystal was mounted on a Cryoloop with Paratone oil. Data were collected in a nitrogen gas stream at 100(2) K using φ and $\overline{ω}$ scans. Crystal-to-detector distance was 40 mm and exposure time was 2, or 10 seconds depending on the 2θ range per frame using a scan width of 1.00°. Data collection was 99.4% complete to 67.679° in θ. The data were integrated using the Bruker SAINT Software program and scaled using the SADABS software program. Solution by direct methods (SHELXT) produced a complete phasing model consistent with the proposed structure. All nonhydrogen atoms were refined anisotropically by full-matrix least-squares (SHELXL-2014). All carbon bonded hydrogen atoms were placed using a riding model. Their positions were constrained relative to their parent atom using the appropriate HFIX command in SHELXL-2014.

TABLE 4

| | | |
|---|---|---|
| Empirical formula: | $C_{31}H_{45}N_8O_2$ | |
| Molecular weight | 561.75 | |
| Temperature | 100.0 K | |
| Wavelength | 1.54178 Å | |
| Crystal system | Orthorhombic | |
| Space group | $P2_12_12_1$ | |
| Unit cell dimensions: | a = 6.7104(13) Å | α = 90°. |
| | b = 15.482(3) Å | β = 90°. |
| | c = 30.288(6) Å | γ = 90°. |

TABLE 4-continued

| | |
|---|---|
| Volume | 3146.6(11) A3 |
| Z | 4 |
| Density (calculated) | 1.186 Mg/m$^3$ |
| Absorption coefficient | 0.611 mm$^{-1}$ |
| F(000) | 1212 |
| Crystal size | 0.25 × 0.2 × 0.15 mm$^3$ |
| Theta range for data collection | 2.918 to 68.067°. |
| Index ranges | −7 <= h <= 7, −18 <= k <= 18, −36 <= l <= 36 |
| Reflections collected | 27016 |
| Independent reflections | 5698 [R(int) = 0.0296] |
| Completeness to theta = 67.679° | 99.4% |
| Absorption correction | Semi-empirical from equivalents |
| Max. and min. transmission | 0.5201 and 0.4162 |
| Refinement method | Full-matrix least-squares on F$^2$ |
| Data/restraints/parameters | 5698/1/389 |
| Goodness-of-fit on F$^2$ | 1.067 |
| Final R indices [l > 2sigma(l)] | R1 = 0.0726, wR2 = 0.2035 |
| R indices (all data) | R1 = 0.0768, wR2 = 0.2088 |
| Absolute structure parameter | −0.10(10) |
| Largest diff. peak and hole | 0.630 and −0.318e.Å$^3$ |

Example 2: 4-[(1R)-1-aminoethyl]-2-{6-[(5S)-5-ethyl-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one

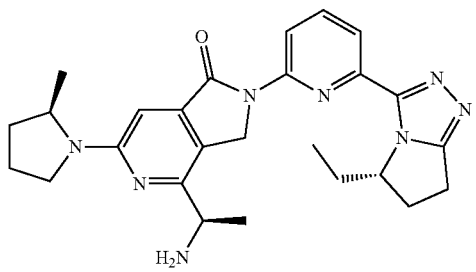 [SMILES: CC[C@H]1CCc2nnc(-c3cccc(N4Cc5c(cc(N6CCC[C@H]6C)nc5[C@@H](C)N)C4=O)n3)n21]

Step 1: (S,S)—N-[(1R)-1-(2-{6-[(5S)-5-ethyl-6,7-dihydro-5H-pyrrolo[2,1-c][1,2,4]triazol-3-yl]pyridin-2-yl}-6-[(2R)-2-methylpyrrolidin-1-yl]-1-oxo-2,3-dihydro-1H-pyrrolo[3,4-c]pyridin-4-yl)ethyl]-2-methylpro pane-2-sulfinamide

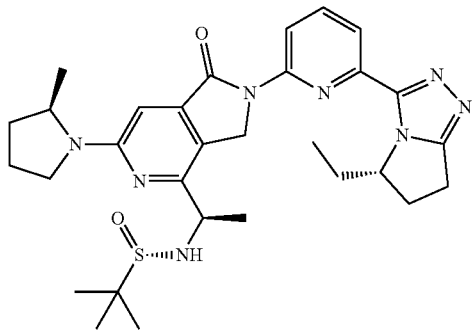 [SMILES: CC[C@H]1CCc2nnc(-c3cccc(N4Cc5c(cc(N6CCC[C@H]6C)nc5[C@@H](C)N[S@@](=O)C(C)(C)C)C4=O)n3)n21]

To a mixture of (S,S)-2-methyl-N-[(1R)-1-{6-[(2R)-2-methylpyrrolidin-1-yl]-1-oxo-2,3-dihydro-1H-pyrrolo[3,4-c]pyridin-4-yl}ethyl]propane-2-sulfinamide (Intermediate 4) (50 mg, 0.14 mmol), (5S)-3-(6-bromopyridin-2-yl)-5-ethyl-6,7-dihydro-5H-pyrrolo[2,1-c][1,2,4]triazole (Intermediate 3) (42.2 mg, 0.144 mmol), and K$_3$PO$_4$ (87.4 mg, 0.412 mmol) in 1,4-dioxane (3 mL) was added Pd$_2$(dba)$_3$ (12.6 mg, 0.014 mmol) and XantPhos (15.9 mg, 0.027 mmol) under N$_2$. After addition, the mixture was bubbled with N$_2$ for 2 min. The resulting mixture was sealed and stirred at 85° C. for 18 h. The reaction mixture was concentrated in vacuo, and the residue was purified by flash chromatography (SiO$_2$, 10% EtOAc/MeOH) to provide the title compound (60 mg, 76% yield) as a yellow solid. $^1$H NMR (400 MHz, CDCl$_3$) δ 8.70 (d, J=8.2 Hz, 1H), 8.18 (d, J=7.4 Hz, 1H), 7.93 (t, J=8.0 Hz, 1H), 6.76 (s, 1H), 5.11-5.02 (m, 2H), 4.99-4.93 (m, 1H), 4.61-4.49 (m, 2H), 4.34-4.27 (m, 1H), 3.67-3.57 (m, 1H), 3.46-3.35 (m, 1H), 3.11-3.01 (m, 3H), 2.65 (td, J=3.7, 7.9 Hz, 1H), 2.19-2.08 (m, 3H), 2.07 (s, 1H), 1.86-1.79 (m, 1H), 1.79 (br. d, J=2.3 Hz, 1H), 1.69 (d, J=6.4 Hz, 3H), 1.31-1.28 (m, 3H), 1.22 (s, 9H), 1.02 (t, J=7.5 Hz, 3H); m/z (ESI+) for (C$_{30}$H$_{40}$N$_8$O$_2$S), 577.5 (M+H)$^+$; [α] D$_{22}$=+85.3° (c=0.1 M, MeOH).

Step 2: Example 2

To a solution of (S,S)—N-[(1R)-1-(2-{6-[(5S)-5-ethyl-6,7-dihydro-5H-pyrrolo[2,1-c][1,2,4]triazol-3-yl]pyridin-2-yl}-6-[(2R)-2-methylpyrrolidin-1-yl]-1-oxo-2,3-dihydro-1H-pyrrolo[3,4-c]pyridin-4-yl)ethyl]-2-methylpro pane-2-sulfinamide (60 mg, 0.10 mmol) in EtOAc (5 mL) was added dropwise 4 M HCl in EtOAc (3 mL) at 0° C. The mixture was stirred at 20° C. for 1 h. The reaction mixture was concentrated in vacuo. To the residue was added EtOAc (10 mL) and water (10 mL). The aqueous layer was basified with saturated NaHCO$_3$ and extracted with DCM (10 mL×3). The combined organic layers were washed with brine (20 mL), dried over Na$_2$SO$_4$, filtered and concentrated in vacuo. The residue was lyophilized for 16 h to provide Example 2 (47 mg, 95%) as pale yellow color solid. $^1$H NMR (400 MHz, DMSO-d$_6$) δ 8.59 (d, J=8.3 Hz, 1H), 8.09-8.02 (m, 1H), 8.02-7.97 (m, 1H), 6.58 (s, 1H), 5.33 (d, J=17.1 Hz, 1H), 5.10 (d, J=17.1 Hz, 1H), 4.99 (br. t, J=6.1 Hz, 1H), 4.29-4.19 (m, 1H), 4.12 (q, J=6.9 Hz, 1H), 3.55 (br. t, J=8.0 Hz, 1H), 3.04-2.85 (m, 3H), 2.58-2.55 (m, 1H), 2.11-1.96 (m, 4H), 1.79-1.66 (m, 2H), 1.36 (d, J=6.5 Hz, 3H), 1.24-1.20 (m, 3H), 0.93 (t, J=7.4 Hz, 3H); m/z (ESI+) for (C$_{26}$H$_{32}$N$_8$O), 473.4 (M+H)$^+$.

Example 3: 4-[(1S)-1-aminoethyl]-2-{6-[(5S)-5-ethyl-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one

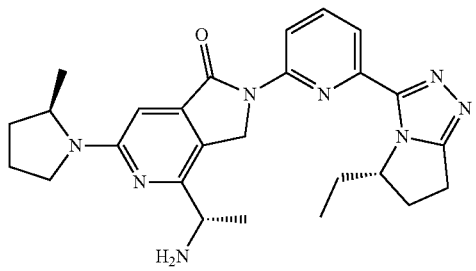 [SMILES: CC[C@H]1CCc2nnc(-c3cccc(N4Cc5c(cc(N6CCC[C@H]6C)nc5[C@H](C)N)C4=O)n3)n21]

Step 1: (S,R)—N-[(1S)-1-(2-{6-[(5S)-5-ethyl-6,7-dihydro-5H-pyrrolo[2,1-c][1,2,4]triazol-3-yl]pyridin-2-yl}-6-[(2R)-2-methylpyrrolidin-1-yl]-1-oxo-2,3-dihydro-1H-pyrrolo[3,4-c]pyridin-4-yl)ethyl]-2-methylpro pane-2-sulfinamide

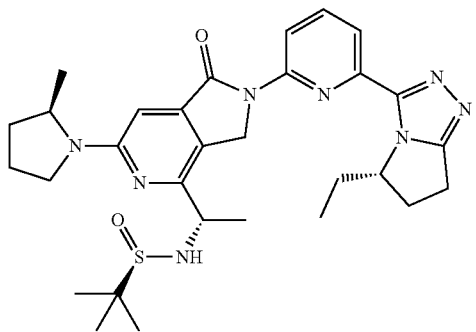 [SMILES: CC[C@H]1CCc2nnc(-c3cccc(N4Cc5c(cc(N6CCC[C@H]6C)nc5[C@H](C)N[S@](=O)C(C)(C)C)C4=O)n3)n21]

To a suspension of (S,R)-2-methyl-N-[(1 S)-1-{6-[(2R)-2-methylpyrrolidin-1-yl]-1-oxo-2,3-dihydro-1H-pyrrolo[3,4-c]pyridin-4-yl}ethyl]propane-2-sulfinamide (Intermediate 14) (2000 mg, 5.487 mmol), (5S)-3-(6-bromopyridin-2-yl)-5-ethyl-6,7-dihydro-5H-pyrrolo[2,1-c][1,2,4]triazole (Intermediate 3) (1610 mg, 5.49 mmol) and K₃PO4 (3490 mg, 16.5 mmol) in 1,4-dioxane (30 mL), Pd₂(dba)₃ (502 mg, 0.549 mmol) and XantPhos (635 mg, 1.10 mmol) were added under N₂. After addition, the mixture was bubbled with Argon for 2 min. The resulting mixture was sealed and allowed to stir at 85° C. for 18 h. TLC analysis showed consumption of the starting material. The mixture was diluted with H₂O (100 mL) with stirring and the resultant suspension was filtered. The aqueous filtrate was separated. The solid was washed with DCM (100 mL). The organic layer was dried over Na₂SO4, filtered and concentrated to provide a yellow residue (3 g) which was purified by flash chromatography (SiO₂, 0-10% MeOH in EtOAc) to provide a yellow solid. The solid was dissolved in DCM (50 mL) and silica-SH (4 g) was added. The yellow mixture was refluxed for 20 min. The mixture was filtered, and the filter cake was washed with DCM/MeOH (10:1). The filtrate was concentrated. The treatment with silica-SH was repeated three additional times to provide the title compound (2.3 g, 72.7%) as a yellow solid. $^1$H NMR (400 MHz, CDCl₃) δ 8.71 (dd, J=0.7, 8.4 Hz, 1H), 8.18 (dd, J=0.7, 7.6 Hz, 1H), 7.97-7.87 (m, 1H), 6.76 (s, 1H), 5.19-5.11 (m, 1H), 5.03-4.94 (m, 2H), 4.65-4.57 (m, 1H), 4.57-4.51 (m, 1H), 4.24 (br t, J=6.1 Hz, 1H), 3.66-3.56 (m, 1H), 3.48-3.39 (m, 1H), 3.13-2.98 (m, 3H), 2.71-2.59 (m, 1H), 2.21-2.03 (m, 4H), 1.87-1.75 (m, 2H), 1.68 (d, J=6.5 Hz, 4H), 1.30 (d, J=6.2 Hz, 3H), 1.24 (s, 9H), 1.02 (t, J=7.5 Hz, 3H). m/z (ESI) for (C₃₀H₄₀NaO₂S), 577.5 (M+H)⁺.

Step 2: Example 3

To a solution of (S,R)—N-[(1S)-1-(2-{6-[(5S)-5-ethyl-6,7-dihydro-5H-pyrrolo[2,1-c][1,2,4]triazol-3-yl]pyridin-2-yl}-6-[(2R)-2-methylpyrrolidin-1-yl]-1-oxo-2,3-dihydro-1H-pyrrolo[3,4-c]pyridin-4-yl)ethyl]-2-methylpro pane-2-sulfinamide (2300 mg, 3.988 mmol) in EtOAc (10 mL) was added 4M HCl in EtOAc (20 mL) at 0° C. After addition, the mixture was stirred at 15° C. for 1 h. The reaction was monitored by LCMS. The resulting yellow suspension was concentrated to provide a residue which was dissolved in H₂O (30 mL) and extracted with EtOAc (25 mL). The aqueous layer was basified with a solution of saturated NaHCO₃ to pH~ 8 and extracted with DCM (3×35 mL). The combined organic layers were washed with brine (20 mL), dried over Na₂SO4, filtered and concentrated to provide a solid to which DCM (50 mL) was added. The solution was filtered through glass microfiber filter GF/F (~0.7 μm) four times. The filtrate was concentrated to provide a yellow solid which was purified by prep. HPLC (Column: Agela DuraShell C18 150*40 mm*5 μm, water (0.05% ammonia hydroxide v/v)-CAN, Gradient Time 12 min, Flow Rate 25 mL/min). This provided Example 3 (1.5 g, 79.6%) as a yellow solid. $^1$H NMR (400 MHz, DMSO-d₆) δ 8.55 (d, J=8.0 Hz, 1H), 8.08-7.90 (m, 2H), 6.51 (s, 1H), 5.26 (d, J=16.8 Hz, 1H), 5.08-4.92 (m, 2H), 4.23 (br. t, J=5.8 Hz, 1H), 4.09 (q, J=6.5 Hz, 1H), 3.53 (br. t, J=7.5 Hz, 1H), 3.30-3.23 (m, 1H), 3.07-2.83 (m, 3H), 2.62-2.53 (m, 1H), 2.16-1.85 (m, 6H), 1.77-1.64 (m, 2H), 1.33 (d, J=6.5 Hz, 3H), 1.21 (d, J=6.0 Hz, 3H), 0.93 (t, J=7.3 Hz, 3H). m/z (ESI) for (C₂₆H₃₂N₈O), 473.4 (M+H)⁺.

Example 4: 4-[(1R)-1-aminoethyl]-2-{6-[(5S)-5-ethyl-6,7-dihydro-5H-pyrrolo[2,1-c][1,2,4]triazol-3-yl]pyridin-2-yl}-6-[methyl(propan-2-yl)amino]-2,3-dihydro-1H-pyrrolo[3,4-c]pyridin-1-one

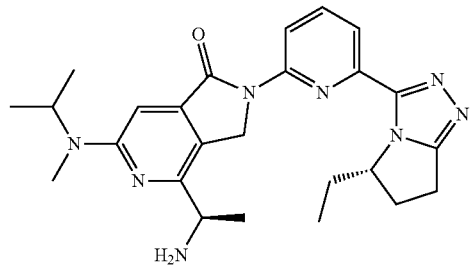 [SMILES: CC[C@H]1CCc2nnc(-c3cccc(N4Cc5c(cc(N(C)C(C)C)nc5[C@@H](C)N)C4=O)n3)n21]

Step 1: (S,S)—N-[(1R)-1-(2-{6-[(5S)-5-ethyl-6,7-dihydro-5H-pyrrolo[2,1-c][1,2,4]triazol-3-yl]pyridin-2-yl}-6-[methyl(propan-2-yl)amino]-1-oxo-2,3-dihydro-1H-pyrrolo[3,4-c]pyridin-4-yl)ethyl]-2-methylpropane-2-sulfinamide

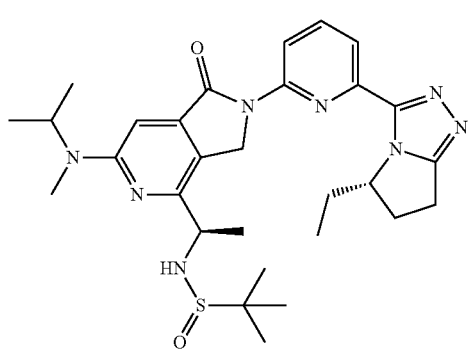 [SMILES: CC[C@H]1CCc2nnc(-c3cccc(N4Cc5c(cc(N(C)C(C)C)nc5[C@@H](C)NS(=O)C(C)(C)C)C4=O)n3)n21]

A solution of (S,S)-2-methyl-N-[(1R)-1-{6-[methyl(propan-2-yl)amino]-1-oxo-2,3-dihydro-1H-pyrrolo[3,4-c]pyridin-4-yl}ethyl]propane-2-sulfinamide (Intermediate 13) (627 mg, 1.78 mmol), (5S)-3-(6-bromopyridin-2-yl)-5-ethyl-6,7-dihydro-5H-pyrrolo[2,1-c][1,2,4]triazole (Intermediate 3) (521 mg, 1.78 mmol), $K_3PO_4$ (1.13 g, 5.34 mmol), $Pd_2(dba)_3$ (102 mg, 0.178 mmol) and XantPhos (206 mg, 0.356 mmol) in 1,4-dioxane (17.8 mL, c=0.1 M) was heated at 100° C. in a 100 mL flask with condenser under $N_2$ for 18 h. The mixture was cooled to RT, filtered and washed with DCM (20 mL). The filtrate was concentrated under reduced pressure. The residue was purified by flash chromatography (24 g, $SiO_2$, 0-10% MeOH/DCM) to provide the title compound as a pale-yellow color solid (808 mg, 80%). m/z (APCI+) for ($C_{29}H_{40}NaO_2S$), 565.3 (M+H)$^+$.

Step 2: Example 4

A 4 N solution of HCl in 1,4-dioxane (1.07 mL, 4.29 mmol) was added to a solution of (S,S)—N-[(1R)-1-(2-{6-[(5S)-5-ethyl-6,7-dihydro-5H-pyrrolo[2,1-c][1,2,4]triazol-3-yl]pyridin-2-yl}-6-[methyl(propan-2-yl)amino]-1-oxo-2,3-dihydro-1H-pyrrolo[3,4-c]pyridin-4-yl)ethyl]-2-methylpropane-2-sulfinamide (808 mg, 1.43 mmol) in MeOH (14.3 mL, c=0.1 M). The mixture was stirred at RT for 2 hr. The volatile materials were removed under reduced pressure. The crude product was purified by Chiral SFC (Phenomenex Lux Cellulose-1 21×250 mm column, 30% MeOH+10 mM $NH_3$ in $CO_2$ held at 120 bar, 100 mL/min) to provide Example 4 (345 mg, 52% yield, >99% de, >99% pure) as pale yellow color solid. $^1$H NMR (400 MHz, DMSO-$d_6$) δ 8.56 (dd, J=1.0, 8.1 Hz, 1H), 8.07-8.01 (m, 1H), 8.00-7.93 (m, 1H), 6.78 (s, 1H), 5.34-5.28 (m, 1H), 5.17-5.10 (m, 1H), 5.02-4.95 (m, 1H), 4.89 (td, J=6.7, 13.4 Hz, 1H), 4.18 (q, J=6.7 Hz, 1H), 3.01-2.94 (m, 2H), 2.93 (s, 3H), 2.62-2.54 (m, 2H), 2.09-1.97 (m, 1H), 1.84-1.72 (m, 1H), 1.41 (d, J=6.6 Hz, 3H), 1.20 (d, J=6.6 Hz, 6H), 0.92 (t, J=7.5 Hz, 3H); m/z (APCI+) for ($C_{25}H_{32}N_8O$), 461.3 (M+H)$^+$. $[α]_D^{22}$=+120.5° (c=0.1 M, MeOH).

Example 5: 4-[(1R)-1-aminopropyl]-2-{3-[(5S)-5-methyl-6,7-dihydro-5H-pyrrolo[2,1-c][1,2,4]triazol-3-yl]phenyl}-6-[methyl(propan-2-yl)amino]-2,3-dihydro-1H-pyrrolo[3,4-c]pyridin-1-one

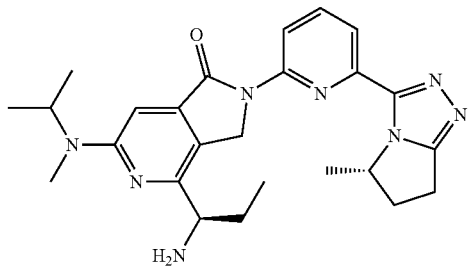 [SMILES: CC[C@@H](N)c1nc(N(C)C(C)C)cc2c1CN(c1cccc(-c3nnc4n3[C@@H](C)CC4)n1)C2=O]

Step 1: (S,S)-2-methyl-N-[(1R)-1-(2-{3-[(5S)-5-methyl-6,7-dihydro-5H-pyrrolo[2,1-c][1,2,4]triazol-3-yl]phenyl}-6-[methyl(propan-2-yl)amino]-1-oxo-2,3-dihydro-1H-pyrrolo[3,4-c]pyridin-4-yl)propyl]propane-2-sulfinamide

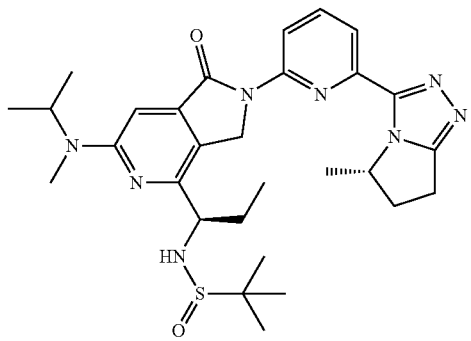 [SMILES: CC[C@@H](NS(=O)C(C)(C)C)c1nc(N(C)C(C)C)cc2c1CN(c1cccc(-c3nnc4n3[C@@H](C)CC4)n1)C2=O]

A mixture of (S,S)-2-methyl-N-(1-{6-[methyl(propan-2-yl)amino]-1-oxo-2,3-dihydro-1H-pyrrolo[3,4-c]pyridin-4-yl}propyl)propane-2-sulfinamide (Intermediate 10) (63 mg, 0.17 mmol), (5S)-3-(3-bromophenyl)-5-methyl-6,7-dihydro-5H-pyrrolo[2,1-c][1,2,4]triazole (Intermediate 2) (48 mg, 0.172 mmol), $K_3PO_4$ (109 mg, 0.516 mmol), $Pd_2(dba)_3$ (9.88 mg, 0.0172 mmol) and XantPhos (19.9 mg, 0.0344 mmol) in 1,4-dioxane (4.5 mL, c=0.1 M) was heated at 100° C. in a 40 mL vial (capped) for 18 h. The volatiles were removed under reduced pressure. The residue was purified by flash chromatography (12 g, $SiO_2$, 0-10% MeOH/DCM) to provide the title compound as a pale-yellow color foam (74.0 mg, 76%). m/z (APCI+) for ($C_{29}H_{40}NaO_2S$), 565.3 (M+H)$^+$.

Step 2: Example 5

A 4 N solution of HCl in 1,4-dioxane (0.164 mL, 0.655 mmol) was added to a solution of (S,S)-2-methyl-N-[(1R)-1-(2-{3-[(5S)-5-methyl-6,7-dihydro-5H-pyrrolo[2,1-c][1,2,4]triazol-3-yl]phenyl}-6-[methyl(propan-2-yl)amino]-1-oxo-2,3-dihydro-1H-pyrrolo[3,4-c]pyridin-4-yl)propyl]propane-2-sulfinamide (74 mg, 0.13 mmol) in MeOH (5.0 mL, c=0.026 M). The mixture was stirred at RT for 2 h. The volatiles were removed under reduced pressure. The crude product was purified by Chiral SFC (Phenomenex Lux Cellulose-1 4.6×100 mm 3 μm column 5-60% MeOH+10 mM NH₃ in CO₂ ramping over 3.0 minutes @ 120 bar, 4 mL/min) to provide Example 5 (11.6 mg, 19% yield, >99% de, >95% pure) as pale yellow color solid. ¹H NMR (600 MHz, DMSO-d₆) δ 8.54 (d, J=8.3 Hz, 1H), 8.35 (br. s, 2H), 8.07 (t, J=8.0 Hz, 1H), 8.00-7.90 (m, 1H), 6.91 (d, J=0.9 Hz, 1H), 5.27-5.07 (m, 3H), 5.01 (br. s, 1H), 4.37 (br. s, 1H), 3.14-2.97 (m, 2H), 2.94 (d, J=1.5 Hz, 3H), 2.92-2.85 (m, 1H), 2.42-2.35 (m, 1H), 2.06-1.91 (m, 2H), 1.50 (d, J=6.1 Hz, 3H), 1.19 (d, J=6.6 Hz, 3H), 1.15 (d, J=6.6 Hz, 3H), 0.92 (t, J=7.3 Hz, 3H); m/z (APCI+) for (C₂₅H₃₂N₈O), 461.3 (M+H)⁺. [α]D₂₂=+75.9° (c=0.2 M, MeOH).

Example 6: 4-[(1)-1-amino-2-methoxyethyl]-6-(1-methylcyclopropyl)-2-{6-[(5S)-5-methyl-6,7-dihydro-5H-pyrrolo[2,1-c][1,2,4]triazol-3-yl]pyridin-2-yl}-2,3-dihydro-1H-pyrrolo[3,4-c]pyridin-1-one Example 6(a) Example 6(b)

Example 6(a)

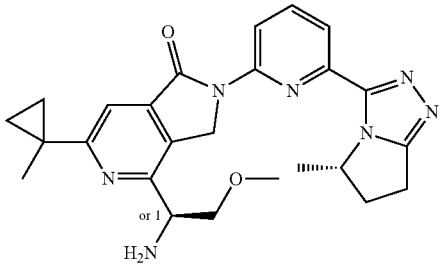

Example 6(b)

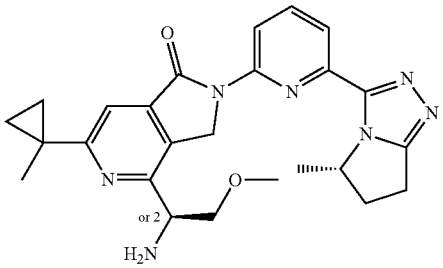

Stereochemistry of 6a and 6b is arbitrarily depicted with the understanding that the two isomers were separated (see description preceding intermediates section).

Step 1: tert-butyl {2-methoxy-1-[6-(1-methylcyclopropyl)-2-{6-[(5S)-5-methyl-6,7-dihydro-5H-pyrrolo[2,1-c][1,2,4]triazol-3-yl]pyridin-2-yl}-1-oxo-2,3-dihydro-1H-pyrrolo[3,4-c]pyridin-4-yl]ethyl}carbamate

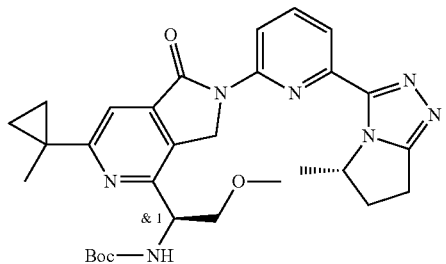 [SMILES: COC[C@@H](NC(=O)OC(C)(C)C)c1nc(C2(C)CC2)cc2c1CN(c1cccc(-c3nnc4n3[C@@H](C)CC4)n1)C2=O]

A solution of tert-butyl {2-methoxy-1-[6-(1-methylcyclopropyl)-1-oxo-2,3-dihydro-1H-pyrrolo[3,4-c]pyridin-4-yl]ethyl}carbamate (Intermediate 15) (136 mg, 0.376 mmol), (5S)-3-(6-bromopyridin-2-yl)-5-ethyl-6,7-dihydro-5H-pyrrolo[2,1-c][1,2,4]triazole (Intermediate 2) (105 mg, 0.376 mmol), K₃PO₄ (240 mg, 1.13 mmol), and 1,4-dioxane (12 mL) was bubbled with nitrogen for 2 min. To this mixture was added Pd₂(dba)₃ (34.5 mg, 0.038 mmol) and XantPhos (43.5 mg, 0.075 mmol). The reaction was heated to 85° C. and was allowed to stir at this temperature for 18 h. The reaction was cooled and combined with an identical reaction run on a 43 mg scale (Intermediate 15). The combined mixture was concentrated and purified via flash chromatography (SiO₂, 10:1 EtOAc/MeOH) followed by prep. TLC (SiO₂, 10:1 EtOAc/MeOH) to provide the title compound as a yellow solid (170 mg, 61%). ¹H NMR (400 MHz, CDCl₃) δ 8.67 (dd, J=12.2, 8.3 Hz, 1H), 8.20-8.10 (m, 1H), 8.01-7.84 (m, 1H), 5.66 (d, J=8.0 Hz, 1H), 5.35-5.11 (m, 3H), 5.03 (d, J=11.7 Hz, 1H), 3.60-3.46 (m, 2H), 3.27 (d, J=8.5 Hz, 3H), 3.16-2.94 (m, 4H), 2.50 (d, J=8.7 Hz, 2H), 2.39 (s, 2H), 1.71 (s, 3H), 1.43 (s, 9H), 1.33 (q, J=2.3 Hz, 2H), 0.92 (t, J=2.6 Hz, 2H). m/z (ESI) for (C₃₀H₃₇N₇O₄), 460.2 (M+H)⁺.

Step 2: Example 6

To a solution of tert-butyl {2-methoxy-1-[6-(1-methylcyclopropyl)-2-{6-[(5S)-5-methyl-6,7-dihydro-5H-pyrrolo[2,1-c][1,2,4]triazol-3-yl]pyridin-2-yl}-1-oxo-2,3-dihydro-1H-pyrrolo[3,4-c]pyridin-4-yl]ethyl}carbamate (170 mg, 0.304 mmol) in DCM (5 mL) was added dropwise a 4 M solution of HCl in EtOAc (3 mL) at 0° C. The reaction was stirred at 20° C. for 1 h and was then concentrated. The resulting residue was diluted with H₂O (15 mL) and was basified to pH~8 with a solution of saturated NaHCO₃. The mixture was extracted with DCM (3×8 mL) and the combined organic layer was washed with brine (20 mL), dried over Na₂SO₄, filtered and concentrated to provide a yellow solid. The resulting solid was purified via prep. SFC (column: Daicel Chiralpak 250 mm*30 mm*10 μm, 0.1% NH₃—H₂O EtOH) to provide:

The first-eluting isomer as Example 6a (30 mg, 21%). ¹H NMR (400 MHz, DMSO-d₆) δ 8.56 (d, J=7.9 Hz, 1H), 8.08 (t, J=7.8 Hz, 1H), 7.99 (d, J=7.8 Hz, 1H), 7.57 (s, 1H), 5.48 (d, J=18.1 Hz, 1H), 5.30 (d, J=18.1 Hz, 1H), 5.12 (br. t, J=6.5 Hz, 1H), 4.30 (t, J=6.3 Hz, 1H), 3.65-3.52 (m, 2H), 3.30-3.26 (m, 3H), 3.13-2.86 (m, 3H), 2.40 (br. dd, J=8.4, 11.9

Hz, 3H), 1.59-1.52 (m, 6H), 1.31-1.24 (m, 2H), 0.89 (d, J=2.9 Hz, 2H). m/z (ESI) for ($C_{25}H_{29}N_7O$), 560.3 (M+H)$^+$. [α] $D_{22}$=+66.1° (c=0.1 M, MeOH).

The second-eluting isomer as Example 6b (33 mg, 23%). $^1$H NMR (400 MHz, DMSO-d$^6$) δ 8.58 (d, J=7.9 Hz, 1H), 8.07 (t, J=7.9 Hz, 1H), 7.99 (d, J=7.3 Hz, 1H), 7.55 (s, 1H), 5.44 (d, J=18.1 Hz, 1H), 5.31 (d, J=18.1 Hz, 1H), 5.16 (br. t, J=6.6 Hz, 1H), 4.29 (t, J=6.4 Hz, 1H), 3.55 (d, J=6.4 Hz, 2H), 3.25 (s, 3H), 3.13-2.86 (m, 3H), 2.40 (br. dd, J=8.2, 11.6 Hz, 1H), 2.12 (br. s, 2H), 1.59-1.48 (m, 6H), 1.30-1.23 (m, 2H), 0.88 (d, J=3.1 Hz, 2H). m/z (ESI) for ($C_{25}H_{29}N_7O$), 560.2 (M+H)$^+$. [α] $D_{22}$=+41.5°.

Additional compounds of the invention were prepared by modifications of the methods exemplified herein and are presented in Tables 5, 6, and 7. Except where otherwise indicated, all compounds having chiral carbons were prepared and/or isolated as a single enantiomer as depicted in the structure. Chirality is further indicated by the compound name which designates specific stereochemistry as (R) or (S) for each chiral carbon. When all chiral carbons are so designated as known stereochemistry, the stereochemistry is based on the use of known chiral starting materials and/or confirmation of resolved enantiomers through X-ray crystallography. Some compounds were prepared from racemic intermediates and resolved into single enantiomers by an appropriate chiral preparative SFC method. Where stereochemistry is not known but enantiomers are separated, "or1," or "or2" is at the chiral carbon atom. In the name, the carbon with the resolved but not confirmed stereochemical center, is identified with the symbol "ξ". The bond drawn at that carbon is a representation of the stereochemistry; meaning, the carbon would have that bond configuration drawn (solid wedge) or the opposite configuration (hashed wedge). See, e.g., Examples 101 and 102. When obtained, the optical rotation (α$D_{22}$ or α$D_{20}$) is provided after the IUPAC name, provided simply as a.

TABLE 5

| Ex # | Structure | IUPAC Name, and rotation | LRMS (m/z) (M + H)$^{+\wedge}$ | $^1$H NMR |
|---|---|---|---|---|
| 7 (F)* | 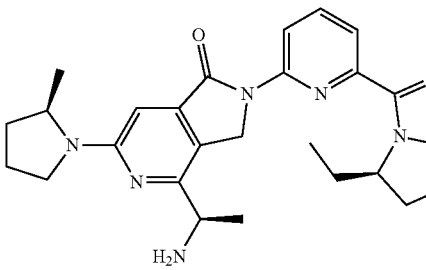 | 4-[(1R)-1-aminoethyl]-2-{6-[(5R)-5-ethyl-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one α = −144.8° | 473.2 | $^1$H NMR (400 MHz, DMSO-d$_6$) δ 8.58 (dd, J = 0.9, 8.2 Hz, 1H), 8.07-8.01 (m, 1H), 8.00-7.96 (m, 1H), 6.55 (s, 1H), 5.30 (d, J = 16.9 Hz, 1H), 5.06 (d, J = 16.9 Hz, 1H), 5.00 (br. t, J = 6.1 Hz, 1H), 4.23 (br. t, J = 5.9 Hz, 1H), 4.11 (q, J = 6.6 Hz, 1H), 3.54 (br. dd, J = 7.5, 9.7 Hz, 1H), 3.02-2.89 (m, 3H), 2.57 (br. d, J = 11.4 Hz, 1H), 2.15-1.89 (m, 5H), 1.77-1.66 (m, 2H), 1.33 (d, J = 6.7 Hz, 3H), 1.22 (d, J = 6.2 Hz, 3H), 0.93 (t, J = 7.4 Hz, 3H). |
| 8 (F)* | 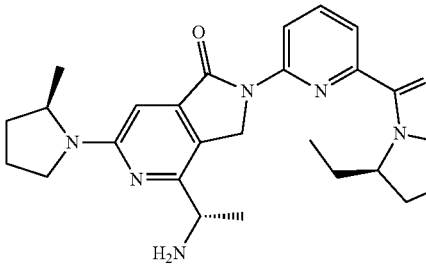 | 4-[(1S)-1-aminoethyl]-2-{6-[(5R)-5-ethyl-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one α = −99.9° | 473.3 | $^1$H NMR (400 MHz, DMSO-d$_6$) δ 8.58 (d, J = 7.5 Hz, 1H), 8.10-8.02 (m, 1H), 8.01-7.95 (m, 1H), 6.57 (s, 1H), 5.31 (d, J = 17.1 Hz, 1H), 5.09 (d, J = 16.8 Hz, 1H), 4.98 (br. s, 1H), 4.24 (br. t, J = 6.0 Hz, 1H), 4.11 (q, J = 6.7 Hz, 1H), 3.60-3.52 (m, 1H), 3.03-2.86 (m, 3H), 2.57 (br. d, J = 11.5 Hz, 1H), 2.17-1.89 (m, 5H), 1.80-1.66 (m, 2H), 1.36 (d, J = 6.8 Hz, 3H), 1.21 (d, J = 6.3 Hz, 3H), 0.93 (t, J = 7.4 Hz, 3H). |
| 9 (F)* | 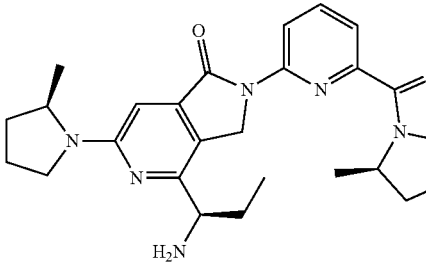 | 4-[(1R)-1-aminopropyl]-2-{6-[(5R)-5-methyl-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one α = −125.4° | 473.2 | $^1$H NMR (400 MHz, DMSO-d$_6$) δ 8.51 (dd, J = 0.7, 8.3 Hz, 1H), 8.08-7.96 (m, 1H), 7.93-7.84 (m, 1H), 6.53 (s, 1H), 5.35-5.00 (m, 3H), 4.18 (quin, J = 6.3 Hz, 1H), 3.93 (br. s, 1H), 3.49 (ddd, J = 2.4, 7.3, 9.8 Hz, 1H), 3.10-2.78 (m, 4H), 2.37-2.30 (m, 1H), 2.04-1.87 (m, 3H), 1.74 (dt, J = 7.0, 13.8 Hz, 1H), 1.67-1.56 (m, 2H), 1.44 (d, J = 6.4 Hz, 3H), 1.15 (d, J = 6.2 Hz, 3H), 0.84 (t, J = 7.4 Hz, |

TABLE 5-continued

| Ex # | Structure | IUPAC Name, and rotation | LRMS (m/z) (M + H)+^ | 1H NMR |
|---|---|---|---|---|
| | | | | 3H). |
| 10 (F)* | 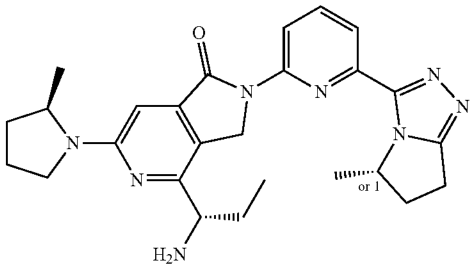 [SMILES: CC[C@H](N)c1nc(N2CCC[C@H]2C)cc2c1CN(c1cccc(-c3nnc4n3[C@@H](C)CC4)n1)C2=O] | 4-[(1S)-1-aminopropyl]-2-{6-[(5ξ)-5-methyl-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one α = +28.8° | 473.2 | 1H NMR (600 MHz, DMSO-d6) δ 8.52-8.43 (m, 1H), 8.04-7.97 (m, 1H), 7.90 (d, J = 7.7 Hz, 1H), 6.70-6.60 (m, 1H), 5.22-5.13 (m, 1H), 5.11-5.00 (m, 2H), 4.31-4.19 (m, 2H), 3.57-3.51 (m, 2H), 3.09-2.89 (m, 2H), 2.87-2.74 (m, 1H), 2.38-2.21 (m, 1H), 2.11-1.87 (m, 5H), 1.73-1.61 (m, 1H), 1.44 (d, J = 6.4 Hz, 3H), 1.20-1.11 (m, 3H), 0.86 (t, J = 7.4 Hz, 3H). |
| 11 (F)* | 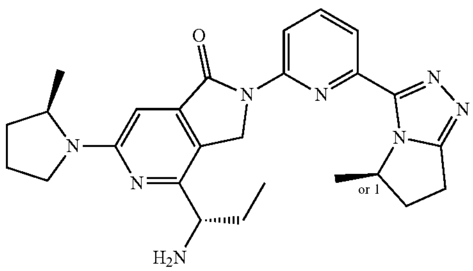 [SMILES: CC[C@H](N)c1nc(N2CCC[C@H]2C)cc2c1CN(c1cccc(-c3nnc4n3[C@H](C)CC4)n1)C2=O] | 4-[(1S)-1-aminopropyl]-2-{6-[(ξ)-5-methyl-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one α = −117.6° | 473.7 | 1H NMR (600 MHz, DMSO-d6) δ 8.47 (d, J = 8.3 Hz, 1H), 8.06-7.93 (m, 1H), 7.90-7.82 (m, 1H), 6.55 (s, 1H), 5.30-5.13 (m, 1H), 5.09-5.02 (m, 2H), 4.22 (br. s, 1H), 4.03-3.89 (m, 1H), 3.54-3.49 (m, 2H), 3.07-2.97 (m, 2H), 2.93 (qd, J = 8.8, 12.2 Hz, 2H), 2.83 (dd, J = 8.9, 15.1 Hz, 1H), 2.38-2.29 (m, 1H), 2.06-1.95 (m, 2H), 1.94-1.88 (m, 1H), 1.87-1.79 (m, 1H), 1.74 (td, J = 6.7, 13.5 Hz, 1H), 1.65 (d, J = 2.2 Hz, 1H), 1.45 (d, J = 6.4 Hz, 3H), 1.13 (d, J = 6.2 Hz, 2H), 0.83 (t, J = 7.3 Hz, 2H). |
| 12 (F)* | 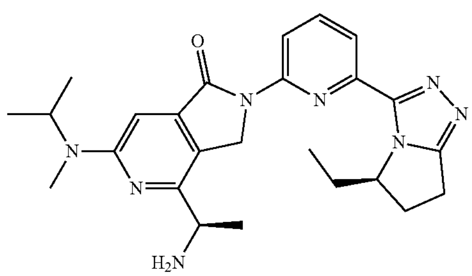 [SMILES: CC[C@@H]1CCc2nnc(-c3cccc(N4Cc5c(cc(N(C)C(C)C)nc5[C@@H](C)N)C4=O)n3)n21] | 4-[(1R)-1-aminoethyl]-2-{6-[(5R)-5-ethyl-6,7-dihydro-5H-pyrrolo[2,1-c][1,2,4]triazol-3-yl]pyridin-2-yl}-6-[methyl(propan-2-yl)amino]-2,3-dihydro-1H-pyrrolo[3,4-c]pyridin-1-one α = −86.9° | 461.2 | 1H NMR (600 MHz, DMSO-d6) δ 8.74 (s, 1 H) 8.62 (d, J = 8.25 Hz, 1 H) 8.10 (t, J = 8.17 Hz, 1 H) 8.01 (d, J = 7.70 Hz, 1 H) 6.71 (s, 1 H) 5.17 (s, 2 H) 4.49-4.61 (m, 4 H) 4.34 (br. s, 1 H) 3.61-3.63 (m, 2 H) 2.55 (br. s, 1 H) 2.02-2.13 (m, 2 H) 1.95-2.02 (m, 1 H) 1.82-1.93 (m, 2 H) 1.64-1.80 (m, 1 H) 1.52 (br. d, J = 6.05 Hz, 3 H) 1.29-1.40 (m, 1 H) 1.11-1.28 (m, 4 H) 0.88-0.98 (m, 3 H). |
| 13 (F)* | 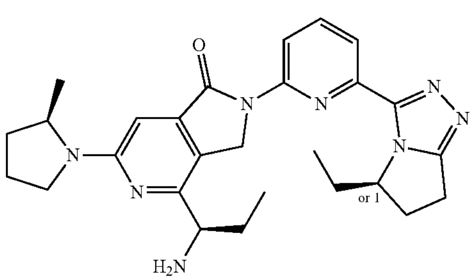 [SMILES: CC[C@@H]1CCc2nnc(-c3cccc(N4Cc5c(cc(N6CCC[C@H]6C)nc5[C@H](N)CC)C4=O)n3)n21] | 4-[(1R)-1-aminopropyl]-2-{6-[(5ξ)-5-ethyl-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one α = +48.1° | 487.2 | 1H NMR (400 MHz, DMSO-d6) δ 8.62-8.52 (m, 1H), 8.10-8.02 (m, 1H), 8.01-7.89 (m, 1H), 6.63 (s, 1H), 5.29 (d, J = 16.6 Hz, 1H), 5.08 (d, J = 16.8 Hz, 1H), 5.04-4.89 (m, 1H), 4.33-4.20 (m, 1H), 4.06-3.92 (m, 1H), 3.65-3.52 (m, 1H), 3.47-3.36 (m, 1H), 3.00-2.92 (m, 3H), 2.66-2.55 (m, 1H), 2.17-2.07 (m, 2H), 2.04-1.94 (m, 2H), 1.92-1.71 (m, 4H), 1.26 (d, J = 6.1 Hz, 3H), 0.98-0.88 (m, 6H). |

TABLE 5-continued

| Ex # | Structure | IUPAC Name, and rotation | LRMS (m/z) (M + H)+^ | 1H NMR |
|---|---|---|---|---|
| 14 (F)* | 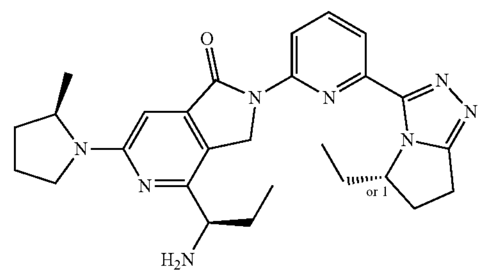 | 4-[(1R)-1-aminopropyl]-2-{6-[(5ξ)-5-ethyl-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one α = −108.8° | 487.2 | 1H NMR (400 MHz, DMSO-d6) δ 8.62-8.52 (m, 1H), 8.10-8.02 (m, 1H), 8.01-7.89 (m, 1H), 6.63 (s, 1H), 5.29 (d, J = 16.6 Hz, 1H), 5.08 (d, J = 16.8 Hz, 1H), 5.04-4.89 (m, 1H), 4.33-4.20 (m, 1H), 4.06-3.92 (m, 1H), 3.65-3.52 (m, 1H), 3.47-3.36 (m, 1H), 3.00-2.92 (m, 3H), 2.66-2.55 (m, 1H), 2.17-2.07 (m, 2H), 2.04-1.94 (m, 2H), 1.92-1.71 (m, 4H), 1.26 (d, J = 6.1 Hz, 3H), 0.98-0.88 (m, 6H). |
| 15 (F)* | 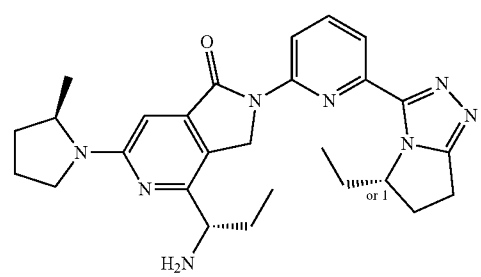 [SMILES: CC[C@H]1CCc2nnc(-c3cccc(N4Cc5c(cc(N6CCC[C@H]6C)nc5[C@@H](N)CC)C4=O)n3)n21] | 4-[(1S)-1-aminopropyl]-2-{6-[(5ξ)-5-ethyl-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one | 487.2 | 1H NMR (600 MHz, DMSO-d6) δ 8.54-8.46 (m, 1H), 8.02-7.95 (m, 1H), 7.93-7.83 (m, 1H), 6.49 (s, 1H), 5.24-5.12 (m, 1H), 4.98 (d, J = 16.5 Hz, 1H), 4.88 (br. s, 1H), 4.18 (br. s, 1H), 3.48 (br. s, 1H), 2.99-2.77 (m, 4H), 2.57-2.46 (m, 1H), 2.08-1.87 (m, 4H), 1.80-1.72 (m, 1H), 1.72-1.53 (m, 3H), 1.21-1.11 (m, 4H), 0.90-0.78 (m, 6H). |
| 16 (F)* | 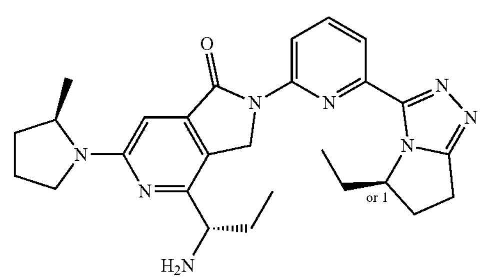 [SMILES: CC[C@@H]1CCc2nnc(-c3cccc(N4Cc5c(cc(N6CCC[C@H]6C)nc5[C@@H](N)CC)C4=O)n3)n21] | 4-[(1S)-1-aminopropyl]-2-{6-[(5ξ)-5-ethyl-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one α = +52.4° | 487.2 | 1H NMR (600 MHz, DMSO-d6) δ 8.56-8.46 (m, 1H), 8.04-7.95 (m, 1H), 6.50 (s, 1H), 5.31-5.13 (m, 1H), 4.93 (d, J = 15.4 Hz, 2H), 4.19 (br. s, 1H), 3.48 (br. s, 2H), 2.97-2.78 (m, 4H), 2.50 (d, J = 11.0 Hz, 1H), 2.09-1.86 (m, 4H), 1.78-1.69 (m, 1H), 1.68-1.50 (m, 3H), 1.17-1.10 (m, 4H), 0.86 (t, J = 7.2 Hz, 3H), 0.81 (t, J = 6.4 Hz, 3H). |
| 17 (H)* | 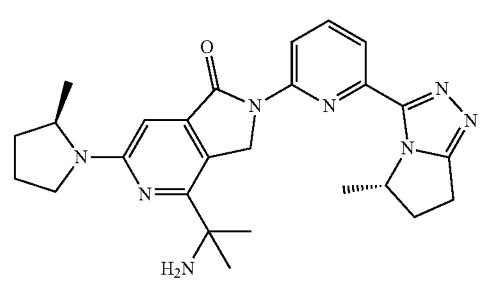 [SMILES: C[C@@H]1CCCN1c1cc2c(c(C(C)(C)N)n1)CN(c1cccc(-c3nnc4n3[C@@H](C)CC4)n1)C2=O] | 4-(2-aminopropan-2-yl)-2-{6-[(5S)-5-methyl-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one | 473.1 | 1H NMR (400 MHz, DMSO-d6) δ 8.62 (d, J = 8.1 Hz, 1H), 8.41 (br. s, 3H), 8.14-8.07 (m, 1H), 8.07-8.02 (m, 1H), 6.76 (s, 1H), 5.45 (d, J = 16.3 Hz, 1H), 5.27-5.16 (m, 2H), 4.39 (br. d, J = 2.0 Hz, 1H), 3.72-3.61 (m, 1H), 3.18-3.08 (m, 1H), 3.07-2.91 (m, 2H), 2.42 (br. d, J = 6.4 Hz, 1H), 2.13-1.98 (m, 3H), 1.76-1.67 (m, 7H), 1.53 (d, J = 6.5 Hz, 3H), 1.20 (d, J = 6.2 Hz, 3H); |

| Ex # | Structure | IUPAC Name, and rotation | LRMS (m/z) (M + H)+^ | 1H NMR |
|---|---|---|---|---|
| 18 (J)* | 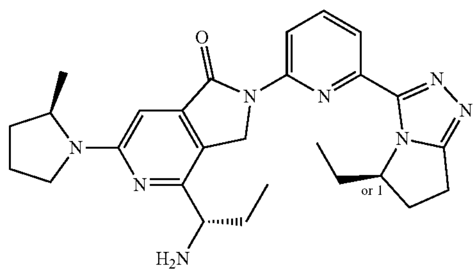 [SMILES: CC[C@@H]1CCc2nnc(-c3cccc(N4Cc5c(cc(N6CCC[C@H]6C)nc5[C@@H](N)CC)C4=O)n3)n21] | 4-[(1ξ)-1-aminoethyl]-2-{6-[(5R)-5-(fluoromethyl)-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one α = +23.8° | 477.4 | 1H NMR (400 MHz, DMSO-d6) δ 8.58 (d, J = 8.0 Hz, 1H), 8.43-8.33 (m, 3H), 8.11 (t, J = 7.9 Hz, 1H), 8.02 (d, J = 7.8 Hz, 1H), 6.73 (s, 1H), 5.42-5.31 (m, 1H), 5.24 (d, J = 16.5 Hz, 1H), 5.11-4.99 (m, 2H), 4.92-4.86 (m, 1H), 4.63-4.55 (m, 1H), 4.40-4.33 (m, 1H), 3.66-3.60 (m, 1H), 3.11-2.91 (m, 3H), 2.78-2.69 (m, 1H), 2.53-2.52 (m, 1H), 2.15-1.96 (m, 3H), 1.78-1.70 (m, 1H), 1.56 (d, J = 6.7 Hz, 3H), 1.22 (d, J = 6.1 Hz, 3H). |
| 19 (J)* | 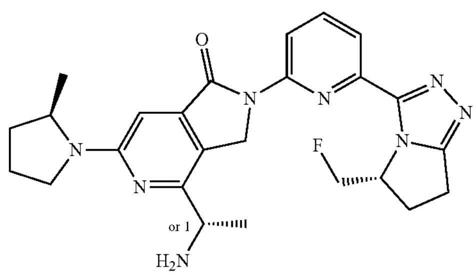 [SMILES: C[C@H](N)c1nc(N2CCC[C@H]2C)cc2c1CN(c1cccc(-c3nnc4n3[C@@H](CF)CC4)n1)C2=O] | 4-[(1ξ)-1-aminoethyl]-2-{6-[(5R)-5-(fluoromethyl)-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one α = −3.1° | 477.0 | 1H NMR (400 MHz, DMSO-d6) δ 8.63 (d, J = 8.0 Hz, 1H), 8.56-8.43 (m, 3H), 8.15-8.04 (m, 2H), 6.73 (s, 1H), 5.53-5.36 (m, 1H), 5.08-5.00 (m, 2H), 4.97-4.88 (m, 1H), 4.69-4.61 (m, 1H), 4.37 (br. s, 1H), 3.67-3.62 (m, 1H), 3.45-3.37 (m, 1H), 3.13-2.95 (m, 3H), 2.79-2.72 (m, 1H), 2.14-1.96 (m, 3H), 1.79-1.70 (m, 1H), 1.56 (d, J = 6.5 Hz, 3H), 1.20 (d, J = 6.3 Hz, 3H). |
| 20 (J)* | 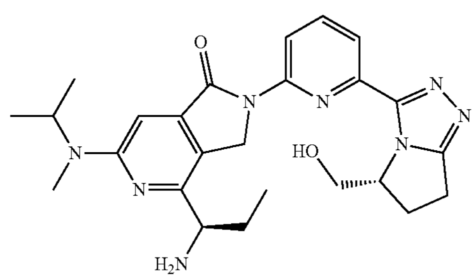 [SMILES: CC[C@@H](N)c1nc(N(C)C(C)C)cc2c1CN(c1cccc(-c3nnc4n3[C@@H](CO)CC4)n1)C2=O] | 4-[(1R)-1-aminopropyl]-2-{6-[(5R)-5-(hydroxymethyl)-6,7-dihydro-5H-pyrrolo[2,1-c][1,2,4]triazol-3-yl]pyridin-2-yl}-6-[methyl(propan-2-yl)amino]-2,3-dihydro-1H-pyrrolo[3,4-c]pyridin-1-one | 477.2 | 1H NMR (400 MHz, DMSO-d6) δ 8.57 (d, J = 7.9 Hz, 1H), 8.06 (t, J = 8.0 Hz, 1H), 7.98 (d, J = 7.4 Hz, 1H), 6.74 (s, 1H), 5.28 (d, J = 17.1 Hz, 1H), 5.07 (d, J = 17.1 Hz, 1H), 5.04-4.98 (m, 1H), 4.98-4.89 (m, 1H), 3.91-3.83 (m, 3H), 3.02-2.82 (m, 6H), 2.77-2.69 (m, 1H), 1.77 (br. d, J = 7.2 Hz, 1H), 1.71-1.59 (m, 1H), 1.15 (d, J = 6.6 Hz, 6H), 0.89 (t, J = 7.4 Hz, 3H). |
| 21 (F)* | 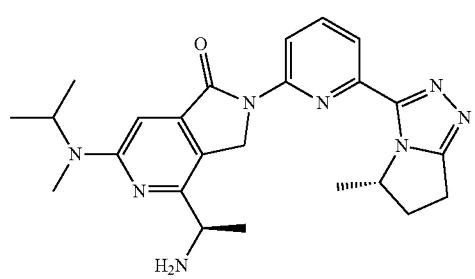 [SMILES: CC(C)N(C)c1cc2c(c([C@@H](C)N)n1)CN(c1cccc(-c3nnc4n3[C@@H](C)CC4)n1)C2=O] | 4-[(1R)-1-aminoethyl]-2-{6-[(5S)-5-methyl-6,7-dihydro-5H-pyrrolo[2,1-c][1,2,4]triazol-3-yl]pyridin-2-yl}-6-[methyl(propan-2-yl)amino]-2,3-dihydro-1H-pyrrolo[3,4-c]pyridin-1-one | 446.6 | 1H NMR (600 MHz, DMSO-d6) δ 8.44-8.51 (m, 1H) 7.96 (t, J = 8.20 Hz, 1H) 7.88 (br. d, J = 6.60 Hz, 1H) 6.64 (br. s, 1H) 5.28 (br. d, J = 16.69 Hz, 1H) 5.10 (br. d, J = 16.32 Hz, 1H) 5.04 (br. s, 1H) 4.84 (br. s, 2H) 2.97-3.04 (m, 2H) 2.87-2.95 (m, 2H) 2.80-2.83 (m, 3H) 2.27-2.37 (m, 2H) 1.42-1.56 (m, 3H) 1.26-1.42 (m, 3H) 1.09 (br. d, J = 4.77 Hz, 6H). |

TABLE 5-continued

| Ex # | Structure | IUPAC Name, and rotation | LRMS (m/z) (M + H)+^ | 1H NMR |
|---|---|---|---|---|
| 22 (H)* | 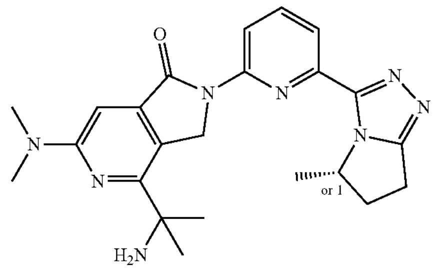 [SMILES: C[C@H]1CCc2nnc(-c3cccc(N4Cc5c(cc(N(C)C)nc5C(C)(C)N)C4=O)n3)n21] | 4-(2-aminopropan-2-yl)-6-(dimethyl-amino)-2-{6-[(5ξ)-5-methyl-6,7-dihydro-5H-pyrrolo[2,1-c][1,2,4]triazol-3-yl]pyridin-2-yl}-2,3-dihydro-1H-pyrrolo[3,4-c]pyridin-1-one α = +80.7° | 433.2 | 1H NMR (600 MHz, DMSO-d6) δ 8.50 (d, J = 8.4 Hz, 1H), 8.02-7.93 (m, 1H), 7.91-7.83 (m, 1H), 6.68 (s, 1H), 5.47-5.24 (m, 2H), 5.12-5.01 (m, 1H), 3.03 (s, 6H), 3.01-2.96 (m, 1H), 2.95-2.86 (m, 1H), 2.85-2.78 (m, 1H), 2.31 (dd, J = 8.3, 12.3 Hz, 1H), 1.44 (d, J = 6.4 Hz, 3H), 1.42 (s, 3H), 1.40 (s, 3H). |
| 23 (H)* | 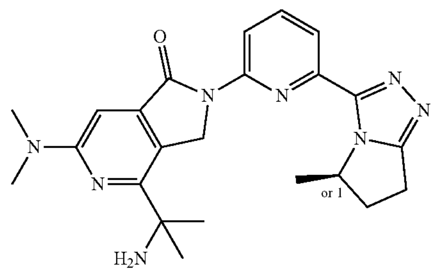 [SMILES: C[C@@H]1CCc2nnc(-c3cccc(N4Cc5c(cc(N(C)C)nc5C(C)(C)N)C4=O)n3)n21] | 4-(2-aminopropan-2-yl)-6-(dimethyl-amino)-2-{6-[(5ξ)-5-methyl-6,7-dihydro-5H-pyrrolo[2,1-c][1,2,4]triazol-3-yl]pyridin-2-yl}-2,3-dihydro-1H-pyrrolo[3,4-c]pyridin-1-one α = −64.6° | 433.2 | 1H NMR (600 MHz, DMSO-d6) δ 8.50 (d, J = 8.4 Hz, 1H), 8.02-7.94 (m, 1H), 7.90 (d, J = 7.7 Hz, 1H), 6.69 (s, 1H), 5.49-5.23 (m, 2H), 5.06 (quin, J = 6.5 Hz, 1H), 3.03 (s, 6H), 3.02-2.97 (m, 1H), 2.91 (qd, J = 8.8, 12.4 Hz, 1H), 2.85-2.79 (m, 1H), 2.31 (dd, J = 8.3, 11.9 Hz, 1H), 1.44 (d, J = 6.4 Hz, 3H), 1.43 (s, 3H), 1.41 (s, 3H). |
| 24 (F)* | 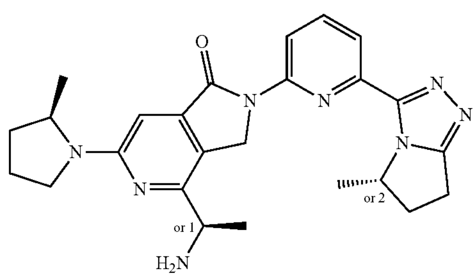 [SMILES: C[C@@H]1CCCN1c1cc2c(c([C@@H](C)N)n1)CN(c1cccc(-c3nnc4n3[C@@H](C)CC4)n1)C2=O] | 4-[(1ξ)-1-aminoethyl]-2-{6-[(5ξ)-5-methyl-6,7-dihydro-5H-pyrrolo[2,1-c][1,2,4]triazol-3-yl]pyridin-2-yl}-6-[(2R)-2-methylpyrroli-din-1-yl]-2,3-dihydro-1H-pyrrolo[3,4-c]pyridin-1-one α = 140.8° | 459.2 | 1H NMR (400 MHz, DMSO-d6) δ 8.57 (dd, J = 0.7, 8.3 Hz, 1H), 8.10-8.03 (m, 1H), 7.97 (dd, J = 0.7, 7.6 Hz, 1H), 6.59 (s, 1H), 5.35 (d, J = 17.1 Hz, 1H), 5.22-5.10 (m, 2H), 4.56 (s, 1H), 4.29-4.21 (m, 1H), 4.19-4.11 (m, 1H), 3.61-3.50 (m, 1H), 3.16-2.81 (m, 4H), 2.44-2.31 (m, 2H), 2.11-2.01 (m, 2H), 1.99-1.93 (m, 1H), 1.74-1.67 (m, 1H), 1.53 (d, J = 6.6 Hz, 3H), 1.40 (br. d, J = 6.4 Hz, 3H), 1.25-1.18 (m, 3H). |
| 25 (F)* | 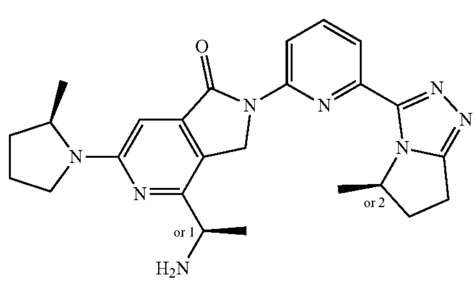 [SMILES: C[C@@H]1CCCN1c1cc2c(c([C@@H](C)N)n1)CN(c1cccc(-c3nnc4n3[C@H](C)CC4)n1)C2=O] | 4-[(1ξ)-1-aminoethyl]-2-{6-[(5ξ)-5-methyl-6,7-dihydro-5H-pyrrolo[2,1-c][1,2,4]triazol-3-yl]pyridin-2-yl}-6-[(2R)-2-methylpyrroli-din-1-yl]-2,3-dihydro-1H-pyrrolo[3,4-c]pyridin-1-one α = +46.6° | 459.2 | 1H NMR (400 MHz, DMSO-d6) δ 8.56 (d, J = 7.9 Hz, 1H), 8.05 (t, J = 7.6 Hz, 1H), 7.97 (d, J = 7.1 Hz, 1H), 6.58 (s, 1H), 5.38-5.29 (m, 1H), 5.22-5.07 (m, 2H), 4.55 (s, 1H), 4.29-4.13 (m, 2H), 3.54 (br. d, J = 2.4 Hz, 2H), 3.13-2.79 (m, 4H), 2.43-2.30 (m, 1H), 2.11-2.02 (m, 2H), 1.98-1.93 (m, 1H), 1.73-1.63 (m, 1H), 1.51 (d, J = 6.6 Hz, 3H), 1.39 (d, J = 6.6 Hz, 3H), 1.20 (d, J = 6.1 Hz, 3H). |

TABLE 5-continued

| Ex # | Structure | IUPAC Name, and rotation | LRMS (m/z) (M + H)+^ | 1H NMR |
|---|---|---|---|---|
| 26 (F)* | 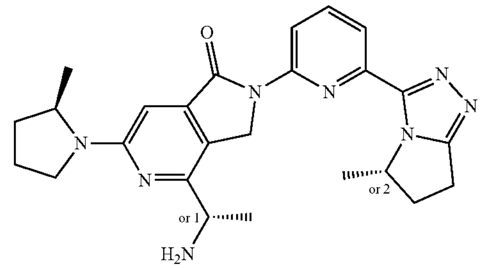 [SMILES: C[C@H](N)c1nc(N2CCC[C@H]2C)cc2c1CN(c1cccc(-c3nnc4n3[C@@H](C)CC4)n1)C2=O] | 4-[(1ξ)-1-aminoethyl]-2-{6-[(5ξ)-5-methyl-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one α = −94.9° | 459.2 | 1H NMR (400 MHz, DMSO-d6) δ 8.58 (dd, J = 0.7, 8.3 Hz, 1H), 8.09-8.02 (m, 1H), 8.00-7.96 (m, 1H), 6.59 (s, 1H), 5.39-5.30 (m, 1H), 5.23-5.11 (m, 2H), 4.56 (s, 1H), 4.24 (br. d, J = 5.4 Hz, 2H), 3.64-3.50 (m, 1H), 3.14-2.84 (m, 4H), 2.43-2.28 (m, 2H), 2.13-2.03 (m, 2H), 1.97 (br. s, 1H), 1.71 (br. d, J = 2.2 Hz, 1H), 1.52 (d, J = 6.4 Hz, 3H), 1.39 (br. d, J = 6.4 Hz, 3H), 1.22 (d, J = 6.1 Hz, 3H). |
| 27 (F)* | 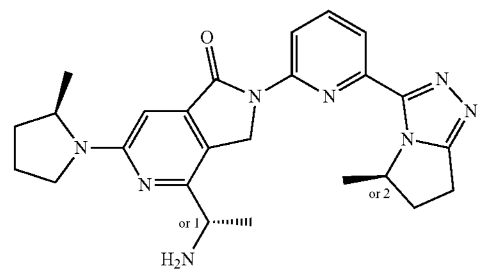 [SMILES: C[C@H](N)c1nc(N2CCC[C@H]2C)cc2c1CN(c1cccc(-c3nnc4n3[C@H](C)CC4)n1)C2=O] | 4-[(1ξ)-1-aminoethyl]-2-{6-[(5ξ)-5-methyl-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one α = +17.4° | 459.2 | 1H NMR (400 MHz, DMSO-d6) δ 8.58 (d, J = 8.1 Hz, 1H), 8.09-8.03 (m, 1H), 7.99-7.95 (m, 1H), 6.57 (s, 1H), 5.37-5.29 (m, 1H), 5.23-5.10 (m, 2H), 4.56 (s, 1H), 4.25 (br. s, 1H), 4.19-4.13 (m, 1H), 3.56 (br. d, J = 2.0 Hz, 1H), 3.15-2.84 (m, 4H), 2.42-2.30 (m, 2H), 2.12-2.01 (m, 2H), 1.96 (br. s, 1H), 1.74-1.66 (m, 1H), 1.52 (d, J = 6.4 Hz, 3H), 1.37 (br. d, J = 6.4 Hz, 3H), 1.21 (d, J = 6.1 Hz, 3H). |
| 28 (F)* | 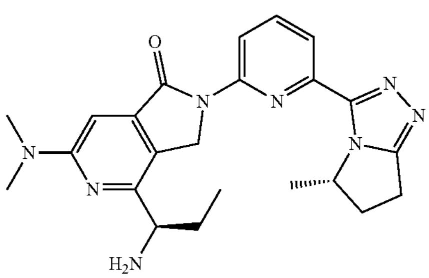 [SMILES: CC[C@@H](N)c1nc(N(C)C)cc2c1CN(c1cccc(-c3nnc4n3[C@@H](C)CC4)n1)C2=O] | 4-[(1R)-1-aminopropyl]-6-(dimethylamino)-2-{6-[(5S)-5-methyl-6,7-dihydro-5H-pyrrolo[2,1-c][1,2,4]triazol-3-yl]pyridin-2-yl}-2,3-dihydro-1H-pyrrolo[3,4-c]pyridin-1-one α = +99.9° | 433.3 | 1H NMR (600 MHz, DMSO-d6) δ 8.47 (d, J = 8.3 Hz, 1H), 8.05-7.97 (m, 1H), 7.92 (d, J = 7.5 Hz, 1H), 6.82 (s, 1H), 5.19-5.02 (m, 3H), 4.21 (br. t, J = 6.2 Hz, 1H), 3.10 (s, 6H), 3.07-2.93 (m, 3H), 2.90-2.80 (m, 1H), 2.41-2.30 (m, 1H), 2.01-1.82 (m, 2H), 1.46 (d, J = 6.4 Hz, 3H), 0.87 (t, J = 7.4 Hz, 3H). |
| 29 (J)* | 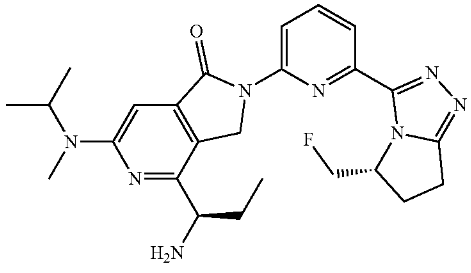 [SMILES: CC[C@@H](N)c1nc(N(C)C(C)C)cc2c1CN(c1cccc(-c3nnc4n3[C@@H](CF)CC4)n1)C2=O] | 4-[(1R)-1-aminoethyl]-2-{6-[(5R)-5-(fluoromethyl)-6,7-dihydro-5H-pyrrolo[2,1-c][1,2,4]triazol-3-yl]pyridin-2-yl}-6-[methyl(propan-2-yl)amino]-2,3-dihydro-1H-pyrrolo[3,4-c]pyridin-1-one | 465.2 | 1H NMR (400 MHz, DMSO-d6) δ 8.58 (d, J = 8.19 Hz, 1H), 8.07-8.13 (m, 1H), 8.00-8.06 (m, 1H), 6.92 (s, 1H), 5.29-5.38 (m, 1H), 5.18-5.26 (m, 1H), 4.96-5.05 (m, 3H), 4.85-4.90 (m, 1H), 4.48-4.60 (m, 1H), 3.00-3.07 (m, 2H), 2.93-2.96 (m, 3H), 2.69-2.81 (m, 3H), 2.20-2.34 (m, 1H), 1.55 (d, J = 6.72 Hz, 3H), 1.15-1.19 (m, 6H). |

TABLE 5-continued

| Ex # | Structure | IUPAC Name, and rotation | LRMS (m/z) (M + H)+^ | 1H NMR |
|---|---|---|---|---|
| 30 (J)* | 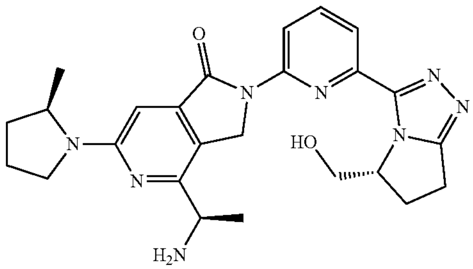 [SMILES: C[C@@H]1CCCN1c1cc2c(c([C@@H](C)N)n1)CN(c1cccc(-c3nnc4n3[C@@H](CO)CC4)n1)C2=O] | 4-[(1R)-1-aminoethyl]-2-{6-[(5R)-5-(hydroxymethyl)-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one α = +50.8° | 475.2 | 1H NMR (600 MHz, DMSO-d6) δ 8.55 (d, J = 8.3 Hz, 1H), 8.08-8.01 (m, 1H), 7.99-7.95 (m, 1H), 6.57 (s, 1H), 5.27 (d, J = 16.9 Hz, 1H), 5.09 (d, J = 16.9 Hz, 1H), 5.04-4.99 (m, 1H), 4.29-4.21 (m, 1H), 4.18 (q, J = 6.3 Hz, 1H), 3.89-3.81 (m, 2H), 3.57-3.52 (m, 1H), 3.05-2.81 (m, 4H), 2.71 (br. dd, J = 9.4, 11.5 Hz, 1H), 2.55-2.51 (m, 1H), 2.13-2.01 (m, 2H), 2.00-1.92 (m, 1H), 1.70 (br. dd, J = 2.4, 5.0 Hz, 1H), 1.38 (d, J = 6.6 Hz, 3H), 1.21 (d, J = 6.2 Hz, 3H). |
| 31 (J)* | 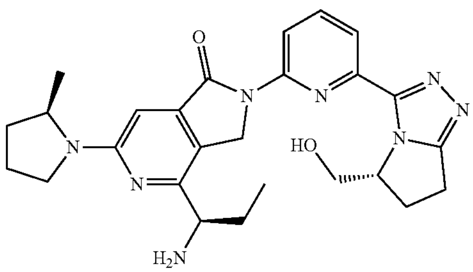 [SMILES: CC[C@@H](N)c1nc(N2CCC[C@H]2C)cc2c1CN(c1cccc(-c3nnc4n3[C@@H](CO)CC4)n1)C2=O] | 4-[(1R)-1-aminopropyl]-2-{6-[(5R)-5-(hydroxymethyl)-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one | 489.4 | 1H NMR (400 MHz, DMSO-d6) δ 8.67-8.59 (m, 1H), 8.42 (br. s, 3H), 8.17-8.10 (m, 1H), 8.04 (dd, J = 0.8, 7.6 Hz, 1H), 6.74 (s, 1H), 5.25-5.10 (m, 3H), 4.42 (br. d, J = 5.8 Hz, 1H), 4.33 (br. s, 1H), 3.93 (br. d, J = 2.8 Hz, 1H), 3.91 (br. d, J = 2.5 Hz, 1H), 3.63-3.57 (m, 1H), 3.43 (br. d, J = 9.0 Hz, 1H), 3.18-3.06 (m, 1H), 3.03-2.91 (m, 2H), 2.82-2.72 (m, 1H), 2.14-1.92 (m, 5H), 1.74 (br. d, J = 6.6 Hz, 1H), 1.22 (d, J = 6.1 Hz, 3H), 0.92 (t, J = 7.4 Hz, 3H); |
| 32 (J)* | 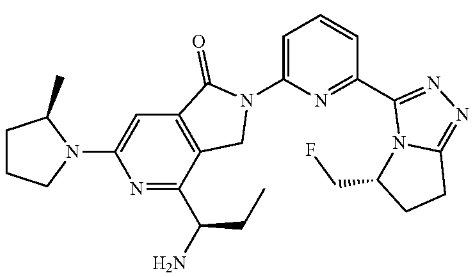 [SMILES: CC[C@@H](N)c1nc(N2CCC[C@H]2C)cc2c1CN(c1cccc(-c3nnc4n3[C@@H](CF)CC4)n1)C2=O] | 4-[(1R)-1-aminopropyl]-2-{6-[(5R)-5-(fluoromethyl)-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one | 491.2 | 1H NMR (400 MHz, DMSO-d6) δ 8.57 (d, J = 8.31 Hz, 1H), 8.05-8.14 (m, 1H), 7.97-8.04 (m, 1H), 6.71 (s, 1H), 5.33-5.39 (m, 1H), 5.26-5.33 (m, 1H), 5.14-5.23 (m, 1H), 5.03-5.12 (m, 1H), 4.96-5.04 (m, 1H), 4.83-4.92 (m, 1H), 4.29 (br. d, J = 5.87 Hz, 2H), 3.60 (br. t, J = 7.83 Hz, 1H), 3.36-3.46 (m, 2H), 2.89-3.10 (m, 3H), 2.67-2.77 (m, 1H), 1.85-2.17 (m, 5H), 1.72 (br. s, 1H), 1.21 (br. d, J = 6.11 Hz, 3H), 0.91 (br. t, J = 7.27 Hz, 3H). |
| 33 (J)* | 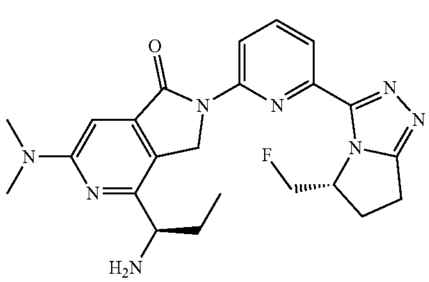 [SMILES: CC[C@@H](N)c1nc(N(C)C)cc2c1CN(c1cccc(-c3nnc4n3[C@@H](CF)CC4)n1)C2=O] | 4-[(1R)-1-aminopropyl]-6-(dimethylamino)-2-{6-[(5R)-5-(fluoromethyl)-6,7-dihydro-5H-pyrrolo[2,1-c][1,2,4]triazol-3-yl]pyridin-2-yl}-2,3-dihydro-1H-pyrrolo[3,4-c]pyridin-1-one α = +58.7° | 451.3 | 1H NMR (400 MHz, DMSO-d6) δ 8.58 (d, J = 8.3 Hz, 1H), 8.16-8.06 (m, 1H), 8.04-7.97 (m, 1H), 6.90 (s, 1H), 5.44-5.27 (m, 1H), 5.24-5.07 (m, 2H), 5.05-4.96 (m, 1H), 4.94-4.82 (m, 1H), 4.33-4.19 (m, 1H), 3.16 (s, 6H), 3.13-2.93 (m, 3H), 2.79-2.62 (m, 1H), 2.07-1.79 (m, 2H), 0.90 (br. t, J = 7.3 Hz, 3H). |

TABLE 5-continued

| Ex # | Structure | IUPAC Name, and rotation | LRMS (m/z) (M + H)+^ | 1H NMR |
|---|---|---|---|---|
| 34 (J)* | 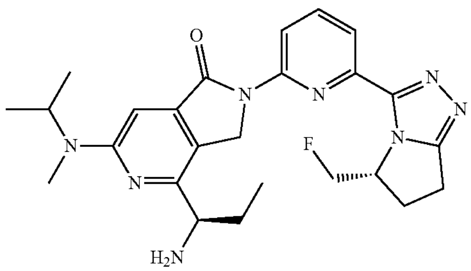 | 4-[(1R)-1-aminopropyl]-2-{6-[(5R)-5-(fluoromethyl)-6,7-dihydro-5H-pyrrolo[2,1-c][1,2,4]triazol-3-yl]pyridin-2-yl}-6-[methyl(propan-2-yl)amino]-2,3-dihydro-1H-pyrrolo[3,4-c]pyridin-1-one | 479.4 | 1H NMR (400 MHz, DMSO-d6) δ 8.59 (d, J = 8.0 Hz, 1H), 8.43 (br. s, 3H), 8.15-8.08 (m, 1H), 8.03 (d, J = 7.5 Hz, 1H), 6.93 (s, 1H), 5.44-5.28 (m, 1H), 5.21-5.06 (m, 2H), 5.05-4.93 (m, 2H), 4.93-4.83 (m, 1H), 4.35 (br. d, J = 6.3 Hz, 1H), 3.13-2.96 (m, 3H), 2.94 (s, 3H), 2.77-2.70 (m, 1H), 2.05-1.91 (m, 2H), 1.17 (dd, J = 6.7, 15.4 Hz, 6H), 0.90 (t, J = 7.4 Hz, 3H). |
| 35 (J)* | 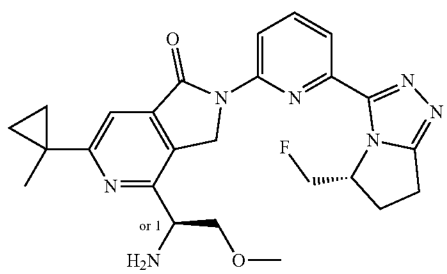 [SMILES: COC[C@@H](N)c1nc(C2(C)CC2)cc2c1CN(c1cccc(-c3nnc4n3[C@@H](CF)CC4)n1)C2=O] | 4-[(1ξ)-1-amino-2-methoxyethyl]-2-{6-[(5R)-5-(fluoromethyl)-6,7-dihydro-5H-pyrrolo[2,1-c][1,2,4]triazol-3-yl]pyridin-2-yl}-6-(1-methylcyclopropyl)-2,3-dihydro-1H-pyrrolo[3,4-c]pyridin-1-one α = +91.2° | 478.1 | 1H NMR (400 MHz, CDCl3) δ 8.70 (dd, J = 0.7, 8.4 Hz, 1H), 8.20 (dd, J = 0.7, 7.6 Hz, 1H), 8.01-7.90 (m, 1H), 7.71 (s, 1H), 5.32-5.16 (m, 2H), 5.16-5.05 (m, 1H), 5.02-4.73 (m, 2H), 4.34 (t, J = 6.5 Hz, 1H), 3.69-3.58 (m, 2H), 3.43-3.35 (m, 3H), 3.22-3.03 (m, 3H), 2.96-2.86 (m, 1H), 1.61 (s, 3H), 1.41-1.31 (m, 2H), 0.91 (q, J = 3.1 Hz, 2H). |
| 36 (F)* | 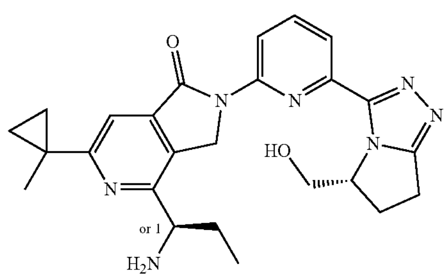 [SMILES: CC[C@@H](N)c1nc(C2(C)CC2)cc2c1CN(c1cccc(-c3nnc4n3[C@@H](CO)CC4)n1)C2=O] | 4-[(1ξ)-1-aminopropyl]-2-{6-[(5R)-5-(hydroxymethyl)-6,7-dihydro-5H-pyrrolo[2,1-c][1,2,4]triazol-3-yl]pyridin-2-yl}-6-(1-methylcyclopropyl)-2,3-dihydro-1H-pyrrolo[3,4-c]pyridin-1-one α = +152.9° | [M + Na]+ 482.1 | 1H NMR (400 MHz, DMSO-d6) δ 8.59-8.52 (m, 1H), 8.10-8.03 (m, 1H), 8.01-7.96 (m, 1H), 7.53 (s, 1H), 5.39 (d, J = 18.0 Hz, 1H), 5.18 (d, J = 18.0 Hz, 1H), 5.06-4.97 (m, 1H), 4.00 (t, J = 6.6 Hz, 1H), 3.87 (d, J = 3.6 Hz, 2H), 3.07-2.81 (m, 3H), 2.77-2.69 (m, 1H), 1.85-1.73 (m, 1H), 1.71-1.61 (m, 1H), 1.56 (s, 3H), 1.31-1.22 (m, 2H), 0.92-0.81 (m, 5H). |
| 37 (F)* | 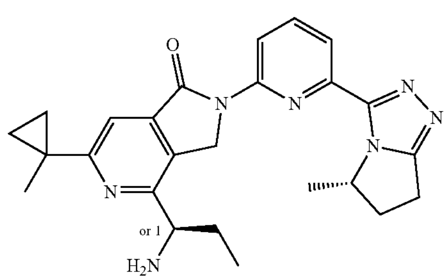 [SMILES: CC[C@@H](N)c1nc(C2(C)CC2)cc2c1CN(c1cccc(-c3nnc4n3[C@@H](C)CC4)n1)C2=O] | 4-[(1ξ)-1-aminopropyl]-6-(1-methylcyclopropyl)-2-{6-[(5S)-5-methyl-6,7-dihydro-5H-pyrrolo[2,1-c][1,2,4]triazol-3-yl]pyridin-2-yl}-2,3-dihydro-1H-pyrrolo[3,4-c]pyridin-1-one α = +92.8° | 444.1 | 1H NMR (400 MHz, DMSO-d6) δ 8.56 (d, J = 8.3 Hz, 1H), 8.10-8.02 (m, 1H), 8.00-7.94 (m, 1H), 7.52 (s, 1H), 5.46 (d, J = 18.1 Hz, 1H), 5.26 (d, J = 18.1 Hz, 1H), 5.12 (quin, J = 6.4 Hz, 1H), 3.98 (t, J = 6.5 Hz, 1H), 3.14-2.84 (m, 3H), 2.40 (br. dd, J = 8.4, 11.7 Hz, 1H), 1.80 (quind, J = 6.9, 13.9 Hz, 1H), 1.72-1.61 (m, 1H), 1.59-1.47 (m, 6H), 1.30-1.21 (m, 2H), 0.93-0.81 (m, 5H). |

TABLE 5-continued

| Ex # | Structure | IUPAC Name, and rotation | LRMS (m/z) (M + H)+^ | 1H NMR |
|---|---|---|---|---|
| 38 (F)* | 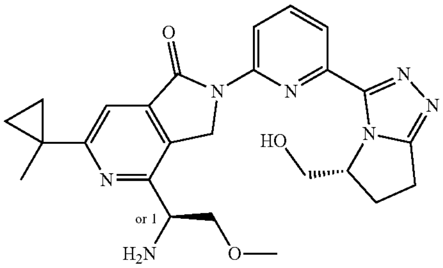 [SMILES: COC[C@@H](N)c1nc(C2(C)CC2)cc2c1CN(c1cccc(-c3nnc4n3[C@@H](CO)CC4)n1)C2=O] | 4-[(1ξ)-1-amino-2-methoxyethyl]-2-{6-[(5R)-5-(hydroxymethyl)-6,7-dihydro-5H-pyrrolo[2,1-c][1,2,4]triazol-3-yl]pyridin-2-yl}-6-(1-methylcyclopropyl)-2,3-dihydro-1H-pyrrolo[3,4-c]pyridin-1-one α = +82.7° | 476.3 | 1H NMR (600 MHz, DMSO-d6) δ 8.60-8.51 (m, 1H), 8.13-8.05 (m, 1H), 8.00 (d, J = 7.5 Hz, 1H), 7.56 (s, 1H), 5.39 (br. d, J = 17.8 Hz, 1H), 5.22 (br. d, J = 17.8 Hz, 1H), 5.03 (br. d, J = 3.1 Hz, 1H), 4.35-4.21 (m, 1H), 3.94-3.82 (m, 2H), 3.66-3.52 (m, 2H), 3.28 (br. s, 3H), 3.04-2.89 (m, 2H), 2.85 (dd, J = 9.2, 14.1 Hz, 1H), 2.74-2.67 (m, 1H), 1.57 (s, 3H), 1.28-1.23 (m, 3H), 0.91-0.86 (m, 2H). |

*Letter within parentheses is the Method by which Example was prepared.
^[M + H]+ unless otherwise indicated.

Example 100: 4-(2-aminopropan-2-yl)-2-[6-(4-ethyl-4H-1,2,4-triazol-3-yl)pyridin-2-yl]-6-[(2R)-2-methylpyrrolidin-1-yl]-2,3-dihydro-1H-pyrrolo[3,4-c]pyridin-1-one

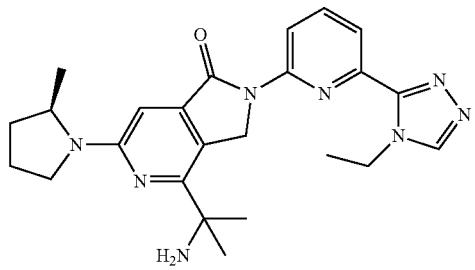 [SMILES: CCn1cnnc1-c1cccc(N2Cc3c(cc(N4CCC[C@H]4C)nc3C(C)(C)N)C2=O)n1]

A mixture of 4-(2-aminopropan-2-yl)-6-[(2R)-2-methylpyrrolidin-1-yl]-2,3-dihydro-1H-pyrrolo[3,4-c]pyridin-1-one (Intermediate 6) (63.0 mg, 0.23 mmol), 2-bromo-6-(4-ethyl-4H-1,2,4-triazol-3-yl)pyridine (Intermediate 1) (58.1 mg, 0.230 mmol), $K_2CO_3$ (69.8 mg, 0.505 mmol), CuI (10.9 mg, 0.058 mmol), and N,N-dimethylethylenediamine (0.115 mmol, 0.0125 mL) in $CH_3CN$ (3.0 mL) was heated at 120° C. with microwave irradiation for 30 min. The volatile material was removed, and the residue was purified by flash chromatography ($SiO_2$, 0-10% MeOH/DCM). The product was further purified by HPLC (Phenemonex Gemini NX C18 column, 150×21.2 mm, 5 μm. Mobile A: Water+10 mM Ammonium Acetate, Mobile B: Acetonitrile) to provide Example 100 as a pale yellow solid (49.3 mg, 49% yield). 1H NMR (600 MHz, DMSO-d6) δ 8.74 (s, 1H), 8.62 (d, J=8.4 Hz, 1H), 8.11-8.04 (m, 1H), 8.03-7.90 (m, 1H), 6.55 (s, 1H), 5.40 (s, 2H), 4.65 (q, J=7.2 Hz, 2H), 4.24-4.19 (m, 1H), 3.29-3.33 (m, 2H, assumed; partially obscured by water peak), 2.16-2.03 (m, 2H), 1.98-1.89 (m, 1H), 1.71-1.69 (m, 1H), 1.50 (t, J=7.1 Hz, 3H), 1.47 (d, J=5.9 Hz, 6H), 1.22 (d, J=6.2 Hz, 3H); m/z (APCI+) for ($C_{24}H_{30}N_8O$), 447.3 (M+H)+.

TABLE 6

| Ex. # | Structure, separation method | IUPAC Name, rotation | LRMS (m/z) (M + H)+^ | 1H NMR |
|---|---|---|---|---|
| 101 (E)* | Peak 1 (separated by SFC on Phenomenex Lux Cell-1, 40% methanol with 10 mM NH3) | 4-[(1ξ)-1-aminoethyl]-6-[(2R)-2-methylpyrrolidin-1-yl]-2-[6-(4-propyl-4H-1,2,4-triazol-3-yl)pyridin-2-yl]-2,3-dihydro-1H-pyrrolo[3,4-c]pyridin-1-one | 447.2 | 1H NMR (600 MHz, DMSO-d6) δ 8.72 (s, 1H), 8.60 (td, J = 2.3, 8.3 Hz, 1H), 8.09-8.02 (m, 1H), 7.99 (br. d, J = 7.7 Hz, 1H), 6.57 (s, 1H), 5.17 (br. s, 2H), 4.59-4.53 (m, 3H), 4.29-4.18 (m, 2H), 3.22-3.18 (m, 1H), 2.10-2.01 (m, 2H), 1.96 (br. s, 1H), 1.91-1.82 (m, 2H), 1.70 (br. s, 1H), 1.39 (br. d, J = 4.2 Hz, 3H), 1.35-1.31 (m, 1H), 1.21 (br. d, J = 5.7 Hz, 4H), 0.94 (br. t, J = 7.2 Hz, 3H). |

TABLE 6-continued

| Ex. # | Structure, separation method | IUPAC Name, rotation | LRMS (m/z) (M + H)+^ | 1H NMR |
|---|---|---|---|---|
| 102 (E)* | Peak 2 (separated by SFC on Phenomenex Lux Cell-1, 40% methanol with 10 mM NH3) | 4-[(1ξ)-1-aminoethyl]-6-[(2R)-2-methylpyrrolidin-1-yl]-2-[6-(4-propyl-4H-1,2,4-triazol-3-yl)pyridin-2-yl]-2,3-dihydro-1H-pyrrolo[3,4-c]pyridin-1-one | 447.2 | 1H NMR (600 MHz, DMSO-d6) δ 8.74 (s, 1H), 8.62 (d, J = 8.3 Hz, 1H), 8.12-8.07 (m, 1H), 8.00 (d, J = 7.7 Hz, 1H), 6.70 (s, 1H), 5.16 (s, 2H), 4.58-4.52 (m, 4H), 4.33 (br. s, 1H), 3.64-3.60 (m, 2H), 2.12-2.02 (m, 2H), 1.98 (br. d, J = 4.2 Hz, 1H), 1.90-1.83 (m, 2H), 1.75-1.70 (m, 1H), 1.52 (br. d, J = 6.1 Hz, 3H), 1.23-1.18 (m, 4H), 0.93 (t, J = 7.4 Hz, 3H). |
| 103 (A)* | | 4-[(1ξ)-1-aminoethyl]-2-[6-(4-cyclobutyl-4H-1,2,4-triazol-3-yl)pyridin-2-yl]-6-(1-methylcyclopropyl)-2,3-dihydro-1H-pyrrolo[3,4-c]pyridin-1-one α = +8.4° | 430.1 | 1H NMR (400 MHz, CDCl3) δ 8.75 (d, J = 8.3 Hz, 1H), 8.50 (s, 1H), 8.14-8.07 (m, 1H), 8.02-7.91 (m, 1H), 7.71 (s, 1H), 5.78 (quin, J = 8.4 Hz, 1H), 5.28 (d, J = 2.8 Hz, 2H), 4.33 (q, J = 6.6 Hz, 1H), 2.73-2.58 (m, 2H), 2.52-2.35 (m, 2H), 2.10-1.98 (m, 1H), 1.97-1.84 (m, 1H), 1.62 (s, 3H), 1.49 (d, J = 6.8 Hz, 3H), 1.37 (br. d, J = 3.5 Hz, 2H), 0.91 (d, J = 2.8 Hz, 2H). |
| 104 (A)* | | 4-[(1ξ)-1-aminoethyl]-2-[6-(4-cyclobutyl-4H-1,2,4-triazol-3-yl)pyridin-2-yl]-6-(1-methylcyclopropyl)-2,3-dihydro-1H-pyrrolo[3,4-c]pyridin-1-one α = +1.5° | 430.1 | 1H NMR (400 MHz, CDCl3) δ 8.75 (d, J = 8.5 Hz, 1H), 8.50 (s, 1H), 8.10 (d, J = 7.8 Hz, 1H), 8.01-7.91 (m, 1H), 7.71 (s, 1H), 5.78 (quin, J = 8.5 Hz, 1H), 5.28 (d, J = 2.8 Hz, 2H), 4.33 (q, J = 6.6 Hz, 1H), 2.72-2.60 (m, 2H), 2.51-2.36 (m, 2H), 2.11-1.98 (m, 1H), 1.97-1.86 (m, 1H), 1.62 (s, 3H), 1.49 (d, J = 6.5 Hz, 3H), 1.41-1.33 (m, 2H), 0.91 (d, J = 2.8 Hz, 2H). |
| 105 (A)* | | 4-[(1ξ)-1-aminopropyl]-2-[6-(4-cyclobutyl-4H-1,2,4-triazol-3-yl)pyridin-2-yl]-6-(1-methylcyclopropyl)-2,3-dihydro-1H-pyrrolo[3,4-c]pyridin-1-one α = −1.9° | 444.1 | 1H NMR (400 MHz, CDCl3) δ 8.75 (d, J = 8.3 Hz, 1H), 8.50 (s, 1H), 8.10 (d, J = 7.5 Hz, 1H), 8.02-7.92 (m, 1H), 7.71 (s, 1H), 5.78 (quin, J = 8.4 Hz, 1H), 5.33-5.18 (m, 2H), 4.06 (t, J = 6.7 Hz, 1H), 2.73-2.59 (m, 2H), 2.43 (quin, J = 10.4 Hz, 2H), 2.04 (q, J = 9.6 Hz, 1H), 1.97-1.84 (m, 2H), 1.84-1.74 (m, 1H), 1.62 (s, 3H), 1.37 (q, J = 3.2 Hz, 2H), 0.95 (t, J = 7.4 Hz, 3H), 0.91 (q, J = 3.4 Hz, 2H). |

TABLE 6-continued

| Ex. # | Structure, separation method | IUPAC Name, rotation | LRMS (m/z) (M + H)+^ | 1H NMR |
|---|---|---|---|---|
| 106 (A)* |  | 4-[(1ξ)-1-aminopropyl]-2-[6-(4-cyclobutyl-4H-1,2,4-triazol-3-yl)pyridin-2-yl]-6-(1-methylcyclopropyl)-2,3-dihydro-1H-pyrrolo[3,4-c]pyridin-1-one α = +22.4° | 441.1 | 1H NMR (400 MHz, CDCl3) δ 8.75 (d, J = 8.5 Hz, 1H), 8.50 (s, 1H), 8.10 (d, J = 7.5 Hz, 1H), 8.02-7.92 (m, 1H), 7.71 (s, 1H), 5.78 (quin, J = 8.5 Hz, 1H), 5.34-5.18 (m, 2H), 4.06 (t, J = 6.7 Hz, 1H), 2.72-2.59 (m, 2H), 2.52-2.35 (m, 2H), 2.04 (q, J = 10.0 Hz, 1H), 1.98-1.85 (m, 2H), 1.78 (dd, J = 7.0, 14.1 Hz, 1H), 1.62 (s, 3H), 1.37 (q, J = 3.1 Hz, 2H), 0.95 (t, J = 7.5 Hz, 3H), 0.91 (q, J = 3.3 Hz, 2H). |
| 107 (G)* |  | 2-[6-(4-ethyl-5-methyl-4H-1,2,4-triazol-3-yl)pyridin-2-yl]-4-[(1ξ)-1-(methylamino)ethyl]-6-[(2R)-2-methylpyrrolidin-1-yl]-2,3-dihydro-1H-pyrrolo[3,4-c]pyridin-1-one α = +2.1° | 461.1 | 1H NMR (400 MHz, CDCl3) δ 8.74 (d, J = 8.5 Hz, 1H), 8.14 (d, J = 7.5 Hz, 1H), 7.93 (t, J = 8.0 Hz, 1H), 6.72 (s, 1H), 5.11 (d, J = 2.0 Hz, 2H), 4.61 (q, J = 7.3 Hz, 2H), 4.29 (br. t, J = 6.0 Hz, 1H), 3.79 (q, J = 6.6 Hz, 1H), 3.66-3.60 (m, 1H), 3.45-3.38 (m, 1H), 2.60 (s, 3H), 2.37 (s, 3H), 2.21-2.00 (m, 3H), 1.55 (t, J = 7.2 Hz, 3H), 1.43 (d, J = 6.8 Hz, 3H), 1.28 (d, J = 6.3 Hz, 3H). |
| 108 (G)* |  | 2-[6-(4-ethyl-5-methyl-4H-1,2,4-triazol-3-yl)pyridin-2-yl]-4-[(1ξ)-1-(methylamino)ethyl]-6-[(2R)-2-methyl-pyrrolidin-1-yl]-2,3-dihydro-1H-pyrrolo[3,4-c]pyridin-1-one α = −80.5° | 461.2 | 1H NMR (400 MHz, CDCl3) δ 8.73 (d, J = 8.5 Hz, 1H), 8.13 (d, J = 7.5 Hz, 1H), 7.93 (t, J = 8.0 Hz, 1H), 6.72 (s, 1H), 5.10 (s, 2H), 4.61 (q, J = 7.1 Hz, 2H), 4.30-4.22 (m, 1H), 3.76 (q, J = 6.7 Hz, 1H), 3.62 (br. t, J = 7.3 Hz, 1H), 3.47-3.38 (m, 1H), 2.59 (s, 3H), 2.37 (s, 3H), 2.20-2.01 (m, 3H), 1.55 (t, J = 7.2 Hz, 3H), 1.44 (d, J = 6.8 Hz, 3H), 1.29 (br. d, J = 6.3 Hz, 3H). |
| 109 (E)* |  | 2-[6-(4-ethyl-4H-1,2,4-triazol-3-yl)pyridin-2-yl]-4-[(1ξ)-1-(methylamino)ethyl]-6-[(2R)-2-methyl-pyrrolidin-1-yl]-2,3-dihydro-1H-pyrrolo[3,4-c]pyridin-1-one α = −1.5° | 447.1 | 1H NMR (400 MHz, CDCl3) δ 8.67 (d, J = 8.4 Hz, 1H), 8.20 (s, 1H), 8.08 (d, J = 7.3 Hz, 1H), 7.86 (t, J = 8.0 Hz, 1H), 6.64 (s, 1H), 5.02 (d, J = 1.6 Hz, 2H), 4.63 (q, J = 7.2 Hz, 2H), 4.23-4.16 (m, 1H), 3.71 (q, J = 6.8 Hz, 1H), 3.57-3.50 (m, 1H), 3.42-3.29 (m, 1H), 2.29 (s, 3H), 2.07-1.92 (m, 3H), 1.69 (br. d, J = 3.0 Hz, 1H), 1.55-1.50 (m, 3H), 1.35 (d, J = 6.8 Hz, 3H), 1.19 (d, J = 6.3 Hz, 3H). |

| Ex. # | Structure, separation method | IUPAC Name, rotation | LRMS (m/z) (M + H)+^ | 1H NMR |
|---|---|---|---|---|
| 110 (E)* | | 2-[6-(4-ethyl-4H-1,2,4-triazol-3-yl)pyridin-2-yl]-4-[(1ξ)-1-(methylamino)ethyl]-6-[(2R)-2-methyl-pyrrolidin-1-yl]-2,3-dihydro-1H-pyrrolo[3,4-c]pyridin-1-one α = −88.2° | 447.1 | 1H NMR (400 MHz, CDCl3) δ 8.66 (d, J = 8.5 Hz, 1H), 8.19 (s, 1H), 8.08 (d, J = 7.6 Hz, 1H), 7.86 (t, J = 8.1 Hz, 1H), 6.63 (s, 1H), 5.05-4.97 (m, 2H), 4.62 (q, J = 7.2 Hz, 2H), 4.22-4.13 (m, 1H), 3.68 (q, J = 6.5 Hz, 1H), 3.58-3.47 (m, 1H), 3.38-3.28 (m, 1H), 2.28 (s, 3H), 2.08-1.92 (m, 3H), 1.74-1.69 (m, 1H), 1.53 (t, J = 7.3 Hz, 3H), 1.35 (d, J = 6.6 Hz, 3H), 1.20 (d, J = 6.3 Hz, 3H). |
| 111 (A)* | | 2-[6-(4-ethyl-4H-1,2,4-triazol-3-yl)pyridin-2-yl]-4-[(1R)-1-(methylamino)ethyl]-6-(1-methylcyclo-propyl)-2,3-dihydro-1H-pyrrolo[3,4-c]pyridin-1-one α = +16.2° | 418.2 | 1H NMR (500 MHz, DMSO-d6) δ 8.77 (s, 1H), 8.63 (dd, J = 0.7, 8.3 Hz, 1H), 8.11 (t, J = 7.9 Hz, 1H), 8.03 (d, J = 7.5 Hz, 1H), 7.57 (s, 1H), 5.32 (s, 2H), 4.71-4.61 (m, 2H), 4.05-3.87 (m, 1H), 2.27 (s, 3H), 1.57 (s, 3H), 1.53 (t, J = 7.2 Hz, 3H), 1.36 (d, J = 6.6 Hz, 3H), 1.32-1.23 (m, 2H), 0.92-0.85 (m, 2H). |
| 112 (A)* | | 2-[6-(4-ethyl-4H-1,2,4-triazol-3-yl)pyridin-2-yl]-4-[(1S)-1-(methylamino)ethyl]-6-(1-methylcyclo-propyl)-2,3-dihydro-1H-pyrrolo[3,4-c]pyridin-1-one α = −19.7° | 418.2 | 1H NMR (500 MHz, DMSO-d6) δ 8.77 (s, 1H), 8.63 (d, J = 8.0 Hz, 1H), 8.11 (t, J = 8.0 Hz, 1H), 8.03 (d, J = 7.4 Hz, 1H), 7.59 (s, 1H), 5.32 (s, 2H), 4.65 (quind, J = 6.7, 13.6 Hz, 2H), 4.14-3.94 (m, 1H), 2.37-2.26 (m, 3H), 1.57 (s, 3H), 1.52 (t, J = 7.2 Hz, 3H), 1.38 (br. d, J = 6.7 Hz, 3H), 1.34-1.25 (m, 2H), 0.89 (d, J = 2.7 Hz, 2H). |
| 113 (A)* | | 4-[(1S)-1-(methylamino)ethyl]-6-(1-methylcyclo-propyl)-2-[6-(4-propyl-4H-1,2,4-triazol-3-yl)pyridin-2-yl]-2,3-dihydro-1H-pyrrolo[3,4-c]pyridin-1-one α = −18.3° | 432.2 | 1H NMR (400 MHz, DMSO-d6) δ 8.75 (s, 1H), 8.63 (d, J = 8.3 Hz, 1H), 8.10 (t, J = 7.9 Hz, 1H), 8.02 (d, J = 7.5 Hz, 1H), 7.55 (s, 1H), 5.29 (s, 2H), 4.65-4.54 (m, 2H), 3.87-3.85 (m, 1H), 2.21 (s, 3H), 1.95-1.83 (m, 2H), 1.56 (s, 3H), 1.32 (br. d, J = 6.8 Hz, 3H), 1.28-1.22 (m, 2H), 0.93 (t, J = 7.3 Hz, 3H), 0.88 (s, 2H). |
| 114 (C)* | | 4-(2-aminopropan-2-yl)-2-[6-(4-ethyl-4H-1,2,4-triazol-3-yl)pyridin-2-yl]-6-(1-methylcyclo-propyl)-2,3-dihydro-1H-pyrrolo[3,4-c]pyridin-1-one | 418.2 | 1H NMR (600 MHz, DMSO-d6) δ 8.71-8.80 (m, 1H), 8.61 (d, J = 8.3 Hz, 1H), 8.07-8.17 (m, 1H), 7.93-8.05 (m, 1H), 7.57 (s, 1H), 5.48 (s, 2H), 4.64 (q, J = 7.1 Hz, 2H), 1.56 (s, 3H), 1.47-1.54 (m, 9H), 1.32 (br. s, 2H), 0.86-0.95 (m, 2H). |

TABLE 6-continued

| Ex. # | Structure, separation method | IUPAC Name, rotation | LRMS (m/z) (M + H)+^ | 1H NMR |
|---|---|---|---|---|
| 115 (A)* | | 4-[(1R)-1-aminoethyl]-2-[6-(4-ethyl-4H-1,2,4-triazol-3-yl)pyridin-2-yl]-6-(1-methylcyclopropyl)-2,3-dihydro-1H-pyrrolo[3,4-c]pyridin-1-one α = +10.1° | 404.3 | 1H NMR (400 MHz, DMSO-d$_6$) δ 8.69 (s, 1H), 8.55 (d, J = 8.3 Hz, 1H), 8.05-7.99 (m, 1H), 7.99-7.93 (m, 1H), 7.46 (s, 1H), 5.36-5.24 (m, 2H), 4.57 (q, J = 7.1 Hz, 2H), 4.15 (q, J = 6.6 Hz, 1H), 1.49 (s, 3H), 1.45 (t, J = 7.1 Hz, 3H), 1.28 (d, J = 6.8 Hz, 3H), 1.24-1.18 (m, 2H), 0.80 (d, J = 3.1 Hz, 2H). |
| 116 (A)* | | 4-[(1S)-1-aminoethyl]-2-[6-(4-ethyl-4H-1,2,4-triazol-3-yl)pyridin-2-yl]-6-(1-methylcyclopropyl)-2,3-dihydro-1H-pyrrolo[3,4-c]pyridin-1-one α = −10.4° | 404.3 | 1H NMR (400 MHz, DMSO-d$_6$) δ 8.76 (s, 1H), 8.61 (d, J = 8.3 Hz, 1H), 8.12-8.05 (m, 1H), 8.05-8.00 (m, 1H), 7.52 (s, 1H), 5.37 (d, J = 4.5 Hz, 2H), 4.64 (q, J = 7.3 Hz, 2H), 4.22 (d, J = 6.8 Hz, 1H), 1.55 (s, 3H), 1.52 (t, J = 7.2 Hz, 3H), 1.35 (d, J = 6.8 Hz, 3H), 1.28-1.23 (m, 2H), 0.87 (d, J = 3.0 Hz, 2H). |
| 117 (A)* | | 4-[(1ξ)-1-aminoethyl]-6-(1-methylcyclopropyl)-2-[6-(4-propyl-4H-1,2,4-triazol-3-yl)pyridin-2-yl]-2,3-dihydro-1H-pyrrolo[3,4-c]pyridin-1-one α = +4.6° | 418.2 | 1H NMR (400 MHz, DMSO-d$_6$) δ 8.75 (s, 1H), 8.63 (d, J = 7.8 Hz, 1H), 8.10 (t, J = 7.4 Hz, 1H), 8.03 (d, J = 7.4 Hz, 1H), 7.54 (s, 1H), 5.34 (s, 2H), 4.58 (br. t, J = 7.2 Hz, 2H), 4.21 (d, J = 6.7 Hz, 1H), 1.96-1.83 (m, 2H), 1.56 (s, 3H), 1.34 (d, J = 6.6 Hz, 3H), 1.30-1.25 (m, 2H), 0.94 (t, J = 7.3 Hz, 3H), 0.87 (d, J = 3.2 Hz, 2H). |
| 118 (A)* | | 4-[(1ξ)-1-aminoethyl]-6-(1-methylcyclopropyl)-2-[6-(4-propyl-4H-1,2,4-triazol-3-yl)pyridin-2-yl]-2,3-dihydro-1H-pyrrolo[3,4-c]pyridin-1-one α = +3.5° | 418.2 | 1H NMR (400 MHz, DMSO-d$_6$) δ 8.75 (s, 1H), 8.63 (d, J = 7.9 Hz, 1H), 8.10 (t, J = 7.7 Hz, 1H), 8.02 (d, J = 7.4 Hz, 1H), 7.54 (s, 1H), 5.41-5.28 (m, 2H), 4.65-4.52 (m, 2H), 4.21 (q, J = 6.6 Hz, 1H), 1.99-1.82 (m, 2H), 1.56 (s, 3H), 1.34 (d, J = 6.7 Hz, 3H), 1.30-1.22 (m, 2H), 0.94 (t, J = 7.4 Hz, 3H), 0.87 (d, J = 3.1 Hz, 2H). |
| 119 (A)* | | 4-[(1ξ)-1-aminopropyl]-2-[6-(4-ethyl-4H-1,2,4-triazol-3-yl)pyridin-2-yl]-6-(1-methylcyclopropyl)-2,3-dihydro-1H-pyrrolo[3,4-c]pyridin-1-one α = −1.6° | 418.2 | 1H NMR (400 MHz, DMSO-d$_6$) δ 8.76 (s, 1H), 8.62 (d, J = 8.3 Hz, 1H), 8.11 (t, J = 8.0 Hz, 1H), 8.02 (d, J = 7.6 Hz, 1H), 7.55 (s, 1H), 5.39-5.28 (m, 2H), 4.64 (dq, J = 2.6, 7.0 Hz, 2H), 3.99 (t, J = 6.5 Hz, 1H), 1.85-1.72 (m, 1H), 1.66 (td, J = 7.1, 13.8 Hz, 1H), 1.31-1.23 (m, 2H), 0.92-0.82 (m, 5H). |

TABLE 6-continued

| Ex. # | Structure, separation method | IUPAC Name, rotation | LRMS (m/z) (M + H)+^ | 1H NMR |
|---|---|---|---|---|
| 120 (A)* | | 4-[(1ξ)-1-aminopropyl]-2-[6-(4-ethyl-4H-1,2,4-triazol-3-yl)pyridin-2-yl]-6-(1-methylcyclopropyl)-2,3-dihydro-1H-pyrrolo[3,4-c]pyridin-1-one α = −2.4° | 418.2 | 1H NMR (400 MHz, DMSO-$d_6$) δ 8.76 (s, 1H), 8.62 (d, J = 8.2 Hz, 1H), 8.10 (t, J = 8.0 Hz, 1H), 8.02 (d, J = 7.6 Hz, 1H), 7.54 (s, 1H), 5.39-5.28 (m, 2H), 4.64 (dq, J = 2.1, 7.0 Hz, 2H), 3.97 (t, J = 6.5 Hz, 1H), 2.31-1.89 (m, 2H), 1.84-1.73 (m, 1H), 1.70-1.60 (m, 1H), 1.56 (s, 3H), 1.52 (t, J = 7.1 Hz, 3H), 1.31-1.23 (m, 2H), 0.90-0.82 (m, 5H). |
| 121 (A)* | | 4-[(1ξ)-1-aminopropyl]-6-(1-methylcyclopropyl)-2-[6-(4-propyl-4H-1,2,4-triazol-3-yl)pyridin-2-yl]-2,3-dihydro-1H-pyrrolo[3,4-c]pyridin-1-one α = +7.9° | 432.1 | 1H NMR (400 MHz, DMSO-$d_6$) δ 8.75 (s, 1H), 8.63 (d, J = 8.0 Hz, 1H), 8.12-8.06 (m, 1H), 8.06-8.01 (m, 1H), 7.54 (s, 1H), 5.30 (s, 2H), 4.58 (q, J = 6.8 Hz, 2H), 3.97 (t, J = 6.7 Hz, 1H), 1.96-1.83 (m, 2H), 1.83-1.72 (m, 1H), 1.70-1.60 (m, 1H), 1.56 (s, 3H), 1.32-1.21 (m, 2H), 0.95 (t, J = 7.3 Hz, 3H), 0.91-0.83 (m, 5H). |
| 122 (A)* | | 4-[(1ξ)-1-aminopropyl]-6-(1-methylcyclopropyl)-2-[6-(4-propyl-4H-1,2,4-triazol-3-yl)pyridin-2-yl]-2,3-dihydro-1H-pyrrolo[3,4-c]pyridin-1-one α = −101.4° | 432.1 | 1H NMR (400 MHz, DMSO-$d_6$) δ 8.76 (s, 1H), 8.64 (d, J = 8.5 Hz, 1H), 8.12 (t, J = 7.7 Hz, 1H), 8.03 (d, J = 7.5 Hz, 1H), 7.61 (s, 1H), 5.36-5.25 (m, 2H), 4.64-4.52 (m, 2H), 4.17 (br. t, J = 6.4 Hz, 1H), 1.94-1.81 (m, 3H), 1.79-1.70 (m, 1H), 1.58 (s, 3H), 1.41-1.27 (m, 2H), 0.94 (t, J = 7.4 Hz, 3H), 0.90 (br. d, J = 2.5 Hz, 2H), 0.89-0.84 (m, 3H). |
| 123 (D)* | | 4-(2-aminopropan-2-yl)-6-[ethyl(methyl)amino]-2-[6-(4-ethyl-5-methyl-4H-1,2,4-triazol-3-yl)pyridin-2-yl]-2,3-dihydro-1H-pyrrolo[3,4-c]pyridin-1-one | 435.3 | 1H NMR (600 MHz, DMSO-$d_6$) δ 8.53 (d, J = 8.25 Hz, 1H), 7.93-8.04 (m, 1H), 7.90 (d, J = 7.70 Hz, 1H), 6.65 (s, 1H), 5.31 (s, 2H), 4.48 (q, J = 6.97 Hz, 2H), 3.54-3.58 (m, 2H), 2.98 (s, 3H), 2.42 (s, 3H), 1.35-1.43 (m, 9H), 1.03 (t, J = 6.97 Hz, 3H). |
| 124 (C)* | | 4-(2-aminopropan-2-yl)-6-[ethyl(methyl)amino]-2-[6-(4-ethyl-4H-1,2,4-triazol-3-yl)pyridin-2-yl]-2,3-dihydro-1H-pyrrolo[3,4-c]pyridin-1-one | 421.3 | 1H NMR (400 MHz, DMSO-$d_6$) δ 8.74 (s, 1H), 8.63 (dd, J = 8.19, 0.86 Hz, 1H), 8.05-8.18 (m, 1H), 7.98-8.04 (m, 1H), 6.73 (s, 1H), 5.41 (s, 2H), 4.65 (q, J = 7.09 Hz, 2H), 3.64 (q, J = 6.97 Hz, 2H), 3.06 (s, 3H), 1.51 (t, J = 7.15 Hz, 3H), 1.46 (s, 6H), 1.11 (t, J = 6.97 Hz, 3H). |

TABLE 6-continued

| Ex. # | Structure, separation method | IUPAC Name, rotation | LRMS (m/z) (M + H)+^ | 1H NMR |
|---|---|---|---|---|
| 125 (A)* | | 4-[(1ξ)-1-aminoethyl]-6-(1-methyl-cyclopropyl)-2-{6-[4-(pentan-3-yl)-4H-1,2,4-triazol-3-yl]pyridin-2-yl}-2,3-dihydro-1H-pyrrolo[3,4-c]pyridin-1-one α = −7.9° | 446.3 | 1H NMR (400 MHz, DMSO-d6) δ 8.92 (s, 1H), 8.64 (d, J = 8.4 Hz, 1H), 8.11 (t, J = 8.0 Hz, 1H), 7.96 (d, J = 7.6 Hz, 1H), 7.54 (s, 1H), 5.50-5.27 (m, 3H), 4.20 (br. d, J = 6.4 Hz, 1H), 1.97-1.84 (m, 4H), 1.56 (s, 3H), 1.34 (d, J = 6.8 Hz, 3H), 1.31-1.23 (m, 2H), 0.87 (br. d, J = 2.9 Hz, 2H), 0.84-0.73 (m, 6H). |
| 126 (A)* | | 4-[(1ξ)-1-aminoethyl]-6-(1-methyl-cyclopropyl)-2-{6-[4-(pentan-3-yl)-4H-1,2,4-triazol-3-yl]pyridin-2-yl}-2,3-dihydro-1H-pyrrolo[3,4-c]pyridin-1-one α = +0.32° | 446.3 | 1H NMR (400 MHz, DMSO-d6) δ 8.93 (s, 1H), 8.64 (d, J = 8.0 Hz, 1H), 8.12 (t, J = 8.0 Hz, 1H), 7.96 (d, J = 7.0 Hz, 1H), 7.55 (s, 1H), 5.46-5.28 (m, 3H), 4.23 (q, J = 6.4 Hz, 1H), 1.99-1.82 (m, 4H), 1.56 (s, 3H), 1.35 (d, J = 6.8 Hz, 3H), 1.31-1.25 (m, 2H), 0.87 (d, J = 2.8 Hz, 2H), 0.82-0.75 (m, 6H). |
| 127 (G)* | | 4-[(1ξ)-1-aminoethyl]-6-[ethyl(methyl)amino]-2-[6-(4-ethyl-5-methyl-4H-1,2,4-triazol-3-yl)pyridin-2-yl]-2,3-dihydro-1H-pyrrolo[3,4-c]pyridin-1-one α = −18.6° | 421.4 | 1H NMR (400 MHz, Methanol-d4) δ 8.66 (br. d, J = 8.2 Hz, 1H), 8.05-7.89 (m, 2H), 6.84-6.73 (m, 1H), 5.12 (br. s, 2H), 4.65 (q, J = 7.1 Hz, 2H), 4.14 (q, J = 6.4 Hz, 1H), 3.71 (br. d, J = 6.7 Hz, 2H), 3.16-3.07 (m, 3H), 2.60 (s, 3H), 1.56 (t, J = 7.1 Hz, 3H), 1.49 (d, J = 6.6 Hz, 3H), 1.20 (t, J = 7.0 Hz, 3H). |
| 128 (G)* | | 4-[(1ξ)-1-aminoethyl]-6-[ethyl(methyl)amino]-2-[6-(4-ethyl-5-methyl-4H-1,2,4-triazol-3-yl)pyridin-2-yl]-2,3-dihydro-1H-pyrrolo[3,4-c]pyridin-1-one α = +24.1° | 421.2 | 1H NMR (400 MHz, Methanol-d4) δ 8.73-8.59 (m, 1H), 8.06-7.86 (m, 2H), 6.86-6.69 (m, 1H), 5.12 (br. s, 2H), 4.65 (q, J = 7.0 Hz, 2H), 4.13 (br. d, J = 6.6 Hz, 1H), 3.71 (br. d, J = 6.7 Hz, 2H), 3.11 (br. d, J = 1.6 Hz, 3H), 2.60 (s, 3H), 1.56 (t, J = 7.1 Hz, 3H), 1.49 (d, J = 6.7 Hz, 3H), 1.20 (t, J = 6.9 Hz, 3H). |
| 129 (E)* | | 4-[(1ξ)-1-aminoethyl]-6-[ethyl(methyl)amino]-2-[6-(4-ethyl-4H-1,2,4-triazol-3-yl)pyridin-2-yl]-2,3-dihydro-1H-pyrrolo[3,4-c]pyridin-1-one α = +8.4° | 407.3 | 1H NMR (400 MHz, DMSO-d6) δ 8.74 (s, 1H), 8.61 (dd, J = 0.9, 8.3 Hz, 1H), 8.13-8.05 (m, 1H), 8.03-7.97 (m, 1H), 6.73 (s, 1H), 5.32-5.17 (m, 2H), 4.63 (q, J = 7.1 Hz, 2H), 4.10 (q, J = 6.7 Hz, 1H), 3.64 (q, J = 7.0 Hz, 2H), 3.05 (s, 3H), 2.11 (br. s, 2H), 1.50 (t, J = 7.2 Hz, 3H), 1.35 (d, J = 6.7 Hz, 3H), 1.10 (t, J = 7.0 Hz, 3H). |

TABLE 6-continued

| Ex. # | Structure, separation method | IUPAC Name, rotation | LRMS (m/z) (M + H)+^ | 1H NMR |
|---|---|---|---|---|
| 130 (E)* | 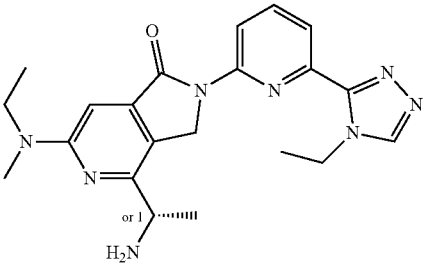 [SMILES: CCN(C)c1cc2c(c([C@H](C)N)n1)CN(c1cccc(-c3nncn3CC)n1)C2=O] | 4-[(1ξ)-1-aminoethyl]-6-[ethyl(methyl)amino]-2-[6-(4-ethyl-4H-1,2,4-triazol-3-yl)pyridin-2-yl]-2,3-dihydro-1H-pyrrolo[3,4-c]pyridin-1-one α = −16.0° | 407.2 | 1H NMR (400 MHz, DMSO-d6) δ 8.76 (s, 1H), 8.62 (dd, J = 0.7, 8.3 Hz, 1H), 8.32 (br. s, 2H), 8.15-8.08 (m, 1H), 8.00 (dd, J = 0.7, 7.6 Hz, 1H), 6.89 (s, 1H), 5.26-5.13 (m, 2H), 4.69-4.56 (m, 3H), 3.71 (sxt, J = 7.3 Hz, 2H), 3.12 (s, 3H), 1.55 (d, J = 6.8 Hz, 3H), 1.48 (t, J = 7.2 Hz, 3H), 1.12 (t, J = 7.0 Hz, 3H). |
| 131 (C)* | 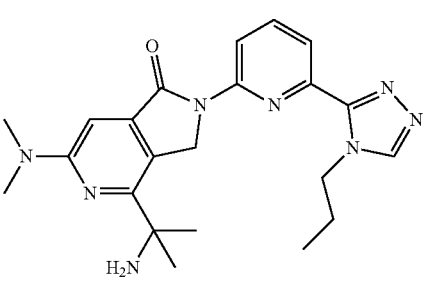 [SMILES: CCCn1cnnc1-c1cccc(N2Cc3c(cc(N(C)C)nc3C(C)(C)N)C2=O)n1] | 4-(2-aminopropan-2-yl)-6-(dimethylamino)-2-[6-(4-propyl-4H-1,2,4-triazol-3-yl)pyridin-2-yl]-2,3-dihydro-1H-pyrrolo[3,4-c]pyridin-1-one | 421.2 | 1H NMR (600 MHz, DMSO-d6) δ 8.73 (s, 1H), 8.63 (dd, J = 0.9, 8.3 Hz, 1H), 8.15-8.05 (m, 1H), 8.02-7.95 (m, 1H), 6.78 (s, 1H), 5.39 (s, 2H), 4.59 (t, J = 7.0 Hz, 2H), 3.11 (s, 6H), 1.93-1.83 (m, 2H), 1.47 (s, 6H), 0.90 (t, J = 7.4 Hz, 3H). |
| 132 (C)* | 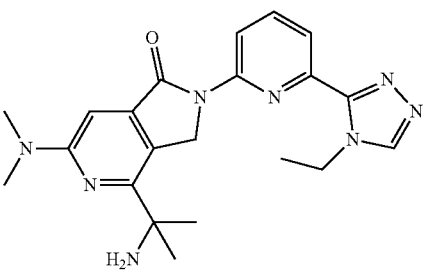 [SMILES: CCn1cnnc1-c1cccc(N2Cc3c(cc(N(C)C)nc3C(C)(C)N)C2=O)n1] | 4-(2-aminopropan-2-yl)-6-(dimethylamino)-2-[6-(4-ethyl-4H-1,2,4-triazol-3-yl)pyridin-2-yl]-2,3-dihydro-1H-pyrrolo[3,4-c]pyridin-1-one | 407.3 | 1H NMR (600 MHz, DMSO-d6) δ 8.67 (s, 1H), 8.54 (d, J = 8.2 Hz, 1H), 8.04-7.96 (m, 1H), 7.95-7.85 (m, 1H), 6.67 (s, 1H), 5.33 (s, 2H), 4.57 (q, J = 7.1 Hz, 2H), 3.02 (s, 6H), 1.43 (t, J = 7.2 Hz, 3H), 1.39 (s, 6H). |
| 133 (I)* | 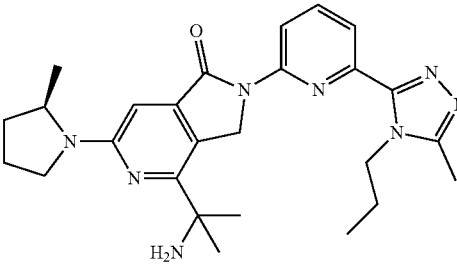 | 4-(2-aminopropan-2-yl)-2-[6-(5-methyl-4-propyl-4H-1,2,4-triazol-3-yl)pyridin-2-yl]-6-[(2R)-2-methylpyrrolidin-1-yl]-2,3-dihydro-1H-pyrrolo[3,4-c]pyridin-1-one | 475.3 | 1H NMR (600 MHz, DMSO-d6) δ 8.60 (d, J = 8.4 Hz, 1H), 8.05 (t, J = 8.0 Hz, 1H), 7.94 (dd, J = 0.8, 7.6 Hz, 1H), 6.56 (s, 1H), 5.51-5.26 (m, 2H), 4.50 (t, J = 7.2 Hz, 2H), 4.22 (t, J = 5.8 Hz, 1H), 3.30-3.32 (m, 2H assumed; partially obscured by water peak) 2.48 (s, 3H), 2.15-2.02 (m, 2H), 1.97 (br. s, 1H), 1.77 (qd, J = 7.4, 14.6 Hz, 2H), 1.69-1.71 (m, 1H) 1.47 (s, 3H), 1.46 (s, 3H), 1.22 (d, J = 6.2 Hz, 3H), 0.92-0.85 (m, 3H). |

TABLE 6-continued

| Ex. # | Structure, separation method | IUPAC Name, rotation | LRMS (m/z) (M + H)+^ | 1H NMR |
|---|---|---|---|---|
| 134 (I)* | | 4-(2-aminopropan-2-yl)-2-[6-(4-ethyl-5-methyl-4H-1,2,4-triazol-3-yl)pyridin-2-yl]-6-[(2R)-2-methylpyrrolidin-1-yl]-2,3-dihydro-1H-pyrrolo[3,4-c]pyridin-1-one | 461.3 | 1H NMR (400 MHz, DMSO-d6) δ 8.55 (dd, J = 0.9, 8.3 Hz, 1H), 8.09-7.96 (m, 1H), 7.93-7.80 (m, 1H), 6.49 (s, 1H), 5.33 (s, 2H), 4.49 (q, J = 7.1 Hz, 2H), 4.19-4.08 (m, 1H), 3.58-3.42 (m, 1H), 3.23-3.25 (m, 1H, assumed; partially obscured by water peak), 2.42 (br. s, 3H), 2.09-1.85 (m, 3H), 1.65-1.55 (m, 1H), 1.44-1.36 (m, 9H), 1.15 (d, J = 6.2 Hz, 3H). |
| 135 (I)* | Peak 2 (separated using a Phenomenex Lux Cellulose-1, 21 × 250 mm, 5 um column at 35° C., Eluted with 20% MeOH + 10 mM ammonium acetate in CO2. Pressure held at 120 bar with flow rate of 100 mL/min.) | 4-[(1ξ)-1-aminoethyl]-2-[6-(5-methyl-4-propyl-4H-1,2,4-triazol-3-yl)pyridin-2-yl]-6-[(2R)-2-methylpyrrolidin-1-yl]-2,3-dihydro-1H-pyrrolo[3,4-c]pyridin-1-one | 461.8 | 1H NMR (400 MHz, DMSO-d6) δ 8.63 (d, J = 8.3 Hz, 1H), 8.07 (t, J = 7.9 Hz, 1H), 7.98-7.90 (m, 1H), 6.58 (s, 1H), 5.20 (s, 2H), 4.53-4.41 (m, 2H), 4.31-4.22 (m, 1H), 4.10-4.06 (m, 2H), 3.59-3.54 (m, 1H), 2.50-2.49 (m, 3H), 2.11-2.03 (m, 2H), 1.99-1.91 (m, 1H), 1.86-1.78 (m, 2H), 1.73-1.69 (m, 1H), 1.35 (d, J = 6.6 Hz, 3H), 1.22 (d, J = 6.2 Hz, 3H), 0.96 (t, J = 7.5 Hz, 3H). |
| 136 (C)* | Peak 1 (separated using a Phenomenex Lux Cellulose-1, 21 × 250 mm, 5 um column at 35° C., Eluted with 20% MeOH + 10 mM ammonium acetate in CO2. Pressure held at 120 bar with flow rate of 100 mL/min.) | 4-[(1ξ)-1-aminoethyl]-2-[6-(5-methyl-4-propyl-4H-1,2,4-triazol-3-yl)pyridin-2-yl]-6-[(2R)-2-methylpyrrolidin-1-yl]-2,3-dihydro-1H-pyrrolo[3,4-c]pyridin-1-one | 461.8 | 1H NMR (400 MHz, DMSO-d6) δ 8.61 (d, J = 8.3 Hz, 1H), 8.06 (t, J = 7.9 Hz, 1H), 7.96 (d, J = 7.6 Hz, 1H), 6.57 (s, 1H), 5.19 (s, 2H), 4.53-4.43 (m, 2H), 4.29-4.18 (m, 1H), 4.13-4.03 (m, 1H), 3.62-3.52 (m, 1H), 2.49 (br. s, 3H), 2.09-2.03 (m, 2H), 1.96 (br. d, J = 2.9 Hz, 1H), 1.84-1.77 (m, 2H), 1.70 (br. d, J = 2.7 Hz, 1H), 1.34 (br. d, J = 6.1 Hz, 3H), 1.22 (d, J = 6.4 Hz, 3H), 0.95 (t, J = 7.3 Hz, 3H), 0.90-0.89 (m, 1H). |
| 137 (C)* | | 4-[(1S)-1-aminoethyl]-6-(dimethylamino)-2-[6-(4-propyl-4H-1,2,4-triazol-3-yl)pyridin-2-yl]-2,3-dihydro-1H-pyrrolo[3,4-c]pyridin-1-one α = −4.5° | 406.2 | 1H NMR (600 MHz, DMSO-d6) δ 8.72 (d, J = 2.0 Hz, 1H), 8.63-8.56 (m, 1H), 8.10-8.02 (m, 1H), 8.01-7.97 (m, 1H), 6.85-6.61 (m, 1H), 5.18 (br. s, 2H), 4.56 (br. t, J = 7.2 Hz, 2H), 4.10 (br. s, 1H), 3.09 (d, J = 3.1 Hz, 6H), 1.97-1.84 (m, 2H), 1.34 (br. d, J = 5.9 Hz, 3H), 1.00-0.85 (m, 3H). |

| Ex. # | Structure, separation method | IUPAC Name, rotation | LRMS (m/z) (M + H)+^ | ¹H NMR |
|---|---|---|---|---|
| 138 (C)* | | 4-[(1R)-1-aminoethyl]-6-(dimethylamino)-2-[6-(4-propyl-4H-1,2,4-triazol-3-yl)pyridin-2-yl]-2,3-dihydro-1H-pyrrolo[3,4-c]pyridin-1-one α = +4.9° | 406.2 | ¹H NMR (600 MHz, DMSO-d₆) δ 8.72 (s, 1H), 8.59 (br. d, J = 7.9 Hz, 1H), 8.07-8.01 (m, 1H), 7.98 (d, J = 7.3 Hz, 1H), 6.71 (s, 1H), 5.17 (br. d, J = 2.2 Hz, 2H), 4.64-4.49 (m, 2H), 4.09 (br. d, J = 4.8 Hz, 1H), 3.08 (s, 6H), 1.95-1.84 (m, 2H), 1.34 (br. d, J = 6.6 Hz, 3H), 0.94 (br. t, J = 7.2 Hz, 3H). |
| 139 (I)* | | 4-(2-aminopropan-2-yl)-6-[methyl(propan-2-yl)amino]-2-[6-(5-methyl-4-propyl-4H-1,2,4-triazol-3-yl)pyridin-2-yl]-2,3-dihydro-1H-pyrrolo[3,4-c]pyridin-1-one | 463.5 | ¹H NMR (400 MHz, DMSO-d₆) δ 8.72 (d, J = 8.3 Hz, 1H), 8.59 (br. s, 3H), 8.19 (t, J = 8.0 Hz, 1H), 7.98 (d, J = 7.5 Hz, 1H), 6.93 (s, 1H), 5.26 (s, 2H), 4.97 (br. s, 1H), 4.60 (br. t, J = 7.3 Hz, 2H), 2.94 (s, 3H), 2.70 (s, 3H), 1.92-1.78 (m, 2H), 1.72 (s, 6H), 1.17 (d, J = 6.5 Hz, 6H), 0.91 (t, J = 7.3 Hz, 3H). |
| 140 (E)* | | 4-[(1R)-1-aminopropyl]-2-[6-(4-ethyl-4H-1,2,4-triazol-3-yl)pyridin-2-yl]-6-[(2R)-2-methylpyrrolidin-1-yl]-2,3-dihydro-1H-pyrrolo[3,4-c]pyridin-1-one | 447.2 | ¹H NMR (600 MHz, DMSO-d₆) δ 8.73-8.62 (m, 1H), 8.55 (d, J = 8.3 Hz, 1H), 8.08-7.98 (m, 1H), 7.93 (d, J = 7.6 Hz, 1H), 6.50 (s, 1H), 5.14 (d, J = 1.7 Hz, 2H), 4.57 (dq, J = 3.4, 7.0 Hz, 2H), 4.22-4.08 (m, 1H), 3.77 (br. t, J = 6.1 Hz, 1H), 3.55-3.41 (m, 1H), 3.30-3.25 (m, 1H, assumed; partially obscured by water peak), 2.00 (d, J = 5.3 Hz, 1H), 1.92-1.87 (m, 1H), 1.76-1.51 (m, 4H), 1.44 (t, J = 7.2 Hz, 3H), 1.15 (d, J = 6.2 Hz, 3H), 0.82 (t, J = 7.4 Hz, 3H). |
| 141 (E)* | | 4-[(1S)-1-aminopropyl]-2-[6-(4-ethyl-4H-1,2,4-triazol-3-yl)pyridin-2-yl]-6-[(2R)-2-methylpyrrolidin-1-yl]-2,3-dihydro-1H-pyrrolo[3,4-c]pyridin-1-one | 447.2 | ¹H NMR (400 MHz, DMSO-d₆) δ 8.67 (s, 1H), 8.55 (dd, J = 0.7, 8.4 Hz, 1H), 8.11-7.99 (m, 1H), 7.93 (dd, J = 0.7, 7.6 Hz, 1H), 6.52 (s, 1H), 5.12 (s, 2H), 4.66-4.50 (m, 2H), 4.26-4.07 (m, 1H), 3.87-3.71 (m, 1H), 3.56-3.45 (m, 1H), 3.27-3.29 (m 1H, assumed; partially obscured by water peak,) 2.05-1.95 (m, 2H), 1.93-1.86 (m, 1H), 1.79-1.68 (m, 1H), 1.65-1.51 (m, 2H), 1.44 (t, J = 7.2 Hz, 3H), 1.14 (d, J = 6.2 Hz, 3H), 0.82 (t, J = 7.4 Hz, 3H). |

TABLE 6-continued

| Ex. # | Structure, separation method | IUPAC Name, rotation | LRMS (m/z) (M + H)+∧ | 1H NMR |
|---|---|---|---|---|
| 142 (E)* | | 4-[(1ξ)-1-aminopropyl]-6-(dimethylamino)-2-[6-(4-propyl-4H-1,2,4-triazol-3-yl)pyridin-2-yl]-2,3-dihydro-1H-pyrrolo[3,4-c]pyridin-1-one α = −3.8° | 421.2 | 1H NMR (600 MHz, DMSO-d6) δ 8.75 (s, 1H), 8.62 (d, J = 8.3 Hz, 1H), 8.10 (t, J = 8.0 Hz, 1H), 8.01 (d, J = 7.5 Hz, 1H), 6.92 (d, J = 2.0 Hz, 1H), 5.24-5.05 (m, 2H), 4.68-4.57 (m, 1H), 4.56-4.46 (m, 1H), 4.34 (br. s, 1H), 3.17 (s, 6H), 2.07-1.81 (m, 4H), 0.92 (td, J = 7.3, 15.0 Hz, 6H). |
| 143 (E)* | | 4-[(1ξ)-1-aminopropyl]-6-(dimethylamino)-2-[6-(4-propyl-4I-1,2,4-triazol-3-yl)pyridin-2-yl]-2,3-dihydro-1I-pyrrolo[3,4-c]pyridin-1-one α = +5.6° | 421.2 | 1H NMR (600 MHz, DMSO-d6) δ 8.65 (s, 1H), 8.52 (dd, J = 2.9, 8.3 Hz, 1H), 7.98 (dt, J = 2.1, 7.8 Hz, 1H), 7.92 (d, J = 7.5 Hz, 1H), 6.66 (d, J = 3.7 Hz, 1H), 5.08 (br. s, 2H), 4.60-4.41 (m, 2H), 3.87-3.67 (m, 1H), 3.02 (s, 6H), 1.81 (sxt, J = 7.0 Hz, 2H), 1.75-1.65 (m, 1H), 1.57 (br. s, 1H), 0.88 (t, J = 7.3 Hz, 3H), 0.82 (t, J = 6.3 Hz, 3H). |
| 144 (E)* | | 4-[(1R)-1-aminopropyl]-6-[(2R)-2-methylpyrrolidin-1-yl]-2-[6-(4-propyl-4H-1,2,4-triazol-3-yl)pyridin-2-yl]-2,3-dihydro-1H-pyrrolo[3,4-c]pyridin-1-one | 461.2 | 1H NMR (400 MHz, DMSO-d6) δ 8.66 (s, 1H), 8.56 (dd, J = 0.7, 8.3 Hz, 1H), 8.07-7.98 (m, 1H), 7.96-7.84 (m, 1H), 6.50 (s, 1H), 5.11 (s, 2H), 4.62-4.41 (m, 2H), 4.15 (t, J = 5.7 Hz, 1H), 3.77 (br. s, 1H), 3.56-3.42 (m, 1H), 3.30-3.27 (m, 1H, assumed; partially obscured by water peak), 2.08-1.92 (m, 3H), 1.86-1.76 (m, 2H), 1.75-1.46 (m, 3H), 1.15 (d, J = 6.2 Hz, 3H), 0.88 (t, J = 7.4 Hz, 3H), 0.82 (t, J = 7.3 Hz, 3H). |
| 145 (E)* | | 4-[(1S)-1-aminopropyl]-6-[(2R)-2-methylpyrrolidin-1-yl]-2-[6-(4-propyl-4H-1,2,4-triazol-3-yl)pyridin-2-yl]-2,3-dihydro-1H-pyrrolo[3,4-c]pyridin-1-one | 461.2 | 1H NMR (600 MHz, DMSO-d6) δ 8.66 (s, 1H), 8.56 (d, J = 8.3 Hz, 1H), 8.10-7.98 (m, 1H), 7.96-7.88 (m, 1H), 6.52 (s, 1H), 5.17-5.00 (m, 2H), 4.62-4.39 (m, 2H), 4.27-4.06 (m, 1H), 3.87-3.71 (m, 1H), 3.56-3.43 (m, 1H), 3.30-3.29 (m 1H, assumed; partially obscured by water peak) 2.07-1.95 (m, 2H), 1.92-1.70 (m, 4H), 1.66-1.51 (m, 2H), 1.14 (d, J = 6.1 Hz, 3H), 0.88 (t, J = 7.4 Hz, 3H), 0.81 (t, J = 7.3 Hz, 3H). |

TABLE 6-continued

| Ex. # | Structure, separation method | IUPAC Name, rotation | LRMS (m/z) (M + H)+∧ | 1H NMR |
|---|---|---|---|---|
| 146 (E)* | | 4-[(1ξ)-1-aminopropyl]-6-(dimethyl-amino)-2-[6-(4-ethyl-4H-1,2,4-triazol-3-yl)pyridin-2-yl]-2,3-dihydro-1H-pyrrolo[3,4-c]pyridin-1-one α = +1.2° | 407.2 | 1H NMR (600 MHz, DMSO-d$_6$) δ 8.71 (s, 1H), 8.54 (d, J = 8.3 Hz, 1H), 8.50-8.40 (m, 2H), 8.04 (t, J = 8.0 Hz, 1H), 7.93 (d, J = 7.3 Hz, 1H), 6.85 (s, 1H), 5.29-4.99 (m, 2H), 4.70-4.49 (m, 2H), 4.39-4.24 (m, 1H), 3.10 (s, 6H), 2.07-1.82 (m, 2H), 1.42 (t, J = 7.2 Hz, 3H), 0.82 (t, J = 7.4 Hz, 3H). |
| 147 (E)* | | 4-[(1ξ)-1-aminopropyl]-6-(dimethyl-amino)-2-[6-(4-ethyl-4H-1,2,4-triazol-3-yl)pyridin-2-yl]-2,3-dihydro-1H-pyrrolo[3,4-c]pyridin-1-one α = −0.4° | 407.2 | 1H NMR (600 MHz, DMSO-d$_6$) δ 8.69 (s, 1H), 8.53 (d, J = 8.3 Hz, 1H), 8.18 (br. s, 2H), 8.02 (t, J = 8.0 Hz, 1H), 7.95-7.85 (m, 1H), 6.91-6.76 (m, 1H), 5.22-4.97 (m, 2H), 4.70-4.47 (m, 2H), 4.45-4.27 (m, 1H), 3.10 (s, 6H), 2.04-1.75 (m, 2H), 1.42 (t, J = 7.1 Hz, 3H), 0.84 (t, J = 7.4 Hz, 3H). |
| 148 (G)* | | 4-[(1ξ)-1-aminoethyl]-6-[methyl(propan-2-yl)amino]-2-[6-(5-methyl-4-propyl-4H-1,2,4-triazol-3-yl)pyridin-2-yl]-2,3-dihydro-1H-pyrrolo[3,4-c]pyridin-1-one α = +3.8° | 449.3 | 1H NMR (400 MHz, DMSO-d$_6$) δ 8.58 (d, J = 8.3 Hz, 1H), 8.02 (t, J = 7.5 Hz, 1H), 7.94 (d, J = 8.0 Hz, 1H), 6.71 (s, 1H), 5.15 (s, 2H), 4.96-4.85 (m, 1H), 4.45 (br. dd, J = 6.3, 8.8 Hz, 2H), 4.07 (d, J = 6.8 Hz, 1H), 2.86 (s, 3H), 2.48-2.43 (m, 3H), 1.88-1.76 (m, 2H), 1.33 (d, J = 6.5 Hz, 3H), 1.15 (d, J = 6.5 Hz, 6H), 0.94 (t, J = 7.3 Hz, 3H). |
| 149 (G)* | | 4-[(1ξ)-1-aminoethyl]-6-[methyl(propan-2-yl)amino]-2-[6-(5-methyl-4-propyl-4H-1,2,4-triazol-3-yl)pyridin-2-yl]-2,3-dihydro-1H-pyrrolo[3,4-c]pyridin-1-one α = −10.6° | 449.3 | 1H NMR (400 MHz, DMSO-d$_6$) δ 8.62 (d, J = 8.3 Hz, 1H), 8.06 (t, J = 8.0 Hz, 1H), 7.96 (d, J = 7.5 Hz, 1H), 6.75 (s, 1H), 5.19 (s, 2H), 4.93 (s, 1H), 4.47 (br. dd, J = 6.0, 8.5 Hz, 2H), 4.11 (d, J = 6.5 Hz, 1H), 2.89 (s, 3H), 2.50-2.48 (m, 3H), 1.90-1.76 (m, 2H), 1.35 (d, J = 6.8 Hz, 3H), 1.17 (d, J = 6.8 Hz, 6H), 0.96 (t, J = 7.4 Hz, 3H). |

TABLE 6-continued

| Ex. # | Structure, separation method | IUPAC Name, rotation | LRMS (m/z) (M + H)+^ | 1H NMR |
|---|---|---|---|---|
| 150 (E)* | | 4-[(1ξ)-1-aminoethyl]-2-[6-(4-ethyl-4H-1,2,4-triazol-3-yl)pyridin-2-yl]-6-[(2R)-2-methylpyrrolidin-1-yl]-2,3-dihydro-1H-pyrrolo[3,4-c]pyridin-1-one α = −29.3° | 433.1 | 1H NMR (400 MHz, DMSO-d6) δ 8.73 (s, 1H), 8.59 (d, J = 8.3 Hz, 1H), 8.09-8.04 (m, 1H), 7.99 (d, J = 7.5 Hz, 1H), 6.56 (s, 1H), 5.21 (br. s, 2H), 4.63 (q, J = 7.2 Hz, 2H), 4.55 (s, 1H), 4.23 (br. s, 2H), 3.51 (br. s, 3H), 2.09-2.02 (m, 2H), 1.96 (br. d, J = 2.4 Hz, 1H), 1.70 (br. dd, J = 2.4, 4.8 Hz, 1H), 1.50 (t, J = 7.2 Hz, 3H), 1.39 (br. d, J = 6.4 Hz, 3H), 1.23-1.18 (m, 3H). |
| 151 (E)* | | 4-[(1ξ)-1-aminoethyl]-2-[6-(4-ethyl-4H-1,2,4-triazol-3-yl)pyridin-2-yl]-6-[(2R)-2-methylpyrrolidin-1-yl]-2,3-dihydro-1H-pyrrolo[3,4-c]pyridin-1-one α = −49.4° | 433.1 | 1H NMR (400 MHz, DMSO-d6) δ 8.76 (s, 1H), 8.59 (d, J = 8.3 Hz, 1H), 8.36-8.32 (m, 2H), 8.12-8.05 (m, 1H), 7.98 (d, J = 7.5 Hz, 1H), 6.70 (s, 1H), 5.16 (br. d, J = 2.8 Hz, 2H), 4.67-4.55 (m, 3H), 4.39-4.31 (m, 1H), 3.68-3.54 (m, 2H), 2.07 (br. s, 2H), 2.01-1.94 (m, 1H), 1.76-1.67 (m, 1H), 1.56 (d, J = 6.6 Hz, 3H), 1.48 (t, J = 7.2 Hz, 3H), 1.19 (d, J = 6.2 Hz, 3H). |
| 152 (E)* | | 4-[(1ξ)-1-aminoethyl]-6-(dimethylamino)-2-[6-(4-ethyl-4H-1,2,4-triazol-3-yl)pyridin-2-yl]-2,3-dihydro-1H-pyrrolo[3,4-c]pyridin-1-one α = +13.7° | 393.3 | 1H NMR (600 MHz, DMSO-d6) δ 8.73 (s, 1H), 8.62-8.56 (m, 1H), 8.10-8.01 (m, 1H), 7.98 (br. d, J = 7.7 Hz, 1H), 6.75 (s, 1H), 5.32-5.13 (m, 2H), 4.62 (q, J = 7.0 Hz, 2H), 4.27-4.06 (m, 1H), 3.12-3.03 (m, 6H), 1.49 (br. t, J = 7.1 Hz, 3H), 1.41-1.19 (m, 3H). |
| 153 (E)* | | 4-[(1ξ)-1-aminoethyl]-6-(dimethylamino)-2-[6-(4-ethyl-4H-1,2,4-triazol-3-yl)pyridin-2-yl]-2,3-dihydro-1H-pyrrolo[3,4-c]pyridin-1-one α = −10.9° | 393.3 | 1H NMR (600 MHz, DMSO-d6) δ 8.76 (s, 1H), 8.60 (d, J = 8.3 Hz, 1H), 8.09 (t, J = 8.1 Hz, 1H), 7.99 (d, J = 7.5 Hz, 1H), 6.90 (d, J = 2.2 Hz, 1H), 5.24-5.08 (m, 2H), 4.73-4.54 (m, 3H), 3.16 (d, J = 1.8 Hz, 6H), 1.54 (d, J = 6.8 Hz, 3H), 1.47 (t, J = 7.2 Hz, 3H). |
| 154 (G)* | | 4-[(1ξ)-1-aminoethyl]-2-[6-(4-ethyl-5-methyl-4H-1,2,4-triazol-3-yl)pyridin-2-yl]-6-[(2R)-2-methylpyrrolidin-1-yl]-2,3-dihydro-1H-pyrrolo[3,4-c]pyridin-1-one α = −48.5° | 447.2 | 1H NMR (400 MHz, DMSO-d6) δ 8.62-8.57 (m, 1H), 8.31 (br. s, 2H), 8.08 (t, J = 8.0 Hz, 1H), 7.95 (d, J = 7.7 Hz, 1H), 6.73-6.70 (m, 1H), 5.18 (br. s, 2H), 4.60-4.47 (m, 3H), 4.39-4.31 (m, 1H), 3.67-3.58 (m, 1H), 3.36-3.35 (m, 1H), 2.50 (s, 3H), 2.11-2.03 (m, 2H), 2.00-1.96 (m, 1H), 1.76-1.71 (m, 1H), 1.56 (d, J = 6.8 Hz, 3H), 1.43 (t, J = 7.1 |

TABLE 6-continued

| Ex. # | Structure, separation method | IUPAC Name, rotation | LRMS (m/z) (M + H)+^ | 1H NMR |
|---|---|---|---|---|
| | | | | Hz, 3H), 1.19 (d, J = 6.2 Hz, 3H). |
| 155 (G)* | 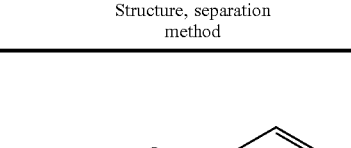 | 4-[(1ξ)-1-aminoethyl]-2-[6-(4-ethyl-5-methyl-4H-1,2,4-triazol-3-yl)pyridin-2-yl]-6-[(2R)-2-methyl-pyrrolidin-1-yl]-2,3-dihydro-1H-pyrrolo[3,4-c]pyridin-1-one α = −35.6° | 447.2 | 1H NMR (400 MHz, DMSO-d6) δ 8.58 (br. d, J = 8.3 Hz, 1H), 8.04 (t, J = 7.9 Hz, 1H), 7.95 (br. d, J = 7.7 Hz, 1H), 6.53 (s, 1H), 5.22 (br. d, J = 8.8 Hz, 2H), 4.60-4.48 (m, 3H), 4.21 (br. s, 1H), 3.58-3.50 (m, 3H), 3.17 (br. s, 1H), 2.49-2.47 (m, 3H), 2.08-2.00 (m, 2H), 1.95 (br. s, 1H), 1.69 (br. d, J = 2.2 Hz, 1H), 1.45 (br. t, J = 6.5 Hz, 3H), 1.43-1.29 (m, 3H), 1.20 (br. d, J = 5.5 Hz, 3H). |

*Letter within parentheses is the Method by which Example was prepared.
^[M + H]+ unless otherwise indicated.

Example 200: 2-{6-[(5S)-5-ethyl-6,7-dihydro-5H-pyrrolo[2,1-c][1,2,4]triazol-3-yl]pyridin-2-yl}-4-[(methylamino)methyl]-6-[(2R)-2-methylpyrrolidin-1-yl]-2,3-dihydro-1H-pyrrolo[3,4-c]pyridin-1-one

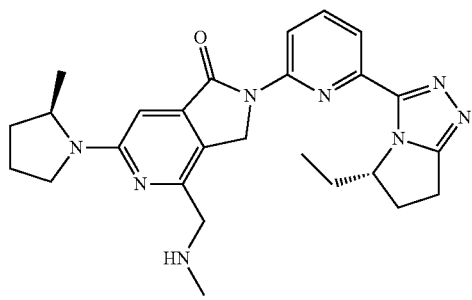 [SMILES: CC[C@H]1CCc2nnc(-c3cccc(N4Cc5c(cc(N6CCC[C@H]6C)nc5CNC)C4=O)n3)n21]

Step 1: tert-butyl [(2-{6-[(5S)-5-ethyl-6,7-dihydro-5H-pyrrolo[2,1-c][1,2,4]triazol-3-yl]pyridin-2-yl}-6-[(2R)-2-methylpyrrolidin-1-yl]-1-oxo-2,3-dihydro-1H-pyrrolo[3,4-c]pyridin-4-yl)methyl]methylcarbamate

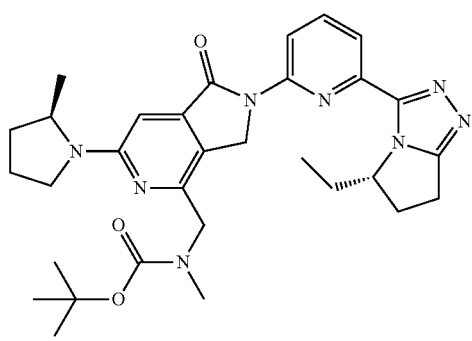 [SMILES: CC[C@H]1CCc2nnc(-c3cccc(N4Cc5c(cc(N6CCC[C@H]6C)nc5CN(C)C(=O)OC(C)(C)C)C4=O)n3)n21]

A mixture of tert-butyl methyl({6-[(2R)-2-methylpyrrolidin-1-yl]-1-oxo-2,3-dihydro-1H-pyrrolo[3,4-c]pyridin-4-yl}methyl)carbamate (Intermediate 8) (752 mg, 2.09 mmol), (5S)-3-(6-bromopyridin-2-yl)-5-ethyl-6,7-dihydro-5H-pyrrolo[2,1-c][1,2,4]triazole (Intermediate 3) (612 mg, 2.09 mmol), K3PO4 (1.33 g, 6.26 mmol), Pd2(dba)3 (120 mg, 0.209 mmol), and XantPhos (241 mg, 0.417 mmol) in 1,4-dioxane (20.9 mL, c=0.1 M) was heated at 100° C. in 100 mL flask with condenser under N2 for 18 h. The mixture was cooled to RT, filtered and washed with DCM (20 mL). The filtrate was concentrated under reduced pressure. The residue was purified by flash chromatography (24 g, SiO2, 0-10% MeOH/DCM) to provide the title compound as a pale-yellow solid (1.13 g, 85%). m/z (APCI+) for (C31H40N8O3), 573.30 (M+H)+.

Step 2: Example 200

A 4 N solution of HCl in 1,4-dioxane (4.42 mL, 17.7 mmol) was added to a solution of tert-butyl [(2-{6-[(5S)-5-ethyl-6,7-dihydro-5H-pyrrolo[2,1-c][1,2,4]triazol-3-yl]pyridin-2-yl}-6-[(2R)-2-methylpyrrolidin-1-yl]-1-oxo-2,3-dihydro-1H-pyrrolo[3,4-c]pyridin-4-yl)methyl]methylcarbamate (1.01 g, 1.77 mmol) in DCM (22.1 mL, c=0.08 M). The mixture was stirred at RT for 2 h. The volatile material was removed under reduced pressure. The crude product was purified by SFC (ZymorSPHER HADP column with methanol and 10 mM NH3) to provide Example 200 as a pale-yellow solid (640 mg, 77%). 1H NMR (400 MHz, DMSO-d6) δ 8.97 (br. s, 1H), 8.60 (dd, J=0.9, 8.3 Hz, 1H), 8.17-8.06 (m, 1H), 8.04-7.95 (m, 1H), 6.76 (s, 1H), 5.28 (d, J=16.6 Hz, 1H), 5.09-4.91 (m, 2H), 4.45-4.19 (m, 3H), 3.73-3.61 (m, 1H), 3.49-3.37 (m, 1H), 3.09-2.87 (m, 3H), 2.76 (s, 3H), 2.61-2.54 (m, 1H), 2.15-1.96 (m, 4H), 1.80-1.64 (m, 2H), 1.21 (d, J=6.2 Hz, 3H), 0.93 (t, J=7.4 Hz, 3H). m/z (APCI+) for (C26H32N8O), 473.3 (M+H)+. [α]D22=+76.0° (c=0.1 M, MeOH).

Example 201: 2-{6-[(5S)-5-ethyl-6,7-dihydro-5H-pyrrolo[2,1-c][1,2,4]triazol-3-yl]pyridin-2-yl}-4-[(methylamino)methyl]-6-[methyl(propan-2-yl)amino]-2,3-dihydro-1H-pyrrolo[3,4-c]pyridin-1-one

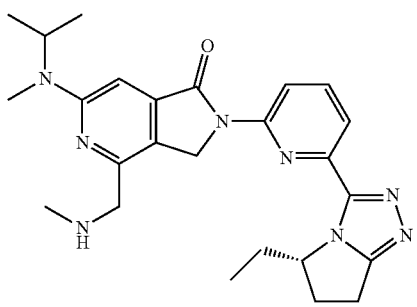 [SMILES: CC[C@H]1CCc2nnc(-c3cccc(N4Cc5c(cc(N(C)C(C)C)nc5CNC)C4=O)n3)n21]

Step 1: tert-butyl [(2-{6-[(5S)-5-ethyl-6,7-dihydro-5H-pyrrolo[2,1-c][1,2,4]triazol-3-yl]pyridin-2-yl}-6-[methyl(propan-2-yl)amino]-1-oxo-2,3-dihydro-1H-pyrrolo[3,4-c]pyridin-4-yl)methyl]methylcarbamate

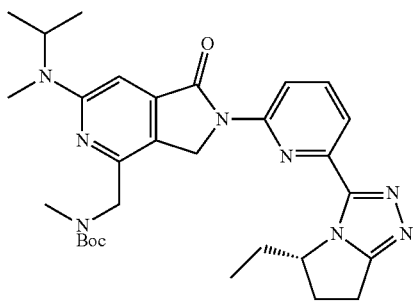 [SMILES: CC[C@H]1CCc2nnc(-c3cccc(N4Cc5c(cc(N(C)C(C)C)nc5CN(C)C(=O)OC(C)(C)C)C4=O)n3)n21]

To a screw-cap flask equipped with a magnetic stir bar was added tert-butyl methyl({6-[methyl(propan-2-yl)amino]-1-oxo-2,3-dihydro-1H-pyrrolo[3,4-c]pyridin-4-yl}methyl)carbamate (Intermediate 9) (294 mg, 0.84 mmol), (5S)-3-(6-bromopyridin-2-yl)-5-ethyl-6,7-dihydro-5H-pyrrolo[2,1-c][1,2,4]triazole (Intermediate 3) (260 mg, 0.88 mmol), $K_3PO_4$ (537 mg, 2.53 mmol), $Pd_2(dba)_3$ (78.0 mg, 0.084 mmol), XantPhos (97.6 mg, 0.17 mmol), and 1,4-dioxane (16.9 mL, 0.05 M). The mixture was bubbled with $N_2$ for 5 minutes before sealing the flask and heating to 85° C. for 22 h. LCMS analysis showed consumption of the starting material. The reaction mixture was concentrated, and the residue was purified by flash chromatography ($SiO_2$, 100% heptane to 1:10 MeOH/EtOAc) to provide the title compound (344 mg, 73% yield) as a yellow solid. $^1$H NMR (400 MHz, $CDCl_3$) δ=8.72-8.65 (m, 1H), 8.13 (d, J=7.5 Hz, 1H), 7.91 (t, J=7.9 Hz, 1H), 6.89 (s, 1H), 5.13-4.85 (m, 4H), 4.25-4.08 (m, 1H), 3.10-2.96 (m, 6H), 2.96-2.93 (m, 3H), 2.66-2.58 (m, 1H), 2.07-1.94 (m, 1H), 1.87-1.74 (m, 1H), 1.53 (s, 1H), 1.50-1.35 (m, 9H), 1.23 (dd, J=2.8, 6.6 Hz, 6H), 1.00-0.87 (m, 3H); LCMS m/z (APCI) for ($C_{30}H_{40}N_8O_3$), 561.3 (M+H)$^+$.

Step 2: Example 201

To a flask equipped with a magnetic stir bar and containing tert-butyl [(2-{6-[(5S)-5-ethyl-6,7-dihydro-5H-pyrrolo[2,1-c][1,2,4]triazol-3-yl]pyridin-2-yl}-6-[methyl(propan-2-yl)amino]-1-oxo-2,3-dihydro-1H-pyrrolo[3,4-c]pyridin-4-yl)methyl]methylcarbamate (344 mg, 0.62 mmol) and $CH_2Cl_2$ (12.3 mL, 0.05 M) was added HCl (4 M in 1,4-dioxane, 1.53 mL, 6.2 mmol). After stirring at RT for 20 h, LCMS analysis showed consumption of starting material. Toluene (5 mL) was added to the reaction flask and the reaction mixture was concentrated. The crude residue was passed over a strong ion exchange (SCX) column to remove residual HCl and concentrated to provide Example 201 (278 mg, 98% yield) as a yellow solid. $^1$H NMR (400 MHz, $CDCl_3$) δ=8.59 (d, J=7.8 Hz, 1H), 8.11-8.03 (m, 1H), 8.00-7.96 (m, 1H), 6.77 (s, 1H), 5.76 (s, 1H), 5.25 (s, 1H), 5.08 (s, 3H), 3.84 (s, 2H), 3.01-2.88 (m, 6H), 2.61-2.54 (m, 1H), 2.39 (s, 3H), 2.05-1.93 (m, 1H), 1.80-1.67 (m, 1H), 1.16 (d, J=6.7 Hz, 6H), 0.92 (t, J=7.4 Hz, 3H); LCMS m/z (APCI) for ($C_{25}H_{32}N_8O$), 461.3 (M+H)$^+$.

Example 202: 2-{6-[(5R)-5-(fluoromethyl)-6,7-dihydro-5H-pyrrolo[2,1-c][1,2,4]triazol-3-yl]pyridin-2-yl}-4-[(methylamino)methyl]-6-[(2R)-2-methylpyrrolidin-1-yl]-2,3-dihydro-1H-pyrrolo[3,4-c]pyridin-1-one

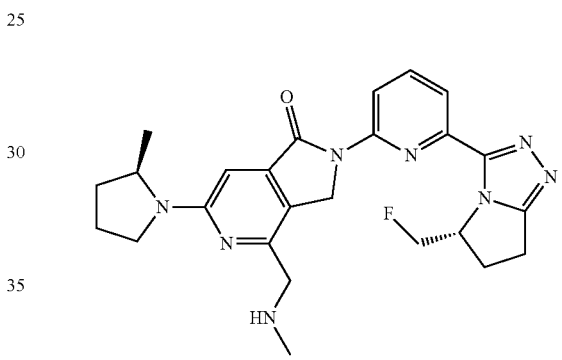

Step 1: tert-butyl [(2-{6-[(5R)-5-(fluoromethyl)-6,7-dihydro-5H-pyrrolo[2,1-c][1,2,4]triazol-3-yl]pyridin-2-yl}-6-[(2R)-2-methylpyrrolidin-1-yl]-1-oxo-2,3-dihydro-1H-pyrrolo[3,4-c]pyridin-4-yl)methyl]methylcarbamate

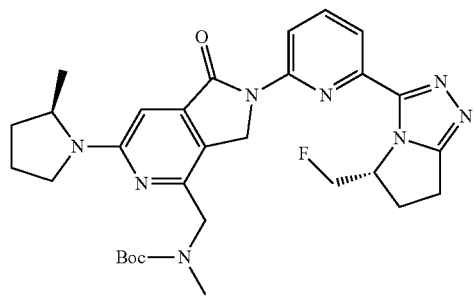 [SMILES: C[C@@H]1CCCN1c1cc2c(c(CN(C)C(=O)OC(C)(C)C)n1)CN(c1cccc(-c3nnc4n3[C@@H](CF)CC4)n1)C2=O]

To a mixture of tert-butyl methyl({6-[(2R)-2-methylpyrrolidin-1-yl]-1-oxo-2,3-dihydro-1H-pyrrolo[3,4-c]pyridin-4-yl}methyl)carbamate (Intermediate 8) (90 mg, 0.25 mmol), (5S)-3-(6-bromopyridin-2-yl)-5-ethyl-6,7-dihydro-5H-pyrrolo[2,1-c][1,2,4]triazole (Intermediate 7) (74.2 mg, 0.250 mmol), and $K_3PO_4$ (159 mg, 0.749 mmol) in 1,4-dioxane (8 mL) was added $Pd_2(dba)_3$ (22.9 mg, 0.025 mmol)

and XantPhos (28.9 mg, 0.0499 mmol) under $N_2$. After addition, the mixture was bubbled with $N_2$ for 2 min. The resulting mixture was sealed and stirred at 85° C. for 18 h. To the reaction mixture was added brine (30 mL). The mixture was extracted with EtOAc (20 mL×2). The combined organic layers were dried over $Na_2SO_4$, filtered and concentrated in vacuo to provide a brown solid (250 mg). The material was purified by flash chromatography ($SiO_2$, DCM/EtOAc=1:1) to provide the title compound (120 mg, 83%) as a yellow solid. $^1$H NMR (400 MHz, $CDCl_3$) δ 8.69 (d, J=8.3 Hz, 1H), 8.16 (d, J=7.6 Hz, 1H), 7.96-7.86 (m, 1H), 6.72 (s, 1H), 5.40 (d, J=30.1 Hz, 1H), 5.01 (dd, J=48.3, 16.6 Hz, 4H), 4.71 (d, J=14.5 Hz, 1H), 4.26-4.05 (m, 1H), 3.59 (t, J=8.7 Hz, 1H), 3.39 (q, J=9.0, 8.4 Hz, 1H), 3.22-3.05 (m, 3H), 3.02 (s, 3H), 2.92-2.82 (m, 1H), 2.19-1.96 (m, 4H), 1.77-1.71 (m, 1H), 1.43 (s, 9H), 1.26 (d, J=6.3 Hz, 3H). LCMS m/z (ESI) for ($C_{30}H_{37}FN_8O_3$), 577.2 (M+H)$^+$.

Step 2: Example 202

To a suspension of tert-butyl [(2-{6-[(5R)-5-(fluoromethyl)-6,7-dihydro-5H-pyrrolo[2,1-c][1,2,4]triazol-3-yl]pyridin-2-yl}-6-[(2R)-2-methylpyrrolidin-1-yl]-1-oxo-2,3-dihydro-1H-pyrrolo[3,4-c]pyridin-4-yl)methyl] methylcarbamate (120 mg, 0.208 mmol) in DCM (8 mL) was added HCl in EtOAc (4 mL, 4 M) dropwise at 0° C. The mixture was stirred at RT for 2 h and was monitored by LCMS. The reaction mixture was then cooled to 0° C. and HCl in EtOAc (5.0 mL, 4 M) was added. The mixture was stirred at RT for 30 min. The mixture was concentrated in vacuo to provide a yellow solid (100 mg). To the residue was added water (10 mL) and washed with EtOAc (10 mL). The aqueous layer was lyophilized for 16 h to provide Example 202 (94 mg, 88%, HCl salt) as a yellow solid. $^1$H NMR (400 MHz, DMSO-$d_6$) δ 9.21-9.00 (m, 2H), 8.61 (d, J=8.3 Hz, 1H), 8.14-8.08 (m, 1H), 8.06-8.02 (m, 1H), 6.75 (s, 1H), 5.43-5.29 (m, 1H), 5.23 (d, J=16.6 Hz, 1H), 5.09-4.91 (m, 3H), 4.40-4.29 (m, 3H), 3.70-3.59 (m, 1H), 3.13-2.92 (m, 3H), 2.79-2.71 (m, 4H), 2.15-1.96 (m, 3H), 1.77-1.70 (m, 1H), 1.21 (d, J=6.3 Hz, 3H). LCMS m/z (ESI) for ($C_{26}H_{29}FN_8O$), 477.4 (M+H)$^+$.

TABLE 7

| Ex. # | Structure | IUPAC Name, rotation | LRMS (m/z) (M + H)$^{+\wedge}$ | $^1$H NMR |
|---|---|---|---|---|
| 203 (B)* | [Structure] | 2-{6-[(5R)-5-ethyl-6,7-dihydro-5H-pyrrolo[2,1-c][1,2,4]triazol-3-yl]pyridin-2-yl}-4-[(methylamino)methyl]-6-[(2R)-2-methylpyrrolidin-1-yl]-2,3-dihydro-1H-pyrrolo[3,4-c]pyridin-1-one α = −155.8° | 473.3 | $^1$H NMR (400 MHz, $CDCl_3$) δ 8.59 (d, J = 7.8 Hz, 1H), 8.11-8.03 (m, 1H), 8.00-7.96 (m, 1H), 6.77 (s, 1H), 5.76 (s, 1H), 5.25 (s, 1H), 5.08 (s, 3H), 3.84 (s, 2H), 3.01-2.88 (m, 2H), 2.61-2.54 (m, 1H), 2.39 (s, 3H), 2.05-1.93 (m, 1H), 1.80-1.67 (m, 1H), 1.16 (d, J = 6.7 Hz, 6H), 0.92 (t, J = 7.4 Hz, 3H). |
| 204 (B)* | [Structure] | 2-{6-[(5R)-5-ethyl-6,7-dihydro-5H-pyrrolo[2,1-c][1,2,4]triazol-3-yl]pyridin-2-yl}-4-[(methylamino)methyl]-6-[methyl(propan-2-yl)amino]-2,3-dihydro-1H-pyrrolo[3,4-c]pyridin-1-one α = +210.0° | 461.1 | $^1$H NMR (400 MHz, $CDCl_3$) δ 8.70 (d, J = 8.3 Hz, 1H), 8.15 (d, J = 7.3 Hz, 1H), 7.91 (t, J = 8.0 Hz, 1H), 6.88 (s, 1H), 5.14-5.03 (m, 2H), 4.98-4.91 (m, 2H), 3.94-3.85 (m, 2H), 3.09-2.98 (m, 2H), 2.95 (s, 3H), 2.64-2.58 (m, 1H), 2.56 (s, 3H), 2.10 (ddd, J = 3.4, 7.5, 13.7 Hz, 1H), 1.78-1.74 (m, 1H), 1.23 (d, J = 6.7 Hz, 6H), 1.01 (t, J = 7.5 Hz, 3H). |
| 205 (K)* | [Structure] | 2-{6-[(5R)-5-(fluoromethyl)-6,7-dihydro-5H-pyrrolo[2,1-c][1,2,4]triazol-3-yl]pyridin-2-yl}-4-[(methylamino)methyl]-6-[methyl(propan-2-yl)amino]-2,3-dihydro-1H-pyrrolo[3,4-c]pyridin-1-one | 465.4 | $^1$H NMR (400 MHz, DMSO-$d_6$) δ 9.26 (br. s, 2H), 8.59 (d, J = 8.3 Hz, 1H), 8.10 (t, J = 7.9 Hz, 1H), 8.03 (d, J = 7.8 Hz, 1H), 6.91 (s, 1H), 5.42 (br. d, J = 8.0 Hz, 1H), 5.25 (d, J = 16.6 Hz, 1H), 5.09-4.93 (m, 4H), 4.40-4.27 (m, 2H), 3.12-2.95 (m, 3H), 2.93 (s, 3H), 2.77-2.70 (m, 4H), 1.17 (d, J = 6.5 Hz, 6H). |

TABLE 7-continued

| Ex. # | Structure | IUPAC Name, rotation | LRMS (m/z) (M + H)+^ | 1H NMR |
|---|---|---|---|---|
| 206 (B)* | 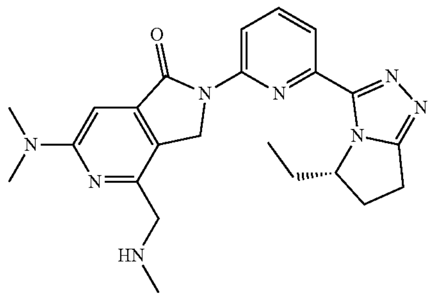 [SMILES: CC[C@H]1CCc2nnc(-c3cccc(N4Cc5c(cc(N(C)C)nc5CNC)C4=O)n3)n21] | 6-(dimethylamino)-2-{6-[(5S)-5-ethyl-6,7-dihydro-5H-pyrrolo[2,1-c][1,2,4]triazol-3-yl]pyridin-2-yl}-4-[(methylamino)methyl]-2,3-dihydro-1H-pyrrolo[3,4-c]pyridin-1-one α = +70.7° | 433.2 | 1H NMR (400 MHz, DMSO-d6) δ 8.58 (d, J = 8.3 Hz, 1H), 8.10-8.03 (m, 1H), 7.99 (d, J = 7.6 Hz, 1H), 6.84 (s, 1H), 5.27 (d, J = 17.1 Hz, 1H), 5.08-4.94 (m, 2H), 4.06-3.94 (m, 2H), 3.15 (br. s, 6H), 3.05-2.87 (m, 4H), 2.81 (s, 1H), 2.49-2.47 (m, 3H), 2.04-1.89 (m, 1H), 1.79-1.67 (m, 1H), 0.91 (t, J = 7.3 Hz, 3H). |
| 207 (B)* | 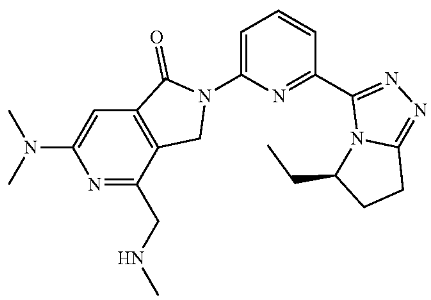 [SMILES: CC[C@@H]1CCc2nnc(-c3cccc(N4Cc5c(cc(N(C)C)nc5CNC)C4=O)n3)n21] | 6-(dimethylamino)-2-{6-[(5R)-5-ethyl-6,7-dihydro-5H-pyrrolo[2,1-c][1,2,4]triazol-3-yl]pyridin-2-yl}-4-[(methylamino)methyl]-2,3-dihydro-1H-pyrrolo[3,4-c]pyridin-1-one α = −71.8° | 433.2 | 1H NMR (400 MHz, DMSO-d6) δ 8.58 (d, J = 8.1 Hz, 1H), 8.09-8.01 (m, 1H), 8.00-7.95 (m, 1H), 6.80 (s, 1H), 5.27 (d, J = 17.1 Hz, 1H), 5.10-4.95 (m, 2H), 3.85 (br. s, 2H), 3.11 (s, 6H), 3.03-2.87 (m, 4H), 2.81 (s, 1H), 2.38 (s, 3H), 2.06-1.92 (m, 1H), 1.74 (br. d, J = 8.1 Hz, 1H), 0.91 (t, J = 7.3 Hz, 3H). |
| 208 (B)* | 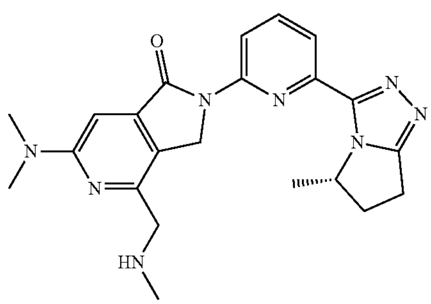 [SMILES: CNCc1nc(N(C)C)cc2c1CN(c1cccc(-c3nnc4n3[C@@H](C)CC4)n1)C2=O] | 6-(dimethylamino)-4-[(methylamino)methyl]-2-{6-[(5S)-5-methyl-6,7-dihydro-5H-pyrrolo[2,1-c][1,2,4]triazol-3-yl]pyridin-2-yl}-2,3-dihydro-1H-pyrrolo[3,4-c]pyridin-1-one α = +58.5° | 419.2 | 1H NMR (400 MHz, DMSO-d6) δ 8.58 (dd, J = 3.2, 8.1 Hz, 1H), 8.09-8.03 (m, 1H), 7.97 (dd, J = 5.3, 7.0 Hz, 1H), 6.81 (d, J = 2.2 Hz, 1H), 5.34-5.23 (m, 1H), 5.19-4.96 (m, 2H), 3.90 (br. d, J = 8.6 Hz, 2H), 3.28-3.26 (m, 3H), 3.14-3.08 (m, 6H), 3.08-2.86 (m, 4H), 2.85-2.79 (m, 1H), 2.45-2.36 (m, 3H). |
| 209 (B)* | 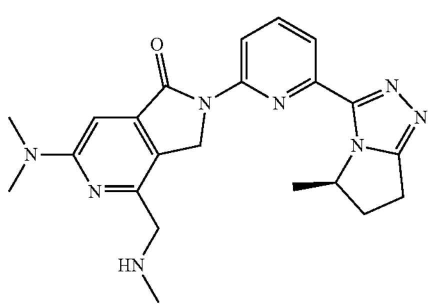 [SMILES: CNCc1nc(N(C)C)cc2c1CN(c1cccc(-c3nnc4n3[C@H](C)CC4)n1)C2=O] | 6-(dimethylamino)-4-[(methylamino)methyl]-2-{6-[(5R)-5-methyl-6,7-dihydro-5H-pyrrolo[2,1-c][1,2,4]triazol-3-yl]pyridin-2-yl}-2,3-dihydro-1H-pyrrolo[3,4-c]pyridin-1-one α = −91.8° | 419.2 | 1H NMR (400 MHz, DMSO-d6) δ 8.58 (ddd, J = 0.7, 3.2, 8.3 Hz, 1H), 8.11-8.00 (m, 1H), 8.01-7.93 (m, 1H), 6.79 (d, J = 1.7 Hz, 1H), 5.34-5.24 (m, 1H), 5.20-4.95 (m, 2H), 3.93-3.73 (m, 2H), 3.28-3.25 (m, 3H), 3.13-3.08 (m, 6H), 3.06-2.77 (m, 4H), 2.70-2.62 (m, 1H), 2.41-2.35 (m, 3H). |

TABLE 7-continued

| Ex. # | Structure | IUPAC Name, rotation | LRMS (m/z) (M + H)+^ | 1H NMR |
|---|---|---|---|---|
| 210 (B)* | 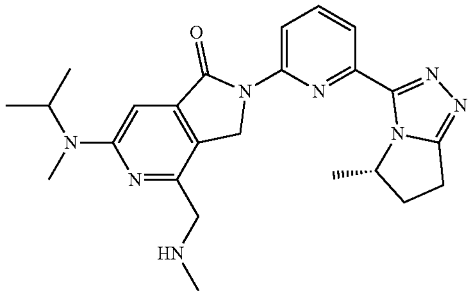 [SMILES: CNCc1nc(N(C)C(C)C)cc2c1CN(c1cccc(-c3nnc4n3[C@@H](C)CC4)n1)C2=O] | 4-[(methyl-amino)methyl]-2-{6-[(5S)-5-methyl-6,7-dihydro-5H-pyrrolo[2,1-c][1,2,4]triazol-3-yl]pyridin-2-yl}-6-[methyl(propan-2-yl)amino]-2,3-dihydro-1H-pyrrolo[3,4-c]pyridin-1-one | 447.4 | 1H NMR (400 MHz, DMSO-d6) δ 8.57 (d, J = 8.1 Hz, 1H), 8.05 (t, J = 8.0 Hz, 1H), 7.96 (d, J = 7.4 Hz, 1H), 6.75 (s, 1H), 5.31-5.21 (m, 1H), 5.20-5.07 (m, 2H), 4.95 (td, J = 6.8, 13.4 Hz, 1H), 3.92-3.79 (m, 2H), 3.17-2.89 (m, 4H), 2.88 (s, 3H), 2.41-2.39 (m, 3H), 1.52 (br. d, J = 6.4 Hz, 3H), 1.15 (d, J = 6.8 Hz, 6H). |
| 211 (L)* | 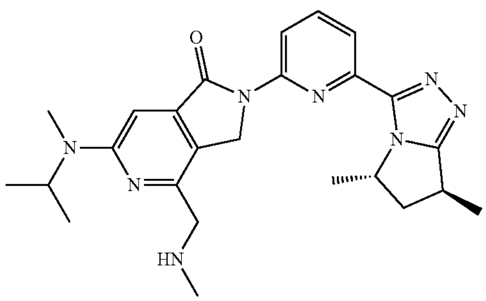 [SMILES: CNCc1nc(N(C)C(C)C)cc2c1CN(c1cccc(-c3nnc4n3[C@@H](C)C[C@@H]4C)n1)C2=O] | 2-{6-[(5S,7S)-5,7-dimethyl-6,7-dihydro-5H-pyrrolo[2,1-c][1,2,4]triazol-3-yl]pyridin-2-yl}-4-[(methyl-amino)methyl]-6-[methyl(propan-2-yl)amino]-2,3-dihydro-1H-pyrrolo[3,4-c]pyridin-1-one | 461.3 | 1H NMR (400 MHz, DMSO-d6) δ 8.58 (d, J = 7.7 Hz, 1H), 8.10-8.05 (m, 1H), 8.01-7.97 (m, 1H), 7.48 (d, J = 8.1 Hz, 1H), 7.11 (d, J = 8.1 Hz, 1H), 6.85 (s, 1H), 5.30-5.22 (m, 1H), 5.15-5.04 (m, 2H), 5.02-4.95 (m, 1H), 4.11 (br. s, 2H), 3.50 (s, 1H), 2.91 (s, 3H), 2.64-2.56 (m, 4H), 2.29 (s, 1H), 1.53 (d, J = 6.5 Hz, 3H), 1.38 (d, J = 6.8 Hz, 3H), 1.16 (d, J = 6.7 Hz, 6H). |
| 212 (L)* | 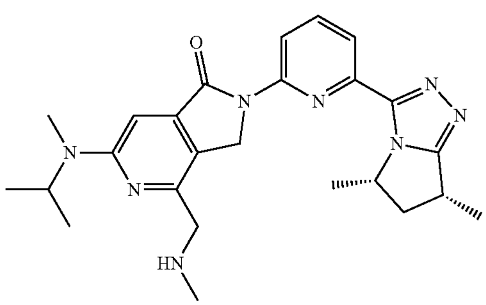 [SMILES: CNCc1nc(N(C)C(C)C)cc2c1CN(c1cccc(-c3nnc4n3[C@@H](C)C[C@H]4C)n1)C2=O] | 2-{6-[(5S,7R)-5,7-dimethyl-6,7-dihydro-5H-pyrrolo[2,1-c][1,2,4]triazol-3-yl]pyridin-2-yl}-4-[(methyl-amino)methyl]-6-[methyl(propan-2-yl)amino]-2,3-dihydro-1H-pyrrolo[3,4-c]pyridin-1-one | 461.2 | 1H NMR (400 MHz, DMSO-d6) δ 8.57 (d, J = 8.3 Hz, 1H), 8.07 (t, J = 8.0 Hz, 1H), 7.96 (d, J = 7.6 Hz, 1H), 7.50-7.44 (m, 1H), 7.10 (d, J = 7.9 Hz, 1H), 6.84 (s, 1H), 5.21 (s, 1H), 5.11-4.93 (m, 3H), 4.11 (br. s, 1H), 2.90 (s, 3H), 2.57 (br. s, 2H), 2.29 (s, 1H), 2.10-2.03 (m, 1H), 1.55 (d, J = 6.4 Hz, 3H), 1.43 (d, J = 6.8 Hz, 3H), 1.16 (d, J = 6.6 Hz, 6H). There are 4 protons missing, all believed to be under the water or DMSO peaks. |

*Letter within parentheses is the Method by which Example was prepared.

^[M + H]+ unless otherwise indicated.

Example 300: 6-(dimethylamino)-4-[(methylamino)methyl]-2-[6-(4-propyl-4H-1,2,4-triazol-3-yl)pyridin-2-yl]-2,3-dihydro-1H-pyrrolo[3,4-c]pyridin-1-one

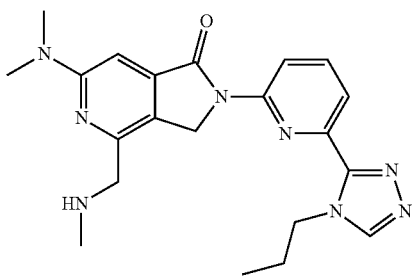 [SMILES: CCCn1cnnc1-c1cccc(N2Cc3c(cc(N(C)C)nc3CNC)C2=O)n1]

Step 1: tert-butyl ({6-(dimethylamino)-1-oxo-2-[6-(4-propyl-4H-1,2,4-triazol-3-yl)pyridin-2-yl]-2,3-dihydro-1H-pyrrolo[3,4-c]pyridin-4-yl}methyl)methylcarbamate

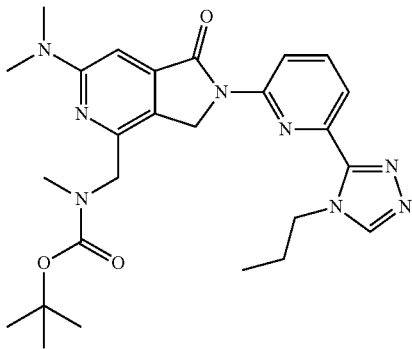 [SMILES: CCCn1cnnc1-c1cccc(N2Cc3c(cc(N(C)C)nc3CN(C)C(=O)OC(C)(C)C)C2=O)n1]

A mixture of tert-butyl {[6-(dimethylamino)-1-oxo-2,3-dihydro-1H-pyrrolo[3,4-c]pyridin-4-yl]methyl}methylcarbamate (Intermediate 11) (1.33 g, 4.15 mmol), 2-bromo-6-(4-propyl-4H-1,2,4-triazol-3-yl)pyridine (Intermediate 12) (1.16 g, 4.36 mmol), $Pd_2(dba)_3$ (380 mg, 0.415 mmol), XantPhos (480 g, 0.830 mmol), and $K_3PO_4$ (2.64 g, 12.5 mmoL) in 1,4-dioxane (46 mL) was degassed with $N_2$ for 5 min and then stirred at 85° C. for 16 h. The reaction was analyzed by LCMS, which showed consumption of the starting material. The mixture was cooled to RT, filtered through a pad of Celite®, and concentrated under vacuum. The residue was slurried with EtOAc (15 mL) for 10 min and the solids were collected by filtration. The filter cake was washed with EtOAc (4×) and then dried under vacuum. The residue was purified by flash chromatography (40 g $SiO_2$, 0-100% EtOAc/heptane then 10% MeOH/EtOAc) to provide a light-yellow solid. The material was dissolved in 1:9 EtOH/DCM and treated with Ultra-pure Si-Thio $SiO_2$ (1.59 g). The mixture was stirred for 2 h and the filtered. The filter cake was washed with 1:9 EtOH/DCM and the combined filtrate was concentrated under vacuum. The residue was dissolved in 1:9 EtOH/DCM and treated with Ultra-pure Si-Thio $SiO_2$ (1.32 g). The mixture was stirred for 3 h and then filtered. The filter cake was washed with 1:9 EtOH/DCM and the combined filtrate was concentrated. The residue was dissolved in 1:9 EtOH and treated with Ultra-pure Si-Thio $SiO_2$ (1.22 g). The mixture was stirred for 16 h and then filtered. The filter cake was washed with 1:9 EtOH/DCM. The combined filtrate was concentrated to dryness provide the title compound (2.08 g, 95% yield) as a light-yellow solid. $^1$H NMR (400 MHz, DMSO-$d_6$) δ 8.74 (s, 1H), 8.61 (d, J=8.4 Hz, 1H), 8.09 (t, J=8.0 Hz, 1H), 7.97 (d, J=7.6 Hz, 1H), 6.82 (s, 1H), 5.05 (d, J=11.7 Hz, 2H), 4.56 (s, 2H), 4.52-4.46 (m, 2H), 3.09 (s, 6H), 2.92 (s, 3H), 1.88-1.76 (m, 2H), 1.40-1.19 (m, 9H), 0.87 (t, J=7.4 Hz, 3H); LCMS m/z (ESI+) for ($C_{26}H_{34}N_8O_3$), 507.4 (M+H)$^+$.

Step 2: Example 300

To a suspension of tert-butyl ({6-(dimethylamino)-1-oxo-2-[6-(4-propyl-4H-1,2,4-triazol-3-yl)pyridin-2-yl]-2,3-dihydro-1H-pyrrolo[3,4-c]pyridin-4-yl}methyl)methylcarbamate (1.96 g, 3.87 mmol) in MeOH (20 mL) was added a solution of HCl (4.0 M in 1,4-dioxane, 19.3 mL, 77.4 mmol) slowly at 0° C. The mixture was stirred for 3 h at 0° C. and then allow to warm slowly to RT. The mixture was stirred at RT for 16 h. The reaction was concentrated to dryness. The solids were dissolved in 1:9 MeOH/DCM (80 mL), cooled to 0° C., and then stirred with a saturated solution of $Na_2CO_3$ (25 mL) for 20 min. The mixture was separated. The aqueous layer was extracted with 1:19 MeOH/DCM (3×50 mL). The combined organic layers were washed with $H_2O$ (2×30 mL), dried over $Na_2SO_4$, filtered, and concentrated. The solids were slurried in EtOAc at 40° C. for 40 min. The solids were collected by filtration. The filter cake was washed with EtOAc and then dried for 16 h in a vacuum oven at 30° C. to provide Example 300 (1.42 g, 90% yield) as a yellow solid. $^1$H NMR (400 MHz, DMSO-$d_6$) δ 8.73 (s, 1H), 8.62 (dd, J=8.4, 1.0 Hz, 1H), 8.11-8.04 (m, 1H), 8.00 (dd, J=7.7, 1.0 Hz, 1H), 6.78 (s, 1H), 5.14 (s, 2H), 4.57 (dd, J=7.9, 6.5 Hz, 2H), 3.80 (s, 2H), 3.09 (s, 6H), 2.35 (s, 3H), 1.88 (h, J=7.4 Hz, 2H), 0.93 (t, J=7.4 Hz, 3H); LCMS m/z (ESI+) for ($C_{21}H_{26}N_8O$), 407.3 (M+H)$^+$.

Biological Assays and Data

HPK1 Biochemical Enzyme Assay

HPK1 enzyme inhibition was measured by using the fluorescence-based chelation-enhanced fluorescence (CHEF) method (1), and by using a proprietary fluorescent peptide substrate, in which a cysteine residue is alkylated with a sulfonamido-oxine-based derivative to afford an amino acid termed C-Sox (CSx). The reactions were conducted in 50 μL volumes in 96-well plates, and contained 0.5 nM human full-length autophosphorylated recombinant HPK1 (see below for production method), 3 μM phospho-acceptor peptide substrate (Ac-[CSx]HSLPRFNR-amide peptide substrate, also known as AQT0178, AssayQuant Technologies Inc., Hopkinton, Mass.), test compound (11-dose 3-fold serial dilutions, 2% DMSO final) or DMSO only, 0.002% Tween-20, 1 mM DTT and 2.5 mM $MgCl_2$ in 50 mM MOPS (3-(N-morpholino)propanesulfonic acid) buffer, pH 7.8, and were initiated by the addition of 45 μM ATP, following a 20-min preincubation. Initial reaction velocities were determined by following the peptide fluorescence ($\lambda_{ex}$=360 nm, $\lambda_{em}$=500 nm) at 30° C. for 15 min in a Tecan M1000 plate reader (Tecan Group Ltd., Mannedorf, Zurich, Switzerland). The inhibition constant ($K_i$) values were calculated by fitting initial reaction velocities to the Morrison equation (2) for tight-binding competitive inhibition by using a non-linear regression method and an experimentally measured apparent ATP $K_m$ (19 μM). The inhibitors were shown to be ATP-competitive from kinetic and crystallographic studies.

Production of Autophosphorylated Full-Length Recombinant HPK1

The DNA sequence encoding full-length human HPK1 (Genbank NM_001042600.2) was synthesized at GenScript and contained a limited number of silent base changes to eliminate certain restriction endonuclease enzyme recognition sites, and fused to a DNA sequence encoding a Tobacco Etch Virus (TEV)-cleavable N-terminal polyhistidine purification tag. A recombinant baculovirus was prepared by using the Bac-to-Bac method (InVitrogen) and was used to infect 9 L of Sf21 insect cells. All purification steps were carried out at 4° C. Cells containing recombinant HPK1 were lysed in 50 mM HEPES-NaOH, pH 7.5, 250 mM NaCl, 1 mM tris(2-carboxyethyl)phosphine (TCEP), 10 μM leupeptin (Sigma), 10 μM E-64 (Sigma), and one 'EDTA-free' protease inhibitor tablet (Roche) per 75 mL buffer, centrifuged at 15,000×g for 1 h and the supernatant passed over 5 mL of ProBond IMAC resin (InVitrogen). After washing, HPK1 was eluted with 12.5 mL of 50 mM HEPES-NaOH, pH 7.5, 400 mM NaCl, 250 mM imidazole-HCl pH 7.5, 1 mM TCEP, 2 μM leupeptin, and 2 μM E-64. The eluted HPK1 was dialyzed overnight against 0.8 L of 50 mM HEPES-NaOH, pH 7.5, 400 mM NaCl, 20 mM imidazole-HCl pH 7.5, 1 mM TCEP, 2 μM leupeptin, 2 μM E-64, 2 mM ATP-NaOH pH 7.3, 5 mM $MgCl_2$ and 1 mg TEV (this step simultaneously allows for reduction of the imidazole concentration in preparation for the subsequent reverse IMAC chromatography step, removal of the polyhistidine purification tag by TEV protease, and autophosphorylation of HPK1 in the presence of MgATP). The de-tagged and autophosphorylated HPK1 was adjusted to 40 mM imidazole-HCl, pH 7.5, and passed through a 10 mL column of ProBond resin similarly equilibrated. The de-tagged HPK1 that passed through the column was concentrated to approximately 7 mL and purified further by gel filtration over a Superdex 26/60 size exclusion column (GE Healthcare) equilibrated and processed in 41.7 mM HEPES-NaOH buffer. pH 7.5, containing 417 mM NaCl, and 0.417 mM TCEP. The peak fractions containing HPK1 were pooled and concentrated to approximately 2.5 mL by using a centrifugal concentrator (Millipore). The concentrated HPK1 was adjusted to 20% (v/v) glycerol by the addition of 50% (v/v) glycerol, resulting in a final formulation of 25 mM HEPES-NaOH pH 7.5, 250 mM NaCl, 0.25 mM TCEP and 20% (v/v) glycerol. The final protein concentration was approximately 1 mg/mL as determined by the Bradford assay (Pierce reagent) and using bovine serum albumin (Pierce 2 mg/mL standard) as protein standard. Mass spectrogram analysis indicated the autophosphorylated HPK1 to contain an average of 15 phosphates per monomer. Aliquots of the enzyme were flash frozen in liquid nitrogen and stored at −80° C. The final product contains a glycine-serine extension at the N-terminus of the full-length protein, as a result of the cloning strategy.

The final DNA sequence of N-terminally tagged full-length HPK1 (SEQ ID NO. 1) comprised the sequence following the solidus after removal of the purification tag (underlined) which codes for full-length HPK1 with an additional 5'-GGATCC BamH I cloning site sequence (SEQ ID NO. 3):

<u>ATGGCGTCGCATCACCATCACCATCACGATTACGATGGTGCTACGACCGA</u>

<u>AAACCTGTATTTTCAG</u>/

This provides (SEQ ID NO. 1):

GGATCCATGGACGTCGTGGACCCTGACATTTTCAATAGAGACCCCCGGGA
CCACTATGACCTGCTACAGCGGCTGGGTGGCGGCACGTATGGGGAAGTCT
TTAAGGCTCGCGACAAGGTGTCAGGGGACCTGGTGGCACTGAAGATGGTG
AAGATGGAGCCTGATGATGATGTCTCCACCCTTCAGAAGGAAATCCTCAT
ATTGAAAACTTGCCGGCACGCCAACATCGTGGCCTACCACGGGAGTTATC
TCTGGTTGCAGAAACTCTGGATCTGCATGGAGTTCTGTGGGGCTGGTTCT
CTCCAGGACATCTACCAAGTGACAGGCTCCCTGTCAGAGCTCCAGATTAG
CTATGTCTGCCGGGAAGTGCTCCAGGGACTGGCCTATTTGCACTCACAGA
AGAAGATACACAGGGACATCAAGGGAGCTAACATCCTCATCAATGATGCT
GGGGAGGTCAGATTGGCTGACTTTGGCATCTCGGCCCAGATTGGGGCTAC
ACTGGCCAGACGCCTCTCTTTCATTGGGACACCCTACTGGATGGCTCCGG
AAGTGGCAGCTGTGGCCCTGAAGGGAGGATACAATGAGCTGTGTGACATC
TGGTCCCTGGGCATCACGGCCATCGAACTGGCCGAGCTACAGCCACCGCT
CTTTGATGTGCACCCTCTCAGAGTTCTCTTCCTCATGACCAAGAGTGGCT
ACCAGCCTCCCCGACTGAAGGAAAAAGGCAAATGGTCGGCTGCCTTCCAC
AACTTCATCAAAGTCACTCTGACTAAGAGTCCCAAGAAACGACCCAGCGC
CACCAAGATGCTCAGTCATCAACTGGTATCCCAGCCTGGGCTGAATCGAG
GCCTGATCCTGGATCTTCTTGACAAACTGAAGAATCCCGGGAAAGGACCC
TCCATTGGGGACATTGAGGATGAGGAGCCCGAGCTACCCCCTGCTATCCC
TCGGCGGATCAGATCCACCCACCGCTCCAGCTCTCTGGGCATCCCAGATG
CAGACTGCTGTCGGCGGCACATGGAGTTCAGGAAGCTCCGAGGAATGGAG
ACCAGACCCCCAGCCAACACCGCTCGCCTACAGCCTCCCCGAGACCTCAG
GAGCAGCAGCCCCAGGAAGCAACTGTCAGAGTCGTCTGACGATGACTATG
ACGACGTGGACATCCCCACCCCTGCAGAGGACACACCTCCTCCACTTCCC
CCCAAGCCCAAGTTCCGTTCTCCATCAGACGAGGGTCCTGGGAGCATGGG
GGATGATGGGCAGCTGAGCCCGGGGGTGCTGGTCCGGTGTGCCAGTGGGC
CCCCACCAAACAGCCCCGTCCTGGGCCTCCCCATCCACCAGCAGCCCC
CACCTCACCGCCCATTCAGAACCCTCACTCTGGAACCCACCCTCCCGGGA
GCTTGACAAGCCCCCACTTCTGCCCCCCAAGAAGGAAAAGATGAAGAGAA
AGGGATGTGCCCTTCTCGTAAAGTTGTTCAATGGCTGCCCCCTCCGCATC
CACAGCACGGCCGCCTGGACACATCCCTCCACCAAGGACCAGCACCTGCT
CCTGGGGGCAGAGGAAGGCATCTTCATCCTGAACCGGAATGACCAGGAGG
CCACGCTGGAAATGCTCTTTCCTAGCCGGACTACGTGGGTGTACTCCATC
AACAACGTTCTCATGTCTCTCTCAGGAAAGACCCCCCACCTGTATTCTCA
TAGCATCCTTGGCCTGCTGGAACGGAAAGAGACCAGAGCAGGAAACCCCA
TCGCTCACATTAGCCCCCACCGCCTACTGGCAAGGAAGAACATGGTTTCC
ACCAAGATCCAGGACACCAAAGGCTGCCGGGCGTGCTGTGTGGCGGAGGG
TGCGAGCTCTGGGGGCCCGTTCCTGTGCGGTGCATTGGAGACGTCCGTTG
TCCTGCTTCAGTGGTACCAGCCCATGAACAAATTCCTGCTTGTCCGGCAG

```
-continued
GTGCTGTTCCCACTGCCGACGCCTCTGTCCGTGTTCGCGCTGCTGACCGG

GCCAGGCTCTGAGCTGCCCGCTGTGTGCATCGGCGTGAGCCCCGGGCGGC

CGGGGAAGTCGGTGCTCTTCCACACGGTGCGCTTTGGCGCGCTCTCTTGC

TGGCTGGGCGAGATGAGCACCGAGCACAGGGGACCCGTGCAGGTGACCCA

GGTAGAGGAAGATATGGTGATGGTGTTGATGGATGGCTCTGTGAAGCTGG

TGACCCCGGAGGGGTCCCCAGTCCGGGGACTTCGCACACCTGAGATCCCC

ATGACCGAAGCGGTGGAGGCCGTGGCTATGGTTGGAGGTCAGCTTCAGGC

CTTCTGGAAGCATGGAGTGCAGGTGTGGGCTCTAGGCTCGGATCAGCTGC

TACAGGAGCTGAGAGACCCTACCCTCACTTTCCGTCTGCTTGGCTCCCCC

AGGCCTGTAGTGGTGGAGACACGCCCAGTGGATGATCCTACTGCTCCCAG

CAACCTCTACATCCAGGAATGA
```

The final protein sequence of N-terminally tagged full-length HPK1 (SEQ ID NO. 2) comprised the sequence following the solidus after removal of the purification tag (underlined) with an additional N-terminal GlySer sequence encoded from the BamH I cloning site (SEQ ID NO. 4):

<u>MASHHHHHHDYDGATTENLYFQ</u>/

This gives (SEQ ID NO. 2):

```
GSMDVVDPDIFNRDPRDHYDLLQRLGGGTYGEVFKARDKVSGDLVALKMV

KMEPDDDVSTLQKEILILKTCRHANIVAYHGSYLWLQKLWICMEFCGAGS

LQDIYQVTGSLSELQISYVCREVLQGLAYLHSQKKIHRDIKGANILINDA

GEVRLADFGISAQIGATLARRLSFIGTPYWMAPEVAAVALKGGYNELCDI

WSLGITAIELAELQPPLFDVHPLRVLFLMTKSGYQPPRLKEKGKWSAAFH

NFIKVTLTKSPKKRPSATKMLSHQLVSQPGLNRGLILDLLDKLKNPGKGP

SIGDIEDEEPELPPAIPRRIRSTHRSSSLGIPDADCCRRHMEFRKLRGME

TRPPANTARLQPPRDLRSSSPRKQLSESSDDDYDDVDIPTPAEDTPPPLP

PKPKFRSPSDEGPGSMGDDGQLSPGVLVRCASGPPPNSPRPGPPPSTSSP

HLTAHSEPSLWNPPSRELDKPPLLPPKKEKMKRKGCALLVKLFNGCPLRI

HSTAAWTHPSTKDQHLLLGAEEGIFILNRNDQEATLEMLFPSRTTWVYSI

NNVLMSLSGKTPHLYSHSILGLLERKETRAGNPIAHISPHRLLARKNMVS

TKIQDTKGCRACCVAEGASSGGPFLCGALETSVVLLQWYQPMNKFLLVRQ

VLFPLPTPLSVFALLTGPGSELPAVCIGVSPGRPGKSVLFHTVRFGALSC

WLGEMSTEHRGPVQVTQVEEDMVMVLMDGSVKLVTPEGSPVRGLRTPEIP

MTEAVEAVAMVGGQLQAFWKHGVQVWALGSDQLLQELRDPTLTFRLLGSP

RPVVVETRPVDDPTAPSNLYIQE
```

Cell Based Assays
Phospho-SLP-76 (Ser376) Homogeneous Time Resolved Fluorescence (HTRF) Assay Jurkat cells were seeded at 90,000 cells/well in 90 uL of RPMI1640 growth medium containing 10% FBS and incubated at 37° C. with 5% $CO_2$ overnight. The following day, compounds were serially diluted from a 10 mM top dose for an 11-point 3-fold dilution curve in DMSO. Compounds were intermediately diluted 1:100 into growth media prior to diluting 1:10 on cells for final concentration 10 μM to 0.1 nM in 0.1% DMSO. After 30 min pre-treatment with compounds, the cells were stimulated using 200 μg/mL of $F(ab)_2$ complexed anti-CD3 (clone UCTH1) for 15 min at 37° C. with 5% $CO_2$. Stimulation was stopped with ice cold PBS and cells were harvested by centrifugation before lysis in Cisbio lysis buffer (Cisbio, Bedford, Mass.). Lysates were transferred to white, low-volume plates containing anti-phospho-SLP-76-Cryptate plus anti-phospho-SLP-76-d2 HTRF antibodies and incubated overnight at room temperature protected from light according to the manufacturer's protocol (Cisbio, Bedford, Mass.). HTRF was measured on a Perkin Elmer Envision and IC50 values were calculated by concentration-response curve fitting utilizing four-parameter nonlinear regression analyses.

Biological activity data for compounds is provided in Table 8. The data for the HPK1 CHEF are provided in Table 8, with column heading HPK1 Ki (μM). The data for the cellular Phospho-SLP-76 (Ser376) Homogeneous Time Resolved Fluorescence (HTRF) assays are provided in Table 8, with column heading pSLP76 $IC_{50}$ (μM). For each of these two assays, the respective adjacent column provides the number of times the compound was tested in the assay.

Biochemical Selectivity Kinase Assay.

PRKD2 (PKD2) and RPS6KA2 (RSK3) kinase assays were performed with Km-levels of ATP at the Thermo Fisher Scientific, Inc. (Madison, Wis.), using their Invitrogen™ SelectScreen™ fluorescence resonance energy transfer (FRET) Z'-LYTE™ technology, based on the differential sensitivity of phosphorylated and nonphosphorylated peptides to proteolytic cleavage. Human recombinant full-length GST-tagged PRKD2 (PKD2) and RPS6KA2 (RSK3) were produced by Thermo Fisher Scientific, Inc. (Madison, Wis.). The kinase assays were conducted in 10-μL reactions. PRKD2 (PKD2) reactions contained 0.64-5.84 ng enzyme, 25 μM ATP (~Km), 2 μM of Ser/Thr 17 (Z'-LYTE™ peptide substrate), 10 mM $MgCl2$, 0.01% BRIJ-35, 1 mM EGTA in 50 mM HEPES, pH 7.5. RPS6KA2 (RSK3) reactions were conducted similarly, and contained 0.5-9 ng enzyme, or 10 μM ATP (~Km) and 2 μM Ser/Thr 06 peptide. After the 1-hour kinase reaction incubation, 5 μL of a 1:256 and 1:4096 dilution of Z'-LYTE™ Development Reagent A was added to the PRKD2 (PKD2) and RPS6KA2 (RSK3) reactions, respectively. The extent of kinase reactions, resulting in a change of FRET signal of the peptide substrate, was measured, and inhibition for each kinase was measured with respect to DMSO control and reported as an average of duplicate measurements. Each 50% inhibitory concentration ($IC_{50}$) determination was based on 10-dose duplicate measurements, fitted to a standard four-parameter $IC_{50}$ equation using XLfit software from IDBS (Guildford, United Kingdom). The dose response curve was curve fit to model number 205 (sigmoidal dose-response model). A ratio of the PRKD2 $IC_{50}$ to the HPK1 Ki and a ratio of the RSK3 $IC_{50}$ to the HPK1 Ki, is provided in the respective columns adjacent to the columns for PRKD2 $IC_{50}$ and RSK3 $IC_{50}$.

Alpha branched amine analogs, where at least one of $R^{3a}$ and $R^{3b}$ is other than hydrogen, greatly improved selectivity for HPK1 relative to other kinases (including PRKD2 and RSK3) relative to non-alpha branched amine compounds, e.g., Example 300. Cyclic, fused triazoles, e.g., compounds of Formula I-B, where $R^4$ is ($R^4$-ii), provided improvement in biochemical and cellular potency relative to non-cyclic compounds, e.g., Example 300.

TABLE 8

| Ex. # | HPK1 Ki (μM) | # of Runs - HPK1 Ki | pSLP76 IC$_{50}$ (μM) | # of Runs - pSLP76 | PRKD2 IC$_{50}$ (nM) | PRKD2 IC$_{50}$/ HPK1 Ki | RSK3 IC$_{50}$ (nM) | RSK3 IC$_{50}$/ HPK1 Ki |
|---|---|---|---|---|---|---|---|---|
| 1 | <0.00005 | 8 | 0.017 | 6 | 155 | >3100 | 47.0 | >940 |
| 2 | <0.00005 | 3 | 0.03 | 3 | 116 | >2320 | 21.3 | >420 |
| 3 | <0.00005 | 2 | 0.034 | 1 | 6.54 | >130 | 3.33 | >66 |
| 4 | <0.00005 | 2 | 0.036 | 1 | 217 | >4304 | 25.8 | >520 |
| 5 | <0.00005 | 2 | 0.031 | 1 | 251 | >5020 | 53.5 | >1080 |
| 6a | 0.00019 | 1 | 0.069 | 2 | 942 | 4958 | 48.6 | 256 |
| 6b | 0.0061 | 1 | 0.641 | 1 | | | | |
| 7 | 0.0028 | 1 | | | | | | |
| 8 | 0.0056 | 2 | | | | | | |
| 9 | 0.00049 | 2 | 0.115 | 1 | | | | |
| 10 | 0.00013 | 1 | 0.147 | 1 | | | | |
| 11 | 0.00972 | 1 | | | | | | |
| 12 | 0.00198 | 1 | | | | | | |
| 13 | <0.00007 | 3 | 0.036 | 2 | | | | |
| 14 | 0.00093 | 3 | 0.34 | 1 | | | | |
| 15 | 0.00847 | 1 | | | | | | |
| 16 | 0.000093 | 1 | 0.487 | 1 | | | | |
| 17 | <0.00005 | 1 | 0.023 | 2 | | | | |
| 18 | <0.00005 | 2 | 0.042 | 3 | | | | |
| 19 | 0.00015 | 1 | | | | | | |
| 20 | <0.00005 | 2 | 0.023 | 2 | | | | |
| 21 | 0.000064 | 1 | 0.046 | 1 | | | | |
| 22 | 0.00008 | 2 | 0.133 | 2 | | | | |
| 23 | 0.005 | 3 | 0.329 | 2 | | | | |
| 24 | 0.00176 | 1 | | | | | | |
| 25 | <0.00005 | 2 | 0.053 | 5 | | | | |
| 26 | 0.00072 | 1 | 0.133 | 1 | | | | |
| 27 | <0.00005 | 2 | 0.056 | 2 | | | | |
| 28 | <0.000045 | 2 | 0.064 | 1 | | | | |
| 29 | 0.0002 | 3 | 0.072 | 2 | | | | |
| 30 | <0.00005 | 1 | 0.062 | 2 | | | | |
| 31 | <0.00005 | 1 | 0.042 | 1 | | | | |
| 32 | 0.00006 | 1 | 0.046 | 1 | | | | |
| 33 | 0.00021 | 1 | 0.179 | 1 | | | | |
| 34 | 0.00015 | 1 | 0.026 | 2 | | | | |
| 35 | 0.0003 | 1 | 0.181 | 2 | | | | |
| 36 | 0.000074 | 1 | 0.110 | 2 | | | | |
| 37 | <0.00005 | 1 | 0.049 | 1 | | | | |
| 38 | 0.00018 | 1 | 0.197 | 2 | | | | |
| 100 | <0.00005 | 4 | 0.039 | 4 | 51.2 | >1020 | 15.5 | >320 |
| 101 | 0.00017 | 3 | 0.118 | 1 | | | | |
| 102 | 0.00011 | 3 | 0.107 | 1 | | | | |
| 103 | 0.00138 | 2 | | | | | | |
| 104 | 0.00236 | 2 | | | | | | |
| 105 | 0.00201 | 2 | | | | | | |
| 106 | 0.0105 | 1 | | | | | | |
| 107 | 0.00102 | 2 | 0.140 | 1 | | | | |
| 108 | 0.00061 | 2 | 0.084 | 1 | | | | |
| 109 | 0.00031 | 1 | 0.061 | 1 | | | | |
| 110 | 0.00009 | 2 | 0.042 | 2 | | | | |
| 111 | 0.00342 | 1 | 0.470 | 1 | | | | |
| 112 | 0.00077 | 1 | 0.421 | 1 | | | | |
| 113 | 0.00067 | 1 | 0.133 | 2 | | | | |
| 114 | 0.00041 | 2 | 0.148 | 3 | | | | |
| 115 | 0.00056 | 2 | 0.216 | 4 | | | | |
| 116 | 0.00064 | 1 | 0.214 | 1 | | | | |
| 117 | 0.00102 | 1 | 0.270 | 1 | | | | |
| 118 | 0.00150 | 1 | 0.324 | 1 | | | | |
| 119 | 0.00090 | 1 | 0.165 | 2 | | | | |
| 120 | 0.00297 | 1 | 0.531 | 1 | | | | |
| 121 | 0.00412 | 2 | 0.553 | 2 | | | | |
| 122 | 0.00078 | 1 | 0.354 | 1 | | | | |
| 123 | 0.00097 | 1 | 0.243 | 1 | | | | |
| 124 | 0.00037 | 2 | 0.098 | 2 | | | | |
| 125 | 0.00142 | 1 | | | | | | |
| 126 | 0.00178 | 1 | | | | | | |
| 127 | 0.00141 | 1 | | | | | | |
| 128 | 0.00103 | 1 | 0.194 | 1 | | | | |
| 129 | 0.00028 | 1 | 0.097 | 2 | | | | |
| 130 | 0.0004 | 1 | 0.077 | 2 | | | | |
| 131 | 0.00102 | 3 | 0.094 | 1 | | | | |
| 132 | 0.00038 | 1 | 0.148 | 1 | | | | |
| 133 | 0.00012 | 1 | 0.095 | 2 | | | | |
| 134 | 0.00022 | 2 | 0.106 | 2 | | | | |
| 135 | 0.00037 | 1 | 0.143 | 2 | | | | |

TABLE 8-continued

| Ex. # | HPK1 Ki (μM) | # of Runs - HPK1 Ki | pSLP76 IC$_{50}$ (μM) | # of Runs - pSLP76 | PRKD2 IC$_{50}$ (nM) | PRKD2 IC$_{50}$/ HPK1 Ki | RSK3 IC$_{50}$ (nM) | RSK3 IC$_{50}$/ HPK1 Ki |
|---|---|---|---|---|---|---|---|---|
| 136 | 0.00022 | 1 | 0.09 | 2 | | | | |
| 137 | 0.00075 | 1 | 0.189 | 2 | | | | |
| 138 | 0.00096 | 1 | 0.332 | 1 | | | | |
| 139 | 0.00027 | 1 | 0.104 | 2 | | | | |
| 140 | <0.00007 | 3 | 0.053 | 3 | | | | |
| 141 | 0.00044 | 1 | | | | | | |
| 142 | 0.00154 | 1 | | | | | | |
| 143 | 0.00373 | 1 | | | | | | |
| 144 | 0.00011 | 1 | 0.090 | 3 | | | | |
| 145 | 0.00046 | 1 | | | | | | |
| 146 | 0.00314 | 1 | | | | | | |
| 147 | 0.001 | 1 | | | | | | |
| 148 | 0.0004 | 1 | 0.096 | 2 | | | | |
| 149 | 0.0006 | 1 | 0.171 | 2 | | | | |
| 150 | 0.00011 | 1 | 0.059 | 1 | | | | |
| 151 | 0.00012 | 1 | 0.033 | 1 | | | | |
| 152 | 0.00153 | 1 | 0.191 | 1 | | | | |
| 153 | 0.00125 | 1 | | | | | | |
| 154 | 0.00025 | 1 | 0.120 | 1 | | | | |
| 155 | 0.00024 | 1 | 0.113 | 2 | | | | |
| 200 | <0.00005 | 2 | 0.016 | 4 | 7.97 | >160 | 10.1 | >200 |
| 201 | <0.00005 | 1 | 0.037 | 1 | 5.43 | >108 | 6.73 | >134 |
| 202 | 0.00006 | 1 | 0.025 | 2 | 6.54 | 108 | 40.1 | 667 |
| 203 | 0.00104 | 1 | 0.182 | 3 | | | | |
| 204 | 0.00129 | 1 | | | | | | |
| 205 | <0.00005 | 2 | 0.052 | 2 | | | | |
| 206 | 0.00012 | 1 | 0.078 | 2 | | | | |
| 207 | 0.00268 | 1 | | | | | | |
| 208 | 0.0006 | 2 | 0.085 | 2 | | | | |
| 209 | 0.00211 | 1 | | | | | | |
| 210 | <0.00005 | 2 | 0.047 | 3 | | | | |
| 211 | <0.00005 | 1 | 0.078 | 2 | | | | |
| 212 | 0.00032 | 1 | 0.159 | 1 | | | | |
| 300 | 0.00014 | 1 | 0.094 | 4 | 1.93 | 14 | 6.26 | 23 |

An empty box in Table 8 means data was not obtained.

All publications and patent applications cited in the specification are herein incorporated by reference in their entirety. It will be apparent to those of ordinary skill in the art that certain changes and modifications may be made thereto without departing from the spirit or scope of the appended claims.

What is claimed is:

1. A compound of Formula I:

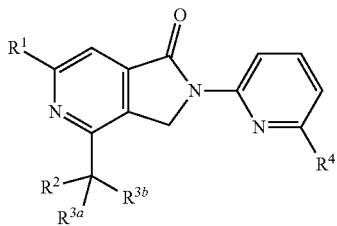

I or a pharmaceutically acceptable salt thereof, wherein:
$R^1$ is $(C_1-C_6)$alkyl, halo$(C_1-C_6)$alkyl, $(C_1-C_6)$alkoxy, halo$(C_1-C_6)$alkoxy, —$N(R^5)(R^6)$, or $(C_3-C_6)$cycloalkyl, wherein said $(C_1-C_6)$alkyl, halo$(C_1-C_6)$alkyl, and $(C_3-C_6)$cycloalkyl are substituted with 0 or 1 substituent that is hydroxy, cyano, $(C_1-C_6)$alkyl, or $(C_1-C_6)$alkoxy, wherein:
  $R^5$ and $R^6$ are each independently hydrogen or $(C_1-C_6)$alkyl that is substituted with 0, 1, or 2 substituents independently selected from the group consisting of halogen, $(C_1-C_6)$alkoxy, cyano, and hydroxy, or
  $R^5$ and $R^6$ taken together with the nitrogen to which they are attached form a (4- to 8-membered)heterocycloalkyl that is substituted with 0, 1, or 2 substituents independently selected from the group consisting of halogen, $(C_1-C_6)$alkyl, halo$(C_1-C_6)$alkyl, $(C_1-C_6)$alkoxy, and halo$(C_1-C_6)$alkoxy;
$R^2$ is $N(R^7)(R^8)$, wherein:
  $R^7$ and $R^8$ are each independently hydrogen or $(C_1-C_6)$alkyl that is substituted with 0, or 1 substituent that is halogen, $(C_1-C_6)$alkoxy, cyano, or hydroxy; or
  $R^7$ is hydrogen or $(C_1-C_6)$alkyl that is substituted with 0, or 1 substituent that is halogen, $(C_1-C_6)$alkoxy, cyano, or hydroxy; and $R^8$ taken together with the nitrogen to which it is attached and taken together with $R^{3a}$ and the carbon to which it is attached form a (4- to 6-membered)heterocycloalkyl that is substituted with 0, 1, or 2 substituents independently selected from halogen, hydroxy, $(C_1-C_3)$alkyl, halo$(C_1-C_3)$alkyl, $(C_1-C_3)$alkoxy, and halo$(C_1-C_6)$alkoxy; or
  $R^7$ and $R^8$ taken together with the nitrogen to which they are attached form a (4- to 6-membered)heterocycloalkyl that is substituted with 0, 1, or 2 substituents independently selected from halogen, hydroxy, $(C_1-C_6)$alkyl, halo$(C_1-C_6)$alkyl, $(C_1-C_6)$alkoxy, and halo$(C_1-C_6)$alkoxy;
$R^{3a}$ is hydrogen, or $(C_1-C_3)$alkyl that is substituted with 0 or 1 substituent that is hydroxy, or $(C_1-C_3)$alkoxy;
$R^{3b}$ is hydrogen, or $(C_1-C_3)$alkyl, provided that $R^{3a}$ and $R^{3b}$ are not both H when $R^4$ is $(R^4$-i$)$;
$R^4$ is $(R^4$-i$)$ or $(R^4$-ii$)$:

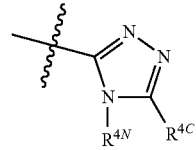

($R^4$-i)

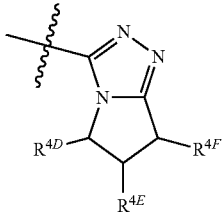

($R^4$-ii)

wherein:
  $R^{4N}$ is $(C_1-C_6)$alkyl, halo$(C_1-C_6)$alkyl, or $(C_3-C_6)$cycloalkyl, wherein said $(C_1-C_6)$alkyl is substituted with 0 or 1 substituent that is hydroxy;
  $R^{4C}$ is hydrogen, $(C_1-C_6)$alkyl, halo$(C_1-C_6)$alkyl, $(C_1-C_6)$alkoxy, halo$(C_1-C_6)$alkoxy, or $(C_3-C_6)$cycloalkyl, wherein said $(C_1-C_6)$alkyl and halo$(C_1-C_6)$alkyl are substituted with 0 or 1 substituent that is hydroxy, cyano, or $(C_1-C_6)$alkoxy;
  $R^{4D}$ is hydrogen, $(C_1-C_6)$alkyl, halo$(C_1-C_6)$alkyl, $(C_1-C_6)$alkoxy, halo$(C_1-C_6)$alkoxy, or $(C_3-C_6)$cycloalkyl, wherein said $(C_1-C_6)$alkyl and halo$(C_1-C_6)$alkyl are substituted with 0 or 1 substituent that is hydroxy, cyano, or $(C_1-C_6)$alkoxy;
  $R^{4E}$ is hydrogen, halogen, cyano, hydroxy, or $(C_1-C_6)$alkyl; and R$^{4F}$ is hydrogen, halogen, cyano, hydroxy, (C$_1$-C$_6$)alkyl, halo(C$_1$-C$_6$)alkyl, (C$_1$-C$_6$)alkoxy, halo(C$_1$-C$_6$)alkoxy, or (C$_3$-C$_6$)cycloalkyl, wherein said (C$_1$-C$_6$)alkyl and halo(C$_1$-C$_6$)alkyl are substituted with 0 or 1 substituent that is hydroxy, cyano, or (C$_1$-C$_6$)alkoxy.

2. The compound of claim 1, or a pharmaceutically acceptable salt thereof, wherein R$^4$ is (R$^4$-i);
R$^{4N}$ is (C$_1$-C$_6$)alkyl, or (C$_3$-C$_6$)cycloalkyl; and
R$^{4C}$ is hydrogen, or (C$_1$-C$_3$)alkyl.

3. The compound of claim 1, or a pharmaceutically acceptable salt thereof, wherein R$^1$ is —N(R$^5$)(R$^6$), or (C$_3$-C$_6$)cycloalkyl, wherein said (C$_3$-C$_6$)cycloalkyl is cyclopropyl and is substituted with 0 or 1 substituent that is (C$_1$-C$_6$)alkyl, wherein said (C$_1$-C$_6$)alkyl is methyl;
R$^5$ and R$^6$ are each independently hydrogen or (C$_1$-C$_3$)alkyl, or
R$^5$ and R$^6$ taken together with the nitrogen to which they are attached form a (5-membered)heterocycloalkyl that is substituted with 0, or 1 substituent that is (C$_1$-C$_6$)alkyl;
R$^2$ is N(R$^7$)(R$^8$), wherein R$^7$ and R$^8$ are each independently hydrogen or (C$_1$-C$_6$)alkyl that is methyl;
R$^{3a}$ is (C$_1$-C$_3$)alkyl that is substituted with 0 or 1 substituent that is (C$_1$-C$_3$)alkoxy; and
R$^{3b}$ is hydrogen, or (C$_1$-C$_3$)alkyl.

4. The compound of claim 1, or a pharmaceutically acceptable salt thereof, wherein R$^4$ is (R$^4$-ii);
R$^{4D}$ is hydrogen, (C$_1$-C$_6$)alkyl, or halo(C$_1$-C$_6$)alkyl, wherein said (C$_1$-C$_6$)alkyl is substituted with 0 or 1 substituent that is hydroxy;
R$^{4E}$ is hydrogen; and
R$^{4F}$ is hydrogen, (C$_1$-C$_6$)alkyl, or halo(C$_1$-C$_6$)alkyl, wherein said (C$_1$-C$_6$)alkyl is substituted with 0 or 1 substituent that is hydroxy.

5. The compound of claim 1, or a pharmaceutically acceptable salt thereof, wherein R$^1$ is —N(R$^5$)(R$^6$), or (C$_3$-C$_6$)cycloalkyl, wherein said (C$_3$-C$_6$)cycloalkyl is cyclopropyl and is substituted with 0 or 1 substituent that is (C$_1$-C$_6$)alkyl, wherein said (C$_1$-C$_6$)alkyl is methyl;
R$^5$ and R$^6$ are each independently hydrogen or (C$_1$-C$_3$)alkyl, or
R$^5$ and R$^6$ taken together with the nitrogen to which they are attached form a (5-membered)heterocycloalkyl that is substituted with 0, or 1 substituent that is (C$_1$-C$_6$)alkyl;
R$^2$ is N(R$^7$)(R$^8$), wherein R$^7$ and R$^8$ are each independently hydrogen or (C$_1$-C$_6$)alkyl that is methyl;
R$^{3a}$ is hydrogen, or (C$_1$-C$_3$)alkyl that is substituted with 0 or 1 substituent that is (C$_1$-C$_3$)alkoxy; and
R$^{3b}$ is hydrogen, or (C$_1$-C$_3$)alkyl.

6. The compound of claim 1, or a pharmaceutically acceptable salt thereof, wherein R$^1$ is 2-methyl-pyrrolidin-1-yl, or 2(R)-methyl-pyrrolidin-1-yl.

7. The compound of claim 1, or a pharmaceutically acceptable salt thereof, wherein R$^7$ and R$^8$ are each hydrogen.

8. The compound of claim 1, or a pharmaceutically acceptable salt thereof, wherein R$^7$ is hydrogen; and R$^8$ is (C$_1$-C$_3$)alkyl.

9. The compound of claim 1, or a pharmaceutically acceptable salt thereof, wherein R$^{35}$ is hydrogen, and wherein orientation of R$^2$, R$^{3a}$, and R$^{3b}$ provide a compound of Formula I(R) or Formula I(S):

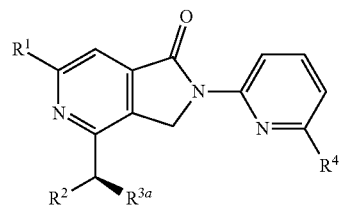

Formula I(R)

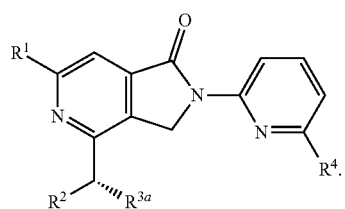

Formula I(S)

10. The compound of claim 1, or a pharmaceutically acceptable salt thereof, wherein R$^4$ is 5-methyl-6,7-dihydro-5H-pyrrolo[2,1-c][1,2,4]triazol-3-yl, (5R)-5-methyl-6,7-dihydro-5H-pyrrolo[2,1-c][1,2,4]triazol-3-yl, (5.5)-5-methyl-6,7-dihydro-5H-pyrrolo[2,1-c][1,2,4]triazol-3-yl, 5-ethyl-6,7-dihydro-5H-pyrrolo[2,1-c][1,2,4]triazol-3-yl, (5S)-5-ethyl-6,7-dihydro-5H-pyrrolo[2,1-c][1,2,4]triazol-3-yl, or (5R)-5-ethyl-6,7-dihydro-5H-pyrrolo[2,1-c][1,2,4]triazol-3-yl.

11. The compound of claim 10, or a pharmaceutically acceptable salt thereof, wherein R$^4$ is (5S)-5-methyl-6,7-dihydro-5H-pyrrolo[2,1-c][1,2,4]triazol-3-yl, or (5S)-5-ethyl-6,7-dihydro-5H-pyrrolo[2,1-c][1,2,4]triazol-3-yl.

12. A compound that is 4-[1-aminopropyl]-2-{6-[5-methyl-6,7-dihydro-5H-pyrrolo[2,1-c][1,2,4]triazol-3-yl]pyridin-2-yl}-6-[2-methylpyrrolidin-1-yl]-2,3-dihydro-1H-pyrrolo[3,4-c]pyridin-1-one;
  4-[1-aminoethyl]-2-{6-[5-ethyl-6,7-dihydro-5H-pyrrolo[2,1-c][1,2,4]triazol-3-yl]pyridin-2-yl}-6-[2-methylpyrrolidin-1-yl]-2,3-dihydro-1H-pyrrolo[3,4-c]pyridin-1-one;
  4-[1-aminoethyl]-2-{6-[5-ethyl-6,7-dihydro-5H-pyrrolo[2,1-c][1s,2,4]triazol-3-yl]pyridin-2-yl}-6-[2-methylpyrrolidin-1-yl]-2,3-dihydro-1H-pyrrolo[3,4-c]pyridin-1-one;
  4-[1-aminoethyl]-2-{6-[5-ethyl-6,7-dihydro-5H-pyrrolo[2,1-c][1,2,4]triazol-3-yl]pyridin-2-yl}-6-[methyl(propan-2-yl)amino]-2,3-dihydro-1H-pyrrolo[3,4-c]pyridin-1-one;
  4-[1-aminopropyl]-2-{3-[5-methyl-6,7-dihydro-5H-pyrrolo[2,1-c][1,2,4]triazol-3-yl]phenyl}-6-[methyl(propan-2-yl)amino]-2,3-dihydro-1H-pyrrolo[3,4-c]pyridin-1-one; or
  4-[1-amino-2-methoxyethyl]-6-(1-methylcyclopropyl)-2-{6-[5-methyl-6,7-dihydro-5H-pyrrolo[2,1-c][1,2,4]triazol-3-yl]pyridin-2-yl}-2,3-dihydro-1H-pyrrolo[3,4-c]pyridin-1-one; or a pharmaceutically acceptable salt thereof.

13. The compound of claim 12, wherein the compound is 4-[(1R)-1-aminopropyl]-2-{6-[(5S)-5-methyl-6,7-dihydro-5H-pyrrolo[2,1-c][1,2,4]triazol-3-yl]pyridin-2-yl}-6-[(2R)-2-methyl pyrrolidin-1-yl]-2,3-dihydro-1H-pyrrolo[3,4-c]pyridin-1-one;
  4-[(1R)-1-aminoethyl]-2-{6-[(5S)-5-ethyl-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one;

4-[(1S)-1-aminoethyl]-2-{6-[(5S)-5-ethyl-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one;

4-[(1R)-1-aminoethyl]-2-{6-[(5S)-5-ethyl-6,7-dihydro-5H-pyrrolo[2,1-c][1,2,4]triazol-3-yl]pyridin-2-yl}-6-[methyl(propan-2-yl)amino]-2,3-dihydro-1H-pyrrolo[3,4-c]pyridin-1-one;

4-[(1R)-1-aminopropyl]-2-{3-[(5S)-5-methyl-6,7-dihydro-5H-pyrrolo[2,1-c][1,2,4]triazol-3-yl]phenyl}-6-[methyl(propan-2-yl)amino]-2,3-dihydro-1H-pyrrolo[3,4-c]pyridin-1-one;

4-[(1R)-1-amino-2-methoxyethyl]-6-(1-methylcyclopropyl)-2-{6-[(5S)-5-methyl-6,7-dihydro-5H-pyrrolo[2,1-c][1,2,4]triazol-3-yl]pyridin-2-yl}-2,3-dihydro-1H-pyrrolo[3,4-c]pyridin-1-one; or 4-[(1S)-1-amino-2-methoxyethyl]-6-(1-methylcyclopropyl)-2-{6-[(5S)-5-methyl-6,7-dihydro-5H-pyrrolo[2,1-c][1,2,4]triazol-3-yl]pyridin-2-yl}-2,3-dihydro-1H-pyrrolo[3,4-c]pyridin-1-one; or a pharmaceutically acceptable salt thereof.

14. A compound having the structure:

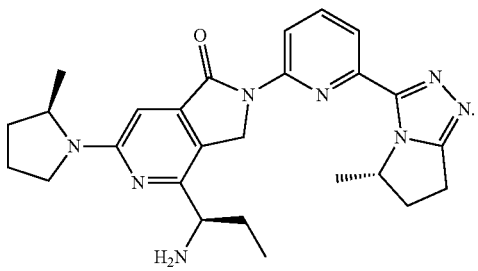 [SMILES: CC[C@@H](N)c1nc(N2CCC[C@H]2C)cc2c1CN(c1cccc(-c3nnc4n3[C@@H](C)CC4)n1)C2=O]

15. A compound that is 4-[(1R)-1-aminopropyl]-2-{6-[(5S)-5-methyl-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one; or a pharmaceutically acceptable salt thereof.

16. A compound that is 4-[(1R)-1-aminoethyl]-2-{6-[(5S)-5-ethyl-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one; or a pharmaceutically acceptable salt thereof.

17. A compound that is 4-[(1.5)-1-aminoethyl]-2-{6-[(5S)-5-ethyl-6,7-dihydro-5H-pyrrolo[2,1-c][1,2,4]triazol-3-yl]pyridin-2-yl}-6-[(2R)-2-methylpyrrolidin-1-yl]-2,3-dihydro-1H-pyrrolo[3,4-c]pyridin-1-one; or a pharmaceutically acceptable salt thereof.

18. A pharmaceutical composition comprising a compound of claim 1, or a pharmaceutically acceptable salt thereof, and a pharmaceutically acceptable carrier or excipient.

19. A method for the treatment of cancer abnormal cell growth in a mammal, comprising administering to the mammal a therapeutically effective amount of a compound of claim 1, or a pharmaceutically acceptable salt thereof, wherein the cancer is selected from the group consisting of breast cancer, ovarian cancer, bladder cancer, uterine cancer, prostate cancer, lung cancer, esophageal cancer, head and neck cancer, colorectal cancer, kidney cancer, liver cancer, pancreatic cancer, stomach cancer, and thyroid cancer.

20. The method of claim 19, wherein the cancer is breast cancer.

21. The method of claim 19, wherein the cancer is ovarian cancer.

22. The method of claim 19, wherein the cancer is bladder cancer.

23. The method of claim 19, wherein the cancer is uterine cancer.

24. The method of claim 19, wherein the cancer is prostate cancer.

25. The method of claim 19, wherein the cancer is lung cancer.

26. The method of claim 19, wherein the cancer is esophageal cancer.

27. The method of claim 19, wherein the cancer is head and neck cancer.

28. The method of claim 19, wherein the cancer is colorectal cancer.

29. The method of claim 19, wherein the cancer is kidney cancer.

30. The method of claim 19, wherein the cancer is liver cancer.

31. The method of claim 19, wherein the cancer is pancreatic cancer.

32. The method of claim 19, wherein the cancer is stomach cancer.

33. The method of claim 19, wherein the cancer is thyroid cancer.

* * * * *

SEQUENCE LISTING

<160> NUMBER OF SEQ ID NOS: 4

<210> SEQ ID NO 1
<211> LENGTH: 2472
<212> TYPE: DNA
<213> ORGANISM: Homo sapiens

<400> SEQUENCE: 1

```
ggatccatgg acgtcgtgga ccctgacatt tcaatagag accccggga ccactatgac      60 ctgctacagc ggctgggtgg cggcacgtat ggggaagtct ttaaggctcg cgacaaggtg     120
tcaggggacc tggtggcact gaagatggtg aagatggagc ctgatgatga tgtctccacc     180
cttcagaagg aaatcctcat attgaaaact gccggcacg ccaacatcgt ggcctaccac     240
gggagttatc tctggttgca gaaactctgg atctgcatgg agttctgtgg ggctggttct     300
ctccaggaca tctaccaagt gacaggctcc ctgtcagagc tccagattag ctatgtctgc     360
cgggaagtgc tccagggact ggcctatttg cactcacaga gaagataca cagggacatc     420 aagggagcta acatcctcat caatgatgct ggggaggtca gattggctga ctttggcatc     480
```

```
tcggcccaga ttggggctac actggccaga cgcctctctt tcattgggac accctactgg    540
atggctccgg aagtggcagc tgtggccctg aagggaggat acaatgagct gtgtgacatc    600
tggtccctgg gcatcacggc catcgaactg gccgagctac agccaccgct ctttgatgtg    660
caccctctca gagttctctt cctcatgacc aagagtggct accagcctcc ccgactgaag    720
gaaaaaggca atggtcggc tgccttccac aacttcatca agtcactct gactaagagt      780 cccaagaaac gacccagcgc caccaagatg ctcagtcatc aactggtatc ccagcctggg    840
ctgaatcgag gcctgatcct ggatcttctt gacaaactga gaatcccgg gaaaggaccc     900 tccattgggg acattgagga tgaggagccc gagctacccc tgctatccc tcggcggatc     960 agatccaccc accgctccag ctctctgggc atccagatgc agactgctg tcggcggcac    1020 atggagttca ggaagctccg aggaatggag accagacccc cagccaacac cgctcgccta   1080
cagcctcccc gagacctcag gagcagcagc cccaggaagc aactgtcaga gtcgtctgac   1140
gatgactatg acgacgtgga catccccacc cctgcagagg acacacctcc tccacttccc   1200
cccaagccca gttccgttc tccatcagac gagggtcctg ggagcatggg ggatgatggg    1260
cagctgagcc cggggggtgct ggtccggtgt gccagtgggc ccccaccaaa cagccccgt    1320 cctgggcctc ccccatccac cagcagcccc cacctcaccg cccattcaga accctcactc   1380
tggaacccac cctcccggga gcttgacaag ccccccacttc tgcccccaa gaaggaaaag   1440 atgaagagaa agggatgtgc ccttctcgta aagttgttca atggctgccc cctccgcatc    1500
cacagcacgg ccgcctggac acatccctcc accaaggacc agcacctgct cctgggggca   1560
gaggaaggca tcttcatcct gaaccggaat gaccaggagg ccacgctgga aatgctcttt    1620
cctagccgga ctacgtgggt gtactccatc aacaacgttc tcatgtctct ctcaggaaag    1680
accccccacc tgtattctca tagcatcctt ggcctgctgg aacggaaaga gaccagagca    1740
ggaaacccca tcgctcacat tagccccac cgcctactgg caaggaagaa catggtttcc     1800
accaagatcc aggacaccaa aggctgccgg gcgtgctgtg tggcggaggg tgcgagctct    1860
gggggcccgt tcctgtgcgg tgcattggag acgtccgttg tcctgcttca gtggtaccag    1920
cccatgaaca aattcctgct tgtccggcag gtgctgttcc cactgccgac gcctctgtcc    1980
gtgttcgcgc tgctgaccgg gccaggctct gagctgcccg ctgtgtgcat cggcgtgagc    2040
cccgggcggc cggggaagtc ggtgctcttc cacacggtgc gctttggcgc gctctcttgc    2100
tggctgggcg agatgagcac cgagcacagg ggacccgtgc aggtgaccca ggtagaggaa    2160
gatatggtga tggtgttgat ggatggctct gtgaagctgg tgaccccgga ggggtcccca    2220
gtccggggac ttcgcacacc tgagatcccc atgaccgaag cggtggaggc cgtggctatg    2280
gttggaggtc agcttcaggc cttctggaag catgagtgc aggtgtgggc tctaggctcg     2340
gatcagctgc tacaggagct gagagaccct accctcactt tccgtctgct ggctcccccc    2400
aggcctgtag tggtggagac acgcccagtg gatgatccta ctgctcccag caacctctac    2460
atccaggaat ga                                                        2472
```

<210> SEQ ID NO 2
<211> LENGTH: 823
<212> TYPE: PRT
<213> ORGANISM: Homo sapiens

<400> SEQUENCE: 2

Gly Ser Met Asp Val Val Asp Pro Asp Ile Phe Asn Arg Asp Pro Arg
1               5                   10                  15

```
Asp His Tyr Asp Leu Leu Gln Arg Leu Gly Gly Gly Thr Tyr Gly Glu
             20                  25                  30

Val Phe Lys Ala Arg Asp Lys Val Ser Gly Asp Leu Val Ala Leu Lys
         35                  40                  45

Met Val Lys Met Glu Pro Asp Asp Val Ser Thr Leu Gln Lys Glu
 50                  55                  60

Ile Leu Ile Leu Lys Thr Cys Arg His Ala Asn Ile Val Ala Tyr His
 65                  70                  75                  80

Gly Ser Tyr Leu Trp Leu Gln Lys Leu Trp Ile Cys Met Glu Phe Cys
                 85                  90                  95

Gly Ala Gly Ser Leu Gln Asp Ile Tyr Gln Val Thr Gly Ser Leu Ser
             100                 105                 110

Glu Leu Gln Ile Ser Tyr Val Cys Arg Glu Val Leu Gln Gly Leu Ala
         115                 120                 125

Tyr Leu His Ser Gln Lys Lys Ile His Arg Asp Ile Lys Gly Ala Asn
130                 135                 140

Ile Leu Ile Asn Asp Ala Gly Glu Val Arg Leu Ala Asp Phe Gly Ile
145                 150                 155                 160

Ser Ala Gln Ile Gly Ala Thr Leu Ala Arg Arg Leu Ser Phe Ile Gly
                165                 170                 175

Thr Pro Tyr Trp Met Ala Pro Glu Val Ala Ala Val Ala Leu Lys Gly
             180                 185                 190

Gly Tyr Asn Glu Leu Cys Asp Ile Trp Ser Leu Gly Ile Thr Ala Ile
         195                 200                 205

Glu Leu Ala Glu Leu Gln Pro Pro Leu Phe Asp Val His Pro Leu Arg
     210                 215                 220

Val Leu Phe Leu Met Thr Lys Ser Gly Tyr Gln Pro Pro Arg Leu Lys
225                 230                 235                 240

Glu Lys Gly Lys Trp Ser Ala Ala Phe His Asn Phe Ile Lys Val Thr
                245                 250                 255

Leu Thr Lys Ser Pro Lys Lys Arg Pro Ser Ala Thr Lys Met Leu Ser
             260                 265                 270

His Gln Leu Val Ser Gln Pro Gly Leu Asn Arg Gly Leu Ile Leu Asp
         275                 280                 285

Leu Leu Asp Lys Leu Lys Asn Pro Gly Lys Gly Pro Ser Ile Gly Asp
     290                 295                 300

Ile Glu Asp Glu Glu Pro Glu Leu Pro Pro Ala Ile Pro Arg Arg Ile
305                 310                 315                 320

Arg Ser Thr His Arg Ser Ser Leu Gly Ile Pro Asp Ala Asp Cys
                325                 330                 335

Cys Arg His Met Glu Phe Arg Lys Leu Arg Gly Met Glu Thr Arg
             340                 345                 350

Pro Pro Ala Asn Thr Ala Arg Leu Gln Pro Pro Arg Asp Leu Arg Ser
         355                 360                 365

Ser Ser Pro Arg Lys Gln Leu Ser Glu Ser Ser Asp Asp Tyr Asp
     370                 375                 380

Asp Val Asp Ile Pro Thr Pro Ala Glu Asp Thr Pro Pro Leu Pro
385                 390                 395                 400

Pro Lys Pro Lys Phe Arg Ser Pro Ser Asp Glu Gly Pro Gly Ser Met
                405                 410                 415

Gly Asp Asp Gly Gln Leu Ser Pro Gly Val Leu Val Arg Cys Ala Ser
             420                 425                 430
```

Gly Pro Pro Asn Ser Pro Arg Pro Gly Pro Pro Ser Thr Ser
        435                 440                 445

Ser Pro His Leu Thr Ala His Ser Glu Pro Ser Leu Trp Asn Pro Pro
450                 455                 460

Ser Arg Glu Leu Asp Lys Pro Leu Leu Pro Pro Lys Lys Glu Lys
465                 470                 475                 480

Met Lys Arg Lys Gly Cys Ala Leu Leu Val Lys Leu Phe Asn Gly Cys
                485                 490                 495

Pro Leu Arg Ile His Ser Thr Ala Ala Trp Thr His Pro Ser Thr Lys
                500                 505                 510

Asp Gln His Leu Leu Gly Ala Glu Gly Ile Phe Ile Leu Asn
        515                 520                 525

Arg Asn Asp Gln Glu Ala Thr Leu Glu Met Leu Phe Pro Ser Arg Thr
530                 535                 540

Thr Trp Val Tyr Ser Ile Asn Asn Val Leu Met Ser Leu Ser Gly Lys
545                 550                 555                 560

Thr Pro His Leu Tyr Ser His Ser Ile Leu Gly Leu Leu Glu Arg Lys
                565                 570                 575

Glu Thr Arg Ala Gly Asn Pro Ile Ala His Ile Ser Pro His Arg Leu
        580                 585                 590

Leu Ala Arg Lys Asn Met Val Ser Thr Lys Ile Gln Asp Thr Lys Gly
        595                 600                 605

Cys Arg Ala Cys Cys Val Ala Glu Gly Ala Ser Ser Gly Gly Pro Phe
        610                 615                 620

Leu Cys Gly Ala Leu Glu Thr Ser Val Val Leu Leu Gln Trp Tyr Gln
625                 630                 635                 640

Pro Met Asn Lys Phe Leu Leu Val Arg Gln Val Leu Phe Pro Leu Pro
                645                 650                 655

Thr Pro Leu Ser Val Phe Ala Leu Leu Thr Gly Pro Gly Ser Glu Leu
                660                 665                 670

Pro Ala Val Cys Ile Gly Val Ser Pro Gly Arg Pro Gly Lys Ser Val
                675                 680                 685

Leu Phe His Thr Val Arg Phe Gly Ala Leu Ser Cys Trp Leu Gly Glu
        690                 695                 700

Met Ser Thr Glu His Arg Gly Pro Val Gln Val Thr Gln Val Glu Glu
705                 710                 715                 720

Asp Met Val Met Val Leu Met Asp Gly Ser Val Lys Leu Val Thr Pro
                725                 730                 735

Glu Gly Ser Pro Val Arg Gly Leu Arg Thr Pro Glu Ile Pro Met Thr
                740                 745                 750

Glu Ala Val Glu Ala Val Ala Met Val Gly Gly Gln Leu Gln Ala Phe
                755                 760                 765

Trp Lys His Gly Val Gln Val Trp Ala Leu Gly Ser Asp Gln Leu Leu
        770                 775                 780

Gln Glu Leu Arg Asp Pro Thr Leu Thr Phe Arg Leu Leu Gly Ser Pro
785                 790                 795                 800

Arg Pro Val Val Val Glu Thr Arg Pro Val Asp Asp Pro Thr Ala Pro
                805                 810                 815

Ser Asn Leu Tyr Ile Gln Glu
            820

<210> SEQ ID NO 3
<211> LENGTH: 66
<212> TYPE: DNA

```
<213> ORGANISM: Homo sapiens

<400> SEQUENCE: 3
atggcgtcgc atcaccatca ccatcacgat tacgatggtg ctacgaccga aaacctgtat    60
tttcag                                                                66

<210> SEQ ID NO 4
<211> LENGTH: 22
<212> TYPE: PRT
<213> ORGANISM: Homo sapiens

<400> SEQUENCE: 4

Met Ala Ser His His His His His His Asp Tyr Asp Gly Ala Thr Thr
1               5                   10                  15

Glu Asn Leu Tyr Phe Gln
            20
```